(12) United States Patent
Ohuchida et al.

(10) Patent No.: US 6,790,866 B2
(45) Date of Patent: Sep. 14, 2004

(54) SULFONAMIDE AND CARBOXAMIDE DERIVATIVES AND DRUGS CONTAINING THE SAME AS THE ACTIVE INGREDIENT

(75) Inventors: Shuichi Ohuchida, Osaka (JP); Yuuki Nagao, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 109 days.

(21) Appl. No.: 10/207,078

(22) Filed: Jul. 30, 2002

(65) Prior Publication Data

US 2003/0060460 A1 Mar. 27, 2003

Related U.S. Application Data

(62) Division of application No. 09/331,327, filed as application No. PCT/JP97/04593 on Dec. 12, 1997, now Pat. No. 6,448,290.

(30) Foreign Application Priority Data

Dec. 18, 1996 (JP) .............................. 8-353818
Oct. 21, 1997 (JP) .............................. 9-305055

(51) Int. Cl.[7] ........................ A61K 31/44; A61K 31/38; A61K 31/34; A61K 31/24
(52) U.S. Cl. ...................... 514/604; 514/346; 514/349; 514/350; 514/438; 514/445; 514/448; 514/472; 514/535; 514/562; 546/291; 546/312; 549/69; 549/71; 549/77; 549/479; 549/480; 549/483; 549/487; 560/13; 560/430; 562/430; 564/92
(58) Field of Search ................. 514/346, 349, 514/350, 438, 445, 448, 472, 535, 562, 604; 546/291, 312; 549/69, 71, 77, 479, 480, 483, 487; 560/13, 430; 562/430; 564/92

(56) References Cited

U.S. PATENT DOCUMENTS

3,655,693 A    4/1972  Shen et al. .............. 260/332.2
5,397,798 A    3/1995  Fitch et al. .................. 514/399

FOREIGN PATENT DOCUMENTS

JP    5916871    1/1984
JP    272150     3/1990
WO    9533461    12/1995
WO    9603380    2/1996
WO    9606822    3/1996
WO    9611902    4/1996

OTHER PUBLICATIONS

Justus Liebigs Ann. Chem. (1909), 367, 133.
Khim. Geterotsikl. Soedin (1974), (6), 760.
Khim. Geterotsikl. Soedin (1972), (10), 1341.
Khim. Geterotsikl. Soedin (1972), (5), 616.
Khim. Geterotsikl. Soedin (1976), (5), 641.
Khim. Geterotsikl. Soedin (1971), (7), 1028.
Khim. Geterotsikl. Soedin (1970), (12), 1597.
Supplemental European Search Report dated Nov. 19, 2001.

Primary Examiner—Peter O'Sullivan
(74) Attorney, Agent, or Firm—Stevens, Davis, Miller & Mosher, L.L.P.

(57) ABSTRACT

The sulfonamide or carboamide derivatives of the formula (I) and a pharmaceutical composition which comprise them as an active ingredient:

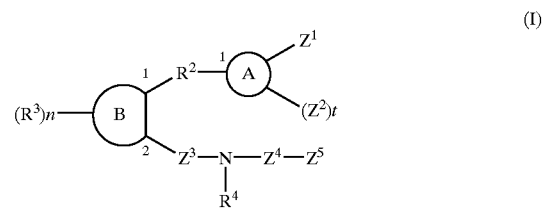

(wherein A ring, B ring is carbocyclic ring, heterocyclic ring; $Z^1$ is —$COR^1$, —CH=CH—$COR^1$ etc.; $Z^2$ is H, alkyl etc.; $Z^3$ is single bond, alkylene; $Z^4$ is $SO_2$, CO; $Z^5$ is alkyl, phenyl, heterocyclic ring etc.; $R^2$ is $CONR^8$, O, S, $NZ^6$, $Z^7$-alkylene, alkylene etc.; $R^3$ is H, alkyl, halogen, $CF_3$ etc.; $R^4$ is H, (substituted) alkyl etc.; n, t is 1–4).

The compounds of the formula (I) can bind to receptors of $PGE_2$ and show antagonistic activity against the action thereof or agonistic activity. Therefore, they are considered to be useful as medicine for inhibition of uterine contraction, analgesics, antidiarrheals, sleep inducers, medicine for increase of vesical capacity or medicine for uterine contraction, cathartic, suppression of gastric acid secretion, antihypertensive or diuretic agents.

13 Claims, No Drawings

SULFONAMIDE AND CARBOXAMIDE DERIVATIVES AND DRUGS CONTAINING THE SAME AS THE ACTIVE INGREDIENT

CROSS-REFERENCE TO RELATED APPLICATIONS

This application is a divisional application of U.S. Ser. No. 09/331,327, filed Jun. 18, 1999, now U.S. Pat. No. 6,448,290, which, in turn, is a §371 application of International Application No. PCT/JP97/04593, filed Dec. 12, 1997, claiming benefit of Japanese priority application Ser. Nos. JP 8-353818, filed Dec. 18, 1996 and JP 9-305055, filed Oct. 21, 1997, the entire disclosures of which are incorporated herein by reference.

FIELD OF TECHNOLOGY

This invention relates to sulfonamide and carboamide derivatives. More particularly, this invention relates to (1) the compounds of the formula (I):

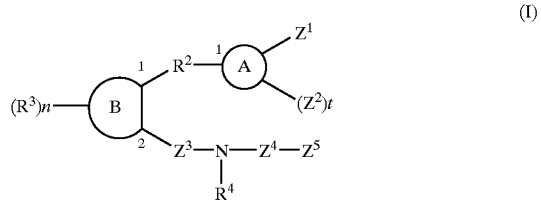

(wherein all symbols are as hereinafter defined.),
(2) processes for preparing them and
(3) Prostaglandin $E_2$ (abbreviated as $PGE_2$) antagonists or agonists which comprise them as an active ingredient.

BACKGROUND $PGE_2$ has been known as metabolite in the arachidonate cascade. It has been known that $PGE_2$ causes uterine contraction, induction of pain, promotion of digestive peristalsis, awakening effect, vesica contraction, suppression of gastric acid secretion or reduction of blood pressure etc. The $PGE_2$ antagonist or $PGE_2$ agonist is expected to show the following actions.

To antagonize against $PGE_2$ means to suppress the effects above mentioned, so such an activity is linked to inhibition of uterine contraction, analgesic action, inhibition of digestive peristalsis, induction of sleep or increase of vesical capacity. Therefore, $PGE_2$ antagonists are considered to be useful for the prevention of abortion, as analgesics, as antidiarrheals, as sleep inducers or as agents for treating pollakiuria.

To show $PGE_2$ agonistic activity means to promote the effects above mentioned, so such an activity is linked to uterine contraction, promotion of digestive peristalsis, suppression of gastric acid secretion or reduction of blood pressure or diuresis. Therefore, $PGE_2$ agonists are considered to be useful as abortifacient, cathartic, antiulcer, antigastritis, antihypertensive or diuretic agents.

A lot of $PGE_2$ agonists including $PGE_2$ itself etc. have been known, but only a few compounds ($PGE_2$ antagonists) possessing the inhibition of activity of $PGE_2$ by antagonizing against $PGE_2$ have been known.

For example, the patent applications relating to PGE antagonists are as follows:

In the specification of WO-96/03380, it is disclosed that the compounds of the formula (A):

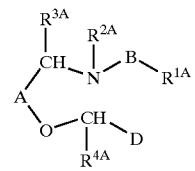

(wherein A is phenyl which may be substituted etc., B is ring system which may be substituted, D is ring system which may be substituted, $R^{1A}$ is carboxyl etc., $R^{2A}$ is H, C1–6 alkyl etc., $R^{3A}$ is H, C1–4 alkyl, $R^{4A}$ is H, C1–4 alkyl (as excerpt).) are active as PGE antagonists.

In the specification of WO-96/06822, it is disclosed that the compounds of the formula (B):

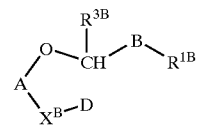

(wherein A is ring system which may be substituted, B is hetero aryl ring which may be substituted or phenyl which may be substituted, D is ring system which may be substituted, $X^B$ is $(CHR^{4B})_{nB}$ or $(CHR^{4B})_p CR^{4B}=CR^{4B} (CHR^{4B})_q$, $R^{1B}$ is carboxyl etc., $R^{3B}$ is H, C1–4 alkyl, $R^{4B}$ is H, C1–4 alkyl (as excerpt)) are active PGE antagonists.

In the specification of WO-96/11902, it is disclosed that the compounds of the formula (C):

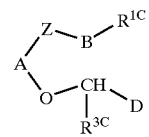

(wherein A, B and D are various ring systems, $R^{1C}$ is carboxyl etc., $R^{3C}$ is H, C1–4 alkyl. Z is —$(CH(R^{5C}))_m$ etc. (as excerpt)) are active as PGE antagonists.

On the other hand, some compounds having a similar structure to the present invention compounds have been known.

For example, the following compound is described in Justus Liebigs Ann. Chem. (1909), 367, 133:

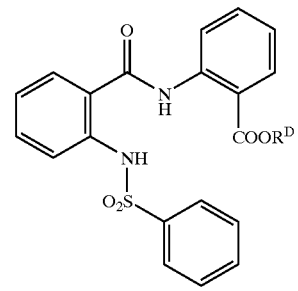

(wherein $R^D$ is H or ethyl.)

The following compound is described in Khim. Geterotsikl. Soedin (1974), (6), 760:

(E)

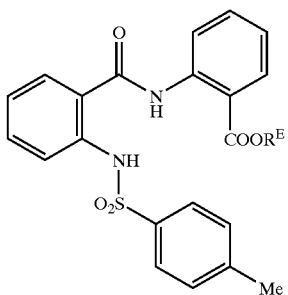

(wherein $R^E$ is phenethyl, benzyl, hexadecyl, decyl, nonyl, butyl, propyl, ethyl, methyl.)

The following compound is described in Khim. Geterotsikl. Soedin (1972), (10), 1341:

(F-1)

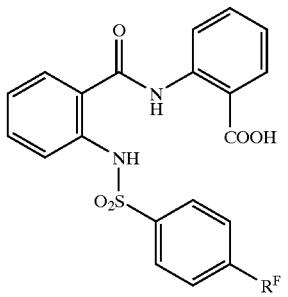

(F-2)

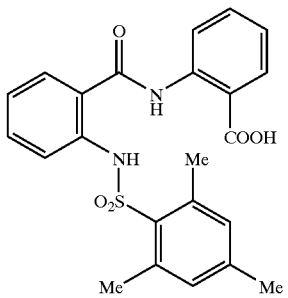

(wherein $R^F$ is nitro or methoxy.)

The following compound is described in Khim. Geterotsikl. Soedin (1972), (5), 616:

(G-1)

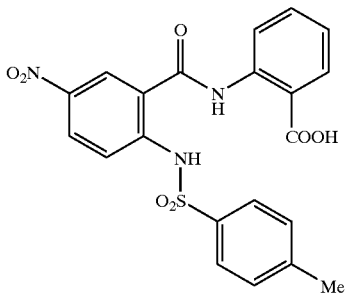

(G-2)

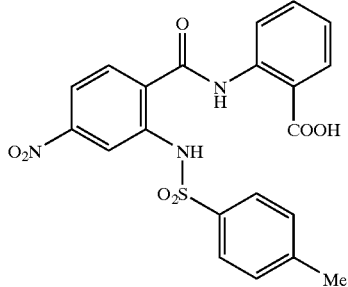

The following compound is described in Khim. Geterotsikl. Soedin (1976), (5), 641:

(H)

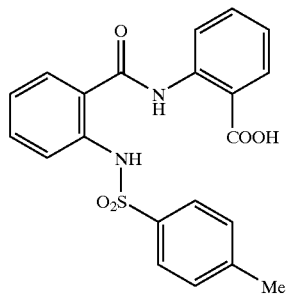

The following compound is described in Khim. Geterotsikl. Soedin (1971), (7), 1028:

(J-1)

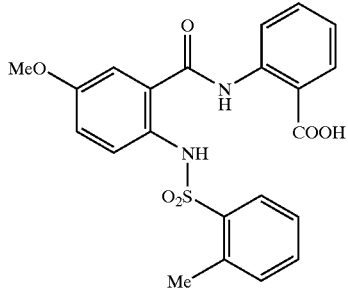

(J-2)

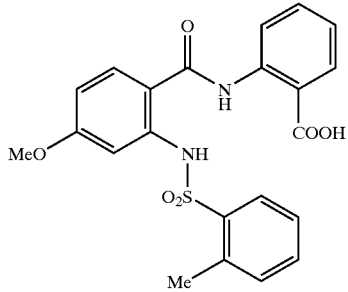

The following compound is described in Khim. Geterotsikl. Soedin (1970), (12), 1597:

(K-1)

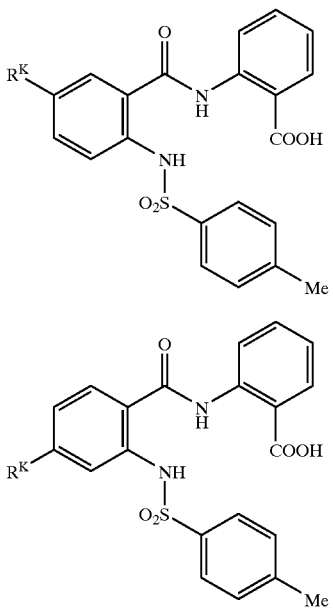

(K-2)

(wherein each $R^K$ is Br or Cl.)

The compounds of the formula (A), (B) and (C) in the related arts possess the same pharmacological activity as the present invention compounds. But there is a difference in structure as follows: The present invention compounds have sulfonamide or carboamide as an essential element in their structure. On the other hand, the compounds described in such related arts have ether or alkylene in the corresponding part. So, it is not easy to predict the present invention compounds from the structure of these related arts.

In addition, the compounds of the formula (D) to (K) relate to the study for synthesis only. In these literature, there is no description on pharmacological activity. The carboxyl group in such compounds is connected at the ortho position, so the present invention compounds are different from such compounds in structure. Therefore, it is not easy to predict the present invention from such compounds possessing the different activity and structure.

THE DISCLOSURE OF THE INVENTION

The present invention relates to (1) sulfonamide or carboamide derivatives of the formula (I)

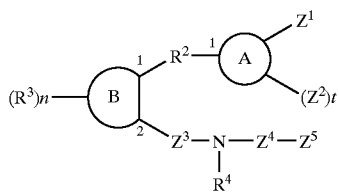

(I)

(wherein

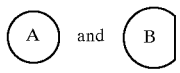

each, independently, is C5–15 carbocyclic ring or 5–7 membered heterocyclic ring containing one or two oxygen, sulfur or nitrogen atom(s), $Z^1$ is

—$COR^1$,

—C1–4 alkylene-$COR^1$,

—CH=CH—$COR^1$,

—C≡$COR^1$, or

—O—C1–3 alkylene-$COR^1$ (wherein $R^1$ is hydroxy, C1–4 alkoxy or formula $NR^6R^7$ (wherein $R^6$ and $R^7$ each, independently, is H or C1–4 alkyl.).), or —C1–5 alkylene-OH, $Z^2$ is H, C1–4 alkyl, C1–4 alkoxy, nitro, halogen, trifluoromethyl, trifluoromethoxy, hydroxy or $COR^1$ (wherein $R^1$ is as hereinbefore defined.), $Z^3$ is single bond or C1–4 alkylene, $Z^4$ is $SO_2$ or CO, $Z^5$ is (1) C1–8 alkyl, C2–8 alkenyl, or C2–8 alkynyl, (2) phenyl, C3–7 cycloalkyl, or 5–7 membered heterocyclic ring containing one or two oxygen, sulfur or nitrogen atom(s), or (3) C1–4 alkyl, C2–4 alkenyl or C2–4 alkynyl substituted by phenyl or C3–7 cycloalkyl (phenyl, C3–7 cycloalkyl, and 5–7 membered heterocyclic ring containing one or two oxygen, sulfur or nitrogen atom(s) mentioned in the above (2) and (3) may be substituted by 1–5 of $R^5$ (wherein $R^5$ (if two or more $R^5$, each independently) is H, C1–6 alkyl, C1–6 alkoxy, C1–6 alkylthio, nitro, halogen, tifluoromethyl, trifluoromethoxy or hydroxy.).), $R^2$ is $CONR^8$, $NR^8CO$, $CONR^8$—C1–4 alkylene, C1–4 alkylene-$CONR^8$, $NR^8CO$—C1–4 alkylene, C1–4 alkylene-$NR^8CO$, C1–3 alkylene-$CONR^8$—C1–3 alkylene, or C1–3 alkylene-$NR^8CO$—C1–3 alkylene (wherein each $R^8$ is H or C1–4 alkyl.),

O, S, $NZ^6$ (wherein $Z^6$ is H or C1–4 alkyl.), $Z^7$-C1–4 alkylene,

C1–4 alkylene-$Z^7$, or

C1–3 alkylene-$Z^7$-C1–3 alkylene (wherein each $Z^7$ is O, S or $NZ^6$ (wherein $Z^6$ is as hereinbefore defined.).),

CO,

CO—C1–4 alkylene,

C1–4 alkylene-CO,

C1–3 alkylene-CO—C1–3 alkylene,

C2–4 alkylene,

C2–4 alkenylene, or

C2–4 alkynylene, $R^3$ is H, C1–6 alkyl, C1–6 alkoxy, C1–6 alkylthio, nitro, halogen, trifluoromethyl, trifluoromethoxy, hydroxy or hydroxymethyl, $R^4$ is (1) H, (2) C1–8 alkyl, C2–8 alkenyl, or C2–8 alkynyl, (3) C1–6 alkyl substituted by one or two substituent(s) selected from the group consisting of $COOZ^8$, CONZ$^9$Z$^{10}$, and OZ$^8$ (wherein Z$^8$, Z$^9$ and Z$^{10}$ each, independently, is H or C1–4 alkyl.) and C1–4 alkoxy-C1–4 alkoxy, (4) C3–7 cycloalkyl, or (5) C1–4 alkyl, C2–4 alkenyl or C2–4 alkynyl substituted by phenyl or C3–7 cycloalkyl (phenyl and C3–7 cycloalkyl mentioned in the above (4) and (5) may be substituted by 1–5 of R$^5$ (wherein R$^5$ is as hereinbefore defined.).), and n and teach, independently, is an integer of 1–4, with the proviso that (1) R$^2$ and Z$^3$ should be connected at the 1- or 2-position of

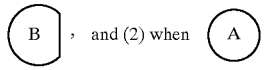, and (2) when is a benzene ring and (Z$^2$)t is other than COR$^1$, Z$^1$ should be connected at the 3- or 4-position of the benzene ring.), or a non-toxic salt thereof, (2) processes for preparing them and (3) PGE$_2$ antagonists or agonists which comprise them as an active ingredient.

DETAILED DESCRIPTION OF THE INVENTION

In the formula (I), C1–4 alkyl in Z$^5$ and R$^4$ and C1–4 alkyl represented by Z$^2$, Z$^6$, Z$^8$, Z$^9$, Z$^{10}$, R$^6$, R$^7$ and R$^8$ means methyl, ethyl, propyl, butyl and isomer thereof.

In the formula (I), C1–6 alkyl in R$^4$ and C1–6 alkyl represented by R$^3$ and R$^5$ means methyl, ethyl, propyl, butyl, pentyl, hexyl and isomer thereof.

In the formula (I), C1–8 alkyl represented by Z$^5$ and R$^4$ means methyl, ethyl, propyl, butyl, pentyl, hexyl, heptyl, octyl and isomer thereof.

In the formula (I), C2–4 alkenyl in Z$^5$ and R$^4$ means vinyl, propenyl, butenyl and isomer thereof.

In the formula (I), C2–8 alkenyl represented by Z$^5$ and R$^4$ means C2–8 alkyl having 1–3 of double bond and, for example, vinyl, propenyl, butenyl, pentenyl, hexenyl, heptenyl, octenyl etc. and isomer thereof.

In the formula (I), C2–4 alkynyl in Z$^5$ and R$^4$ means ethynyl, propynyl, butynyl and isomer thereof.

In the formula (I), C2–8 alkynyl represented by Z$^5$ and R$^4$ means C2–8 alkyl having 1–3 of triple bond and, for example, ethynyl, propynyl, butynyl, pentynyl, hexynyl, heptynyl, octynyl etc. and isomer thereof.

In the formula (I), C1–4 alkoxy in R$^4$ and C1–4 alkoxy represented by Z$^2$ and R$^1$ means methoxy, ethoxy, propoxy, butoxy and isomer thereof.

In the formula (I), C1–6 alkoxy represented by R$^3$ and R$^5$ means methoxy, ethoxy, propoxy, butoxy, pentyloxy, hexyloxy and isomer thereof.

In the formula (I), C1–6 alkylthio represented by R$^3$ and R$^5$ means methylthio, ethylthio, propylthio, butylthio, pentylthio, hexylthio and isomer thereof.

In the formula (I), C1–3 alkylene in Z$^1$ and R$^2$ means methylene, ethylene, trimethylene and isomer thereof.

In the formula (I), C1–4 alkylene in Z$^1$ and R$^2$ and C1–4 alkylene represented by Z$^3$ means methylene, ethylene, trimethylene, tetramethylene and isomer thereof.

In the formula (I), C1–5 alkylene in Z$^1$ means methylene, ethylene, trimethylene, tetramethylene, pentamethylene and isomer thereof.

In the formula (I), C2–4 alkylene represented by R$^2$ means ethylene, trimethylene, tetramethylene and isomer thereof.

In the formula (I), C2–4 alkenylene represented by R$^2$ means vinylene, propenylene, butenylene and isomer thereof.

In the formula (I), C2–4 alkynylene represented by R$^2$ means ethynylene, propynylene, butynylene and isomer thereof.

In the formula (I), C3–7 cycloalkyl in Z$^5$ and R$^4$ and C3–7 cycloalkyl represented by Z$^5$ and R$^4$ means cyclopropyl, cyclobutyl, cyclopentyl, cyclohexyl, cycloheptyl.

In the formula (I), C5–15 carbocyclic ring represented by

means mono-, bi- or tri-ring of C5–15 carbocyclic aryl, or partially or fully saturated ring thereof.

For example, C5–15 carbocyclic aryl includes benzene, pentalene, indene, naphthalene, azulene, fluorene, anthracene etc. Partially or fully saturated ring thereof includes the above mentioned ring which is partially or fully saturated.

As for C5–15 carbocyclic ring, preferably, mono- or bi-ring of C5–10 carbocyclic aryl and the mentioned C5–7 cycloalkyl is listed, and more preferably, benzene, naphthalene, cyclopentyl, cyclohexyl or cycloheptyl.

In the formula (I), 5–7 membered heterocyclic ring containing one or two oxygen, sulfur or nitrogen atom(s) represented by

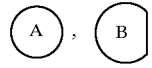

and Z$^5$ means 5–7 membered heterocyclic aryl ring containing one or two oxygen, sulfur or nitrogen atom(s) or partially or fully saturated ring thereof.

5–7 membered heterocyclic aryl ring containing one or two oxygen, sulfur or nitrogen atom(s) includes pyrrole, imidazole, pyrazole, pyridine, pyrazine, pyrimidine, pyridazine, azepine, diazepine, furan, pyran, oxepine, oxazepine, thiophen, thiain (thiopyran), thiepine, oxazole, isoxazole, thiazole, isothiazole, oxadiazole, oxadiazine, oxazepine, oxadiazepine, thiadiazole, thiadiazine, thiadiazepine etc.

5–7 membered heterocyclic aryl ring containing one or two oxygen, sulfur or nitrogen atom(s) which is partially or fully saturated includes pyrroline, pyrrolidine, imidazoline, imidazolidine, pyrazoline, pyrazolidine, piperidine, piperazine, tetrahydropyrimidine, tetrahydropyridazine, dihydroturan, tetrahydrofuran, dihydropyran, tetrahydropyran, dihydrothiophen, tetrahydrothiophen, dihydrothiain (dihydrothiopyran), tetrahydrothiain (tetrahydrothiopyran), dihydroxazole, tetrahydroxazole, dihydroisoxazole, tetrahydroisoxazole, dihydrothiazole, tetrahydrothiazole, dihydroisothiazole, tetrahydroisothiazole, morpholine, thiomorpholine etc.

In the formula (I), halogen represented by Z$^2$, R$^3$ and R$^5$ means chlorine, bromine, fluorine and iodine.

In the formula (I), as for Z$^3$ which represents single bond or C1–4 alkylene, preferably, single bond or methylene is listed and more preferably, single bond.

In the formula (I), as for Z$^4$ which represents SO$_2$ or CO, preferably SO$_2$ is listed.

In the formula (I), as for $R^4$, preferably, every group is listed and more preferably, group other than hydrogen.

Unless otherwise specified, all isomers are included in the invention. For example, alkyl, alkylene and alkenylene includes straight-chain or branched-chain ones. Double bond in alkenylene include structure of configurations E, Z and EZ mixtures. Isomers generated by asymmetric carbon (s) e.g. branched alkyl are also included in the present invention.

In the compounds of the formula (I) of the present invention, the compounds wherein

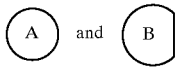

is C5–15 carbocyclic ring and $Z^5$ is C1–8 alkyl, C2–8 alkenyl, C2–8 alkynyl, or group containing phenyl or C3–7 cycloalkyl (each ring may be substituted.) are preferable. The compounds wherein

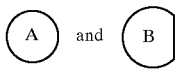

is mono- or bi-ring of C5–10 carbocyclic aryl and C5–7 cycloalkyl and $Z^5$ is the above mentioned group are more preferable.

The compounds wherein at least one of

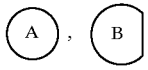

and $Z^5$ is 5–7 membered heterocyclic ring containing one or two oxygen, sulfur or nitrogen atom(s) (each ring may be substituted.) are also preferable. Such compounds include, for example, the compounds wherein (1)

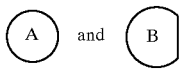

is C5–15 carbocyclic ring and $Z^5$ is 5–7 membered heterocyclic ring containing one or two oxygen, sulfur or nitrogen atom(s) or (2) one of

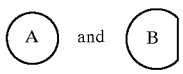

is 5–7 membered heterocyclic ring containing one or two oxygen, sulfur or nitrogen atom(s) and the other is C5–15 carbocyclic ring. The compounds wherein carbocyclic ring represented by

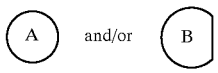

in case of the above (1) and (2) is mono- or bi-ring of C5–10 carbocyclic aryl and C5–7 cycloalkyl are more preferable.

In the compounds of the formula (I) of the present invention, concrete and preferable compounds include the compounds described in the Examples and corresponding esters and amides.

[Salt]

The compounds of the present invention of the formula (I) may be converted into the corresponding salts by methods known per se. Non-toxic and water-soluble salts are preferable. Suitable salts, for example, are as follows: salts of alkali metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine etc.).

[The Method of the Preparation for the Present Invention Compounds]

The compounds of the formula (I) of the present invention may be prepared by the method described in the following, the method described in the Examples as hereinafter or known methods.

(1) In the compounds of the formula (I) of the present invention, the carboxylic acid compounds of the formula (Ia):

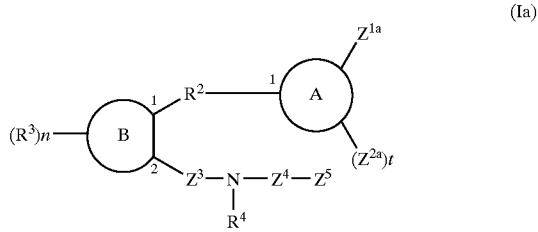

(Ia)

(wherein $Z^{1a}$ and $Z^{2a}$ are as $Z^1$ and $Z^2$, respectively, with the proviso that at least one of them is COOH or a group containing COOH, and the other symbols are as hereinbefore defined.)

may be prepared from the ester compound of the formula (Ib):

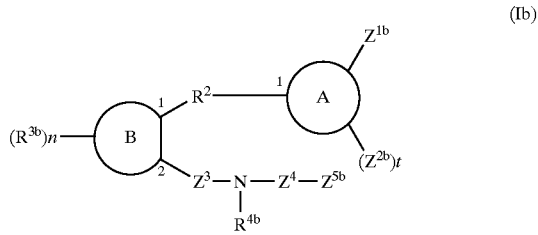

(Ib)

(wherein $Z^{1b}$ and $Z^{2b}$ are as $Z^1$ and $Z^2$, respectively, with the proviso that at least one of them is $COR^{1b}$ or a group containing $COR^{1b}$ (wherein $R^{1b}$ is C1–4 alkoxy or methoxymethoxy (abbreviated as OMOM.).), $R^{3b}$, $R^{4b}$ and $Z^{5b}$ are as $R^3$, $R^4$ and $Z^5$, respectively, with the proviso when $R^3$, $R^4$ or $R^5$ in $Z^5$ is COOH or hydroxy, or a group containing COOH or hydroxy, each COOH and hydroxy is protected by a protecting group which is removable under an acidic, neutral or alkaline condition, and the other symbols are as hereinbefore defined.)

by hydrolysis under an alkaline, acidic or neutral condition, if necessary, followed by hydrolysis under the different condition.

The removal of a protecting group by hydrolysis under an alkaline, acidic or neutral condition is a well-known reaction as hereinafter described.

(2) In the compounds of the formula (I) of the present invention, the ester compounds of the formula (Ic):

(Ic)

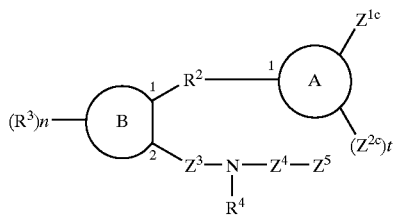

(wherein $Z^{1c}$ and $Z^{2c}$ are as $Z^1$ and $Z^2$, respectively, with the proviso that at least one of them is $COR^{1c}$ or a group containing $COR^{1c}$ (wherein $R^{1c}$ is C1–4 alkoxy.) and the other symbols are as hereinbefore defined.) may be prepared from the compound of the formula (Ia) by esterification.

Esterification is well known, it may be carried out, for example;

(a) by the method using diazoalkane,
(b) by the method using alkyl halide,
(c) by the method using dimethylformamide (DMF)-dialkyl acetal or
(d) by the method reacting corresponding alkanol etc.

Concrete description of the methods described above are as follows:

(a) The method using diazoalkane may be carried out, for example, using corresponding diazoalkane in an organic solvent (diethylether, ethyl acetate, methylene chloride, acetone, methanol or ethanol etc.) at –10~40° C.

(b) The method using alkyl halide may be carried out, for example, in an organic solvent (acetone, DMF, dimethylsufoxide (DMSO) etc.) in the presence of base (potassium carbonate, sodium carbonate, potassium hydrogen carbonate, sodium hydrogen carbonate, calcium oxide etc.) using corresponding alkyl halide at –10~40° C.

(c) The method using DMF-dialkyl acetal may be carried out, for example, in an organic solvent (benzene, toluene etc.) using corresponding DMF-dialkyl acetal at –10~40° C.

(d) The method of reacting corresponding alkanol may be carried out, for example, in corresponding alkanol ($HR^{1c}$ ($R^{1c}$ is as hereinbefore defined.)) using acid (HCl, sulfuric acid, p-toluene sulfonic acid, hydrochloride gas etc.) or condensing agents (DCC, pivaloyl halide, aryl sulfonyl halide, alkyl sulfonyl halide etc.) at 0~40° C.

Of course, an organic solvent (tetrahydrofuran, methylene chloride etc.) which does not relate to the reaction may be added in these esterification.

(3) In the compounds of the formula (I) of the present invention, the amide compounds of the formula (Id):

(Id)

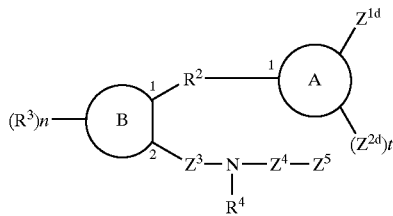

(wherein $Z^{1d}$ and $Z^{2d}$ are as $Z^1$ and $Z^2$, respectively, with the proviso that at least one of them is $COR^{1d}$ or a group containing $COR^{1d}$ (wherein $R^{1d}$ is $NR^6R^7$ (wherein all symbols are as hereinbefore defined.), and the other symbols are as hereinbefore defined.)

may be prepared by reacting the compound of the formula (Ia) with the compound of the formula (III):

$$HNR^6R^7 \quad (III)$$

(wherein all symbols are as hereinbefore defined.) to form the amide bond.

Reaction to form amide-bond is well known, it may be carried out, for example, in an organic solvent (THF, methylene chloride, benzene, acetone, acetonitrile etc.), in the presence or absence of tertiary amine (dimethylaminopyridine, pyridine, triethylamine etc.) using a condensing agent (EDC or DCC etc.) at 0~50° C.

(4) In the compounds of the formula (I) of the present invention, the alcohol compounds of the formula (Ie):

(Ie)

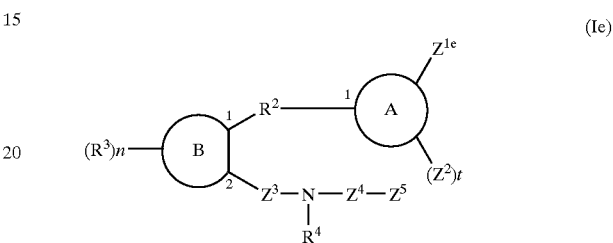

(wherein $Z^{1e}$ is C1–5 alkylene-OH, and the other symbols are as hereinbefore defined.)

may be prepared by the reduction of the compound of the formula (If):

(If)

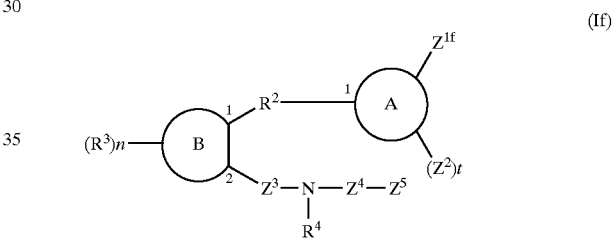

(wherein $Z^{1f}$ is $COOY^f$ for C1–4 alkylene-$COOY^f$ (wherein $Y^f$ is C1–4 alkyl.), and the other symbols are as hereinbefore defined.).

The reductive reaction is known, and for example, this reaction may be carried out in the presence of organic solvent (THF, methylene chloride, diethylether, lower alkanol etc.) using lithium aluminum hydride (LAH) or diisobutyl aluminum hydride (DIBAL) at –78° C. to room temperature.

(5) In the compounds of the formula (Ib), wherein $R^2$ is $CONR^8$, C1–4 alkylene-$CONR^8$, $CONR^8$—C1–4 alkylene, C1–3 alkylene-$CONR^8$—C1–3 alkylene, (wherein all symbols are as hereinbefore defined.), i.e. the compounds of the formula (Ib-1):

(Ib-1)

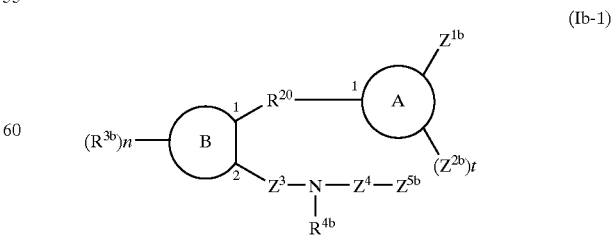

(wherein $R^{20}$ is $CONR^8$, C1–4 alkylene-$CONR^8$, $CONR^8$—C1–4 alkylene, C1–3 alkylene-$CONR^8$—C1–3 alkylene, (wherein all symbols are as hereinbefore defined.), and the other symbols are as hereinbefore defined.)

may be prepared by reacting the compound of the formula (IV):

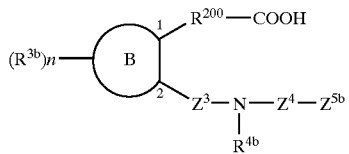
(IV)

(wherein $R^{200}$ is single bond or C1–4 alkylene, and the other symbols are as hereinbefore defined.)

with the formula (V):

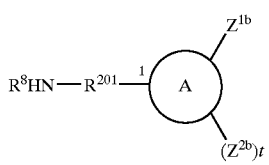
(V)

(wherein $R^{201}$ is single bond or C1–4 alkylene, and the other symbols are as hereinbefore defined.)

to form amide bond.

Reaction to form amide bond may be carried out as the method described in the said (3).

(6) In the compounds of the formula (Ib), wherein $R^2$ is $NR^8CO$, C1–4 alkylene-$NR^8CO$, $NR^8CO$—C1–4 alkylene, C1–3 alkylene-$NR^8CO$—C1–3 alkylene (wherein all symbols are as hereinbefore defined.), i.e. the compounds of the formula (Ib-2):

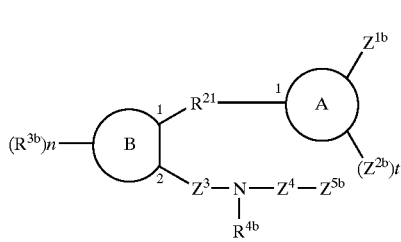
(Ib-2)

(wherein $R^{21}$ is $NR^8CO$, C1–4 alkylene-$NR^8CO$, $NR^8CO$—C1–4 alkylene, C1–3 alkylene-$NR^8CO$—C1–3 alkylene (wherein all symbols are as hereinbefore defined.), and the other symbols are as hereinbefore defined.)

may be prepared by reacting the compound of the formula (VI):

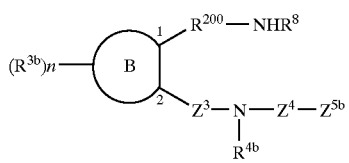
(VI)

(wherein all symbols are as hereinbefore defined.)

with the compound of the formula (VII):

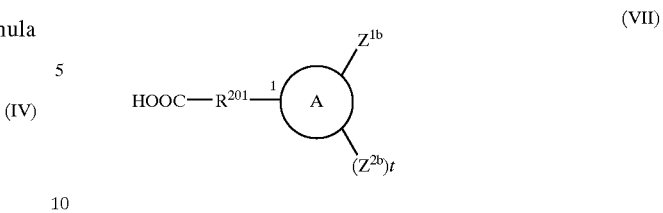
(VII)

(wherein all symbols are as hereinbefore defined.)

to form amide bond.

Reaction to form amide bond may be carried out as the method described in the said (3).

(7) In the compounds of the formula (Ib), wherein $R^2$ is O, S, $NZ^6$, $Z^7$-C1–4 alkylene, C1–4 alkylene-$NZ^7$ or C1–3 alkylene-$NZ^7$-C1–3 alkylene (wherein all symbols are as hereinbefore defined.), i.e. the compounds of the formula (Ib-3)

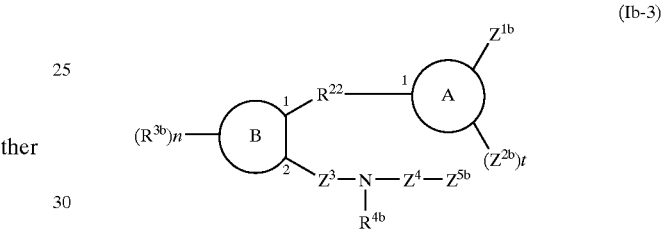
(Ib-3)

(wherein $R^{22}$ is O, S, $NZ^6$, $Z^7$-C1–4 alkylene, C1–4 alkylene-$NZ^7$ or C1–3 alkylene-$NZ^7$-C1–3 alkylene (wherein all symbols are as hereinbefore defined.).)

may be prepared by reacting the compound of the formula (VIII):

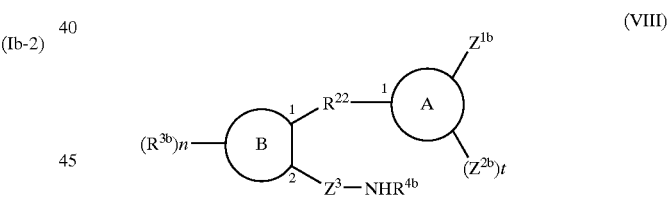
(VIII)

(wherein all symbols are as hereinbefore defined.)

with the compound of the formula (IX):

$$X-Z^4-Z^{5b} \quad (IX)$$

(wherein X is halogen and the other symbols are as hereinbefore defined.) to form sulfonamide bond or carboamide bond.

Reactions to form sulfonamide bond or carboamide bond may be carried out, for example, in an organic solvent (THF, methylene chloride, benzene, acetone, acetonitrile etc.), in the presence or absence of tertiary amine (dimethylaminopyridine, pyridine, triethylamine etc.) at 0~50° C.

(8) In the compounds of the formula (Ib), wherein $R^2$ is $NZ^6$—C1–4 alkylene, C1–4 alkylene-$NZ^6$ or C1–3 alkylene-$NZ^6$—C1–3 alkylene (wherein all symbols are as hereinbefore defined.), i.e. the compounds of the formula (Ib-4):

(Ib-4)

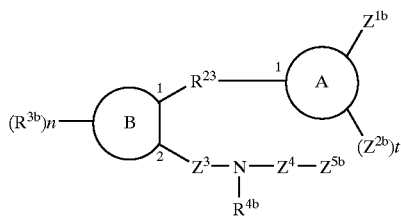

(wherein $R^{23}$ is $NZ^6$—C1–4 alkylene, C1–4 alkylene-$NZ^6$ or C1–3 alkylene-$NZ^6$—C1–3 alkylene (wherein all symbols are as hereinbefore defined.) and the other symbols are as hereinbefore defined.)
may be prepared by
(a) reacting (reductive amination) the compound of the formula (VI-a):

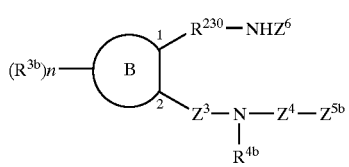

(VI-a)

(wherein $R^{230}$ is single bond or C1–4 alkylene, and the other symbols are as hereinbefore defined.)
with the compound of the formula (VII-a):

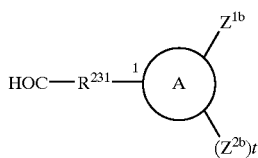

(VII-a)

(wherein $R^{231}$ is single bond or C1–3 alkylene, and the other symbols are as hereinbefore defined.) or
(b) reacting (reductive amination) the compound of the formula (VI-b):

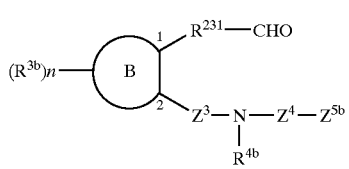

(VI-b)

(wherein all symbols are as hereinbefore defined.)
with the compound of the formula (VII-b):

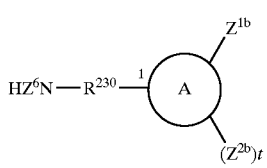

(VII-b)

(wherein all symbols are as hereinbefore defined.).
The reaction of reductive amination described in the above (a) and (b) may carried out, for example, in organic solvent (methanol etc.), in an acidic condition, using a boron reagent such as sodium cyanoborohydride etc. at 0~50° C.

(9) In the compounds of the formula (Ib), wherein $R^2$ is C2–4 alkenylene, i.e. the compounds of the formula (Ib-5):

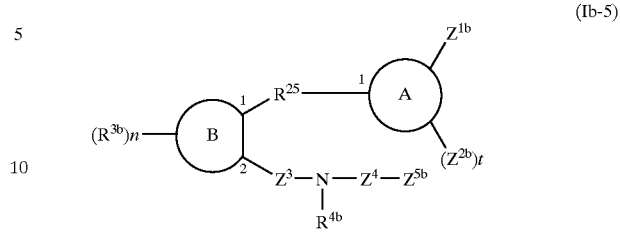

(Ib-5)

(wherein $R^{25}$ is C2–4 alkenylene and the other symbols are as hereinbefore defined.)
may be prepared by reacting the compound of the formula (XI):

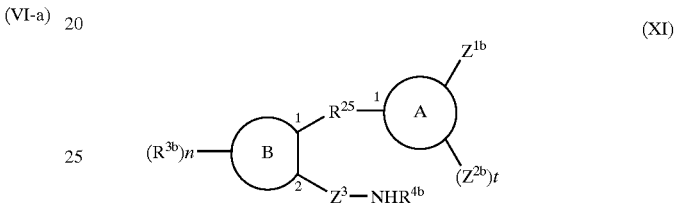

(XI)

(wherein all symbols are as hereinbefore defined.)
with the compound of the formula (IX):

$$X\text{-}Z^4\text{-}Z^{5b}$$ (IX)

(wherein all symbols are as hereinbefore defined.)
to form sulfonamide bond or carboamide bond.
Reaction to form sulfonamide bond or carboamide bond may be carried out as the method described in the said (7).

(10) In the compounds of the formula (Ib), wherein $R^2$ is C2–4 alkylene, i.e. the compounds of the formula (Ib-6):

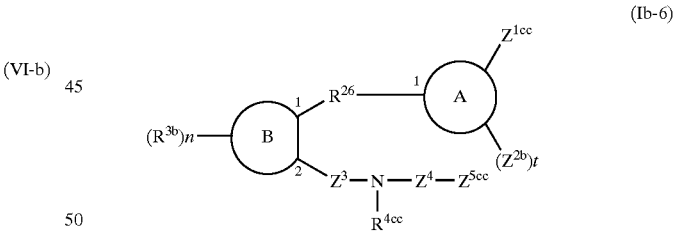

(Ib-6)

(wherein $R^{26}$ is C2–4 alkylene, $Z^{1cc}$, $Z^{5cc}$ and $Z^{4cc}$ are as $Z^{1b}$, $Z^{5b}$ and $Z^{4b}$, respectively, with the proviso that none of $Z^{1cc}$, $Z^{5cc}$ and $Z^{4cc}$ are alkenylene, alkynylene, alkenylene-containing group and alkynylene-containing group, and the other symbols are as hereinbefore defined.)
may be prepared by catalytic reduction of the compound of the formula (Ib-5).
The catalytic reduction is known, and for example, this reaction may be carried out under the condition of atmosphere of hydrogen gas, in an organic solvent (THF, alkanol or acetone etc.), using a reductive catalyst (Pd, Pd—C, Pt or platinum oxide etc.) at 0~50° C.

(11) In the compounds of the formula (Ib), wherein $R^2$ is C2–4 alkynylene, i.e. the compounds of the formula (Ib-7):

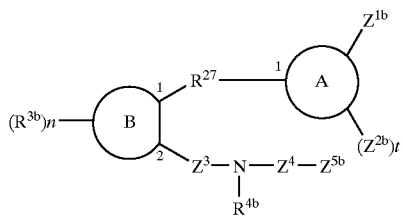
(Ib-7)

(wherein $R^{27}$ is C2–4 alkynylene, and the other symbols are as hereinbefore defined.)

may be prepared by reacting the compound of the formula (XII):

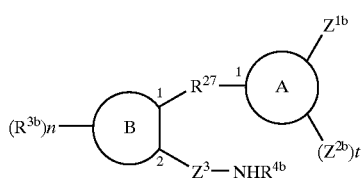
(XII)

(wherein all symbols are as hereinbefore defined.)
with the compound of the formula (IX):

$$X\text{-}Z^4\text{-}Z^{5b} \qquad (IX)$$

(wherein all symbols are as hereinbefore defined.)
to form sulfonamide bond or carboamide bond.

Reaction to form sulfonamide bond or carboamide bond may be carried out as the method described in the said (7).

(12) In the compounds of the formula (Ib), wherein $R^2$ is $NZ^6SO_2$ (wherein all symbols are as hereinbefore defined.), i.e. the compounds of the formula (Ib-8):

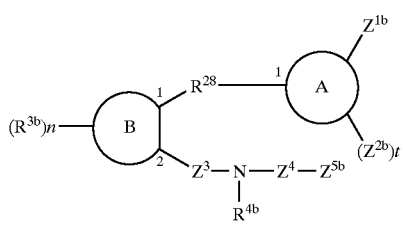
(Ib-8)

(wherein $R^{28}$ is $NZ^6SO_2$ (wherein all symbols are as hereinbefore defined.), and the other symbols are as hereinbefore defined.)

may be prepared by reacting the compound of the formula (Z-1):

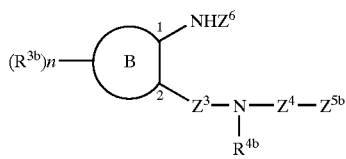
(Z-1)

(wherein all symbols are as hereinbefore defined.)

with the compound of the formula (Z-2):

(Z-2)

(wherein all symbols are as hereinbefore defined.)
to form sulfonamide bond.

Reaction to form sulfonamide bond may be carried out as the method described in the said (7).

(13) In the compounds of the formula (Ib), wherein $R^2$ is CO, CO—C1–4 alkylene, C1–4 alkylene-CO or C1–3 alkylene-CO—C1–3 alkylene, i.e. the compounds of the formula (Ib-9):

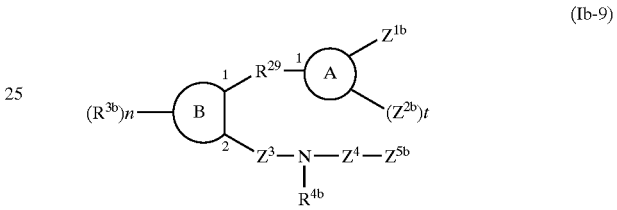
(Ib-9)

(wherein $R^{29}$ is CO, CO—C1–4 alkylene, C1–4 alkylene-CO or C1–3 alkylene-CO—C1–3 alkylene, and the other symbols are as hereinbefore defined.)

may be prepared by reacting the compound of the formula (Z-3):

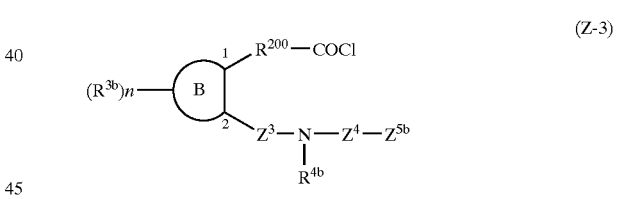
(Z-3)

(wherein all symbols are as hereinbefore defined.)
with the compound of the formula (Z-4):

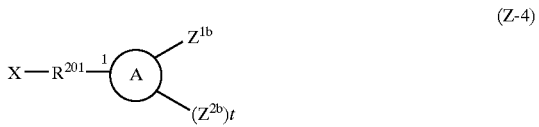
(Z-4)

(wherein all symbols are as hereinbefore defined.).

The reaction may be carried out, for example, in organic solvent (THF, methylene chloride, benzene, acetone, acetonitrile etc.) in the presence of Zn or cyano copper at −78° C. to room temperature.

(14) In the compounds of the formula (Ib), wherein $R^{4b}$ is group other than H, i.e. the compounds of the formula (Ib-10):

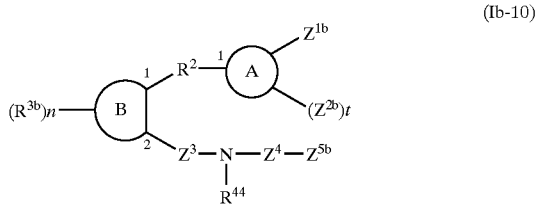

(Ib-10)

(wherein $R^{44}$ is as $R^4$ other than H, and the other symbols are as hereinbefore defined.)
may be prepared by reacting the compound of the formula (Ib-11):

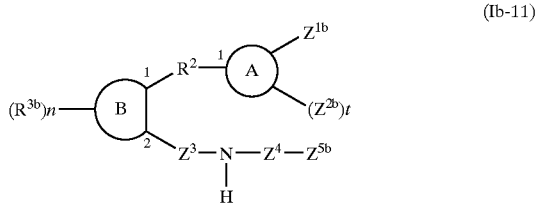

(Ib-11)

(wherein all symbols are as hereinbefore defined.)
and (a) the compound of the formula (Z-5):

X—$R^{44}$ (Z-5)

(wherein all symbols are as hereinbefore defined.)
or (b) the compound of the formula (Z-6):

HO—$R^{44}$ (Z-6)

(wherein all symbols are as hereinbefore defined.).

The above reaction is N-alkylation reaction or corresponding reaction. For example, this reaction (a) in case of using alkyl halide of the formula:

X—$R^{44}$ (wherein all symbols are as hereinbefore defined.),
may be carried out in organic solvent (acetone, THF or methylene chloride etc.), in the presence of base (potassium carbonate etc.) at 0~50° C.

The reaction (b) in case of using alcohol of the formula:

HO—$R^{44}$ (wherein all symbols are as hereinbefore defined.),
may be carried out in organic solvent (acetone, THF or methylene chloride etc.), in the presence of triphenylphosphine and diethyldiazocarboxylate (DEAD) at 0~50° C.

(15) The compounds wherein $R^3$ is hydroxymethyl may be prepared by the method mentioned above or the method described in the Examples hereinafter.

(16) The compounds wherein $Z^4$ is $SO_2$ and $Z^5$ is cyclopentyl, cyclohexyl (each ring may be substituted by 1–5 of $R^5$ ($R^5$ is as hereinbefore defined.).) or isopropyl may be prepared by the method mentioned above or the method described in the Examples hereinafter.

(17) The compounds wherein symbol(s) other than $Z^1$ is/are COOH, COO$Z^a$ (wherein $Z^a$ is C1–4 alkyl) or hydroxy or group containing COOH, COO$Z^a$ (wherein $Z^a$ is as hereinbefore defined.) or hydroxy may be prepared by reacting under the condition that each of the above groups and $Z^1$ if necessary are protected by a protecting group which is removable under an alkaline, acidic or neutral condition and removing a protecting group under an alkaline, acidic or neutral condition or combining removal of protecting groups under different conditions (for example, removal of a protecting group under an acidic condition and removal of a protecting group under an alkaline condition may be carried out successively, either reaction being started first.).

A protecting group of COOH which is removable under an acidic condition includes, for example, silyl containing group such as t-butyldimethylsilyl etc. or t-butyl.

A protecting group of COOH which is removable under an alkaline condition includes alkyl group (for example, methyl etc.) other than t-butyl.

A protecting group of COOH which is removable under both an acidic condition and an alkaline condition includes, for example, methoxymethyl.

A protecting group of COOH which is removable under a neutral condition includes benzyl etc.

A protecting group of hydroxy which is removable under an acidic condition includes, for example, tetrahydropyranyl, silyl containing group such as t-butyldimethylsilyl etc. 1-ethoxyethyl or methoxymethyl etc.

A protecting group of hydroxy which is removable under an alkaline condition includes acyl group such as acetyl etc.

A protecting group of hydroxy which is removable under a neutral condition includes benzyl or silyl containing group such as t-butyldimethylsilyl etc.

The removal of a protecting group under an alkaline condition is well known. For example, this reaction may be carried out in an organic solvent (methanol, THF, dioxane etc.), using a hydroxide of an alkali metal (sodium hydroxide, potassium hydroxide etc.), a hydroxide of an alkaline earth metal (calcium hydroxide etc.) or a carbonate salt (sodium carbonate, potassium carbonate etc.) or an aqueous solution thereof, or mixture thereof at 0~40° C.

The removal of a protecting group under an acidic condition is well known. For example, this reaction may be carried out in a solvent (methylene chloride, dioxane, ethyl acetate, acetic acid, water or mixture thereof etc.), using an organic acid (trifluoroacetic acid etc.) or an inorganic acid (HCl, HBr etc.) at 0~120° C.

The removal of a protecting group under a neutral condition is well known. For example, this reaction using benzyl may be carried out in a solvent (ether (THF, dioxane, dimethoxyethane, diethyl ether etc.), alcohol (methanol, ethanol etc.), benzene (benzene, toluene etc.), ketone (acetone, methylethyl ketone etc.), nitrile (acetonitrile etc.) amide (dimethylformamide etc.) water, ethyl acetate, acetic acid or mixture thereof etc.) in the presence of catalyst (Pd—C, palladium black, PdOH, $PtO_2$, Raney nickel etc.), at ordinary or increased pressure under the condition of atmosphere of hydrogen gas or in the presence of ammonium formate at 0~200° C.

This reaction using silyl containing group such as t-butyldimethylsilyl etc. may be carried out in a solvent such as ether (THF etc.), using tetrabutylammonium fluoride at 0~50° C.

The compounds of the formula (III), (V), (VII), (IX), (VII-a), (VII-b), (Z-2), (Z-4), (Z-5) or (Z-6) are known or may be prepared easily by known methods or the methods described in the Examples hereinafter. The compounds of the formula (IV), (VI), (VIII), (X), (XI), (XII) or (Z-3) may be prepared by the following reaction schemes (A)–(F).

In each reaction scheme, each symbol is as hereinbefore defined, or as defined as follows:

$R^{200}$: single bond or C1–4 alkylene;
$R^{202}$: single bond or C1–4 alkylene;

$R^{203}$: single bond or C1–4 alkylene;
$R^{204}$: single bond or C1 or 2 alkylene;
$R^{205}$: C1, 2 or 3 alkylene;
$R^{206}$: single bond or C1 or 2 alkylene;
$R^{207}$: C1, 2 or 3 alkylene;
$R^{208}$: C1, or 2 alkylene;
$R^{50}$: C1–4 alkyl;
$R^{51}$: trifluoroacetyl;
$X^1, X^2, X^3, X^4$ halogen.
Reaction Scheme (A)
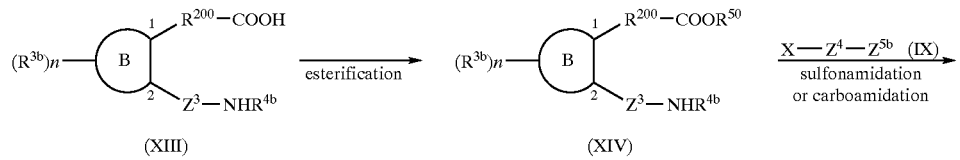
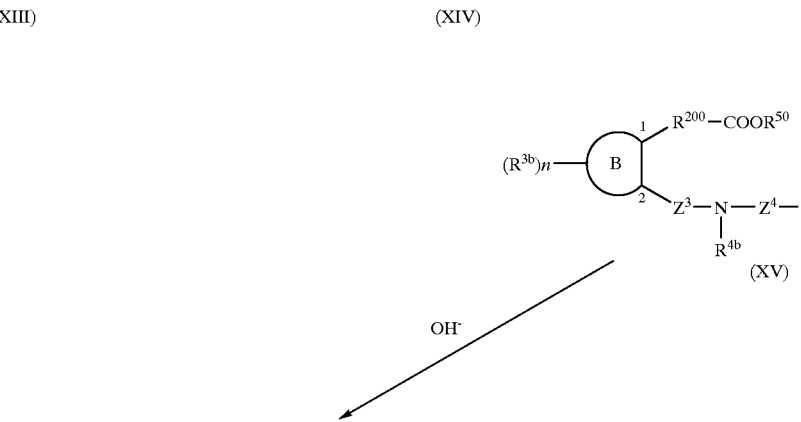
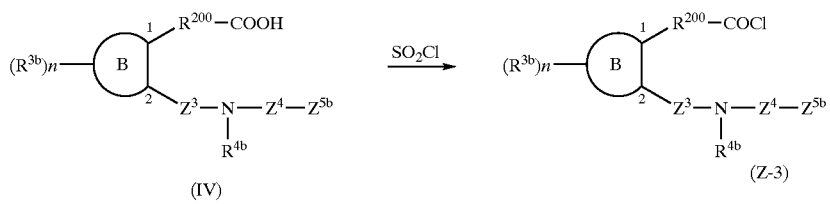
Reaction Scheme (B)
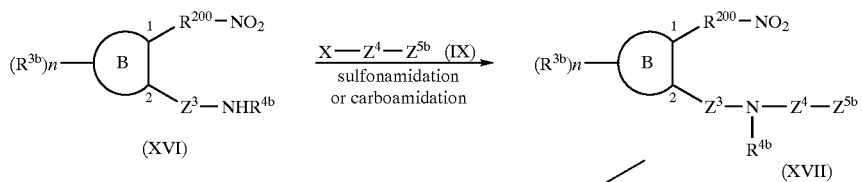
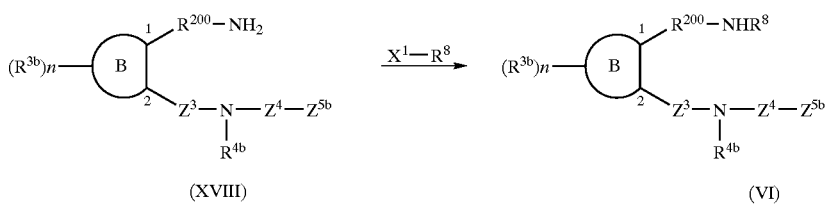

Reaction Scheme (C)
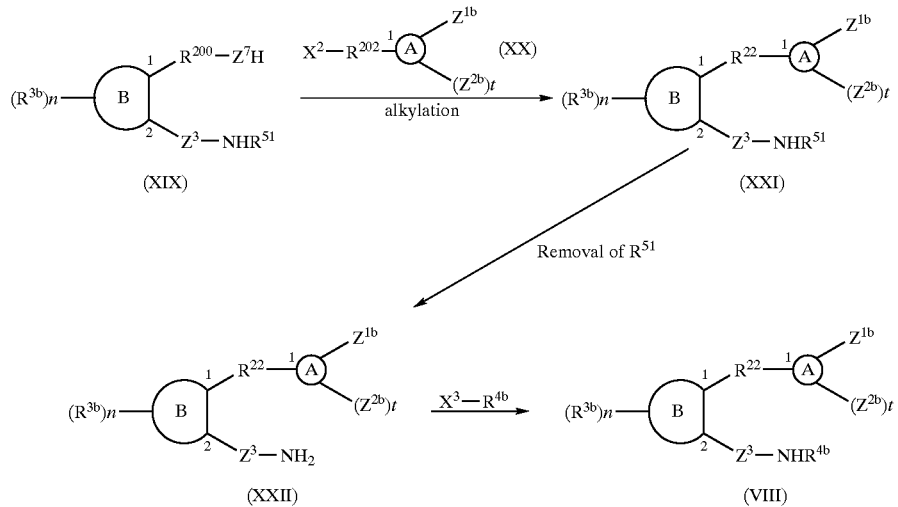
Reaction Scheme (D)
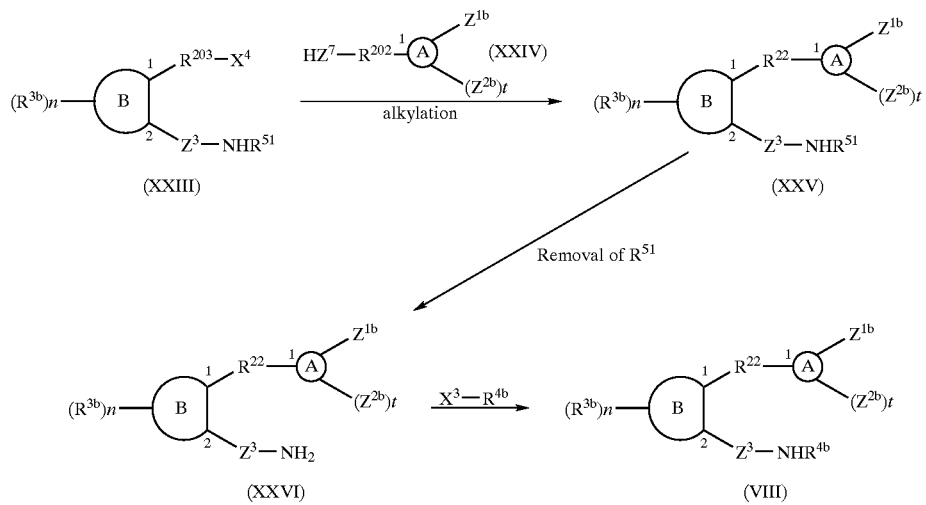
Reaction Scheme (E)
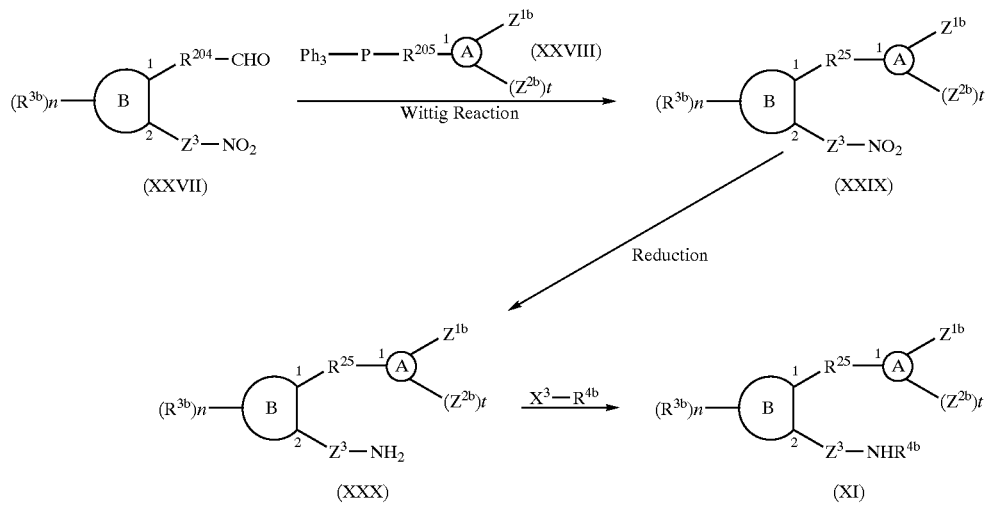

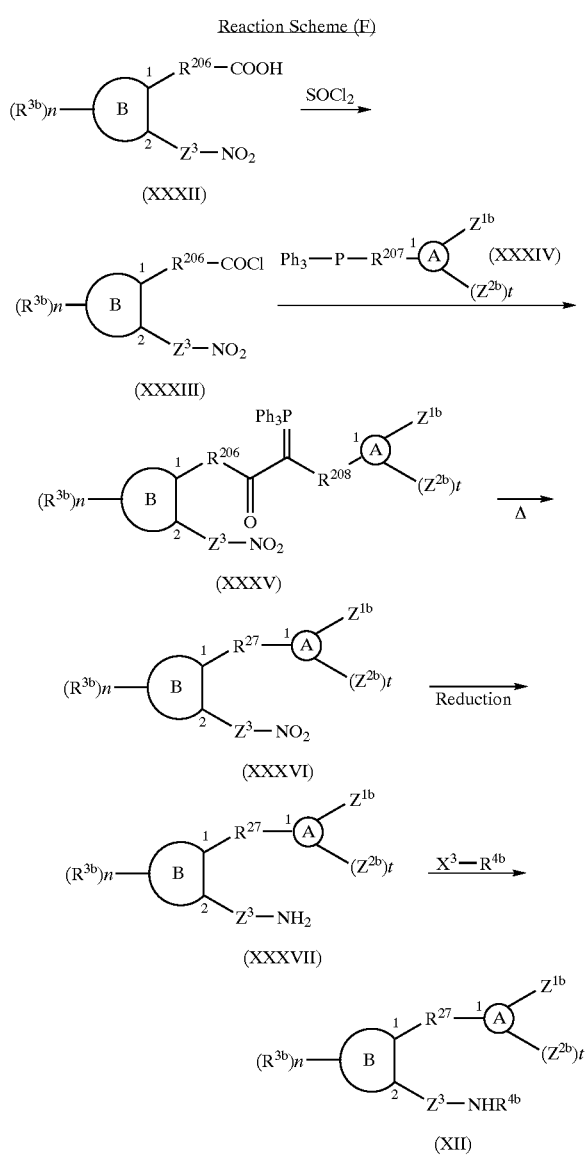

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

[Starting Materials and Reagents]

The other starting materials and reagents in the present invention are known per se or may be prepared by known methods.

Industrial Availability

[Pharmacological Activity of the Present Invention Compounds]

The compounds of the present invention of the formula (I) can bind to the receptors of prostaglandin $E_2$ and show antagonistic activity against the action thereof or agonistic activity, so they are useful as $PGE_2$ antagonists or agonists.

As mentioned hereinbefore, to antagonize against $PGE_2$ is linked to inhibition of uterine contraction, analgesic action, inhibition of digestive peristalsis, induction of sleep or increase of vesical capacity. Therefore, $PGE_2$ antagonists are considered to be useful for the prevention of abortion, as analgesics, as antidiarrheals, as sleep inducers or as agents for treating pollakiuria.

As mentioned hereinbefore, to show $PGE_2$ agonistic activity is linked to uterine contraction, promotion of digestive peristalsis, suppression of gastric acid secretion or reduction of blood pressure or diuresis. Therefore, $PGE_2$ agonists are considered to be useful as abortifacient, cathartic, antiulcer, anti-gastritis, antihypertensive or diuretic agents.

For example, in standard laboratory test, it was confirmed that the compounds of the formula (I) of the present invention can bind to receptor of $PGE_2$ ($EP_1$ receptor) according to assay using expression cell of prostanoid receptor subtype.

(i) Binding Assay Using Expression Cell of Prostanoid Receptor Subtype

The preparation of membrane fraction was carried out according to the method of Sugimoto et al (J. Biol. Chem. 267, 6463–6466 (1992)), using expression CHO cell of prostanoid receptor subtype (mouse EP1).

The standard assay mixture contained membrane fraction (0.5 mg/ml), $^3$H-$PGE_2$ in a final volume of 200 μl was incubated for 1 hour at room temperature. The reaction was terminated by addition of 3 ml of ice-cold buffer. The mixture was rapidly filtered through a glass filter (GF/B). The radioactivity associated with the filter was measured by liquid scintillation counting.

Kd and Bmax values were determined from Scratchard plots (Ann. N.Y. Acad. Sci. 51, 660 (1949)). Non-specific binding was calculated as the bond in the presence of an excess (2.5 μM) of unlabeled $PGE_2$. In the experiment for competition of specific $^3$H-$PGE_2$ was added at a concentration of 2.5 nM and the compound of the present invention was added at a various concentration. The following buffer was used in all reaction.

Buffer: potassium phosphate (pH6.0, 10 mM), EDTA (1 mM), $MgCl_2$ (10 mM), NaCl (0.1M).

The dissociation constant Ki (μM) of each compound was calculated by the following equation.

Ki=IC50/(1+([C]/Kd))

The results were shown in Table 1.

TABLE 1

| Example No. | dissociation constant Ki (μM) |
|---|---|
| 2 (k) | 0.099 |
| 18 (30) | 0.0016 |
| 18 (38) | 0.016 |
| 18 (58) | 0.0062 |
| 18 (75) | 0.0054 |
| 18 (94) | 0.0004 |
| 18 (102) | 0.0002 |
| 20 (20) | 0.0099 |
| 22 (3) | 0.48 |
| 24 | 0.0058 |
| 24 (9) | 0.018 |
| 30 | 0.073 |
| 38 | 0.16 |
| 43 | 0.38 |
| 44 | 0.0013 |
| 48 | 0.01 |

[Toxicity]

The toxicity of the compounds of the present invention is very low and therefore, it is confirmed that these compounds are safe for use as medicine.

[Application for Pharmaceuticals]

The compounds of the present invention of the formula (I) can bind to the receptors of prostaglandin $E_2$ and show antagonistic activity against the action thereof or agonistic activity, so they are useful as $PGE_2$ antagonists or agonists.

As mentioned hereinbefore, to antagonize against $PGE_2$ is linked to inhibition of uterine contraction, analgesic action, inhibition of digestive peristalsis, induction of sleep or increase of vesical capacity. Therefore, $PGE_2$ antagonists are considered to be useful for the prevention of abortion, as analgesics, as antidiarrheals, as sleep inducers or as agents for treating pollakiuria.

As mentioned hereinbefore, to show $PGE_2$ agonistic activity is linked to uterine contraction, promotion of digestive peristalsis, suppression of gastric acid secretion or reduction of blood pressure or diuresis. Therefore, $PGE_2$ agonists are considered to be useful as abortifacient, cathartic, antiulcer, anti-gastritis, antihypertensive or diuretic agents.

The compounds of the present invention can bind to receptors of prostaglandin $E_2$, especially, EP1 receptor strongly, so they are expected to be useful as analgesics or as agents for treating pollakiuria.

For the purpose above described, the compounds of the formula (I), non-toxic salts thereof and hydrates thereof may be normally administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 μg and 100 mg, by oral administration, up to several times per day, and between 0.1 μg and 10 mg, by parenteral administration (preferred into vein) up to several times per day, or continuous administration between 1 and 24 hours per day into vein.

As mentioned above, the doses to be used depend upon various conditions. Therefore, there are cases in which doses lower than or greater than the ranges specified above may be used.

On administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules etc.

Capsules contain hard capsules and soft capsules.

In such solid compositions, one or more of the active compound(s) is or are, admixed with at least one inert diluent such as lactose, mannitol, mannit, glucose, hydroxypropyl cellulose, microcrystalline cellulose, starch, polyvinylpyrrolidone, magnesium metasilicate aluminate. The compositions may also comprise, as is normal practice, additional substances other than inert diluents: e.g. lubricating agents such as magnesium stearate, disintegrating agents such as cellulose calcium glycolate, and assisting agents for dissolving such as glutamic acid or asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent (s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give the title compound isotonicity, isotonic buffer such as sodium chloride, sodium citrate, citric acid. For preparation of such spray compositions, for example, the method described in the U.S. Pat. No. 2,868,691 or 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSORBATE80 (registered trade mark) etc. Such compositions may comprise additional diluents: e.g. preserving agents, wetting agents, emulsifying agents, dispersing agents, stabilizing agent, assisting agents such as assisting agents for dissolving (for example, glutamic acid, asparaginic acid). They may be sterilized for example, by filtration through a bacteria-retaining filter, by incorporation of sterilizing agents in the compositions or by irradiation. They also be manufactured in the form of sterile solid compositions and which can be dissolved in sterile water or some other sterile diluents for injection immediately before used.

Other compositions for parenteral administration include liquids for external use, and endemic liniments, ointment, suppositories and pessaries which comprise one or more of the active compound(s) and may be prepared by known methods.

Best Mode to Practice the Invention

The following reference examples and examples are intended to illustrate, but not limit, the present invention.

The solvents in parentheses show the developing or eluting solvents and the ratios of the solvents used are by volume in chromatographic separations. Without special explanation, NMR data was determined in $CDCl_3$ solution.

REFERENCE EXAMPLE 1

5-chloroanthranilic acid methyl ester

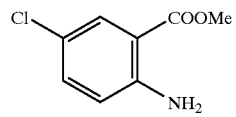

To a suspension of 5-chloroanthranilic acid (6.1 g) in AcOEt-MeOH (20 ml+10 ml), a solution of an excess amount of diazomethane in ether (50 ml) was added at 0° C. After termination of reaction, reaction solvent was evaporated to dryness to give the title compound (6.6 g) having the following physical data.

NMR: δ 7.82 (1H, d), 7.21 (1H, dd), 6.60 (1H, d), 5.73 (2H, brs), 3.88 (3H, s).

REFERENCE EXAMPLE 2
Methyl 2-phenylsulfonylamino-5-chlorobenzoate

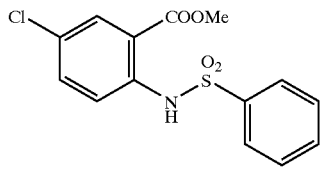

To a solution of 5-chloroanthranilic acid methyl ester (400 mg; prepared in Reference Example 1) and pyridine (0.87 ml) in methylene chloride, benzenesulfonylchloride (0.33 ml) was added at 0° C. The solution was stirred overnight at room temperature. The reaction mixture was poured into diluted HCl and extracted with ethyl acetate. The organic layer was washed, dried over and concentrated under reduced pressure. The residue was purified on silica gel column chromatography (hexane-AcOEt) to give the title compound (664 mg) having the following physical data.

TLC: Rf 0.30 (hexane: AcOEt=4:1); NMR: δ 10.5 (1H, s), 7.90–7.79 (3H, m), 7.79 (1H, d), 7.60–7.37 (4H, m), 3.88 (3H, s).

REFERENCE EXAMPLE 3
2-phenylsulfonylamino-5-chlorobenzoic acid

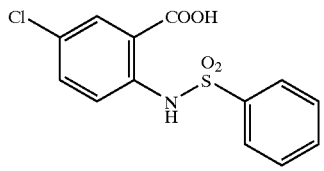

To a solution of methyl 2-phenylsulfonylamino-5-chlorobenzoate (600 mg; prepared in Reference Example 2.) in the mixture of THF-MeOH (6 ml+3 ml), 2N NaOH solution (2 ml) was added. The mixture was stirred for 2 days. To the reaction mixture, 1N HCl (4.5 ml) was added. The mixture was extracted with ethyl acetate. The organic layer was washed and dried over to give the title compound (575 mg) having the following physical data.

NMR: δ 10.31 (1H, s), 7.99 (1H, d), 7.92–7.83 (2H, m), 7.70 (1H, d), 7.63–7.42 (4H, m), 6.20 (1H, brs).

EXAMPLE 1
Methyl 4-(2-phenylsulfonylamino-5-chlorobenzoylamino)benzoate

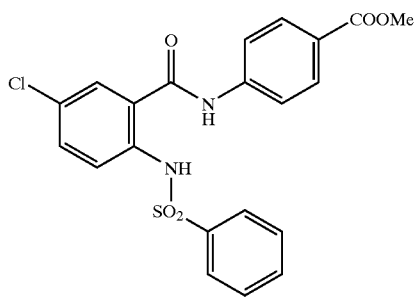

To a suspension of 2-phenylsulfonylamino-5-chlorobenzoic acid (250 mg; prepared in Reference Example 3.) and methyl p-aminobenzoate (133 mg) in methylene chloride (5 ml), EDC (168 mg) and dimethylaminopyridine (20 mg) were added. The mixture was stirred for 3 days at room temperature. The reaction mixture was poured into diluted HCl and extracted with ethyl acetate. The organic layer was washed, dried over and concentrated under reduced pressure. The residue was purified on silica gel column chromatography (AcOEt-benzene) to give the title compound (142 mg) having the following physical data.

TLC: Rf 0.29 (AcOEt:benzene=1:9); NMR (CDCl$_3$+DMSO-d$_6$): δ 10.40 (1H, s), 9.90 (1H, m), 8.03 (2H, d), 7.82–7.70 (5H, m), 7.63 (1H, d), 7.50–7.24 (4H, m), 3.93 (3H, s).

EXAMPLE 2
4-(2-phenylsulfonylamino-5-chlorobenzoylamino)benzoic acid

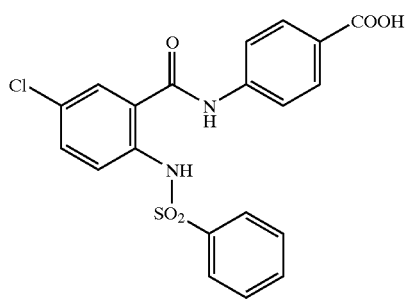

To a solution of methyl 4-(2-phenylsulfonylamino-5-chlorobenzoyl-amino)benzoate (122 mg; prepared in Example 1.) in THF-MeOH (4 ml+2 ml), 2N NaOH aqueous solution (0.5 ml) was added at room temperature. The mixture was stirred overnight. To the reaction mixture, 2N HCl (0.6 ml) and water were added. The mixture was extracted with ethyl acetate. The organic layer was washed, dried over and concentrated under reduced pressure. The residue was purified by recrystallization from the mixture of AcOEt-hexane to give the title compound (80 mg) having the following physical data.

TLC: Rf 0.32 (MeOH: CH$_2$Cl$_2$=15:85); NMR (DMSO-d$_6$): δ 12.74 (1H, brs), 10.61 (1H, s), 10.40 (1H, s), 7.95 (2H, d), 7.85–7.71 (5H, m), 7.64–7.35 (5H, m).

EXAMPLE 2(a)–2(bb)

The title compounds having the following physical data were obtained by the same procedure of Reference Example 1~Reference Example 3 and Examples 1 and 2.

EXAMPLE 2(a)
3-(2-phenylsulfonylaminobenzoylamino)benzoic acid

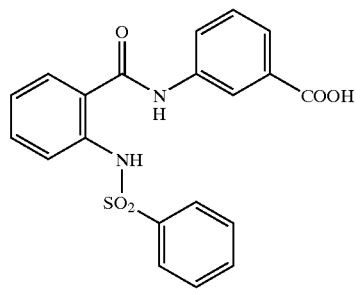

TLC: Rf 0.57 (CHCl$_3$:MeOH:AcOH=100:10:1); NMR (DMSO-d$_6$): δ 13.01 (1H, brs), 10.66 (1H, brs), 10.50 (1H, brs), 8.32 (1H, brs), 7.89 (1H, d), 7.76 (4H, m), 7.51 (6H, m), 7.23 (1H, m).

EXAMPLE 2(b)

3-(2-phenylsulfonylamino-5-chlorobenzoylamino)benzoic acid

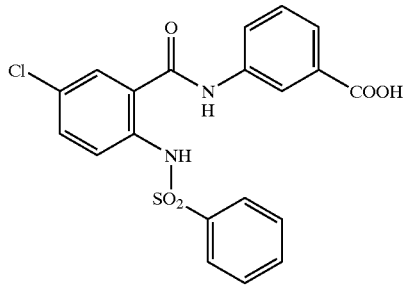

TLC: Rf 0.26 (MeOH:CHCl₃=15:85); NMR (CDCl₃:DMSO-d₆=1:1): δ 12.70 (1H, brs), 10.69 (1H, s), 10.44 (1H, s), 8.27 (1H, t), 7.95–7.69 (5H, m), 7.59–7.36 (6H, m).

EXAMPLE 2(c)

4-(2-phenylsulfonylaminobenzoylamino)benzoic acid

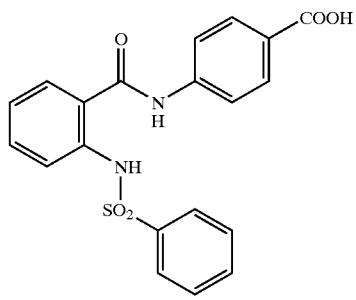

TLC: Rf 0.50 (CHCl₃:MeOH:AcOH=100:10:1); NMR (DMSO-d₆): δ 12.76 (1H, brs), 10.57 (1H, s), 10.49 (1H, s), 7.95 (2H, d), 7.77 (5H, m), 7.28–7.62 (5H, m), 7.24 (1H, m).

EXAMPLE 2(d)

4-[2-(4-chlorophenyl)sulfonylamino-5-chlorobenzoylamino]benzoic acid

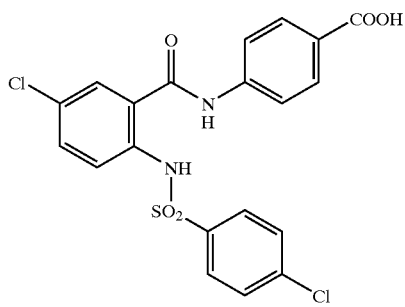

TLC: Rf 0.27 (MeOH:CHCl₃=15:85); NMR (DMSO-d₆): δ 12.70 (1H, br s), 10.59 (1H, s), 10.30 (1H, s), 7.95 (2H, d), 7.83–7.66 (5H, m), 7.62–7.47 (3H, m), 7.34 (1H, d).

EXAMPLE 2(e)

4-[2-(4-chlorophenylsulfonylamino)-4-chlorobenzoylamino]benzoic acid

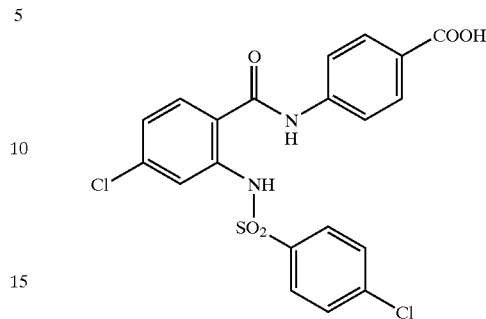

TLC: Rf 0.69 (CHCl₃:MeOH AcOH=17:2:1); NMR (CDCl₃+DMSO-d₆): δ 10.9–10.3 (1H, br), 10.3–9.9 (1H, br), 7.84 (2H, d), 7.7–7.5 (5H, m), 7.45 (1H, s-like), 7.17 (2H, d), 7.0–6.9 (1H, m).

EXAMPLE 2(f)

4-[2-(4-chlorophenylsulfonylamino)-6-chlorobenzoylamino]benzoic acid

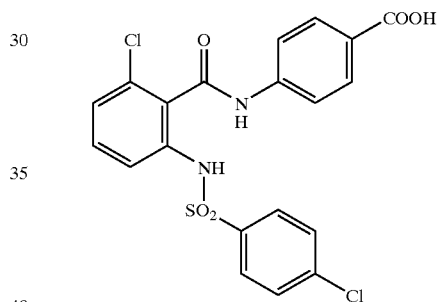

TLC: Rf 0.67 (CHCl₃:MeOH:AcOH=17:2:1); NMR: δ 9.64 (1H, s-like), 7.8–7.7 (2H, m), 7.5–7.3 (4H, m), 7.1–6.9 (5H, m).

EXAMPLE 2(g)

4-[2-(4-chlorophenylsulfonylamino)-3-chlorobenzoylamino]benzoic acid

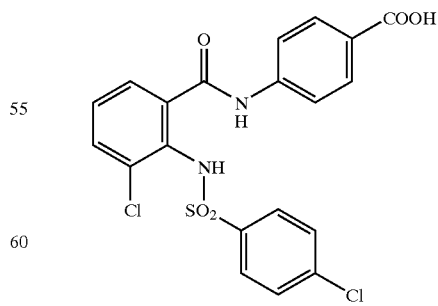

TLC: Rf 0.32 (CHCl₃:MeOH=9:1); NMR (DMSO-d₆): δ 12.8–12.6 (1H, br), 10.7–10.5 (1H, br), 10.12 (1H, s), 7.89 (2H, d), 7.7–7.5 (6H, m), 7.5–7.3 (3H, m).

EXAMPLE 2(h)

4-[2-(2-chlorophenylsulfonylamino)-5-chlorobenzoyl-amino]benzoic acid

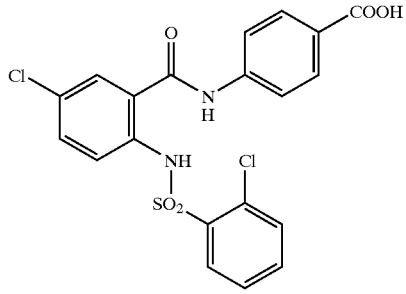

TLC: Rf 0.16 (CHCl$_3$:MeOH=9:1); NMR (DMSO-d$_6$): δ 12.78 (1H, br), 10.80 (2H, br), 8.08–8.03 (1H, m), 7.95 (2H, d), 7.88 (1H, d), 7.80 (2H, d), 7.66–7.46 (4H, m), 7.38 (1H, d).

EXAMPLE 2(i)

4-[2-(3-chlorophenylsulfonylamino)-5-chlorobenzoyl-amino]benzoic acid

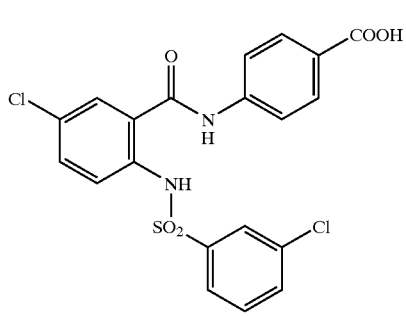

TLC: Rf 0.15 (CHCl$_3$:MeOH=9:1); NMR (DMSO-d$_6$): δ 12.76 (1H, br), 10.62 (1H, brs), 10.36 (1H, brs), 7.92 (2H, d), 7.77–7.73 (4H, m), 7.67–7.44 (4H, m), 7.28 (1H, d).

EXAMPLE 2(j)

4-[2-(4-chlorophenylsulfonylamino)-5-fluorobenzoyl-amino]benzoic acid

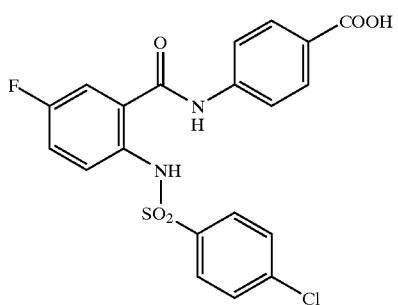

TLC: Rf 0.28 (MeOH:CHCl$_3$=15:85); NMR (DMSO-d$_6$): δ 12.78 (1H, brs), 10.50 (1H, s), 10.09 (1H, s), 7.95 (2H, d), 7.75 (2H, d), 7.68–7.26 (7H, m).

EXAMPLE 2(k)

4-[2-(4-chlorophenylsulfonylamino)-5-bromobenzoyl-amino]benzoic acid

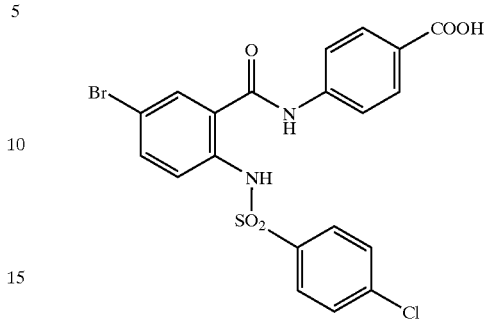

TLC: Rf 0.28 (MeOH:CHCl$_3$=15:85); NMR (DMSO-d$_6$): δ 12.74 (1H, brs), 10.61 (1H, s), 10.33 (1H, s), 7.95 (2H, d), 7.89 (1H, d), 7.81–7.65 (5H, m), 7.53 (2H, d), 7.29 (1H, d).

EXAMPLE 2(l)

4-[2-(4-chlorophenylsulfonylamino)-5-methoxybenzoyl-amino]benzoic acid

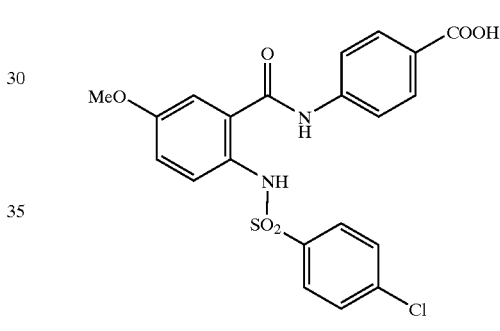

TLC: Rf 0.30 (MeOH:CHCl$_3$=15:85); NMR (DMSO-d$_6$): δ 12.77 (1H, brs), 10.39 (1H, s), 9.79 (1H, s), 7.94 (2H, d), 7.73 (2H, d), 7.59 (2H, d), 7.43 (2H, d), 7.25–7.15 (2H, m), 7.09 (1H, dd).

EXAMPLE 2(m)

4-[2-(4-bromophenylsulfonylamino)-5-chlorobenzoyl-amino]benzoic acid

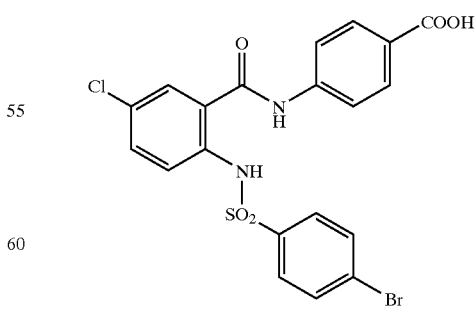

TLC: Rf 0.27 (CHCl$_3$:MeOH=9:1); NMR (DMSO-d$_6$): δ 12.74 (1H, br), 10.55 (1H, brs), 10.27 (1H, brs), 7.92 (2H, d), 7.75–7.71 (3H, m), 7.66–7.51 (5H, m), 7.31 (1H, d).

EXAMPLE 2(n)

4-[2-(4-methylphenylsulfonylamino)-5-chlorobenzoyl-amino]benzoic acid

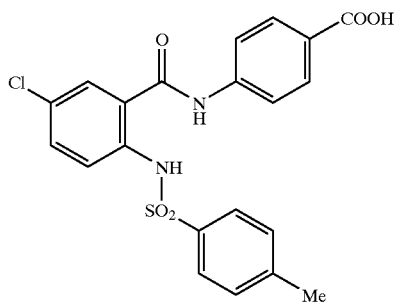

TLC: Rf 0.30 (CHCl$_3$:MeOH=9:1); NMR (DMSO-d$_6$): δ 12.76 (1H, br), 10.56 (1H, brs), 10.23 (1H, brs), 7.93 (2H, d), 7.77–7.73 (3H, m), 7.60–7.51 (3H, m), 7.36 (1H, d), 7.23 (2H, d), 2.24 (3H, s).

EXAMPLE 2(o)

4-[2-(4-methoxyphenylsulfonylamino)-5-chlorobenzoyl-amino]benzoic acid

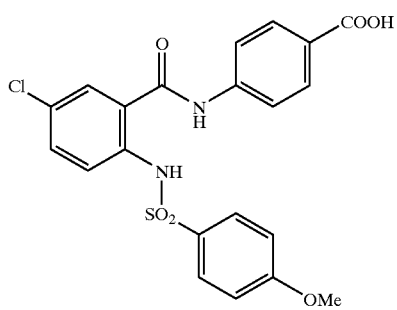

TLC: Rf 0.29 (CHCl$_3$:MeOH=9:1); NMR (DMSO-d$_6$): δ 12.76 (1H, br), 10.57 (1H, brs), 10.16 (1H, brs), 7.93 (2H, d), 7.77–7.73 (3H, m), 7.62 (2H, d), 7.59–7.52 (1H, m), 7.37 (1H, d), 6.93 (2H, d), 3.70 (3H, s).

EXAMPLE 2(p)

4-[2-(4-nitrophenylsulfonylamino)-5-chlorobenzoylamino]benzoic acid

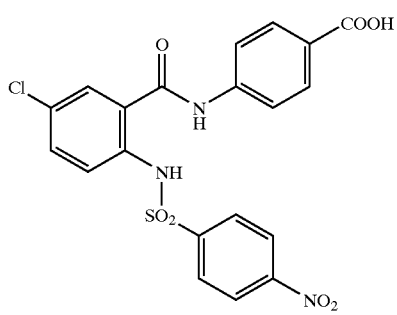

TLC: Rf 0.10 (CHCl$_3$:MeOH=9:1); NMR (DMSO-d$_6$): δ 12.71 (1H, br), 10.55–10.35 (2H, br), 8.19 (2H, d), 7.93–7.86 (4H, m), 7.71–7.64 (3H, m), 7.58–7.52 (1H, m), 7.32 (1H, d).

EXAMPLE 2(q)

4-[2-(2,4-dichlorophenylsulfonylamino)-5-chlorobenzoyl-amino]benzoic acid

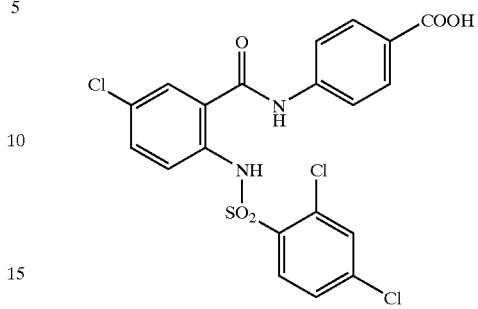

TLC: Rf 0.22 (CHCl$_3$:MeOH=9:1); NMR (DMSO-d$_6$): δ 12.50 (1H, br), 10.73 (2H, br), 7.99–7.91 (3H, m), 7.85 (1H, d-like), 7.79–7.71 (3H, m), 7.58–7.51 (2H, m), 7.36 (1H, d).

EXAMPLE 2(r)

4-[2-(4-butylphenylsulfonylamino)-5-chlorobenzoylamino] benzoic acid

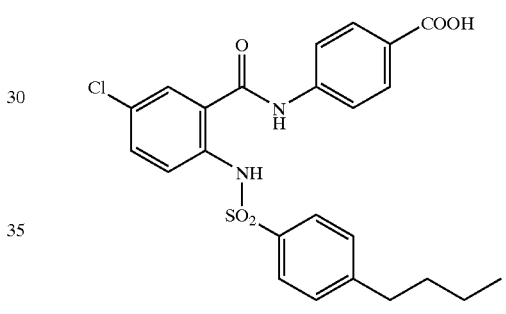

TLC: Rf 0.33 (CHCl$_3$:MeOH=9:1); NMR (DMSO-d$_6$): δ 12.72 (1H, br), 10.55 (1H, brs), 10.24 (1H, s), 7.92 (2H, d), 7.78–7.72 (3H, m), 7.60 (2H, d), 7.57–7.51 (1H, m), 7.37 (1H, d), 7.24 (2H, d), 2.54–2.49 (2H, m), 1.48–1.33 (2H, m), 1.29–1.11 (2H, m), 0.82 (3H, t).

EXAMPLE 2(s)

4-[2-(4-chlorophenylsulfonylamino)benzoylamino]benzoic acid

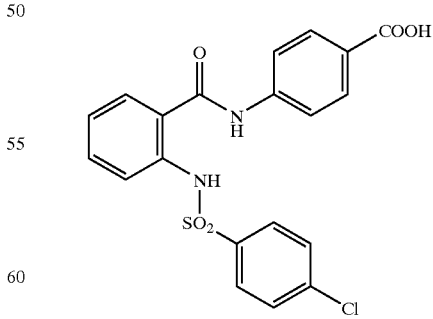

TLC: Rf 0.30 (AcOEt:hexane:AcOH=7:16:1); NMR (DMSO-d$_6$): δ 13.00–12.60 (1H, brs), 10.55 (1H, brs), 10.38 (1H, brs), 7.95 (2H, d), 7.78 (2H, d), 7.74 (1H, m), 7.72 (2H, d), 7.51 (2H, d), 7.50 (1H, m), 7.40–7.24 (2H, m).

EXAMPLE 2(t)

4-(2-phenylsulfonylamino-5-fluorobenzoylamino)benzoic acid

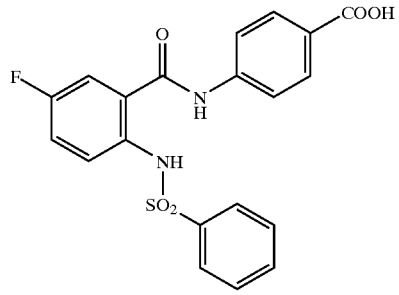

TLC: Rf 0.23 (CHCl$_3$:MeOH=9:1); NMR (DMSO-d$_6$): δ 12.70 (1H, br), 10.52 (1H, br), 10.13 (1H, br), 7.92 (2H, d), 7.74 (2H, d), 7.68–7.64 (2H, m), 7.59–7.27 (6H, m).

EXAMPLE 2(u)

4-(2-phenylsulfonylamino-4-fluorobenzoylamino)benzoic acid

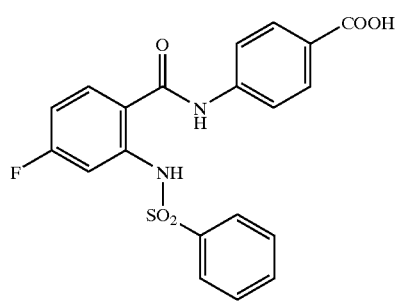

TLC: Rf 0.20 (CHCl$_3$:MeOH=9:1); NMR (DMSO-d$_6$): δ 12.81 (1H, br), 10.85 (1H, br), 10.60 (1H, br), 7.95–7.74 (7H, m), 7.63–7.46 (3H, m), 7.19–7.02 (2H, m).

EXAMPLE 2(v)

4-[2-(4-chlorophenylsulfonylamino)-4-fluorobenzoylamino]benzoic acid

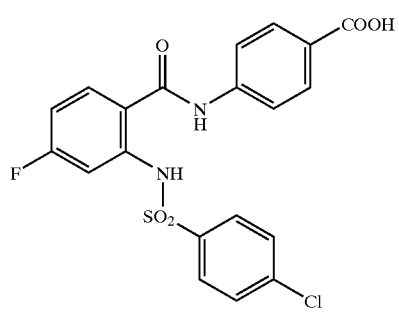

TLC: Rf 0.22 (CHCl$_3$:MeOH=9:1); NMR (DMSO-d$_6$): δ 12.28 (1H, br), 10.75 (1H, br), 10.58 (1H, br), 7.95–7.72 (7H, m), 7.53 (2H, d), 7.19–7.08 (2H, m).

EXAMPLE 2(w)

4-[2-(4-fluorophenylsulfonylamino)-5-chlorobenzoylamino]benzoic acid

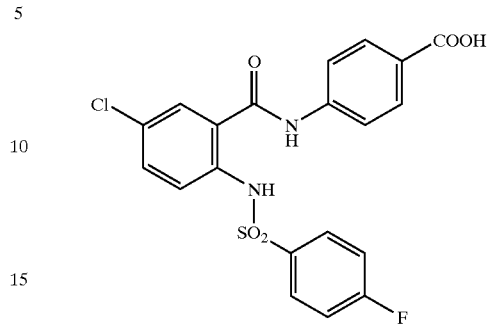

TLC: Rf 0.26 (CHCl$_3$:MeOH=9:1); NMR (DMSO-d$_6$): δ 12.75 (1H, br), 10.58 (1H, br), 10.27 (1H, brs), 7.93 (2H, d), 7.80–7.72 (5H, m), 7.54 (1H, dd), 7.34–7.22 (3H, m).

EXAMPLE 2(x)

4-[2-(4-trifluoromethylphenylsulfonylamino)-5-chlorobenzoylamino]benzoic acid

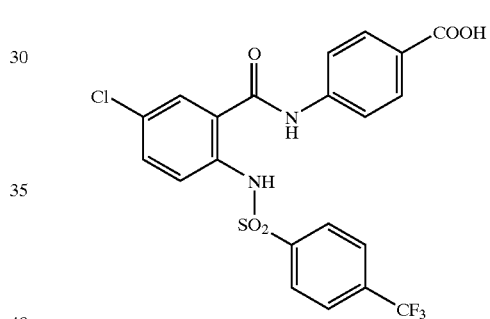

TLC: Rf 0.26 (CHCl$_3$:MeOH=9:1); NMR (DMSO-d$_6$): δ 12.70 (1H, br), 10.56 (1H, br), 10.41 (1H, br), 7.92–7.68 (9H, m), 7.54 (1H, dd-like), 7.31 (1H, d).

EXAMPLE 2(y)

4-(2-phenylsulfonylamino-5-chlorobenzoylaminomethyl)benzoic acid

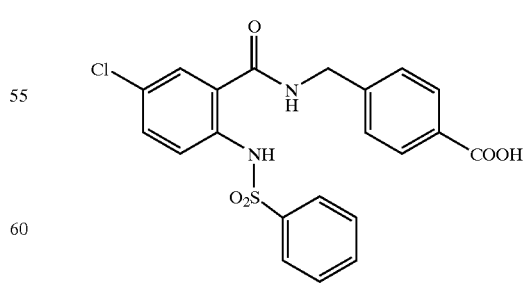

TLC: Rf 0.45 (MeOH:CHCl$_3$=1:4); NMR (DMSO-d$_6$): δ 12.90 (1H, s), 11.47 (1H, s), 9.46 (1H, t), 7.94 (2H, d), 7.86 (1H, d), 7.77–7.36 (9H, m), 4.48 (1H, d).

EXAMPLE 2(z)

4-[2-(2-phenylvinyl)sulfonylamino-5-chlorobenzoylamino]benzoic acid

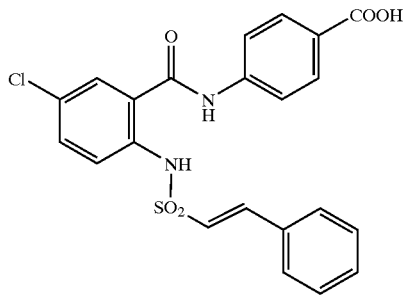

TLC: Rf 0.43 (CHCl₃:MeOH=9:1); NMR (CD3OD): δ 7.98 (2H, d), 7.83 (1H, d), 7.72 (2H, d), 7.63 (1H, d), 7.53 (1H, dd), 7.5–7.2 (6H, m), 7.01 (1H, d).

EXAMPLE 2(aa)

4-[2-(2-phenylethyl)sulfonylamino-5-chlorobenzoylamino]benzoic acid

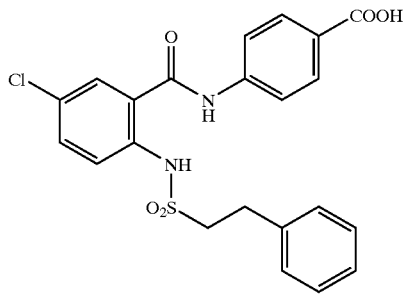

TLC: Rf 0.27 (CHCl₃:MeOH=9:1); NMR (DMSO-d₆): δ 12.75 (1H, br), 10.78 (1H, brs), 10.05 (1H, s), 7.95–7.79 (5H, m), 7.63–7.53 (2H, m), 7.24–7.10 (5H, m), 3.53–3.45 (2H, m), 2.99–2.91 (2H, m).

EXAMPLE 2(bb)

4-[2-(4-chlorophenylsulfonylamino)-5-nitrobenzoylamino]benzoic acid

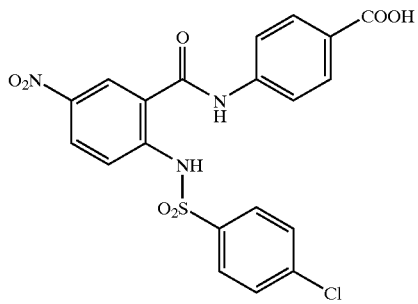

TLC: Rf 0.32 (AcOEt: hexane AcOH=4:12:1); NMR (DMSO-d₆): δ 12.50–10.00 (2H, brs), 8.66 (1H, d), 8.36–8.24 (1H, dd), 8.05–7.87 (4H, m), 7.80 (2H, d), 7.68–7.55 (3H, m).

EXAMPLE 3

4-[2-(4-hydroxyphenylsulfonylamino)-5-chlorobenzoylamino]benzoic acid

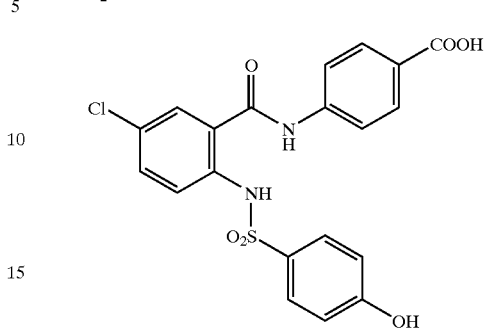

To a mixture solution of methyl 4-[2-(4-pivaroyloxy-phenylsulfonyl-amino)-5-chlorobenzoylamino]benzoate (214 mg; prepared by the same procedure as Reference Examples 1, 2 and 3 and Example 1.) in MeOH-THF (8 ml+3 ml), 2N NaOH aqueous solution (2 ml) was added. The mixture was stirred for one day at 60° C. To the reaction solution, HCl was added. The mixture was extracted with ethyl acetate. The organic layer was washed dried over and purified by recrystallization from the mixture solvent of MeOH-AcOEt-hexane to give the title compound (105 mg) having the following physical data.

TLC: Rf 0.42 (CHCl₃:MeOH:AcOH=45:4:1); NMR (DMSO-d₆): δ 13.0–12.6 (1H, br), 10.64 (1H, s-like), 10.50 (1H, s-like), 10.21 (1H, s), 7.95 (2H, d), 7.9–7.7 (3H, m), 7.6–7.3 (4H, m), 6.76 (2H, d).

REFERENCE EXAMPLE 4

Methyl 4-[2-(2-nitro-5-chlorophenyl)-(EZ)-vinyl]benzoate

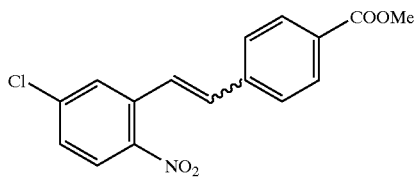

To a solution of 4-methoxycarbonylphenylmethyltriphenylphosphine bromide (4.83 g) in THF (20 ml), potassium t-butoxide (600 mg) was added. The mixture was stirred for 1 hour at room temperature. To the reaction solution, 2-nitro-5-chlorobenzaldehyde (742 mg) was added at 0° C. The mixture was stirred for 30 minutes at room temperature. The reaction mixture was poured into diluted HCl. The mixture was extracted with hexane-AcOEt. The organic layer was washed, dried over and concentrated under the reduced pressure. The residue was purified on silica gel column chromatography (hexane-AcOEt) and recrystallization from the mixture solvent of hexane-AcOEt to give the title compound (680 mg) having the following physical data.

TLC: Rf 0.44 (hexane: AcOEt=4:1).

REFERENCE EXAMPLE 5

Methyl 4-[2-(2-amino-5-chlorophenyl)-(E)-vinyl]benzoate and methyl 4-[2-(2-amino-5-chlorophenyl)-(Z)-vinyl]benzoate

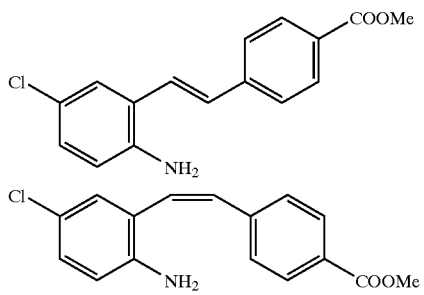

To a solution of methyl 4-[2-(2-nitro-5-chlorophenyl)-(EZ)-vinyl]benzoate (525 mg; prepared in Reference Example 4.) in THF (4 ml), water (1.5 ml), 2N HCl and reduced iron (554 mg) were added. The mixture was stirred overnight at room temperature. Further, to the mixture, 2N HCl (0.2 ml) and reduced iron powder (330 mg) were added. The mixture was stirred for 3 days. The reaction mixture was diluted with ethyl acetate and filtrated. The filtrate was washed, dried over and concentrated under the reduced pressure. The residue was purified on silica gel column chromatography (ether-hexane-AcOEt) to give the title compound having the following physical data.

(E) Type Compound

TLC: Rf 0.37 (AcOEt:benzene=5:95).

(Z) Type Compound

TLC: Rf 0.41 (AcOEt:benzene=5:95).

EXAMPLE 4

Methyl 4-[2-[2-(4-chlorophenylsulfonylamino)-5-chlorophenyl]-(E)-vinyl]benzoate

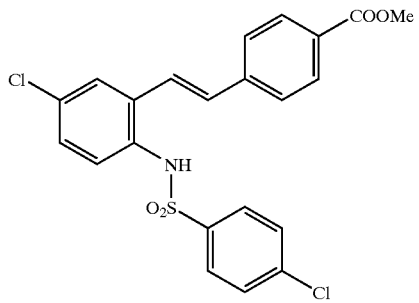

To methyl 4-[2-(2-amino-5-chlorophenyl)-(E)-vinyl]benzoate (130 mg; prepared in Reference Example 5.) in methylene chloride (3 ml), pyridine (0.073 μl) and p-chlorobenzenesulfonylchloride (114 mg) were added. The mixture was stirred overnight at room temperature. The reaction mixture was poured into diluted HCl and extracted with ethyl acetate. The organic layer was washed, dried over and concentrated under the reduced pressure. The residue was purified on silica gel column chromatography (AcOEt-hexane) to give the title compound (205 mg) having the following physical data.

TLC: Rf 0.15 (AcOEt:benzene=4:96); NMR: δ 8.02 (2H, d), 7.63 (2H, d), 7.51 (1H, s), 7.41–7.30 (4H, m), 7.26–7.22 (2H, m), 6.91 (1H, d), 6.81 (1H, d), 6.63 (1H, s), 3.95 (3H, s).

EXAMPLE 4(a)

Methyl 4-[2-[2-(4-chlorophenylsulfonylamino)-5-chlorophenyl]-(Z)-vinyl]-benzoate

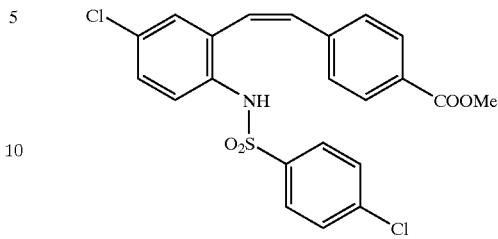

By using Z type compound prepared in Reference Example 5, the title compound having the following physical data was obtained by the same procedure as Example 4.

TLC: Rf 0.23 (AcOEt:benzene=4:96); NMR: δ 7.82 (2H, d), 7.57 (2H, d), 7.46 (1H, d), 7.33 (2H, d), 7.24 (1H, dd), 7.06 (1H, d), 6.99 (2H, d), 6.72 (1H, d), 6.48 (1H, s), 6.20 (1H, d), 3.90 (3H, s).

EXAMPLE 5

4-[2-[2-(4-chlorophenylsulfonylamino)-5-chlorophenyl]-(E)-vinyl]benzoic acid

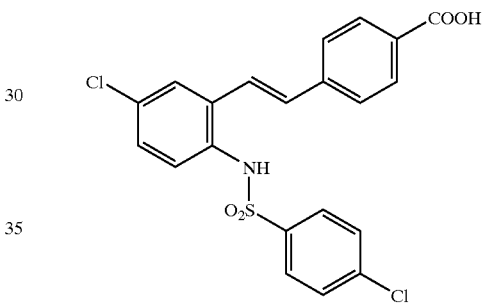

By using methyl 4-[2-[2-(4-chlorophenylsulfonylamino)-5-chlorophenyl]-(E)-vinyl]benzoate (190 mg; prepared in Example 4.), the title compound (168 mg) having the following physical data was obtained by the same procedure as Example 2.

TLC: Rf 0.36 (MeOH:CHCl$_3$=15:85); NMR (DMSO-d$_6$): δ 10.11 (1H, brs), 7.96 (2H, d), 7.80 (1H, d), 7.59 (2H, d), 7.52–7.41 (4H, m), 7.36 (1H, dd), 7.20 (1H, d), 7.15 (1H, d), 7.08 (1H, d).

EXAMPLE 5(a)

4-[2-[2-(4-chlorophenylsulfonylamino)-5-chlorophenyl]-(Z)-vinyl]benzoic acid

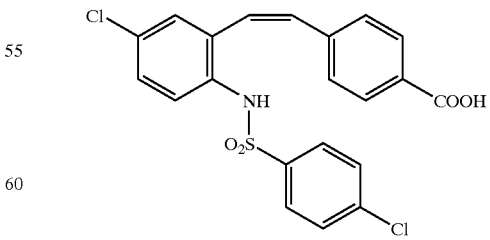

By using methyl 4-[2-[2-(4-chlorophenylsulfonylamino)-5-chlorophenyl]-(Z)-vinyl]benzoate prepared in Example 4(a), the title compound having the following physical data was obtained by the same procedure as Example 2.

TLC: Rf 0.46 (MeOH:CHCl$_3$=15:85); NMR (DMSO-d$_6$): δ 10.05 (1H, brs), 7.79–7.67 (4H, m), 7.55 (2H, d), 7.30 (1H, dd), 7.15 (1H, d), 7.00 (1H, d), 6.91 (1H, d), 6.64 (2H, s).

EXAMPLE 6

4-[2-[2-(4-chlorophenyl)sulfonylamino-5-chlorophenyl]ethyl]benzoic acid

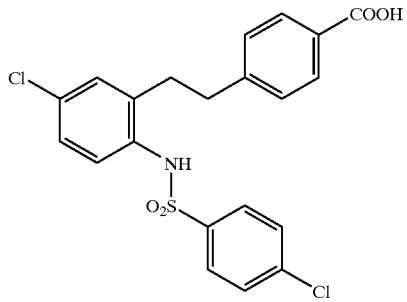

To a solution of 4-[2-[2-(4-chlorophenyl)sulfonylamino-5-chlorophenyl]vinyl]benzoic acid (54 mg; prepared in Example 5.) in THF (4 ml), platinum oxide hydrate (3 mg) was added. The mixture was stirred for 2 hours at room temperature in a stream of hydrogen. The reaction mixture was filtered and the filtrate was concentrated under the reduced pressure. To the residue, methylene chloride was added. The mixture was stirred. The precipitate was collected by filter to give the title compound (46 mg) having the following physical data.

TLC: Rf 0.42 (MeOH:CHCl$_3$=15:85); NMR (DMSO-d$_6$): δ 12.75 (H, s), 9.88 (1H, s), 7.84 (2H, d), 7.72–7.57 (4H, m), 7.32 (1H, d), 7.23 (2H, d), 7.18 (1H, dd), 6.88 (1H, d).

REFERENCE EXAMPLE 6

Methyl 4-(2-trifluoroacetylamino-5-chlorophenoxymethyl)benzoate

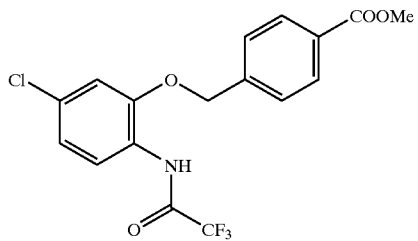

To a solution of 2-trifluoroacetylamino-5-chlorophenol (350 mg) and methyl 4-bromomethylbenzoate (435 mg) in DMF (3 ml), potassium carbonate (263 mg) was added at room temperature. The mixture was stirred for 1.5 hours at 60° C. After the termination of reaction, the reaction mixture was poured into diluted HCl and extracted with ethyl acetate. The organic layer was washed, dried over and concentrated under the reduced pressure. The residue was purified on silica gel column chromatography (AcOEt-benzene) to give the title compound (353 mg) having the following physical data.

TLC: Rf 0.44 (AcOEt:benzene=5:95).

REFERENCE EXAMPLE 7

Methyl 4-(2-amino-5-chlorophenoxymethyl)benzoate

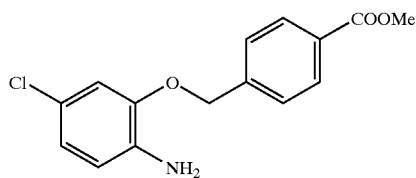

To a solution of methyl 4-(2-trifluoroacetylamino-5-chlorophenoxy-methyl)benzoate (300 mg; prepared in Reference Example 6.) in mixture of THF-MeOH (4 ml+10 ml), a solution of sodium carbonate (440 mg) in water (2 ml) was added. The solution was stirred for 8 hours at 60° C. and overnight at room temperature. The reaction mixture was poured into diluted HCl and extracted with ethyl acetate. The organic layer was washed, dried over and concentrated under the reduced pressure. The residue was purified on silica gel column chromatography (AcOEt-benzene) to give the title compound (194 mg) having the following physical data.

TLC: Rf 0.27 (AcOEt:benzene=5:95).

EXAMPLE 7

Methyl 4-[2-(4-chlorophenylsulfonylamino)-5-chlorophenoxymethyl]benzoate

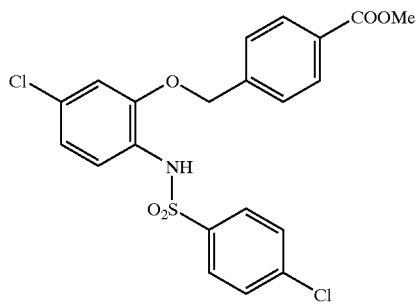

By using methyl 4-(2-amino-5-chlorophenoxymethyl)benzoate (165 mg; prepared in Reference Example 7.), the title compound (259 mg) having the following physical data was obtained by the same procedure as Example 4.

TLC: Rf 0.30 (AcOEt:benzene=5:95); NMR: δ 8.06 (2H, d), 7.59 (2H, d), 7.53 (1H, d), 7.34 (2H, d), 7.18 (2H, d) 6.96 (1H, dd), 6.82 (1H, brs), 6.76 (1H, d), 4.89 (2H, s), 3.96 (3H, s).

EXAMPLE 7(a)

Methyl 4-(2-phenylsulfonylamino-4-chlorophenoxymethyl)benzoate

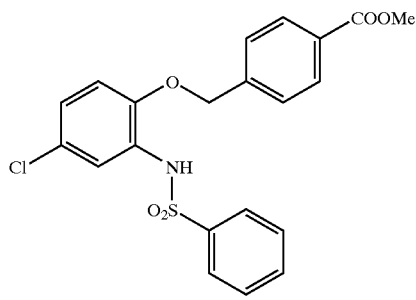

By using 2-trifluoroacetylamino-4-chlorophenol, the title compound having the following physical data was obtained by the same procedure as Reference Example 6→Reference Example 7→Example 4→Example 2.

TLC: Rf 0.37 (hexane:AcOEt=2:1); NMR: δ 8.01 (2H, d, J=8.4 Hz), 7.75 (2H, m), 7.63 (1H, d, J=2.4 Hz), 7.56 (1H, m), 7.43 (2H, m), 7.15 (2H, d, J=8.4 Hz), 6.69 (1H, brs), 6.97 (1H, dd, J=2.4, 8.8 Hz), 6.63 (1H, d, J=8.8 Hz), 4.92 (2H, s), 3.94 (3H, s).

EXAMPLE 8

4-[2-(4-chlorophenylsulfonylamino)-5-chlorophenoxy-methyl]benzoic acid

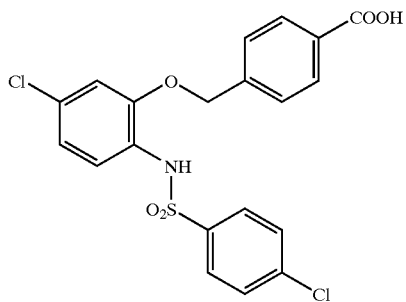

By using methyl 4-[2-(4-chlorophenylsulfonylamino)-5-chlorophenoxy-methyl]benzoate (210 mg; prepared in Example 7.), the title compound (197 mg) having the following physical data was obtained by the same procedure as Example 2.

TLC: Rf 0.43 (MeOH:CHCl$_3$=15:85); NMR (DMSO-d$_6$): δ 9.89 (1H, br s), 7.93 (2H, d), 7.60 (2H, d), 7.42 (2H, d), 7.34 (2H, d), 7.29 (1H, d), 7.06 (1H, d), 7.01 (1H, dd), 4.98 (2H, s).

EXAMPLE 8(a)–8(c)

The title compounds having the following physical data were obtained by the same procedure as Reference Examples 6, 7 and Examples 7 and 8.

EXAMPLE 8(a)

4-(2-phenylsulfonylamino-5-chlorophenoxymethyl)benzoic acid

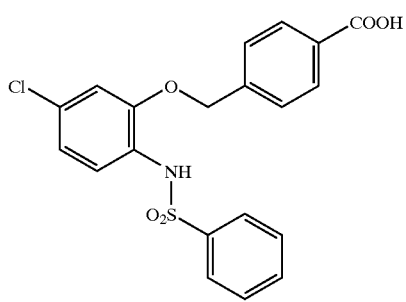

TLC: Rf 0.39 (MeOH:CHCl$_3$=2:8); NMR (DMSO-d$_6$): δ 12.98 (1H, s), 9.78 (1H, s), 7.92 (2H, d), 7.65 (2H, d), 7.55 (1H, t), 7.41 (2H, t), 7.37 (2H, d), 7.28 (1H, d), 7.04 (1H, dz), 6.98 (1H, dd), 4.98 (2H, s).

EXAMPLE 8(b)

4-(2-phenylsulfonylamino-4-chlorophenoxymethyl)benzoic acid

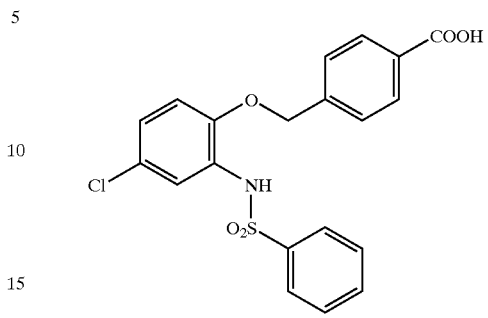

TLC: Rf 0.40 (MeOH:CHCl$_3$=2:8); NMR (DMSO-d$_6$): δ 12.98 (1H, brs), 9.94 (1H, s), 7.90 (2H, d), 7.70 (2H, d), 7.58 (1H, t), 7.44 (2H,), 7.36 (2H, d), 7.28 (1H, d), 7.15 (1H, dd), 6.94 (1H, d), 4.97 (2H, s).

EXAMPLE 8(c)

4-[2-(4-chlorophenylsulfonylamino)-4-chlorophenoxy-methyl]benzoic acid

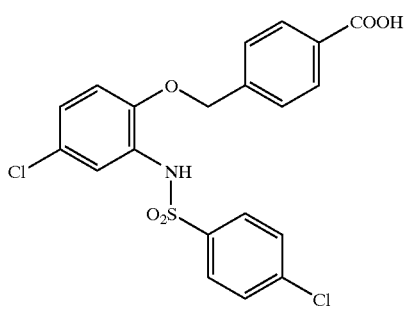

TLC: Rf 0.40 (MeOH:CHCl$_3$=2:8); NMR (DMSO-d$_6$): δ 12.93 (1H, s), 10.02 (1H, s), 7.88 (2H, d), 7.61 (2H, d), 7.42 (2H, d), 7.35–7.22 (3H, m), 7.17 (1H, dd), 6.93 (1H, d), 4.94 (2H, s).

REFERENCE EXAMPLE 8

O-mesyl-2-nitro-5-chlorobenzyl alcohol

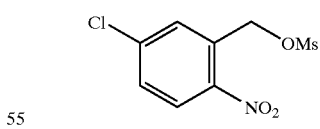

A solution of 2-nitro-5-chlorobenzyl alcohol (400 mg) in methylene chloride (6 ml) was cooled by salt-ice. To this solution, triethylamine(0.6 ml) and mesylchloride (0.25 ml) were added. The mixture was stirred for 15 minutes. To the reaction mixture, water was added. The mixture was extracted with ethyl acetate. The organic layer was washed, dried over and concentrated under the reduced pressure to give the title compound (600 mg) having the following physical data.

TLC: Rf 0.36 (hexane:AcOEt=2:1).

REFERENCE EXAMPLE 9
Methyl 4-(2-nitro-5-chlorophenylmethoxy)benzoate

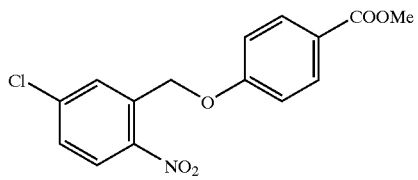

To a solution of O-mesyl-2-nitro-5-chlorobenzyl alcohol (600 mg; prepared in Reference Example 8.) in acetone (10 ml), methyl 4-hydroxy-benzoate (425 mg) and potassium carbonate (900 mg) were added. The mixture was stirred for 1 hour. To the reaction mixture, acetone (10 ml) was added. The mixture was stirred for 22 hours and filtered. The filtrate was concentrated under the reduced pressure. The residue was purified on silica gel column chromatography (hexane-AcOEt) to give the title compound (463 mg) having the following physical data.

TLC: Rf 0.26 (hexane:AcOEt=2:1).

REFERENCE EXAMPLE 10
Methyl 4-(2-amino-5-chlorophenylmethoxy)benzoate

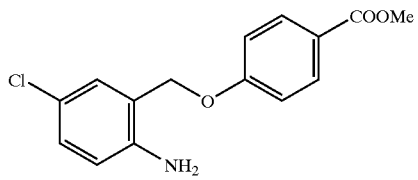

A mixture of methyl 4-(2-nitro-5-chlorophenylmethoxy) benzoate (460 mg; prepared in Reference Example 9.), THF (10 ml), water (3 ml), 1N HCl (0.4 ml) and iron powder (500 mg) was stirred for 13 hours. The reaction mixture was filtered. The filtrate was washed, dried over and concentrated under the reduced pressure. The residue was purified on silica gel column chromatography (hexane-AcOEt) to give the title compound (419 mg) having the following physical data.

TLC: Rf 0.23 (hexane:AcOEt=4:1).

EXAMPLE 9
Methyl 4-[2-(4-chlorophenylsulfonylamino)-5-chlorophenylmethoxy]benzoate

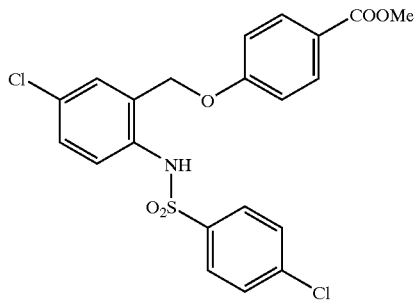

To a solution of methyl 4-(2-amino-5-chlorophenylmethoxy)benzoate (450 mg; prepared in Reference Example 10.) in methylene chloride (4 ml), pyridine (0.24 ml) and 4-chlorobenzenesulfonylchloride (380 mg) were added. The mixture was stirred for 21 hour. To the reaction mixture, water was added. The mixture was extracted with ethyl acetate. The organic layer was washed, dried over and concentrated under the reduced pressure. The residue was purified by recrystallization from hexane-AcOEt mixture solvent to give the title compound (310 mg) having the following physical data.

TLC: Rf 0.45 (benzene:AcOEt=9:1); NMR: δ 8.01 (2H, d), 7.62 (2H, d), 7.40 (2H, d), 7.32–7.26 (3H, m), 7.11 (1H, brs), 6.90 (2H, d), 4.80 (2H, s), 3.90 (3H, s).

EXAMPLE 10
4-[2-(4-chlorophenylsulfonylamino)-5-chlorophenylmethoxy]benzoic acid

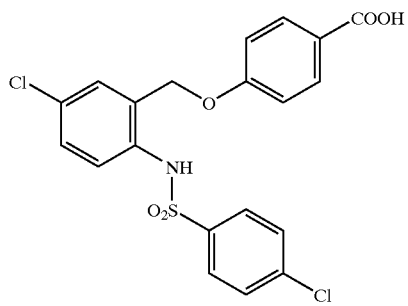

By using methyl 4-[2-(4-chlorophenylsulfonylamino)-5-chlorophenylmethoxy]benzoate (300 mg; prepared in Example 9.), the title compound (187 mg) having the following physical data was obtained by the same procedure as Example 2.

TLC: Rf 0.51 (AcOEt); NMR (DMSO-$d_6$): δ 10.2–10.0 (1H, br), 7.90 (2H, d), 7.69 (2H, d), 7.61 (2H, d), 7.49 (1H, d), 7.36 (1H, dd), 7.01 (1H, d), 6.92 (2H, d), 5.02 (2H, s).

REFERENCE EXAMPLE 11
2-phenylsulfonylamino-5-chloro-1-nitrobenzene

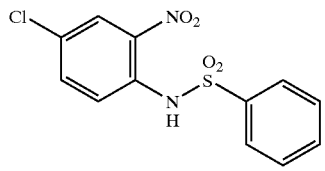

To a solution of 2-nitro-4-chloroaniline (500 mg) and pyridine (2.1 ml in methylene chloride (10 ml), benzenesulfonylchloride (1.2 ml) was added dropwise at 0° C. under an atmosphere of argon. The reaction mixture was stirred for 3 days at room temperature. To the reaction mixture, water was added. The mixture was extracted with ethyl acetate. The organic layer was washed, dried over and concentrated under the reduced pressure. The reside was recrystallized from AcOEt-hexane mixture solvent to give the by-product. The mother liquor was concentrated under the reduced pressure. The residue was purified on silica gel column chromatography (AcOEt-hexane) and recrystallized from AcOEt-hexane mixture solvent to give the title compound (175 mg) having the following physical data.

TLC: Rf 0.37 (AcOEt:hexane=1:5).

REFERENCE EXAMPLE 12

2-phenylsulfonylamino-5-chloroaniline

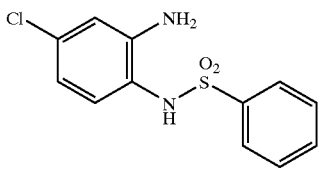

To a solution of 2-phenylsulfonylamino-5-chloro-1-nitrobenzene (172 mg; prepared in Reference Example 11.) in acetic acid (4 ml), reduced iron powder (154 mg) was added at room temperature under an atmosphere of argon. The suspension was stirred for 2 hours at 120° C. The reaction suspension was diluted with ethyl acetate and filtered. The filtrate was concentrated under the reduced pressure. The residue was purified on silica gel column chromatography (AcOEt-hexane) to give the title compound (92 mg) having the following physical data.

TLC: Rf 0.34 (AcOEt:hexane=1:2).

EXAMPLE 11

Methyl 4-(2-phenylsulfonylamino-5-chlorophenylaminocarbonyl)benzoate

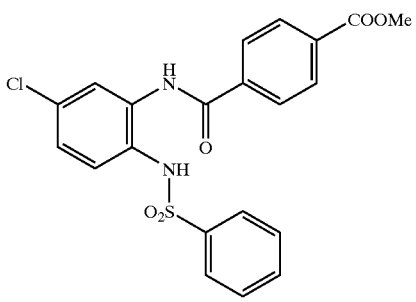

To a solution of 2-phenylsulfonylamino-5-chloroaniline (90 mg; prepared in Reference Example 12.) and pyridine (0.05 ml) in methylene chloride (5 ml), 4-methoxycarbonylbenzoic acid chloride (70 mg) was added at room temperature in a stream of argon. The mixture was stirred for 6 hours. After the termination of reaction, water was added to the reaction mixture. The mixture was extracted with ethyl acetate. The organic layer was washed, dried over and concentrated under the reduced pressure. The residue was purified by the recrystallization from AcOEt-hexane mixture solvent to give the title compound (112 mg) having the following physical data.

TLC: Rf 0.55 (AcOEt:hexane=1:1); NMR (CDCl$_3$+DMSO-d$_6$): δ 9.41 (1H, brs), 8.93 (1H, brs), 8.22 (1H, d), 8.15 (2H, d), 7.98 (2H, d), 7.72–7.62 (2H, m), 7.58–7.45 (1H, m), 7.44–7.32 (2H, m), 6.96 (1H, dd), 6.82 (1H, d).

EXAMPLE 12
4-(2-phenylsulfonylamino-5-chlorophenylaminocarbonyl)benzoic acid

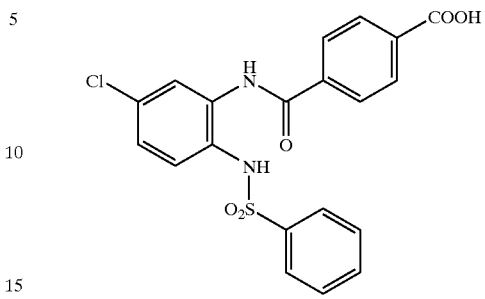

By using methyl 4-(2-phenylsulfonylamino-5-chlorophenylaminocarbonyl)benzoate (110 mg; prepared in Example 11.), the title compound (107 mg) having the following physical data was obtained by the same procedure as Example 2.

TLC: Rf 0.36 (AcOEt:hexane:AcOH=8:10:1); NMR (DMSO-d$_6$): δ 13.00 (1H, brs), 9.80 (1H, brs), 9.65 (1H, s), 8.09 (2H, d), 7.87 (2H, d), 7.81 (1H, d), 7.65–7.50 (3H, m), 7.40 (2H, t), 7.22 (1H, dd), 7.14 (1H, d).

REFERENCE EXAMPLE 13
2-nitro-5-chlorobenzoic acid chloride

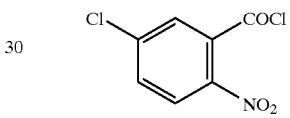

A solution of 2-nitro-5-chlorobenzoic acid (200 mg) in sulfonylchloride (20 ml) was stirred for 4 hours at 99° C. in a stream of argon. After leaving to cool, the solution was concentrated under the reduced pressure to give the title compound.

REFERENCE EXAMPLE 14
1-(2-nitro-5-chlorobenzoyl)-1-(4-methoxycarbonylphenyl)methylidene triphenylphosphoran

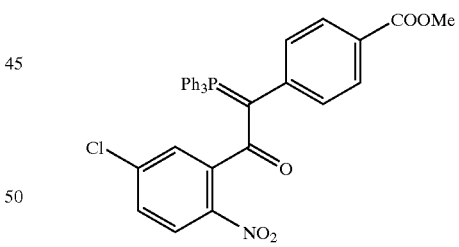

To a solution of 4-methoxycarbonylbenzyltriphenylphosphonium bromide (1.17 g) in THF (8 ml), potassium t-butoxide (246 mg) was added in a stream of argon. The mixture was stirred for 30 minutes. A solution of 2-nitro-5-chlorobenzoic acid chloride (prepared in Reference Example 13.) in THF (4 ml) was added dropwise to the reaction solution. The mixture was stirred for 3 hours at room temperature. The reaction mixture was quenched by adding saturated aqueous ammonium chloride and extracted with chloroform. The organic layer was washed, dried over and concentrated under the reduced pressure. The residue was purified on silica gel column chromatography (CHCl$_3$-MeOH) to give the title compound (619 mg) having the following physical data.

TLC: Rf 0.26 (CHCl$_3$:MeOH=100:1).

REFERENCE EXAMPLE 15
Methyl 4-[2-(2-nitro-5-chlorophenyl)ethynyl]benzoate

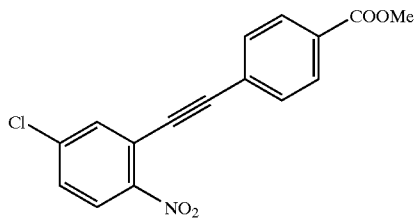

A solution of 1-(2-nitro-5-chlorobenzoyl)-1-(4-methoxycarbonylphenyl)methylidene triphenylphosphoran (513 mg; prepared in Reference Example 14.) in o-dichlorobenzene (10 ml) was refluxed for 9 hours at 180° C. in a stream of argon. The reaction mixture was concentrated under the reduced pressure. The residue was purified on silica gel column chromatography (hexane-AcOEt) to give the title compound (189 mg) having the following physical data.

TLC. Rf 0.39 (hexane:AcOEt=7:1).

REFERENCE EXAMPLE 16
Methyl 4-[2-(2-amino-5-chlorophenyl)ethynyl]benzoate

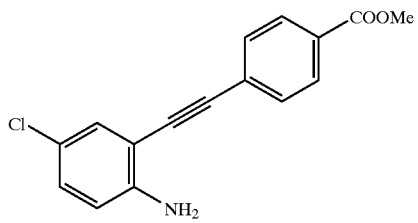

To a solution of methyl 4-[2-(2-nitro-5-chlorophenyl)ethynyl]benzoate (180 mg; prepared in Reference Example 15.) in acetic acid (3.6 ml), reduced iron powder (160 mg) was added. The mixture was refluxed for 30 minutes and filtered. The filtrate was concentrated under the reduced pressure. The residue was purified on silica gel column chromatography (hexane-AcOEt) to give the title compound (144 mg) having the following physical data.

TLC: Rf 0.25 (hexane:AcOEt=5:1).

EXAMPLE 13
Methyl 4-[2-[2-(4-chlorophenylsulfonylamino)-5-chlorophenyl]ethynyl]benzoate

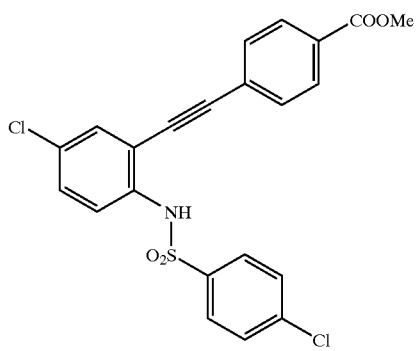

To a solution of methyl 4-[2-(2-amino-5-chlorophenyl)ethynyl]benzoate (136 mg; prepared in Reference Example 16.) in methylene chloride (2 ml), pyridine (77 µl) and 4-chlorobenzenesulfonyl chloride (106 mg) were added at 0° C. under an atmosphere of argon. The mixture was stirred for 24 hours at room temperature. The reaction mixture was diluted with ethyl acetate, washed, dried over and concentrated under the reduced pressure. The residue was purified on silica gel column chromatography (hexane-AcOEt) to give the title compound (207 mg) having the following physical data.

TLC: Rf 0.50 (hexane:AcOEt=3:1); NMR δ 8.07 (2H, d), 7.67 (2H, d), 7.58 (1H, d), 7.49 (2H, d), 7.39 (1H, d), 7.34 (2H, d), 7.32 (1H, dd), 7.07 (1H, brs), 3.96 (3H, s).

EXAMPLE 14
4-[2-[2-(4-chlorophenylsulfonylamino)-5-chlorophenyl]ethynyl]benzoic acid

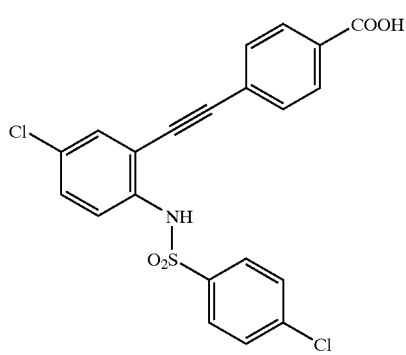

By using methyl 4-[2-[2-(4-chlorophenylsulfonylamino)-5-chlorophenyl]ethynyl]benzoate (199 mg; prepared in Example 13.), the title compound (181 mg) having the following physical data was obtained by the same procedure as Example 2.

TLC: Rf 0.43 (CHCl$_3$:MeOH:AcOH=100:5:1); NMR (DMSO-d$_6$): δ 13.16 (1H, brs), 10.32 (1H, brs), 8.00 (2H, d), 7.65 (2H, d), 7.59 (1H, d), 7.57 (2H, d), 7.50 (1H, dd), 7.43 (2H, d), 7.35 (1H, d).

REFERENCE EXAMPLE 17
Methyl 4-(2-amino-5-trifluoromethylphenoxymethyl)benzoate

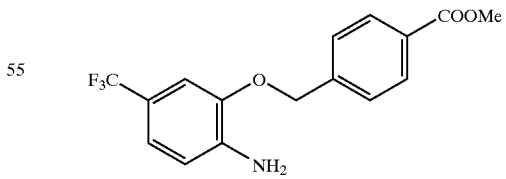

By using 2-nitro-5-trifluoromethylphenol, the title compound having the following physical data was obtained by the same procedure as Reference Example 6→Reference Example 12.

TLC: Rf 0.33 (hexane:AcOEt=3:1).

EXAMPLE 15

Methyl 4-(2-phenylsulfonylamino-5-trifluoromethylphenoxymethyl)benzoate

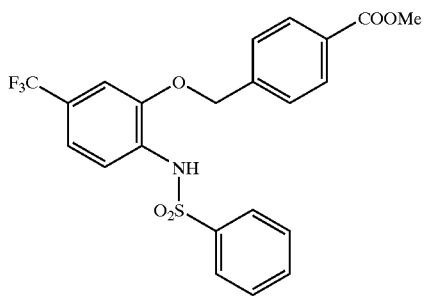

By using methyl 4-(2-amino-5-trifluoromethylphenoxymethyl)benzoate (prepared in Reference Example 17.), the title compound having the following physical data was obtained by the same procedure as Example 7.

TLC: Rf 0.76 (benzene:acetone=9:1); NMR: δ 8.05 (2H, d, J=8.2 Hz), 7.77 (2H, m), 7.69 (1H, d, J=8.6 Hz), 7.58 (1H, m), 7.45 (2H, m), 7.25 (3H, m), 7.18 (1H, m), 6.99 (1H, m), 5.02 (2H, s), 3.95 (1H, s).

EXAMPLE 16

4-(2-phenylsulfonylamino-5-trifluoromethylphenoxymethyl)benzoic acid

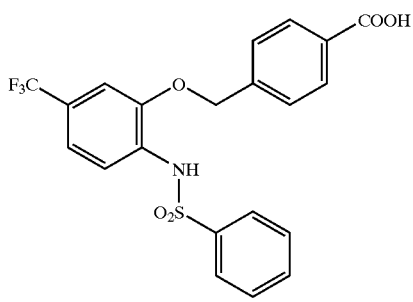

By using methyl 4-(2-phenylsulfonylamino-5-trifluoromethylphenoxymethyl)benzoate (prepared in Example 15.), the title compound having the following physical data was obtained by the same procedure as Example 2.

TLC: Rf 0.52 (CHCl$_3$:MeOH:AcOH=100:5:1); NMR (DMSO-d$_6$): δ 12.95 (1H, brd), 10.10 (1H, brd), 7.93 (2H, d, J=8.0 Hz), 7.75 (2H, m), 7.59 (1H, m), 7.40–7.53 (5H, m), 7.27 (2H, m), 5.14 (2H, s).

EXAMPLE 17

Methyl 4-[2-(N-isopropyl-phenylsulfonylamino)-4-chlorophenoxymethyl]-benzoate

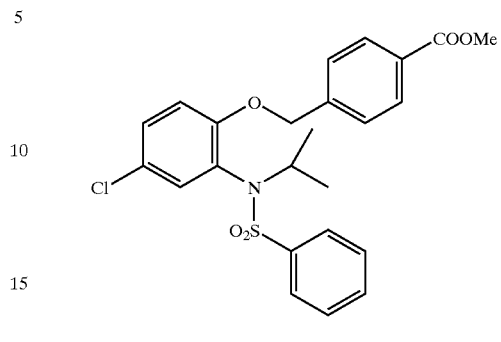

To a solution of methyl 4-(2-phenylsulfonylamino-4-chlorophenoxy-methyl)benzoate (402 mg; prepared in Example 7(a)) in DMF (4 ml), potassium carbonate 256 (mg) and isopropyl iodide (185 μl) were added. The mixture was stirred overnight at room temperature and for 9 hours at 50° C. To the reaction solution, iced water and 2N HCl were added. The mixture was extracted with ethyl acetate. The organic layer was washed, dried over, concentrated after filtration, solidified with ethanol and washed to give the title compound (411 mg) having the following physical data.

TLC: Rf 0.59 (hexane: AcOEt=2:1); NMR: δ 8.05 (2H, d, J=8.8 Hz), 7.83–7.79 (2H, m), 7.55–7.26 (6H, m), 7.08 (1H, d, J=2.8 Hz), 6.89 (1H, d, J=8.8 Hz), 5.04 (2H, s), 4.36 (1H, sept, J=6.8 Hz), 3.93 (3H, s), 1.05 (6H, d, J=6.8 Hz).

EXAMPLE 17(1)–(4)

By using the corresponding compounds, the title compounds having the following physical data were obtained by the same procedure as Reference Example 6→Reference Example 7→Example 7→Example 17 or Reference Example 8→Reference Example 9→Reference Example 10→Example 9→Example 17.

EXAMPLE 17(1)

Methyl 4-[2-(N-isopropyl-phenylsulfonylamino)-5-trifluoromethylphenoxy-methyl]benzoate

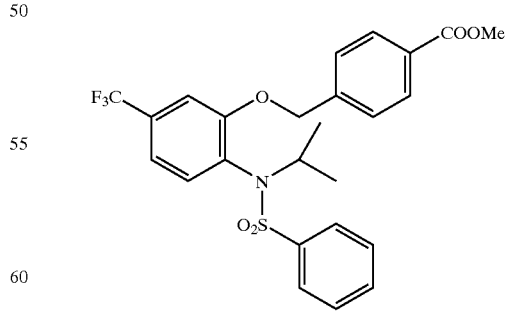

TLC: Rf 0.55 (hexane:AcOEt=2:1); NMR: δ 8.07 (2H, d, J=8.4 Hz), 7.79 (2H, m), 7.44–7.55 (3H, m), 7.32–7.43 (2H, m), 7.18–7.29 (3H, m), 5.10 (2H, s), 4.38 (1H, sept, J=6.6 Hz), 3.94 (3H, s), 1.05 (6H, d, J=6.6 Hz).

EXAMPLE 17(2)

Methyl 4-[2-(N-isopropyl-phenylsulfonylamino)-5-methylphenoxymethyl]-benzoate

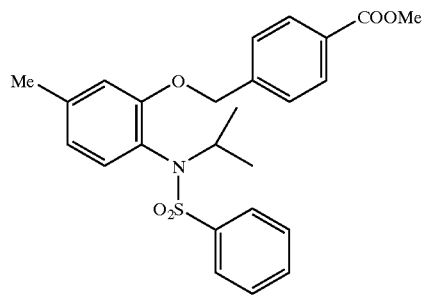

TLC: Rf 0.48 (hexane:AcOEt=2:1); NMR: δ 8.04 (2H, d, J=8.4 Hz), 7.80 (2H, m), 7.41–7.52 (3H, m), 7.28–7.39 (2H, m), 6.97 (1H, d, J=8.6 Hz), 6.73–6.80 (2H, m), 5.00 (2H, s), 4.38 (1H, sept, J=7.0 Hz), 3.93 (3H, s), 2.35 (3H, s), 1.05 (6H, d, J=7.0 Hz).

EXAMPLE 17(3)

Methyl 4-[2-(N-isopropyl-phenylsulfonylamino)-5-chlorophenoxymethyl]-benzoate

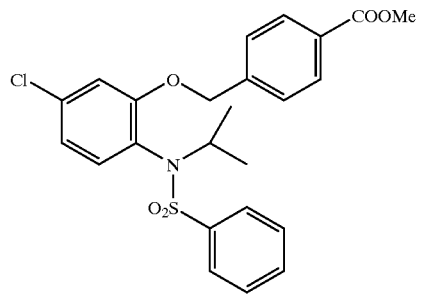

TLC: Rf 0.30 (hexane:AcOEt=4:1); NMR: δ 8.06 (2H, d, J=8.2 Hz), 7.78 (2H, d, J=7.2 Hz), 7.25–7.48 (5H, m), 6.85–7.05 (3H, m), 5.02 (2H, s), 4.37 (1H, sept, J=6.4 Hz), 3.94 (3H, s), 1.04 (6H, d, J=6.4 Hz).

EXAMPLE 17(4)

Methyl 4-[2-(N-isopropyl-2-furanylsulfonylamino)-5-trifluoromethylphenoxymethyl]cinnamate

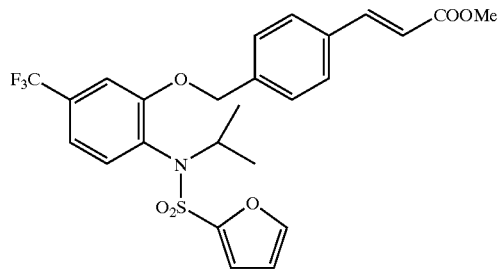

TLC: Rf 0.39 (benzene:AcOEt=19:1); NMR: δ 7.71 (1H, d, J=16 Hz), 7.59–7.45 (5H, m), 7.23–7.20 (3H, m), 6.94–6.92 (1H, m), 6.50–6.42 (2H, m), 5.12 (2H, s), 4.5–4.4 (1H, m), 3.82 (3H, s), 1.09 (6H, dd, J=6.5, 2 Hz).

EXAMPLE 18

4-[2-(N-isopropyl-phenylsulfonylamino)-4-chlorophenoxymethyl]benzoic acid

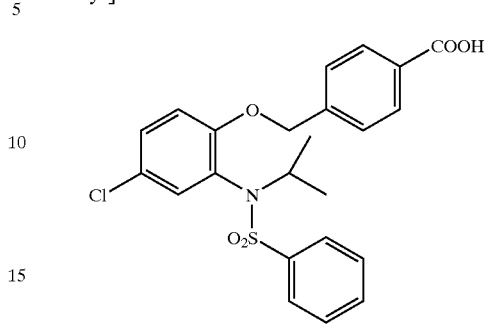

By using methyl 4-[2-(N-isopropyl-phenylsulfonylamino)-4-chlorophenoxymethyl]benzoate (prepared in Example 17.), the title compound having the following physical data was obtained by the same procedure as Example 2.

TLC: Rf 0.43 (CHCl$_3$:MeOH:H$_2$O=9:1:0.1); NMR (DMSO-d$_6$): δ 12.90 (1H, br), 7.94 (2H, d, J=8.4 Hz), 7.78 (2H, d, J=8.4 Hz), 7.66–7.45 (6H, m), 7.23 (1H, d, J=8.4 Hz), 7.07 (1H, d, J=2.4 Hz), 5.13 (2H, s), 4.20 (1H, sept, J=6.6 Hz), 0.99 and 0.96 (each 3H, each d, J=6.6 Hz).

EXAMPLE 18(1)–18(128)

By using the corresponding compounds, the title compounds having the following physical data were obtained by the same procedure as Reference Example 6→Reference Example 7→Example 7→Example 17→Example 2 or Reference Example 8→Reference Example 9→Reference Example 10→Example 9→Example 17→Example 2.

EXAMPLE 18(1)

4-[2-(N-carboxymethyl-phenylsulfonylamino)-4-chlorophenoxymethyl]benzoic acid

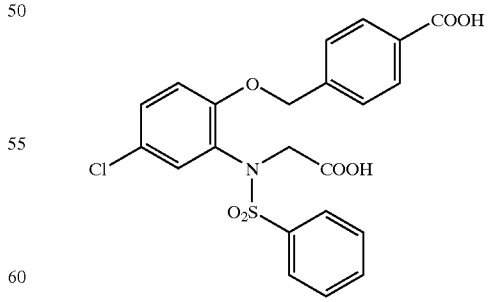

TLC: Rf 0.20 (CHCl$_3$:MeOH:H$_2$O=7:3:0.3); NMR (DMSO-d$_6$): δ 12.93 (2H, br), 7.88 (2H, d, J=8.4 Hz), 7.63–7.37 (7H, m), 7.16–7.06 (3H, m), 4.88 (2H, s), 4.31 (2H, s).

EXAMPLE 18(2)

4-[2-[N-(2-hydroxyethyl)-phenylsulfonylamino]-4-chlorophenoxymethyl]benzoic acid

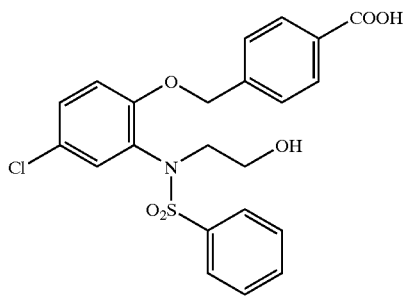

TLC: Rf 0.26 (CHCl$_3$:MeOH:H$_2$O=9:1:0.1); NMR (DMSO-d$_6$): δ 12.71 (1H, br), 7.88 (2H, d, J=8.4 Hz), 7.63–7.32 (7H, m), 7.19–7.08 (3H, m), 4.89 (2H, brs), 4.71 (1H, br), 3.86–3.40 (4H, m).

EXAMPLE 18(3)

4-[2-(N-methyl-phenylsulfonylamino)-4-trifluoromethyl-phenoxymethyl]benzoic acid

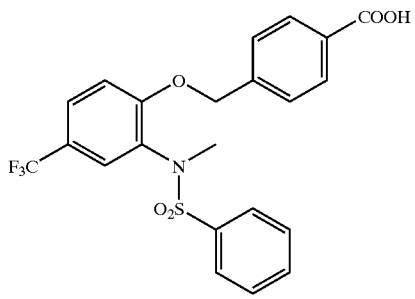

TLC: Rf 0.31 (CHCl$_3$:MeOH:H$_2$O=9:1:0.1); NMR (DMSO-d$_6$): δ 12.90 (1H, br), 7.90 (2H, d, J=8.4 Hz), 7.76–7.70 (1H, dd-like), 7.64–7.43 (6H, m), 7.31 (1H, d, J=8.4 Hz), 7.23 (2H, d, J=8.4 Hz), 5.05 (2H, s), 3.18 (3H, s).

EXAMPLE 18(4)

4-[2-[N-(2-hydroxyethyl)-phenylsulfonylamino]-4-trifluoromethylphenoxymethyl]benzoic acid

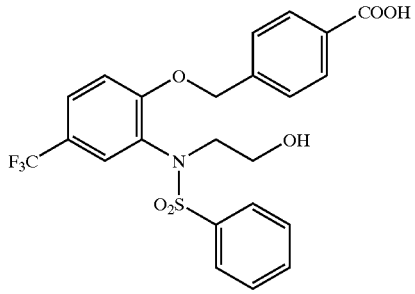

TLC: Rf 0.24 (CHCl$_3$:MeOH:H$_2$O=9:1:0.1); NMR (DMSO-d$_6$): δ 12.51 (1H, br), 7.89 (2H, d, J=8.4 Hz), 7.74 (1H, dd, J=2.2 and 8.4 Hz), 7.62–7.37 (6H, m), 7.28 (1H, d, J=8.4 Hz), 7.20 (2H, d, J=8.4 Hz), 5.00 (2H, brs), 4.70 (1H, br), 3.66–3.28 (4H, m).

EXAMPLE 18(5)

4-[2-[N-(2-hydroxyethyl)-phenylsulfonylamino]-5-trifluoromethylphenoxymethyl]benzoic acid

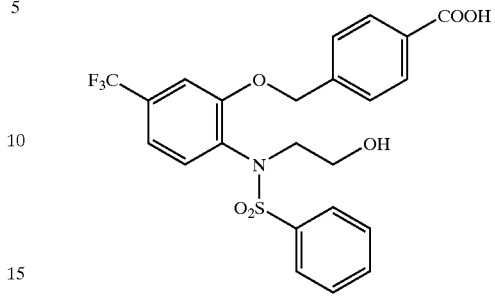

TLC: Rf 0.40 (CHCl$_3$:MeOH:AcOH=100:5:1); NMR (DMSO-d$_6$): δ 12.96 (1H, brd), 7.89 (2H, d, J=8.4 Hz), 7.61 (2H, m), 7.34–7.58 (6H, m), 7.20 (2H, d, J=8.4 Hz), 5.05 (1H, brs), 4.67 (1H, m), 3.60 (2H, m), 3.42 (2H, m).

EXAMPLE 18(6)

4-[2-(N-methyl-phenylsulfonylamino)-5-chlorophenoxymethyl]benzoic acid

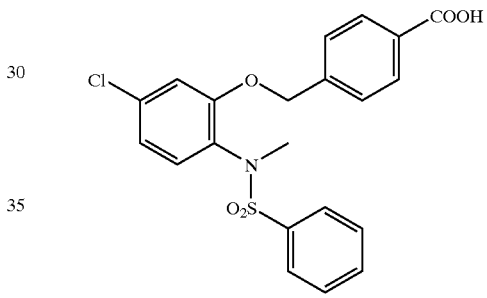

TLC: Rf 0.36 (CHCl$_3$:MeOH:H$_2$O=9:1:0.1); NMR (DMSO-d$_6$): δ 12.63 (1H, br), 7.89 (2H, d, J=8.4 Hz), 7.64–7.41 (5H, m), 7.25–7.19 (4H, m), 7.05 (1H, dd, J=2.2 and 8.4 Hz), 4.98 (2H, s), 3.12 (3H, s).

EXAMPLE 18(7)

4-[2-[N-(2-hydroxyethyl)-phenylsulfonylamino]-5-chlorophenoxymethyl]benzoic acid

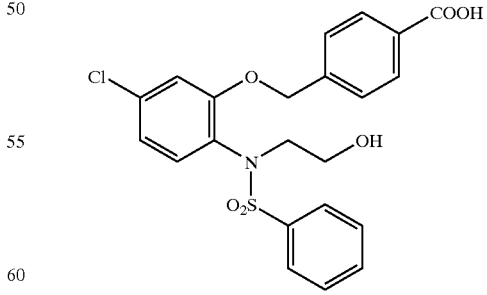

TLC: Rf 0.27 (CHCl$_3$:MeOH H$_2$O=9:1:0.1); NMR (DMSO-d$_6$): δ 12.88 (1H, br), 7.89 (2H, d, J=8.4 Hz), 7.62–7.36 (5H, m), 7.29–7.17 (4H, m), 7.06 (1H, dd, J=2.2 and 8.4 Hz), 4.95 (2H, brs), 4.68 (1H, br), 3.66–3.24 (4H, br).

EXAMPLE 18(8)

4-[2-(N-methyl-phenylsulfonylamino)-5-trifluoromethyl-phenoxymethyl]benzoic acid

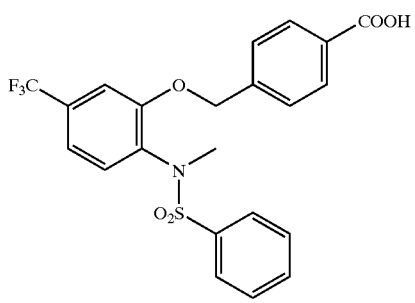

TLC: Rf 0.46 (CHCl$_3$:MeOH:AcOH=100:5:1); NMR: δ 8.08 (2H, d, J=8.0 Hz), 7.68 (2H, m), 7.12–7.53 (8H, m), 4.93 (2H, s), 3.24 (3H, s).

EXAMPLE 18(9)

4-[2-(N-isopropyl-phenylsulfonylamino)-5-trifluoromethyl-phenoxymethyl]benzoic acid

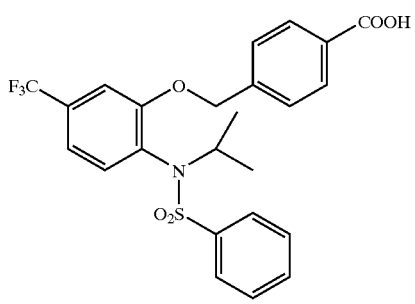

TLC: Rf 0.44 (CHCl$_3$:MeOH:AcOH=100:5:1); NMR: δ 8.15 (2H, d, J=8.6 Hz), 7.81 (2H, m), 7.52 (3H, m), 7.38 (2H, m), 7.24 (3H, m), 5.13 (2H, s), 4.40 (1H, sept, J=6.8 Hz), 1.06 (6H, d, J=6.8 Hz).

EXAMPLE 18(10)

4-[2-(N-isopropyl-phenylsulfonylamino)-5-chlorophenoxymethyl]benzoic acid

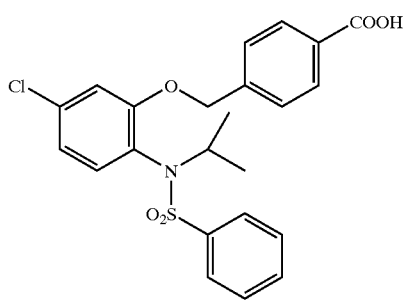

TLC: Rf 0.35 (CHCl$_3$:MeOH:H$_2$O=9:1:0.1); NMR (DMSO-d$_6$): δ 12.96 (1H, br), 7.95 (2H, d, J=8.2 Hz), 7.78–7.74 (2H, m), 7.65–7.43 (5H, m), 7.32 (1H, s), 7.07 (2H, s), 5.21 and 5.07 (each 1H, each d, J=15.6 Hz), 4.21 (1H, sept-like), 0.94 (6H, d, J=6.8 Hz).

EXAMPLE 18(11)

4-[2-(N-isopropyl-phenylsulfonylamino)-4-trifluoromethyl-phenoxymethyl]benzoic acid

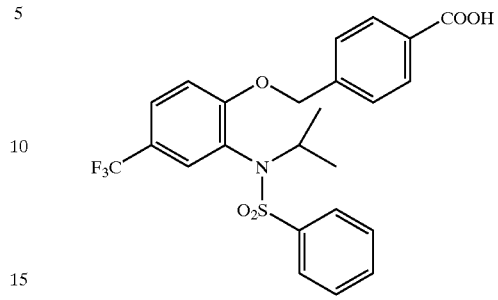

TLC: Rf 0.30 (CHCl$_3$:MeOH:H$_2$O=9:1:0.1); NMR (DMSO-d$_6$): δ 13.03 (1H, br), 7.95 (2H, d, J=8.2 Hz), 7.84–7.74 (3H, m), 7.67–7.39 (6H, m), 7.25 (1H, d, J=2.4 Hz), 5.28 and 5.21 (each 1H, each d, J=16.6 Hz), 4.26 (1H, sept-like), 0.98 and 0.97 (each 3H, each d, J=6.6 Hz).

EXAMPLE 18(12)

4-[2-[N-(2-methoxyethoxymethyl)-phenylsulfonylamino]-4-chlorophenoxymethyl]benzoic acid

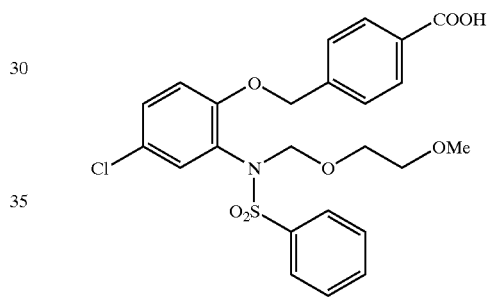

TLC: Rf 0.40 (CHCl$_3$:MeOH:H$_2$O=9:1:0.1); NMR (DMSO-d$_6$): δ 12.98 (1H, br), 7.91 (2H, d, J=8.2 Hz), 7.66–7.52 (3H, m), 7.45–7.38 (3H, m), 7.26–7.22 (3H, m), 7.10 (1H, d, J=8.2 Hz), 5.06 (2H, brs), 4.92 (2H, brs), 3.68–3.63 (2H, t-like), 3.42–3.37 (2H, t-like), 3.21 (3H, s).

EXAMPLE 18(13)

4-[2-[N-(2-methoxyethyl)-phenylsulfonylamino]-4-chlorophenoxymethyl]benzoic acid

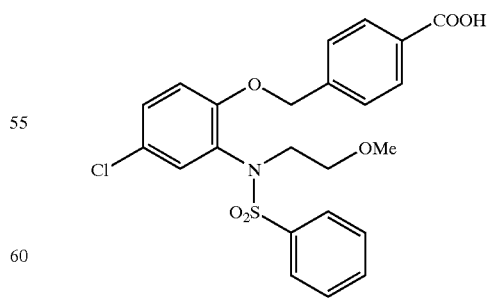

TLC: Rf 0.25 (CHCl$_3$:MeOH:H$_2$O=9:1:0.1); NMR (DMSO-d$_6$): δ 12.92 (1H, br), 7.88 (2H, d, J=8.2 Hz), 7.64–7.39 (6H, m), 7.22–7.10 (4H, m), 4.91 (2H, brs), 3.69 (2H, br), 3.38–3.33 (2H, m), 3.13 (3H, s).

EXAMPLE 18(14)

4-[2-[N-[2-(2-methoxyethoxy)ethyl]-phenylsulfonyl-amino]-4-chlorophenoxymethyl]benzoic acid

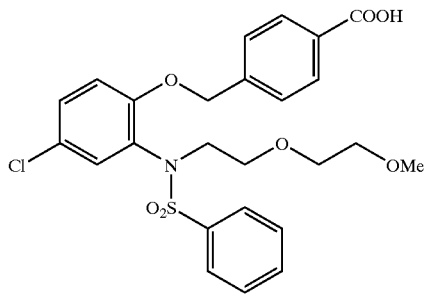

TLC: Rf 0.29 (CHCl$_3$:MeOH:H$_2$O=9:1:0.1); NMR (DMSO-d$_6$): δ 12.95 (1H, br), 7.89 (2H, d, J=8.2 Hz), 7.65–7.39 (6H, m), 7.25 (1H, d, J=2.6 Hz), 7.20 (2H, d, J=8.2 Hz), 7.11 (1H, d, J=8.2 Hz), 4.92 (2H, brs), 3.69 (2H, br), 3.47–3.28 (6H, m), 3.19 (3H, s).

EXAMPLE 18(15)

4-[2-(N-ethyl-phenylsulfonylamino)-4-chlorophenoxymethyl]benzoic acid

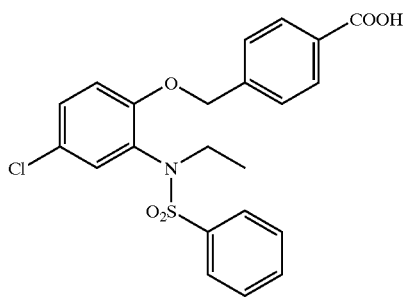

TLC: Rf 0.51 (CHCl$_3$:MeOH=9:1); NMR: δ 8.08 (2H, d, J=8.2 Hz), 7.8–7.6 (2H, m), 7.5–7.2 (7H, m), 6.81 (1H, d, J=9.4 Hz), 4.88 (2H, s), 3.67 (2H, q, J=7.0 Hz), 1.11 (3H, t, J=7.0 Hz).

EXAMPLE 18(16)

4-[2-(N-propyl-phenylsulfonylamino)-4-chlorophenoxymethyl]benzoic acid

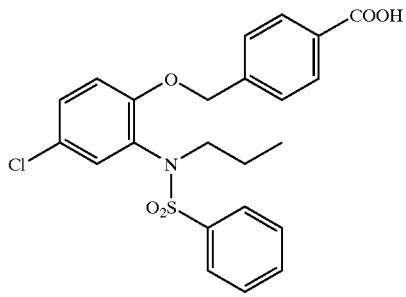

TLC: Rf 0.50 (CHCl$_3$:MeOH=9:1); NMR: δ 8.08 (2H, d, J=8.4 Hz), 7.7–7.6 (2H, m), 7.5–7.2 (7H, m), 6.80 (1H, d, J=9.6 Hz), 4.85 (2H, s), 3.6–3.5 (2H, m), 1.6–1.4 (2H, m), 0.89 (3H, t, J=7.2 Hz).

EXAMPLE 18(17)

4-[2-(N-butyl-phenylsulfonylamino)-4-chlorophenoxymethyl]benzoic acid

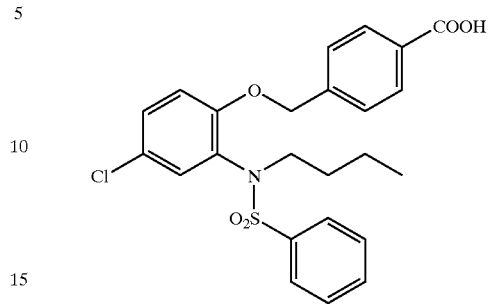

TLC: Rf 0.53 (CHCl$_3$:MeOH=9:1); NMR: δ 8.08 (2H, d, J=8.4 Hz), 7.7–7.6 (2H, m), 7.5–7.2 (7H, m), 6.80 (1H, d, J=9.4 Hz), 4.86 (2H, s), 3.7–3.5 (2H, m), 1.5–1.2 (4H, m), 0.85 (3H, t, J=7.0 Hz).

EXAMPLE 18(18)

4-[2-(N-pentyl-phenylsulfonylamino)-4-chlorophenoxymethyl]benzoic acid

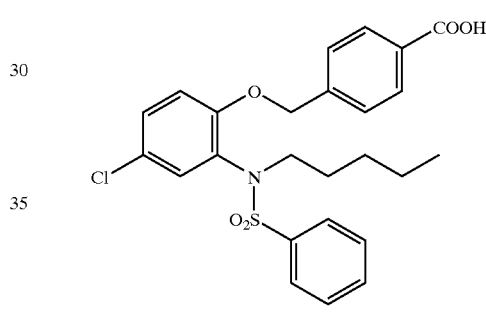

TLC: Rf 0.56 (CHCl$_3$:MeOH=9:1); NMR: δ 8.08 (2H, d, J=8.2 Hz), 7.7–7.6 (2H, m), 7.5–7.2 (7H, m), 6.8–6.7 (1H, m), 4.86 (2H, s), 3.6–3.5 (2H, m), 1.5–1.2 (6H, m), 0.9–0.8 (3H, m).

EXAMPLE 18(19)

4-[2-(N-hexyl-phenylsulfonylamino)-4-chlorophenoxymethyl]benzoic acid

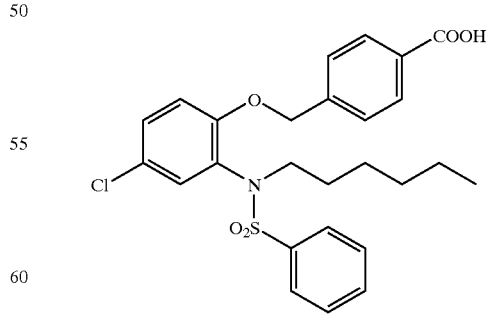

TLC: Rf 0.58 (CHCl$_3$:MeOH=9:1); NMR: δ 8.08 (2H, d, J=8.6 Hz), 7.7–7.6 (2H, m), 7.5–7.2 (7H, m), 6.9–6.8 (1H, m), 4.86 (2H, s), 3.6–3.5 (2H, m), 1.5–1.1 (8H, m), 0.9–0.8 (3H, m).

EXAMPLE 18(20)

4-[2-(N-benzyl-phenylsulfonylamino)-4-chlorophenoxymethyl]benzoic acid

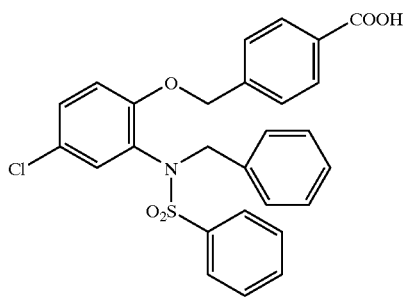

TLC: Rf 0.60 (CHCl$_3$:MeOH=9:1); NMR: δ 8.09 (2H, d, J=8.6 Hz), 7.8–7.7 (2H, m), 7.6–7.3 (3H, m), 7.3–7.1 (9H, m), 6.71 (1H, d, J=8.8 Hz), 4.82 (2H, s), 4.78 (2H, s).

EXAMPLE 18(21)

4-[2-(N-isopropyl-phenylsulfonylamino)-5-methylphenoxymethyl]benzoic acid

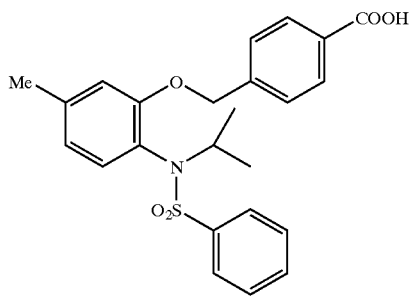

TLC: Rf 0.50 (CHCl$_3$:MeOH:AcOH=100:5:1); NMR: δ 8.13 (2H, d, J=8.2 Hz), 7.82 (2H, m), 7.49 (3H, m), 7.36 (2H, m), 6.98 (1H, d, J=8.6 Hz), 6.77 (2H, m), 5.05 (2H, s), 4.40 (1H, sept, J=6.6 Hz), 2.36 (3H, s), 1.05 (6H, d, J=6.6 Hz).

EXAMPLE 18(22)

4-[2-(N-methyl-phenylsulfonylamino)-5-methylphenoxymethyl]benzoic acid

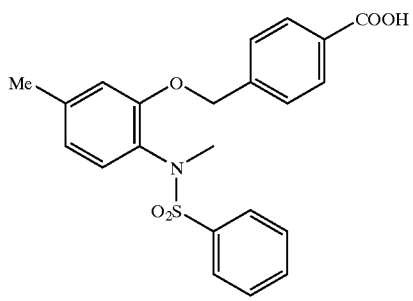

TLC: Rf 0.56 (AcOEt:hexane:AcOH=9:10:1); NMR (DMSO-d$_6$): δ 12.96 (1H, brs), 7.89 (2H, d, J=8.5 Hz), 7.67–7.40 (5H, m), 7.23 (2H, d, J=8.0 Hz), 7.06 (1H, d, J=8.0 Hz), 6.93 (1H, s), 6.78 (1H, d, J=8.0 Hz), 4.93 (2H, s), 3.12 (3H, s), 2.30 (3H, s).

EXAMPLE 18(23)

4-[2-[N-(2-hydroxyethyl)-phenylsulfonylamino]-5-methylphenoxymethyl]benzoic acid

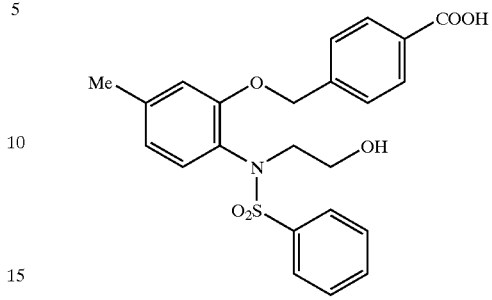

TLC: Rf 0.27 (AcOEt:hexane:AcOH=9:10:1); NMR (DMSO-d$_6$): δ 12.95 (1H, brs), 7.87 (2H, d, J=8.5 Hz), 7.55–7.32 (5H, m), 7.20 (2H, d, J=8.5 Hz), 7.08 (1H, d, J=8.0 Hz), 6.91 (1H, s), 6.77 (1H, d, J=8.0 Hz), 4.89 (2H, brs), 4.63 (1H, t, J=4.0 Hz), 3.50–3.20 (4H, m), 2.29 (3H, s).

EXAMPLE 18(24)

4-[2-[N-(prop-2-enyl)-phenylsulfonylamino]-4-chlorophenoxymethyl]benzoic acid

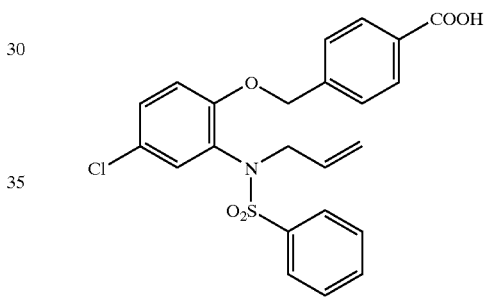

TLC: Rf 0.54 (CHCl$_3$:MeOH=9:1); NMR: δ 8.08 (2H, d, J=8.0 Hz), 7.8–7.6 (2H, m), 7.6–7.2 (7H, m), 6.78 (1H, d, J=9.4 Hz), 5.9–5.6 (1H, m), 5.2–5.0 (2H, m), 4.86 (2H, s), 4.3–4.2 (2H, m).

EXAMPLE 18(25)

4-[2-(N-cyclopentyl-phenylsulfonylamino)-4-chlorophenoxymethyl]benzoic acid

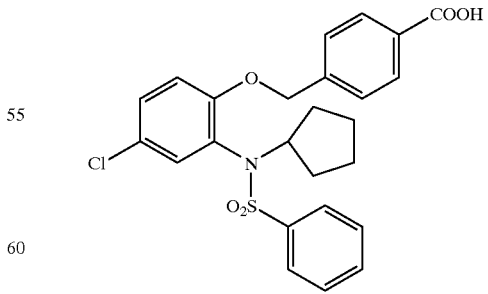

TLC: Rf 0.47 (CHCl$_3$:MeOH=9:1); NMR: δ 8.13 (2H, d, J=8.4 Hz), 7.9–7.8 (2H, m), 7.6–7.2 (6H, m), 7.07 (1H, d, J=2.6 Hz), 6.88 (1H, d, J=8.8 Hz), 5.1–5.0 (2H, m), 4.5–4.3 (1H, m), 2.0–1.7 (2H, m), 1.6–1.2 (6H, m).

EXAMPLE 18(26)

4-[2-[N-(2-methoxyethyl)-phenylsulfonylamino]-5-trifluoromethylphenoxymethyl]benzoic acid

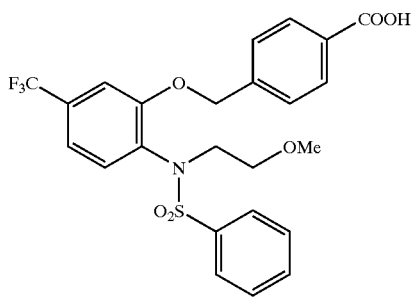

TLC: Rf 0.46 (CHCl$_3$:MeOH:AcOH=100:5:1); NMR: δ 8.07 (2H, d, J=8.4 Hz), 7.66 (2H, m), 7.18–7.53 (7H, m), 7.12 (1H, m), 4.90 (2H, s), 3.81 (2H, m), 3.51 (2H, t, J=6.0 Hz), 3.24 (3H, s).

EXAMPLE 18(27)

4-[2-(N-ethyl-phenylsulfonylamino)-5-trifluoromethyl-phenoxymethyl]benzoic acid

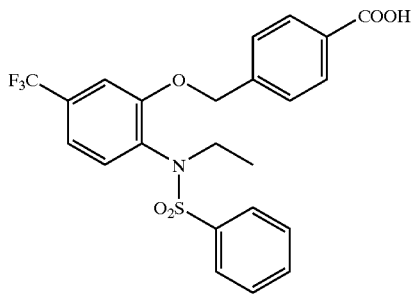

TLC: Rf 0.43 (CHCl$_3$:MeOH=9:1); NMR: δ 8.09 (2H, d, J=8.4 Hz), 7.7–7.6 (2H, m), 7.5–7.2 (7H, m), 7.15 (1H, d, J=1.6 Hz), 4.94 (2H, s), 3.69 (2H, q, J=7.4 Hz), 1.11 (3H, t, J=7.4 Hz).

EXAMPLE 18(28)

4-[2-(N-propyl-phenylsulfonylamino)-5-trifluoromethyl-phenoxymethyl]benzoic acid

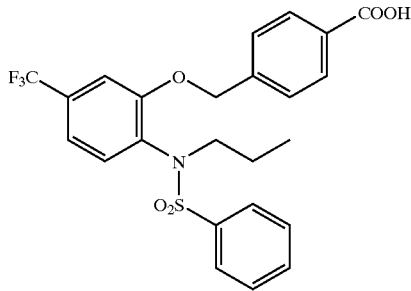

TLC: Rf 0.5 (CHCl$_3$:MeOH=9:1); NMR: δ 8.09 (2H, d, J=8.2 Hz), 7.7–7.6 (2H, m), 7.5–7.2 (7H, m), 7.14 (1H, s), 4.92 (2H, s), 3.59 (2H, t, J=7.4 Hz), 1.6–1.4 (2H, m), 0.88 (3H, t, J=7.4 Hz).

EXAMPLE 18(29)

4-[2-(N-isobutyl-phenylsulfonylamino)-5-trifluoromethyl-phenoxymethyl]benzoic acid

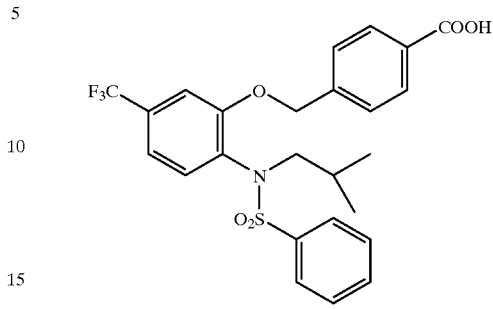

TLC: Rf 0.53 (CHCl$_3$:MeOH=9:1); NMR: δ 8.10 (2H, d, J=8.4 Hz), 7.7–7.6 (2H, m), 7.5–7.2 (7H, m), 7.11 (1H, d, J=1.6 Hz), 5.0–4.8 (2H, m), 3.44 (2H, d, J=7.4 Hz), 1.7–1.5 (1H, m), 0.90 (6H, d, J=6.4 Hz).

EXAMPLE 18(30)

4-[2-(N-cyclopentyl-phenylsulfonylamino)-5-trifluoromethylphenoxymethyl]benzoic acid

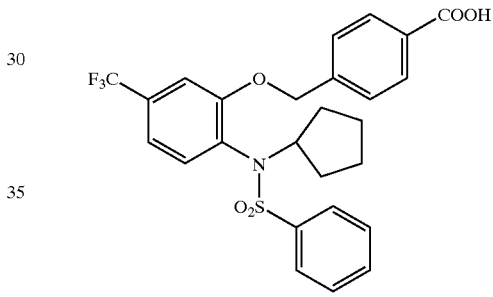

TLC: Rf 0.54 (CHCl$_3$:MeOH=9:1); NMR: δ 8.15 (2H, d, J=8.0 Hz), 7.8–7.7 (2H, m), 7.6–7.3 (5H, m), 7.3–7.2 (3H, m), 5.2–5.0 (2H, m), 4.5–4.3 (1H, m), 2.0–1.8 (2H, m), 1.6–1.2 (6H, m).

EXAMPLE 18(31)

4-[2-[N-(prop-2-enyl)-phenylsulfonylamino]-5-trifluoromethylphenoxymethyl]benzoic acid

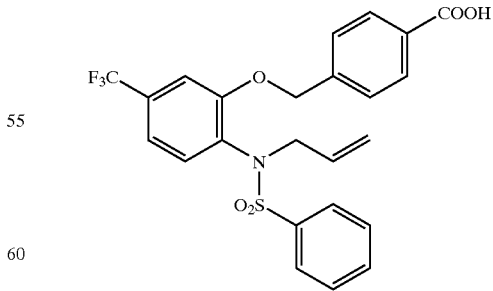

TLC: Rf 0.47 (CHCl$_3$:MeOH=9:1); NMR: δ 8.10 (2H, d, J=8.6 Hz), 7.8–7.6 (2H, m), 7.6–7.2 (7H, m), 7.12 (1H, s), 5.9–5.6 (1H, m), 5.1–5.0 (2H, m), 4.93 (2H, s), 4.24 (2H, d, J=6.2 Hz).

EXAMPLE 18(32)

4-[2-[N-(2-methylprop-2-enyl)-phenylsulfonylamino]-5-trifluoromethylphenoxymethyl]benzoic acid

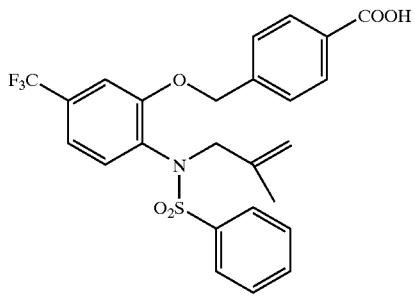

TLC: Rf 0.48 (CHCl₃:MeOH=9:1); NMR: δ 8.10 (2H, d, J=8.4 Hz), 7.7–7.6 (2H, m), 7.5–7.2 (7H, m), 7.10 (1H, s), 4.89 (2H, s), 4.71 (2H, d, J=12.0 Hz), 4.20 (2H, s), 1.74 (3H, s).

EXAMPLE 18(33)

4-[2-(N-isopropyl-4-methylphenylsulfonylamino)-5-trifluoromethylphenoxymethyl]benzoic acid

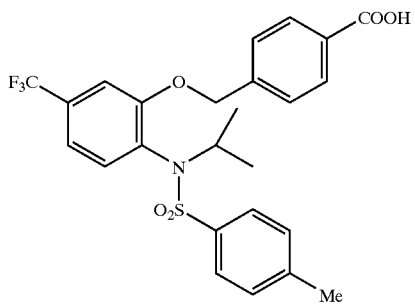

TLC: Rf 0.60 (CHCl₃:MeOH:AcOH=100:5:1); NMR: δ 8.14 (2H, d, J=8.4 Hz), 7.68 (2H, d, J=8.2 Hz), 7.52 (2H, d, J=8.2 Hz), 7.19 (5H, m, arom), 5.14 (2H, s), 4.38 (1H, sept., J=6.8 Hz), 2.38 (3H, s), 1.05 (6H, d, J=6.8 Hz).

EXAMPLE 18(34)

4-[2-(N-isopropyl-4-fluorophenylsulfonylamino)-5-trifluoromethylphenoxymethyl]benzoic acid

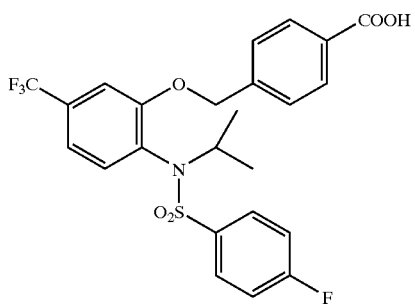

TLC: Rf 0.60 (CHCl₃:MeOH:AcOH=100:5:1); NMR: δ 8.16 (2H, d, J=8.2 Hz), 7.76 (2H, m, arom), 7.52 (2H, d, J=8.2 Hz), 7.26 (3H, m, arom), 7.01 (2H, m, arom), 5.10 (2H, dd, J=11.8, 14.6 Hz), 4.38 (1H, sept., J=6.4 Hz), 1.09 (3H, d, J=6.4 Hz), 1.07 (3H, d J=6.4 Hz).

EXAMPLE 18(35)

4-[2-(N-isopropyl-4-methoxyphenylsulfonylamino)-5-trifluoromethylphenoxymethyl]benzoic acid

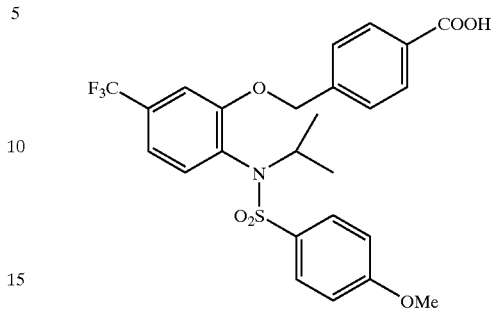

TLC: Rf 0.60 (CHCl₃:MeOH:AcOH=100:5:1); NMR: δ 8.15 (2H, d, J=8.2 Hz), 7.72 (2H, d, J=8.8 Hz), 7.53 (2H, d, J=8.2 Hz), 7.18 (3H, m, arom), 6.81 (2H, d, J=9.2 Hz), 5.14 (2H, s), 4.35 (1H, sept., J=6.4 Hz), 3.83 (3H, s), 1.08 (3H, d, J=6.4 Hz), 1.05 (3H, d, J=6.4 Hz).

EXAMPLE 18(36)

4-[2-(N-isopropyl-phenylsulfonylamino)-5-chlorophenoxy]benzoic acid

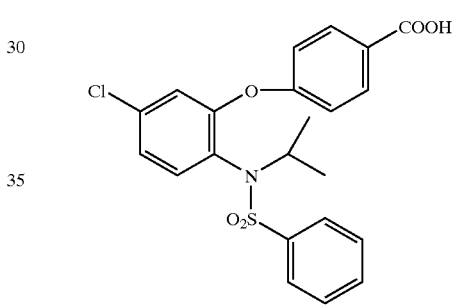

TLC: Rf 0.36 (CHCl₃:MeOH=9:1); NMR: δ 8.11 (2H, d, J=8.6 Hz), 7.8–7.7 (2H, m), 7.6–7.3 (3H, m), 7.2–7.1 (2H, m), 7.02 (2H, d, J=8.6 Hz), 6.92 (1H, d, J=2.0 Hz), 4.6–4.4 (1H, m), 1.14 (3H, d, J=2.4 Hz), 1.11 (3H, d, J=2.4 Hz).

EXAMPLE 18(37)

3-[2-(N-isopropyl-phenylsulfonylamino)-5-chlorophenoxy]cinnamic acid

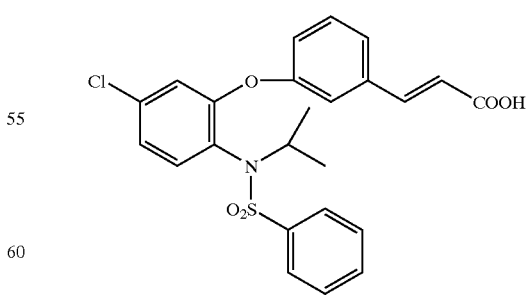

TLC: Rf 0.33 (CHCl₃:MeOH=9:1); NMR: δ 7.9–7.8 (2H, m), 7.73 (1H, d, J=15.8 Hz), 7.6–7.3 (5H, m), 7.2–7.0 (4H, m), 6.78 (1H, d, J=2.2 Hz), 6.42 (1H, d, J=15.8 Hz), 4.6–4.4 (1H, m), 1.17 (3H, d, J=6.8 Hz), 1.13 (3H, d, J=6.8 Hz).

EXAMPLE 18(38)

trans-4-[2-(N-isopropyl-phenylsulfonylamino)-5-trifluoromethylphenoxymethyl]cyclohexanoic acid

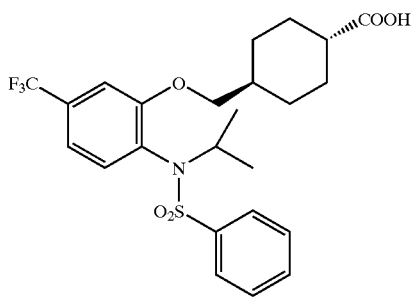

TLC: Rf 0.53 (CHCl$_3$:MeOH:AcOH=100:5:1); NMR: δ 7.81 (2H, m), 7.42–7.63 (3H, m), 7.10–7.24 (3H, m), 4.38 (1H, sept, J=6.8 Hz), 3.79 (2H, m), 2.33 (1H, tt, J=3.8, 10.2 Hz), 2.11 (2H, m), 1.93 (2H, m), 1.71 (1H, m), 1.50 (2H, m), 1.18 (2H, m), 1.07 (3H, d, J=6.8 Hz), 1.02 (3H, d, J=6.8 Hz).

EXAMPLE 18(39)

4-[2-(N-isopropyl-phenylsulfonylamino)-5-chlorophenoxy]phenylacetic acid

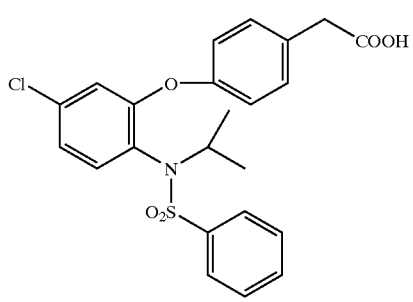

TLC: Rf 0.43 (CHCl$_3$:MeOH=9:1); NMR: δ 7.9–7.8 (2H, m), 7.6–7.4 (3H, m), 7.28 (2H, d, J=7.4 Hz), 7.13 (1H, d, J=8.6 Hz), 7.01 (1H, dd, J=2.2, 8.6 Hz), 6.89 (2H, d, J=8.6 Hz), 6.78 (1H, d, J=2.2 Hz), 4.6–4.4 (1H, m), 3.66 (2H, s), 1.15 (3H, s), 1.12 (3H, s).

EXAMPLE 18(40)

4-[2-(N-isopropyl-phenylsulfonylamino)-5-trifluoromethylphenoxymethyl]cinnamic acid

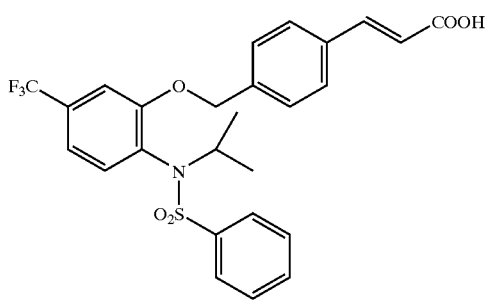

TLC: Rf 0.5 (CHCl$_3$:MeOH=9:1); NMR: δ 7.9–7.8 (3H, m), 7.60 (2H, d, J=8.0 Hz), 7.5–7.3 (5H, m), 7.3–7.2 (3H, m), 6.49 (1H, d, J=15.8 Hz), 5.08 (2H, s), 4.4–4.3 (1H, m), 1.05 (6H, d, J=6.6 Hz).

EXAMPLE 18(41)

3-[4-[2-(N-isopropyl-phenylsulfonylamino)-5-trifluoromethylphenoxymethyl]-phenyl]propionic acid

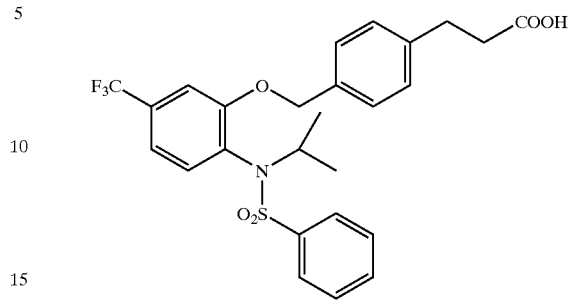

TLC: Rf 0.59 (CHCl$_3$:MeOH=9:1); NMR: δ 7.80 (2H, d, J=7.4 Hz), 7.5–7.4 (1H, m), 7.4–7.2 (9H, m), 4.99 (2H, s), 4.4–4.2 (1H, m), 3.00 (2H, t, J=7.6 Hz), 2.72 (2H, t, J=7.6 Hz), 1.08 (3H, d, J=6.8 Hz), 1.02 (3H, d, J=6.8 Hz).

EXAMPLE 18(42)

3-[2-(N-isopropyl-phenylsulfonylamino)-5-trifluoromethyl-phenoxymethyl]-phenylacetic acid

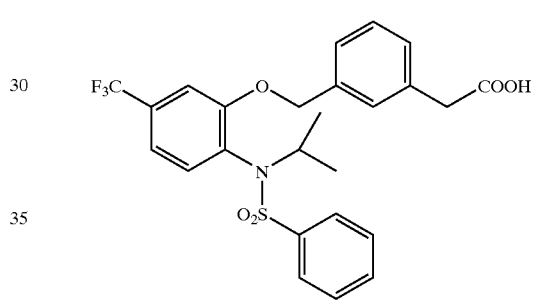

TLC: Rf 0.50 (CHCl$_3$:MeOH=9:1); NMR: δ 7.8–7.7 (2H, m), 7.6–7.2 (10H, m), 5.05 (1H, d, J=11.0 Hz), 4.98 (1H, d, J=1.0 Hz), 4.4–4.2 (1H, m), 3.68 (2H, s), 1.06 (3H, d, J=6.6 Hz), 1.03 (3H, d, J=6.6 Hz).

EXAMPLE 18(43)

4-[2-(N-isopropyl-4-ethoxyphenylsulfonylamino)-5-trifluoromethylphenoxymethyl]benzoic acid

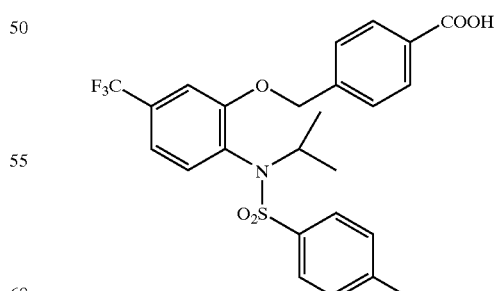

TLC: Rf 0.44 (CHCl$_3$:MeOH=9:1); NMR: δ 8.15 (2H, d, J=8.2 Hz), 7.71 (2H, d, J=8.8 Hz), 7.54 (2H, d, J=8.2 Hz), 7.3–7.2 (3H, m), 6.78 (2H, d, J=8.8 Hz), 5.14 (2H, s), 4.4–4.2 (1H, m), 4.03 (2H, q, J=7.0 Hz), 1.44 (3H, t, J=7.0 Hz), 1.08 (3H, d, J=7.0 Hz), 1.04 (3H, d, J=7.0 Hz).

EXAMPLE 18(44)

4-[2-(N-isobutyl-phenylsulfonylamino)-5-methylphenoxymethyl]benzoic acid

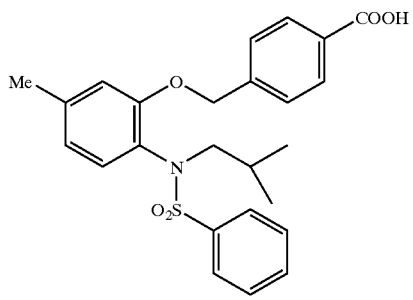

TLC: Rf 0.47 (CHCl$_3$:MeOH:AcOH=100:5:1); NMR: δ 8.07 (2H, d, J=8.2 Hz), 7.63 (2H, m), 7.15–7.44 (6H, m), 6.79 (1H, m), 6.65 (1H, m), 4.80 (2H, m), 3.40 (2H, m), 2.33 (3H, s), 1.63 (1H, m), 0.90 (6H, d, J=6.4 Hz).

EXAMPLE 18(45)

4-[2-(N-isopropyl-phenylsulfonylamino)-5-fluorophenoxymethyl]benzoic acid

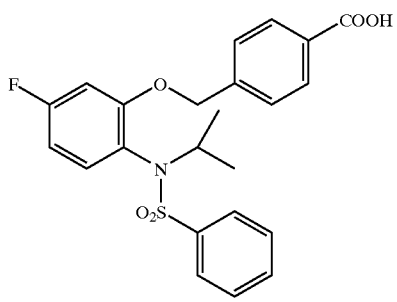

TLC: Rf 0.33 (CHCl$_3$:MeOH=20:1); NMR (DMSO-d$_6$): δ 7.95 (2H, d, J=8.2 Hz), 7.80 (2H, d, J=7.2 Hz), 7.46–7.65 (5H, m), 7.08 (2H, m), 6.82 (1H, m), 5.14 (2H, bs), 4.20 (1H, sept, J=6.6 Hz), 0.94 (6H, d, J=6.6 Hz).

EXAMPLE 18(46)

4-[2-(N-isopropyl-phenylsulfonylamino)-5-methoxyphenoxymethyl]benzoic acid

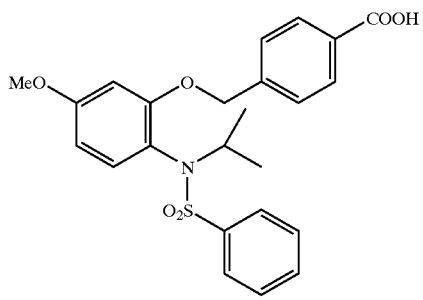

TLC: Rf 0.30 (CHCl$_3$:MeOH=20:1); NMR (DMSO-d$_6$) δ 7.95 (2H, d, J=8.2 Hz), 7.73 (2H, d, J=7.2 Hz), 7.42–7.68 (3H, m), 6.93 (2H, d, J=8.6 Hz), 7.21 (1H, m), 6.56 (2H, dd, J=8.6 Hz, J=2.8 Hz), 5.11 (2H, bs), 4.20 (1H, sept, J=6.6 Hz), 3.79 (3H, s), 0.94 (6H, d, J=6.6 Hz).

EXAMPLE 18(47)

4-[2-(N-propyl-phenylsulfonylamino)-5-methylphenoxymethyl]benzoic acid

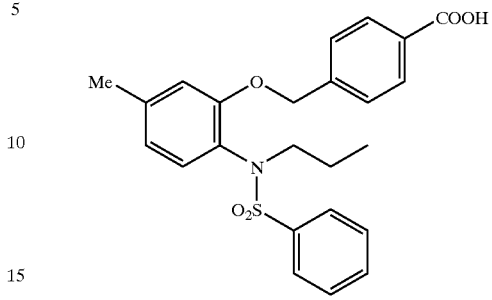

TLC: Rf 0.38 (CHCl$_3$:MeOH:AcOH=100:5:1); NMR: δ 8.07 (2H, d, J=8.6 Hz), 7.67 (2H, m), 7.15–7.45 (6H, m), 6.79 (1H, m), 6.68 (1H, m), 4.83 (2H, brs), 3.57 (2H, m), 2.34 (3H, s), 1.48 (2H, m), 0.88 (3H, t, J=7.4 Hz).

EXAMPLE 18(48)

4-[2-[N-(prop-2-enyl)-phenylsulfonylamino]-5-methylphenoxymethyl]benzoic acid

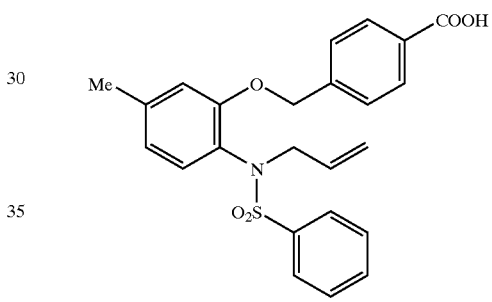

TLC: Rf 0.39 (CHCl$_3$:MeOH:AcOH=100:5:1); NMR: δ 8.07 (2H, d, J=8.0 Hz), 7.69 (2H, m), 7.13–7.48 (6H, m), 6.78 (1H, m), 6.66 (1H, m), 5.80 (1H, tdd, J=6.2, 10.2, 17.2 Hz), 4.98–5.12 (2H, m), 4.84 (2H, brs), 4.23 (2H, m), 2.33 (3H, s).

EXAMPLE 18(49)

4-[2-[N-(2-methylprop-2-enyl)-phenylsulfonylamino]-5-methylphenoxymethyl]benzoic acid

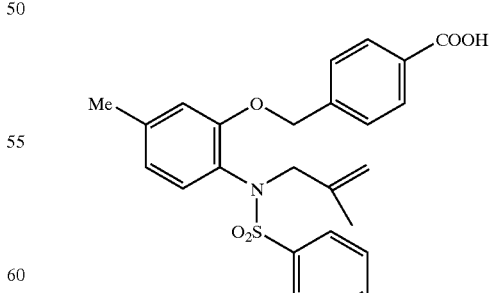

TLC: Rf 0.37 (CHCl$_3$:MeOH:AcOH=100:5:1); NMR: δ 8.07 (2H, d, J=8.2 Hz), 7.66 (2H, m), 7.16–7.47 (6H, m), 6.77 (1H, m), 6.64 (1H, m), 4.80 (2H, brs), 4.71 (2H, m), 4.20 (1H, brs), 2.32 (3H, s), 1.77 (3H, s).

EXAMPLE 18(50)

4-[2-(N-cyclopropylmethyl-phenylsulfonylamino)-5-methylphenoxymethyl]benzoic acid

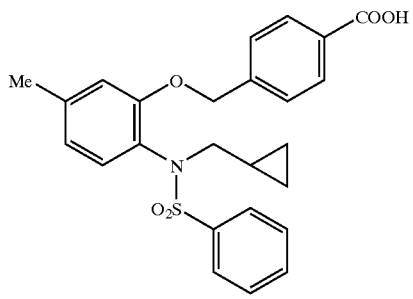

TLC: Rf 0.31 (CHCl$_3$:MeOH:AcOH=100:5:1); NMR: δ 8.06 (2H, d, J=8.0 Hz), 7.68 (2H, m), 7.18–7.44 (6H, m), 6.80 (1H, m), 6.68 (1H, m), 4.84 (2H, brs), 3.48 (2H, m), 2.34 (3H, s), 0.91 (1H, m), 0.38 (2H, m), 0.07 (2H, m).

EXAMPLE 18(51)

4-[2-(N-propyl-phenylsulfonylamino)-5-chlorophenoxymethyl]benzoic acid

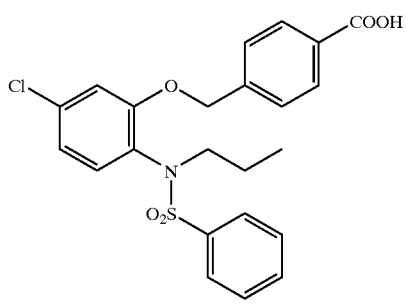

TLC: Rf 0.32 (CHCl$_3$:MeOH=20:1); NMR: δ 8.07 (2H, d, J=7.8 Hz), 7.64 (2H, d, J=6.8 Hz), 7.10–7.41 (6H, m), 6.85–6.99 (2H, m), 4.82 (2H, bs), 3.55 (2H, t, J=6.8 Hz), 1.35–1.52 (2H, m), 0.87 (3H, t, J=7.6 Hz).

EXAMPLE 18(52)

4-[2-(N-isobutyl-phenylsulfonylamino)-5-chlorophenoxymethyl]benzoic acid

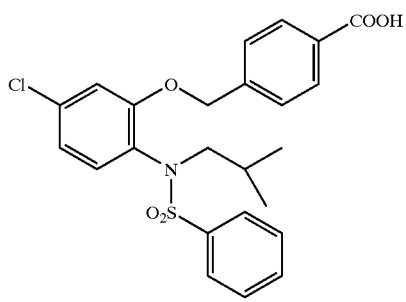

TLC: Rf 0.32 (CHCl$_3$:MeOH=20:1); NMR: δ 8.04 (2H, d, J=7.8 Hz), 7.54 (2H, d, J=7.4 Hz), 7.10–7.41 (6H, m), 6.80–7.01 (2H, m), 4.58–4.95 (2H, bs), 3.34 (2H, d, J=7.0 Hz), 1.46–1.65 (1H, m), 0.83 (6H, d, J=6.4 Hz).

EXAMPLE 18(53)

4-[2-[N-(prop-2-enyl)-phenylsulfonylamino]-5-chlorophenoxymethyl]benzoic acid

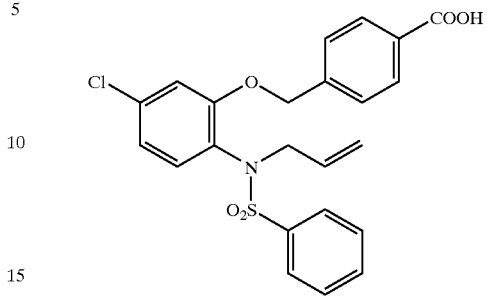

TLC: Rf 0.30 (CHCl$_3$:MeOH=20:1); NMR: δ 8.09 (2H, d, J=8.2 Hz), 7.68 (2H, d, J=6.8 Hz), 7.19–7.52 (6H, m), 6.87–7.01 (2H, m), 5.76 (1H, ddt, J=17.2 Hz, 9.8 Hz, 6.4 Hz) 5.09 (1H, d, J=17.2 Hz), 5.07 (1H, d, J=9.8 Hz), 4.85 (2H, s), 4.21 (2H, d, J=6.4 Hz).

EXAMPLE 18(54)

4-[2-[N-(2-methylprop-2-enyl)-phenylsulfonylamino]-5-chlorophenoxymethyl]benzoic acid

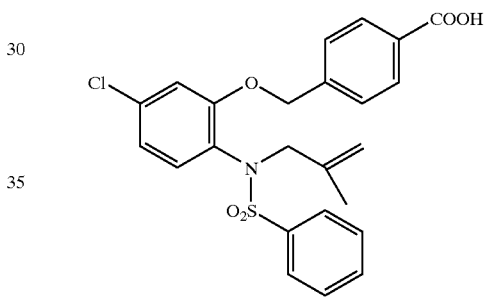

TLC: Rf 0.33 (CHCl$_3$:MeOH=20:1); NMR: δ 8.09 (2H, d, J=8.2 Hz), 7.65 (2H, d, J=6.8 Hz), 7.21–7.51 (6H, m), 6.83–7.00 (2H, m), 4.81(2H, s), 4.74 (1H, s), 4.68 (1H, s), 4.18 (2H,s), 1.75 (3H, s).

EXAMPLE 18(55)

4-[2-(N-cyclopropylmethyl-phenylsulfonylamino)-5-chlorophenoxymethyl]benzoic acid

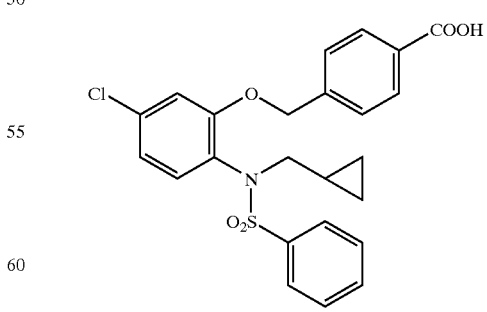

TLC: Rf 0.40 (CHCl$_3$:MeOH=20:1); NMR: δ 8.07 (2H, d, J=8.6 Hz), 7.69 (2H, d, J=7.0 Hz), 7.20–7.48 (6H, m), 6.85–7.09 (2H, m), 4.85(2H, s), 3.47 (2H, bs), 0.85 (1H, m), 0.38 (2H, m), 0.06 (2H, m).

EXAMPLE 18(56)

5-[2-(N-isopropyl-phenylsulfonylamino)-5-methylphenoxymethyl]furan-2-carboxylic acid

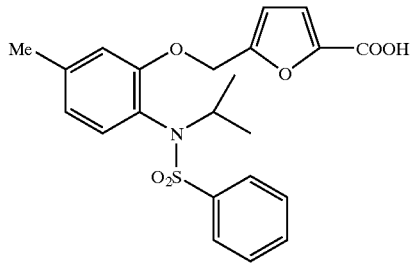

TLC: Rf 0.18 (CHCl$_3$:MeOH=9:1); NMR: δ 7.82 (2H, m), 7.56–7.35 (3H, m), 7.31 (1H, d, J=3.5 Hz), 6.97 (1H, d, J=8.5 Hz), 6.83–6.75 (2H, m), 6.63 (1H, d, J=3.5 Hz), 5.03 (1H, d, J=14 Hz), 4.98 (1H, d, J=14 Hz), 4.37 (1H, m), 2.37 (3H, s), 1.09–0.96 (6H, m).

EXAMPLE 18(57)

4-[2-(N-methoxymethyl-phenylsulfonylamino)-5-trifluoromethylphenoxy-methyl]benzoic acid

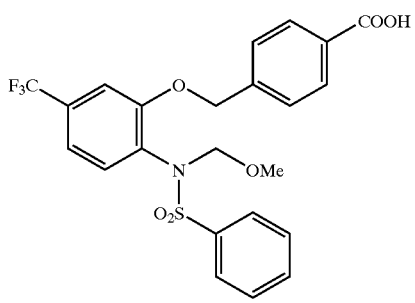

TLC: Rf 0.45 (CHCl$_3$:MeOH:AcOH=100:5:1); NMR: δ 8.09 (2H, d, J=8.0 Hz), 7.65 (2H, m), 7.43–7.53 (2H, m), 7.20–7.40 (5H, m), 7.11 (1H, m), 5.09 (2H, s), 4.89 (2H, s), 3.44 (3H, s).

EXAMPLE 18(58)

4-[2-(N-isopropyl-2-thienylsulfonylamino)-5-chlorophenoxymethyl]benzoic acid

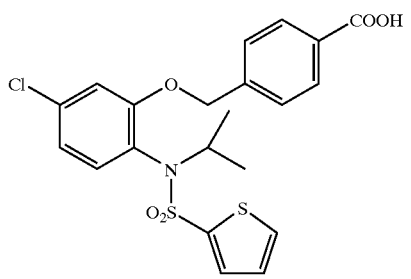

TLC: Rf 0.34 (CHCl$_3$:MeOH=20:1); NMR: δ 8.14 (2H, d, J=8.2 Hz), 7.52–7.57 (4H, m), 6.98–7.03 (4H, m), 5.12 (2H, s), 4.55 (1H, sept, J=6.4 Hz), 1.09 (6H, d, J=6.6 Hz).

EXAMPLE 18(59)

4-[2-(N-isopropyl-2-thienylsulfonylamino)-5-methylphenoxymethyl]benzoic acid

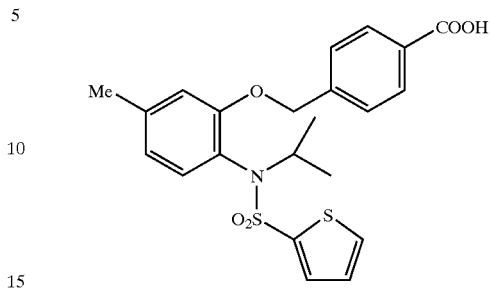

TLC: Rf 0.39 (CHCl$_3$:MeOH=20:1); NMR δ 8.13 (2H, d, J=8.2 Hz), 7.43–7.58 (4H, m), 6.97 (1H, m), 6.80 (2H, m), 5.12 (2H, s), 4.45 (1H, sept, J=6.4 Hz), 1.09 (6H, d, J=6.6 Hz).

EXAMPLE 18(60)

4-[2-(N-isopropyl-2-furanylsulfonylamino)-5-methylphenoxymethyl]benzoic acid

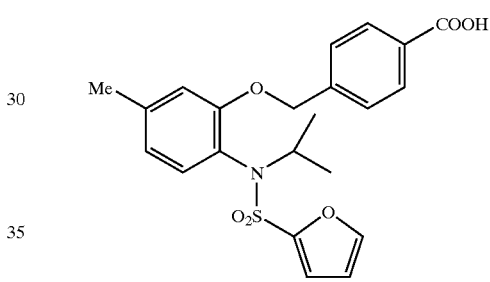

TLC: Rf 0.42 (CHCl$_3$:MeOH:AcOH=100:5:1); NMR: δ 8.14 (2H, d, J=8.2 Hz), 7.58 (2H, d, J=8.2 Hz), 7.44 (1H, dd, J=0.8, 1.6 Hz), 6.88–6.95 (2H, m), 6.72–6.82 (2H, m), 6.41 (1H, dd, J=1.6, 3.4 Hz), 5.12 (2H, s), 4.51 (1H, sept, J=6.6 Hz), 2.31 (3H, s), 1.12 (3H, d, J=6.6 Hz), 1.10 (3H, d, J=6.6 Hz).

EXAMPLE 18(61)

4-[2-(N-isopropyl-2-furanylsulfonylamino)-5-chlorophenoxymethyl]benzoic acid

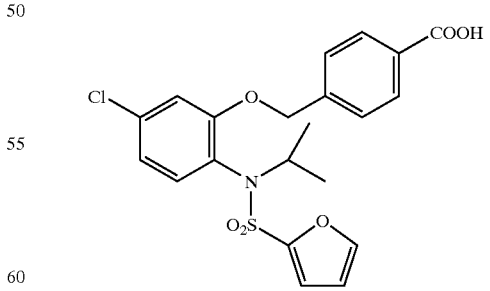

TLC: Rf 0.43 (CHCl$_3$:MeOH:AcOH=100:5:1); NMR: δ 8.16 (2H, d, J=8.4 Hz), 7.57 (2H, d, J=8.4 Hz), 7.45 (1H, dd, J=0.8, 1.6 Hz), 6.95–7.04 (3H, m), 6.92 (1H, d, J=4.4 Hz), 6.43 (1H, dd, J=1.8, 3.4 Hz), 5.13 (2H, s), 4.49 (1H, sept, J=7.0 Hz), 1.11 (3H, d, J=7.0 Hz), 1.09 (3H, d, J=7.0 Hz).

EXAMPLE 18(62)
4-[2-(N-isobutyl-phenylsulfonylamino)-4-methylphenoxymethyl]benzoic acid

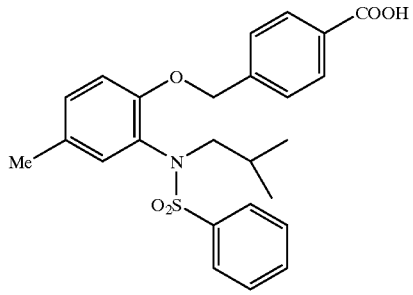

TLC: Rf 0.23 (hexane:AcOEt=1:1); NMR: δ 8.06 (2H, d, J=8 Hz), 7.65–7.61 (2H, m), 7.6–7.4 (7H, m), 6.71 (1H, d, J=8 Hz), 4.9–4.6 (2H, m), 3.5–3.4 (2H, m), 2.29 (3H, s), 1.63 (1H, sept., J=6.5 Hz), 0.91 (6H, d, J=6.5 Hz).

EXAMPLE 18(63)
4-[2-(N-isopropyl-phenylsulfonylamino)-4-methylphenoxymethyl]benzoic acid

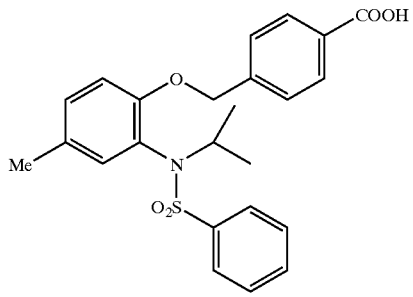

TLC: Rf 0.22 (hexane:AcOEt=1:1); NMR: δ 8.12 (2H, d, J=8 Hz), 7.86–7.81 (2H, m), 7.52–7.30 (5H, m), 7.15–7.10 (1H, m), 6.94 (1H, d, J=1.5 Hz), 6.84 (1H, d, J=8 Hz), 5.02 (2H, s), 4.37 (1H, sept., J=6.5 Hz), 2.28 (3H, s), 1.08 (6H, t, J=6.5 Hz).

EXAMPLE 18(64)
4-[2-[N-(prop-2-enyl)-phenylsulfonylamino]-4-methylphenoxymethyl]benzoic acid

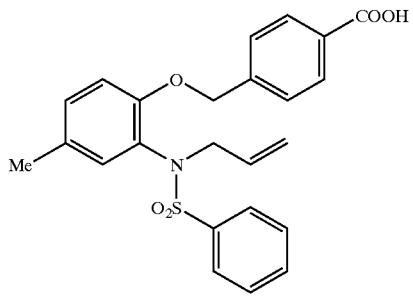

TLC: Rf 0.43 (CHCl$_3$:MeOH:AcOH=100:5:1); NMR (DMSO-d$_6$): δ 7.89 (2H, d, J=8.2 Hz), 7.63 (2H, m), 7.38–7.59 (3H, m), 7.23 (2H, d, J=8.2 Hz), 7.12 (1H, dd, J=1.8, 8.4 Hz), 6.98 (1H, d, J=1.8 Hz), 6.94 (1H, d, J=8.6 Hz), 5.71 (1H, tdd, J=6.4, 10.0, 17.2 Hz), 4.97–5.13 (2H, m), 4.88 (2H, brs), 4.17 (2H, m), 2.22 (3H, s).

EXAMPLE 18(65)
4-[2-(N-isopropyl-4-ethoxyphenylsulfonylamino)-5-chlorophenoxymethyl]benzoic acid

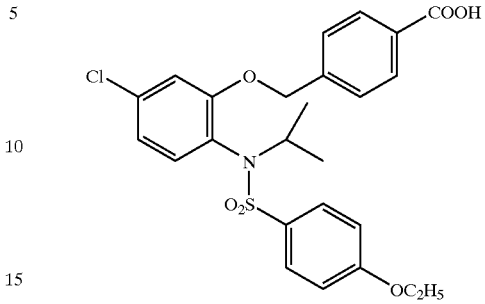

TLC: Rf 0.33 (CHCl$_3$:MeOH=20:1); NMR: δ 8.13 (2H, d, J=8.6 Hz), 7.69 (2H, d, J=9.0 Hz), 7.49 (2H, d, J=8.6 Hz), 6.97–7.09 (3H, m), 6.76 (2H, d, J=9.0 Hz), 5.06 (2H, s), 4.34 (1H, sept, J=6.6 Hz), 4.02 (2H, q, J=7.2 Hz), 1.43 (3H, t, J=7.0 Hz), 1.06 (3H, d, J=6.6 Hz), 1.03 (3H, d, J=6.6 Hz).

EXAMPLE 18(66)
4-[2-(N-isopropyl-4-ethoxyphenylsulfonylamino)-5-methylphenoxymethyl]benzoic acid

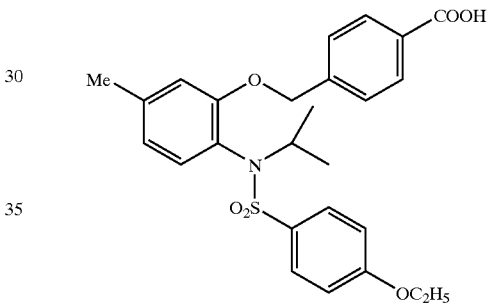

TLC: Rf 0.29 (CHCl$_3$:MeOH=20:1); NMR: δ 8.12 (2H, d, J=8.4 Hz), 7.72 (2H, d, J=8.6 Hz), 7.50 (2H, d, J=8.6 Hz), 7.01 (1H, d, J=8.8 Hz), 6.72–6.80 (4H, m), 5.07 (2H, s), 4.34 (1H, sept, J=6.6 Hz), 4.01 (2H, q, J=7.0 Hz), 2.36 (3H, s), 1.42 (3H, t, J=6.8 Hz), 1.07 (3H, d, J=7.2 Hz), 1.04 (3H, d, J=6.8 Hz).

EXAMPLE 18(67)
4-[2-(N-ethyl-phenylsulfonylamino)-4-methylphenoxymethyl]benzoic acid

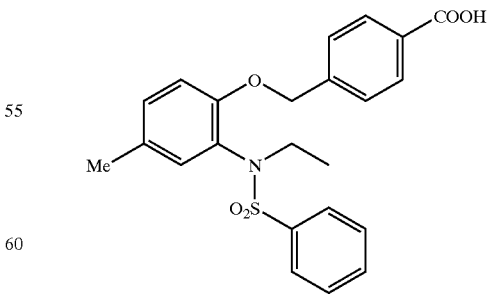

TLC: Rf 0.33 (CHCl$_3$:MeOH=9:1); NMR: δ 8.05 (2H, d, J=8.4 Hz), 7.8–7.6 (2H, m), 7.4–7.2 (5H, m), 7.2–7.0 (2H, m), 6.75 (1H, d, J=8.4 Hz), 4.82 (2H, s), 3.8–3.6 (2H, m), 2.30 (3H, s), 1.11 (3H, t, J=7.0 Hz).

EXAMPLE 18(68)

4-[2-(N-propyl-phenylsulfonylamino)-4-methylphenoxymethyl]benzoic acid

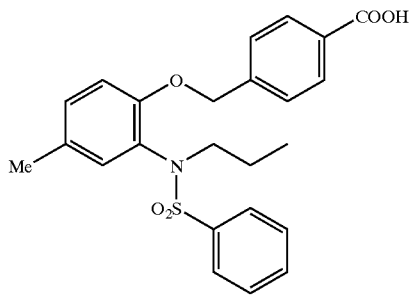

TLC: Rf 0.44 (CHCl$_3$:MeOH=9:1); NMR: δ 8.05 (2H, d, J=8.0 Hz), 7.7–7.6 (2H, m), 7.5–7.0 (7H, m), 6.74 (1H, d, J=8.4 Hz), 4.80 (2H, s), 3.7–3.5 (2H, m), 2.29 (3H, s), 1.6–1.4 (2H, m), 0.89 (3H, t, J=7.4 Hz).

EXAMPLE 18(69)

4-[2-(N-butyl-phenylsulfonylamino)-4-methylphenoxymethyl]benzoic acid

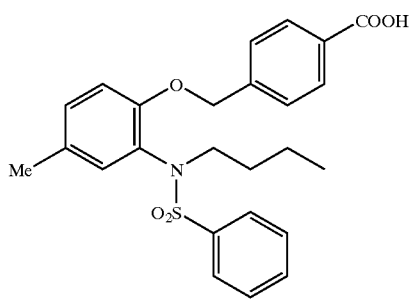

TLC: Rf 0.49 (CHCl$_3$:MeOH=9:1); NMR: δ 8.05 (2H, d, J=8.2 Hz), 7.7–7.6 (2H, m), 7.4–7.2 (5H, m), 7.2–7.0 (2H, m), 6.74 (1H, d, J=8.4 Hz), 4.80 (2H, s), 3.7–3.5 (2H, m), 2.30 (3H, s), 1.6–1.2 (4H, m), 0.85 (3H, t, J=7.0 Hz).

EXAMPLE 18(70)

4-[2-[N-(2-methylprop-2-enyl)-phenylsulfonylamino]-4-methylphenoxymethyl]benzoic acid

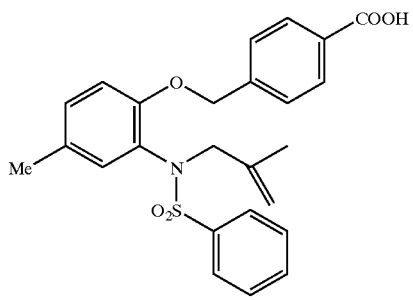

TLC: Rf 0.38 (CHCl$_3$:MeOH=9:1); NMR: δ 8.06 (2H, d, J=8 Hz), 7.65 (2H, m), 7.47–7.25 (3H, m), 7.19 (2H, d, J=8 Hz), 7.13 (1H, d, J=2 Hz), 7.04 (1H, dd, J=8 and 2 Hz), 6.70 (1H, d, J=8 Hz), 4.85–4.65 (4H, m), 4.21 (2H, s), 2.29 (3H, s), 1.78 (3H, s).

EXAMPLE 18(71)

4-[2-(N-cyclopropylmethyl-phenylsulfonylamino)-4-methylphenoxymethyl]benzoic acid

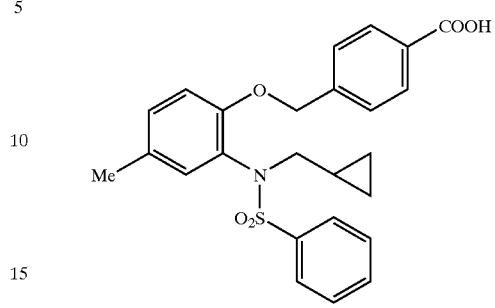

TLC: Rf 0.40 (CHCl$_3$:MeOH:AcOH=100:5:1); NMR (CD$_3$COCD$_3$): δ 7.99(2H, d, J=8.0 Hz), 7.68 (2H, m), 7.26–7.57 (5H, m), 7.15 (2H, m), 6.96 (1H, d, J=8.8 Hz), 4.93 (2H, brs), 3.52 (2H, brd, J=7.0 Hz), 2.28 (3H, s), 0.90 (1H, m), 0.35 (2H, m), 0.06 (2H, m).

EXAMPLE 18(72)

4-[2-(N-isopropyl-propylsulfonylamino)-5-methylphenoxymethyl]benzoic acid

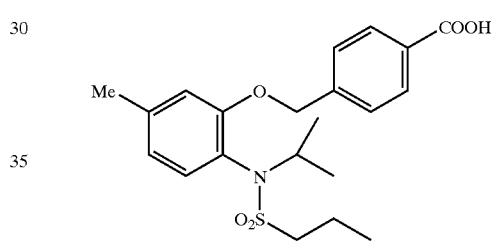

TLC: Rf 0.24 (CHCl$_3$:MeOH=19:1); NMR: δ 8.14 (2H, d, J=8.2 Hz), 7.57 (2H, d, J=8.2 Hz), 7.16 (1H, m), 6.82 (2H, m), 5.13 (2H, s), 4.33 (1H, m), 2.97 (2H, m), 2.36 (3H, s), 1.79 (2H, m), 1.23 (3H, d, J=6.6 Hz), 1.09 (3H, d, J=6.6 Hz), 0.85 (3H, t, J=7.4 Hz).

EXAMPLE 18(73)

4-[2-(N-isopropyl-pentylsulfonylamino)-5-methylphenoxymethyl]benzoic acid

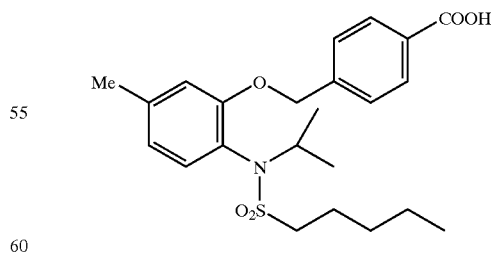

TLC: Rf 0.26 (CHCl$_3$:MeOH=19:1); NMR: δ 8.15 (2H, d, J=8.0 Hz), 7.56 (2H, d, J=8.0 Hz), 7.14 (1H, m), 6.81 (2H, m), 5.12 (2H, s), 4.32 (1H, m), 2.97 (2H, m), 2.36 (3H, s), 1.77 (2H, m), 1.24 (3H, d, J=6.6 Hz), 1.16 (4H, m), 1.09 (3H, d, J=6.6 Hz), 1.12 (3H, d, J=6.6 Hz), 0.83 (3H, t, J=6.4 Hz).

EXAMPLE 18(74)

4-[2-(N-benzyl-methylsulfonylamino)-5-methylphenoxymethyl]benzoic acid

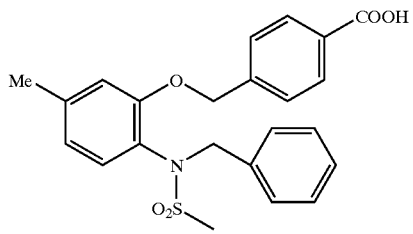

TLC: Rf 0.39 (CHCl₃:MeOH=19:1); NMR: δ 8.17 (2H, d, J=8.0 Hz), 7.53 (2H, d, J=8.0 Hz), 7.25 (5H, s), 6.98 (1H, m), 6.77 (2H, m), 5.17 (2H, s), 4.70 (2H, bs), 2.89 (3H, s), 2.30 (3H, s).

EXAMPLE 18(75)

4-[2-(N-benzyl-propylsulfonylamino)-5-methylphenoxymethyl]benzoic acid

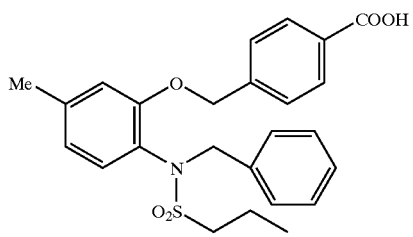

TLC: Rf 0.40 (CHCl₃:MeOH=19:1); NMR: δ 8.17 (2H, d, J=8.2 Hz), 7.55 (2H, d, J=8.2 Hz), 7.23 (5H, s), 6.98 (1H, m), 6.78 (2H, m), 5.16 (2H, s), 4.77 (2H, bs), 2.95 (2H, m), 2.29 (3H, s), 1.81 (2H, m), 0.85 (3H, t, J=7.6 Hz).

EXAMPLE 18(76)

4-[2-(N-isopropyl-cyclopentylsulfonylamino)-5-methylphenoxymethyl]benzoic acid

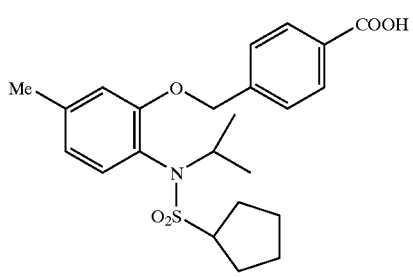

TLC: Rf 0.38 (CHCl₃:MeOH:AcOH=100:5:1); NMR: δ 8.15 (2H, d, J=8.0 Hz), 7.59 (2H, d, J=8.0 Hz), 7.14 (1H, d, J=8.6 Hz), 6.81 (2H, m), 5.12 (2H, s), 4.35 (1H, sept, J=6.6 Hz), 3.51 (1H, m), 2.36 (3H, s), 1.85–2.15 (3H, m), 1.61–1.85 (3H, m), 1.34–1.61 (2H, m), 1.22 (3H, d, J=6.6 Hz), 1.08 (3H, d, J=6.6 Hz).

EXAMPLE 18(77)

4-[2-(N-isobutyl-ethylsulfonylamino)-4-methylphenoxymethyl]benzoic acid

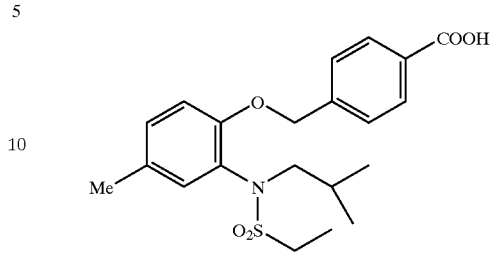

TLC: Rf 0.23 (hexane:AcOEt=1:1); NMR: δ 8.15 (2H, d, J=8 Hz), 7.53 (2H, d, J=8 Hz), 7.21 (1H, d, J=1.5 Hz), 7.08 (1H, dd, J=8.5, 1.5 Hz), 6.86 (1H, d, J=8.5 Hz), 5.17 (2H, s), 3.46 (2H, d, J=7.5 Hz), 2.97 (2H, q, J=7.5 Hz), 2.30 (3H, s), 1.7–1.5 (1H, m), 1.25 (3H, t, J=7.5 Hz), 0.94–0.90 (6H, m).

EXAMPLE 18(78)

4-[2-(N-isobutyl-propylsulfonylamino)-4-methylphenoxymethyl]benzoic acid

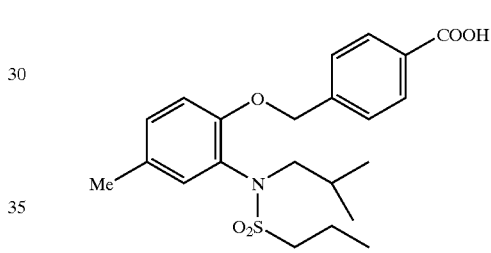

TLC: Rf 0.27 (hexane:AcOEt=1:1); NMR: δ 8.15 (2H, d, J=8 Hz), 7.53 (2H, d, J=8 Hz), 7.20 (1H, d, J=0.5 Hz), 7.08 (1H, dd, J=8, 0.5 Hz), 6.86 (1H, d, J=8 Hz), 5.17 (2H, s), 3.44 (2H, d, J=7 Hz), 2.94–2.86 (2H, m), 2.30 (3H, s), 1.9–1.6 (3H, m), 1.0–0.9(6H, m), 0.85 (3H, t, J=7 Hz).

EXAMPLE 18(79)

4-[2-(N-isobutyl-butylsulfonylamino)-4-methylphenoxymethyl]benzoic acid

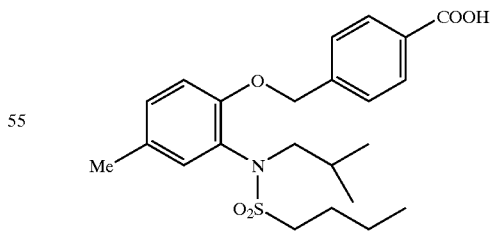

TLC: Rf 0.37 (hexane:AcOEt=1:1); NMR: δ 8.15 (2H, d, J=8 Hz), 7.53 (2H, d, J=8 Hz), 7.20 (1H, d, J=0.5 Hz), 7.08 (1H, dd, J=8.5, 0.5 Hz), 6.86 (1H, d, J=8.5 Hz), 5.16 (2H, s), 3.45 (2H, d, J=7 Hz), 2.97–2.89 (2H, m), 2.30 (3H, s), 1.8–1.5 (3H, m), 1.3–1.1 (2H, m), 1.0–0.9(6H, m), 0.79 (3H, t, J=7 Hz).

EXAMPLE 18(80)

4-[2-(N-isobutyl-propylsulfonylamino)-5-methylphenoxymethyl]benzoic acid

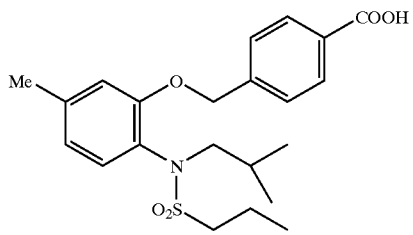

TLC: Rf 0.25 (CHCl$_3$:MeOH=20:1); NMR: δ 8.16 (2H, d, J=8.4 Hz), 7.53 (2H, d, J=8.4 Hz), 7.28 (1H, m), 6.82 (2H, m), 5.18 (2H, s), 3.41 (2H, d, J=7.0 Hz) 2.89 (2H, m), 2.35 (3H, s), 1.78 (2H, m), 1.60 (1H, m), 0.90 (6H, d, J=7.0 Hz), 0.84 (3H, t, 7.6 Hz).

EXAMPLE 18(81)

4-[2-[N-(prop-2-enyl)-propylsulfonylamino]-5-methylphenoxymethyl]benzoic acid

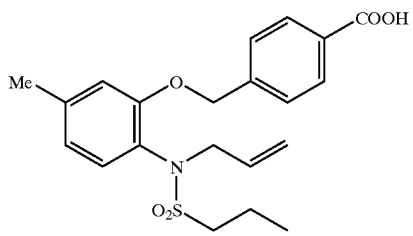

TLC: Rf 0.23 (CHCl$_3$:MeOH=20:1); NMR: δ 8.16 (2H, d, J=8.4 Hz), 7.56 (2H, d, J=8.4 Hz), 7.21 (1H, m), 6.90 (2H, m), 5.80 (1H, m), 5.17 (2H, s), 5.07 (2H, m), 4.21 (2H, d, J=6.2 Hz), 2.94 (2H, m), 2.34 (3H, s), 1.81 (2H, m), 0.86 (3H, t, J=7.4 Hz).

EXAMPLE 18(82)

4-[2-[N-(2-methylprop-2-enyl)-propylsulfonylamino]-5-methylphenoxymethyl]benzoic acid

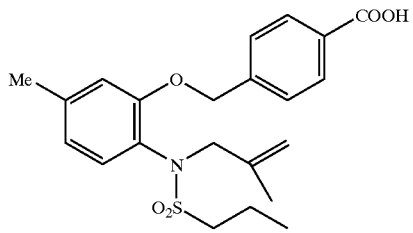

TLC: Rf 0.28 (CHCl$_3$:MeOH=20:1); NMR: δ 8.16 (2H, d, J=8.2 Hz), 7.54 (2H, d, J=8.2 Hz), 7.23 (1H, m), 6.78 (2H, m), 5.17 (2H, s), 4.75 (2H, s), 4.18 (2H, s), 2.88 (2H, m), 2.34 (3H, s), 1.79 (2H, m), 1.78 (3H, s), 0.85 (3H, t, J=7.6 Hz).

EXAMPLE 18(83)

4-[2-(N-isobutyl-phenylsulfonylamino)-4-chlorophenoxymethyl]benzoic acid

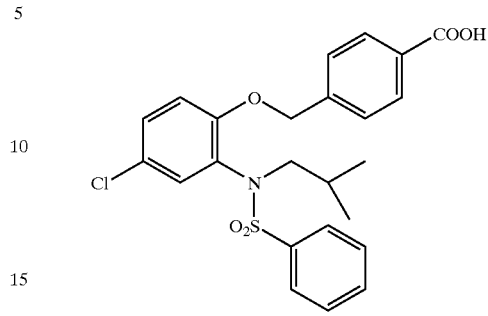

TLC: Rf 0.29 (CHCl$_3$:MeOH=19:1); NMR: δ 8.06 (2H, d, J=8.0 Hz), 7.64 (2H, d, J=8.0 Hz), 7.20–7.40 (7H, m), 6.78 (1H, m), 4.80 (2H, bs), 3.40 (2H, d, J=7.0 Hz), 1.61 (1H, m), 0.90 (6H, d, J=7.0 Hz).

EXAMPLE 18(84)

4-[2-(N-propyl-propylsulfonylamino)-5-methylphenoxymethyl]benzoic acid

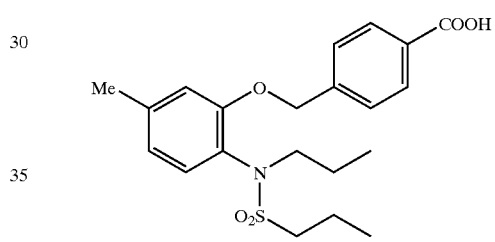

TLC: Rf 0.52 (CHCl$_3$:MeOH=9:1); NMR: δ 8.17 (2H, d, J=8.4 Hz), 7.55 (2H, d, J=8.4 Hz), 7.25 (1H, d, J=8.2 Hz), 6.9–6.8 (2H, m), 5.17 (2H, s), 3.56 (2H, t, J=7.4 Hz), 3.0–2.8 (2H, m), 2.35 (3H, s), 1.9–1.7 (2H, m), 1.6–1.4 (2H, m), 0.89 (3H, t, J=7.2 Hz), 0.84 (3H, t, J=7.4 Hz).

EXAMPLE 18(85)

4-[2-(N-isobutyl-hexylsulfonylamino)-4-methylphenoxymethyl]benzoic acid

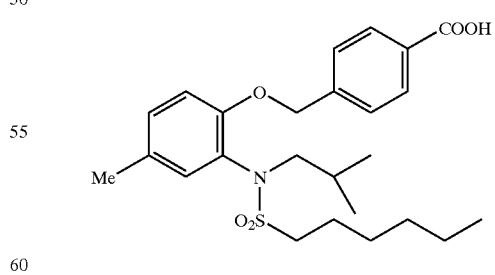

TLC: Rf 0.49 (CHCl$_3$:MeOH=9:1); NMR: δ 8.16 (2H, d, J=8.4 Hz), 7.53 (2H, d, J=8.4 Hz), 7.21 (1H, d, J=2.0 Hz), 7.09 (1H, dd, J=2.0, 8.4 Hz), 6.87 (1H, d, J=8.4 Hz), 5.16 (2H, s), 3.45 (2H, d, J=7.0 Hz), 3.0–2.8 (2H, m), 2.30 (3H, s), 1.8–1.5 (3H, m), 1.3–1.0 (6H, m), 1.0–0.8 (6H, m), 0.83 (3H, t, J=7.0 Hz).

EXAMPLE 18(86)

4-[2-(N-isobutyl-pentylsulfonylamino)-4-methylphenoxymethyl]benzoic acid

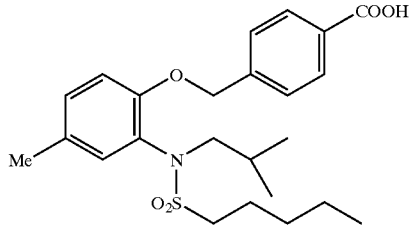

TLC: Rf 0.38 (CHCl$_3$:MeOH:AcOH=100:5:1); NMR: δ 8.16 (2H, d, J=8.4 Hz), 7.53 (2H, d, J=8.4 Hz), 7.21 (1H, d, J=2.2 Hz), 7.09 (1H, dd, J=2.2, 8.6 Hz), 6.87 (1H, d, J=8.6 Hz), 5.16 (2H, s), 3.45 (2H, d, J=7.2 Hz), 2.91 (2H, m), 2.30 (3H, s), 1.74 (2H, m), 1.60 (1H, m), 1.17 (4H, m), 0.92 (6H, m), 0.82 (3H, m).

EXAMPLE 18(87)

4-[2-[N-(prop-2-enyl)-propylsulfonylamino]-5-trifluoromethylphenoxymethyl]benzoic acid

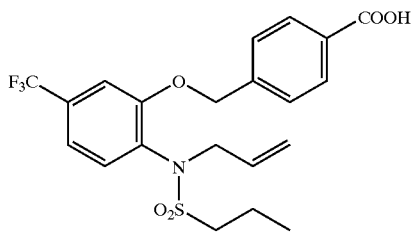

TLC: Rf 0.33 (hexane:AcOEt=1:1); NMR (200 MHz, CDCl$_3$+1drop of CD$_3$OD): δ 8.15–8.11 (2H, m), 7.54–7.44 (3H, m), 7.30–7.24 (2H, m), 5.88–5.68 (1H, m), 5.20 (2H, s), 5.12–5.10 (1H, m), 5.04–5.03 (1H, m), 4.21 (2H, d, J=6.5 Hz), 2.95–2.87 (2H, m), 1.8–1.7 (1H, m), 0.84 (3H, t, J=7.5 Hz).

EXAMPLE 18(88)

4-[2-[N-(2-methylprop-2-enyl)-propylsulfonylamino]-5-trifluoromethylphenoxymethyl]benzoic acid

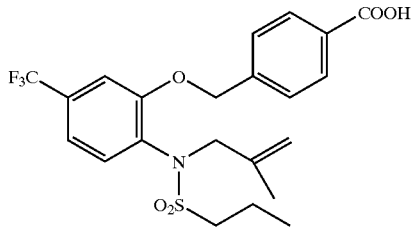

TLC: Rf 0.41 (hexane:AcOEt=1:1); NMR: δ 8.30 (2H, d, J=8 Hz), 7.71–7.67 (2H, m), 7.62–7.56 (1H, m), 7.40–7.35 (2H, m), 5.34 (2H, s), 4.89–4.85 (2H, m), 5.34 (2H, s), 4.89–4.85 (2H, m), 4.31 (2H, s), 3.07–2.99 (2H, m), 2.0–1.8 (2H, m), 1.87 (3H, s), 1.00–0.93 (3H, m).

EXAMPLE 18(89)

4-[2-(N-propyl-2-furanylsulfonylamino)-5-trifluoromethylphenoxymethyl]cinnamic acid

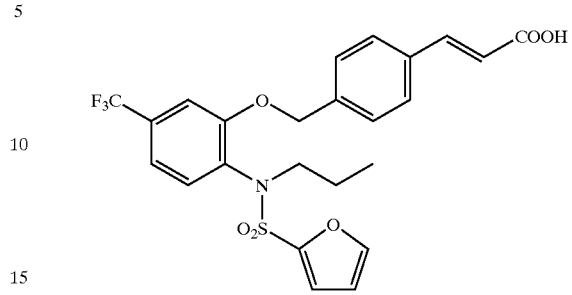

TLC: Rf 0.38 (hexane:AcOEt=1:1); NMR: δ7.81 (1H, d, J=16 Hz), 7.59 (2H, d, J=8 Hz), 7.42–7.37 (3H, m), 7.28–7.24 (2H, m), 7.18 (1H, d, J=1.5 Hz), 6.85 (1H, dd, J=3, 1 Hz),6.49 (1H, d, J=16 Hz), 6.35 (1H, dd, J=3, 2 Hz), 5.03 (2H, s), 3.71–3.64 (2H, m), 1.6–1.4 (2H, m), 0.88 (3H, t, J=7 Hz).

EXAMPLE 18(90)

4-[2-(N-propyl-propylsulfonylamino)-5-trifluoromethylphenoxymethyl]benzoic acid

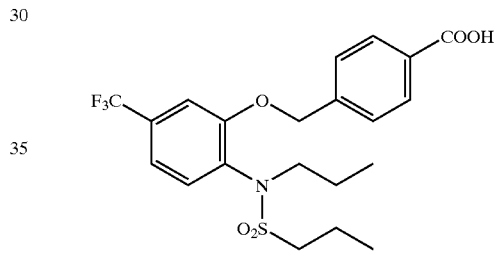

TLC: Rf 0.40 (CHCl$_3$:MeOH=9:1); NMR: δ 8.17 (2H, d, J=8.2 Hz), 7.56 (2H, d, J=8.2 Hz), 7.49 (1H, m), 7.27 (2H, m), 5.22 (2H, s), 3.58 (2H, m), 2.91 (2H, m), 1.79 (2H, m), 1.45 (2H, m), 0.89 (3H, t, J=7.4 Hz), 0.85 (3H, t, J=7.6 Hz).

EXAMPLE 18(91)

4-[2-(N-isobutyl-propylsulfonylamino)-5-trifluoromethylphenoxymethyl]benzoic acid

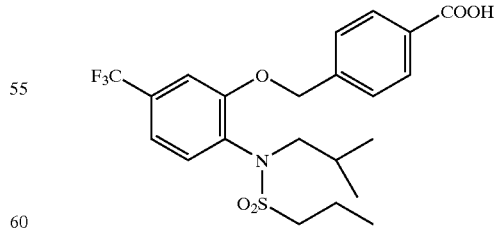

TLC: Rf 0.45 (CHCl$_3$:MeOH=9:1); NMR: δ 8.18 (2H, d, J=8.2 Hz), 7.56 (2H, d, J=8.2 Hz), 7.51 (1H, m), 7.28 (2H, m), 5.23 (2H, s), 3.45 (2H, d, J=7.4 Hz), 2.89 (2H, m), 1.75 (2H, m), 1.58 (1H, m), 0.90 (6H, d, J=6.8 Hz), 0.84 (3H, t, J=7.4 Hz).

EXAMPLE 18(92)

4-[2-(N-propyl-2-furanylsulfonylamino)-5-methylphenoxymethyl]benzoic acid

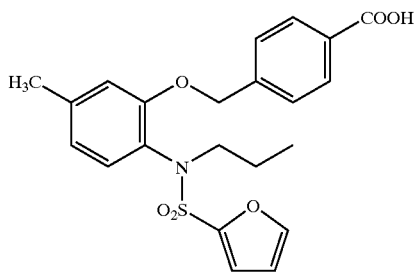

TLC: Rf 0.38 (hexane:AcOEt=1:1); NMR: δ 8.13 (2H, d, J=8 Hz), 7.44 (2H, d, J=8 Hz), 7.25 (1H, m), 7.12 (1H, d, J=8 Hz), 6.83–6.73 (3H, m), 6.33–6.30 (1H, m), 5.01 (2H, s), 3.7–3.6 (2H, m), 2.33 (3H, s), 1.52 (2H, q, J=7 Hz), 0.90 (3H, t, J=7 Hz).

EXAMPLE 18(93)

4-[2-(N-isobutyl-2-furanylsulfonylamino)-5-methylphenoxymethyl]benzoic acid

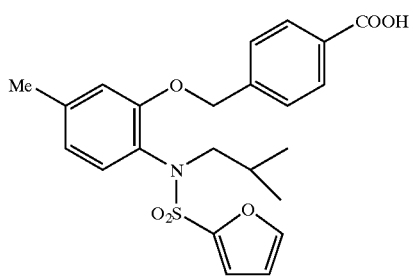

TLC: Rf 0.41 (hexane:AcOEt=1:1); NMR: δ 8.13 (2H, d, J=8 Hz), 7.44 (2H, d, J=8 Hz), 7.25 (1H, m), 7.15 (1H, d, J=8 Hz), 6.80–6.71 (3H, m), 6.31 (1H, m), 5.0 (2H, m), 3.53 (2H, d, J=7 Hz), 1.75–1.60(1H, m), 0.91 (6H, t, J=7 Hz).

EXAMPLE 18(94)

4-[2-(N-isobutyl-2-furanylsulfonylamino)-5-trifluoromethylphenoxymethyl]cinnamic acid

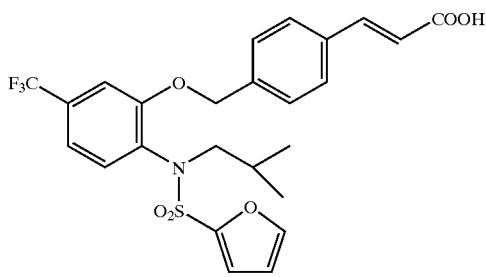

TLC: Rf 0.44 (hexane:AcOEt=1:1); NMR: δ 7.81 (1H, d, J=16 Hz), 7.60 (2H, d, J=8 Hz), 7.41–7.37 (3H, m), 7.27–7.22 (2H, m), 7.17 (1H, m), 6.83 (1H, dd, J=3.5, 1.5 Hz), 6.49 (1H, d, J=16 Hz), 6.35 (1H, dd, J=3.5, 1.5 Hz), 5.02 (2H, s), 3.53 (2H, d, J=7.5 Hz), 1.74–1.50 (1H, m), 0.90 (6H, d, J=6.5 Hz).

EXAMPLE 18(95)

4-[2-(N-propyl-phenylsulfonylamino)-5-methylphenoxymethyl]cinnamic acid

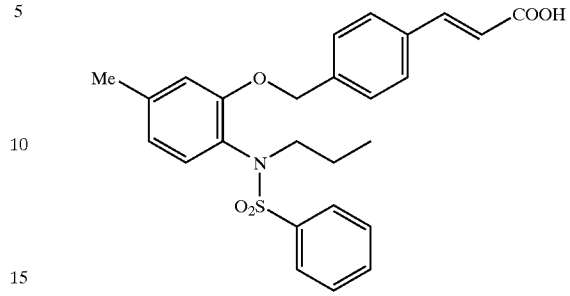

TLC: Rf 0.33 (CHCl$_3$:MeOH:AcOH=100:5:1); NMR: δ 7.79 (1H, d, J=16.0 Hz), 7.67 (2H, m), 7.51 (2H, d, J=8.0 Hz), 7.24–7.43 (3H, m), 7.17 (2H, d, J=8.0 Hz), 7.15 (1H, d, J=8.0 Hz), 6.78 (1H, m), 6.68 (1H, m), 6.47 (1H, d, J=6.0 Hz), 4.79 (2H, brs), 3.55 (2H, m), 2.34 (3H, s), 1.47 (2H, m), 0.87 (3H, t, J=7.2 Hz).

EXAMPLE 18(96)

4-[2-(N-isobutyl-phenylsulfonylamino)-5-methylphenoxymethyl]cinnamic acid

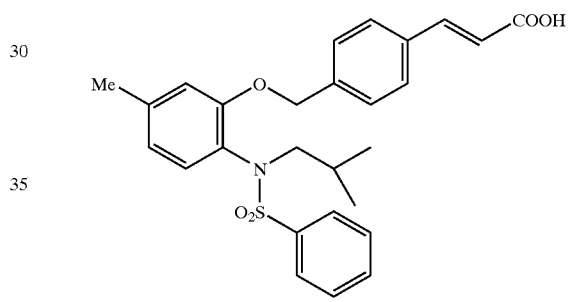

TLC: Rf 0.37 (CHCl$_3$:MeOH:AcOH=100:5:1); NMR: δ 7.79 (1H, d, J=16.0 Hz), 7.63 (2H, m), 7.51 (2H, d, J=8.2 Hz), 7.24–7.46 (3H, m), 7.18 (1H, d, J=7.8 Hz), 7.16 (2H, d, J=8.2 Hz), 6.78 (1H, m), 6.66 (1H, m), 6.48 (1H, d, J=16.0 Hz), 4.74 (2H, m), 3.41 (2H, m), 2.33 (3H, s), 1.61 (1H, m), 0.89 (6H, d, J=6.4 Hz).

EXAMPLE 18(97)

4-[2-(N-isobutyl-propylsulfonylamino)-5-trifluoromethylphenoxymethyl]cinnamic acid

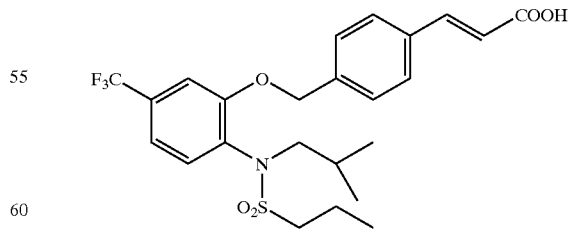

TLC: Rf 0.36 (CHCl$_3$:MeOH:AcOH=100:5:1); NMR: δ 7.80 (1H, d, J=16.0 Hz), 7.62 (2H, d, J=8.4 Hz), 7.44–7.56 (3H, m), 7.24–7.33 (2H, m), 6.50 (1H, d, J=16.0 Hz), 5.17 (2H, s), 3.44 (2H, d, J=7.4 Hz), 2.87 (2H, m), 7.15 (2H, m), 1.55 (1H, m), 0.90 (6H, d, J=6.6 Hz), 0.83 (3H, t, J=7.4 Hz).

EXAMPLE 18(98)

4-[2-(N-methyl-phenylsulfonylamino)-5-trifluoromethyl-phenoxymethyl]cinnamic acid

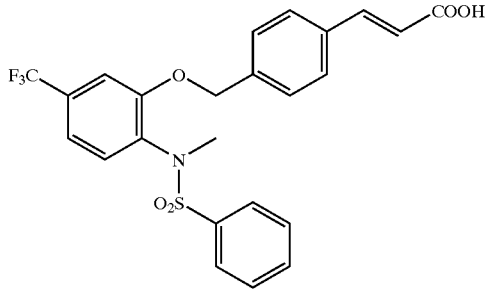

TLC: Rf 0.44 (CHCl$_3$:MeOH=9:1); NMR: δ 7.79 (1H, d, J=16.2 Hz), 7.7–7.6 (2H, m), 7.6–7.2 (7H, m), 7.2–7.1 (3H, m), 6.49 (1H, d, J=16.2 Hz), 4.88 (2H, s), 3.23 (3H, s).

EXAMPLE 18(99)

4-[2-(N-propyl-phenylsulfonylamino)-5-trifluoromethyl-phenoxymethyl]cinnamic acid

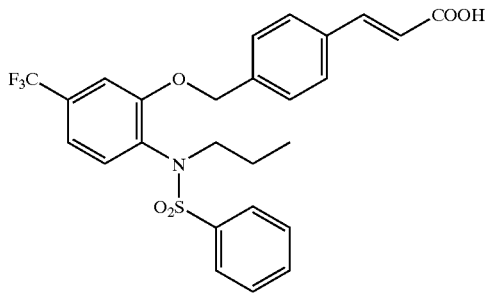

TLC: Rf 0.43 (CHCl$_3$:MeOH=9:1); NMR: δ 7.80 (1H, d, J=16.0 Hz), 7.7–7.6 (2H, m), 7.6–7.1 (10H, m), 6.49 (1H, d, J=16.0 Hz), 4.86 (2H, s), 3.57 (2H, t, J=7.2 Hz), 1.6–1.3 (2H, m), 0.87 (3H, t, J=7.2 Hz).

EXAMPLE 18(100)

4-[2-(N-isobutyl-phenylsulfonylamino)-5-trifluoromethyl-phenoxymethyl]cinnamic acid

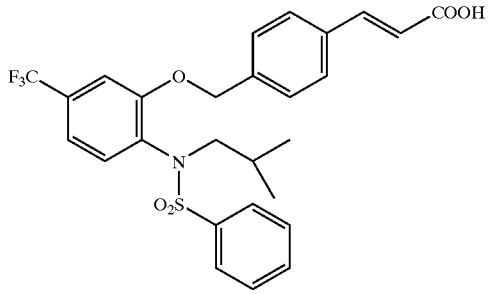

TLC: Rf 0.47 (CHCl$_3$:MeOH=9:1); NMR: δ 7.80 (1H, d, J=16.0 Hz), 7.7–7.1 (12H, m), 6.49 (1H, d, J=16.0 Hz), 4.9–4.7 (2H, br), 3.42 (2H, d, J=7.6 Hz), 1.7–1.5 (1H, m), 0.89 (6H, d, J=6.6 Hz).

EXAMPLE 18(101)

4-[2-(N-isopropyl-propylsulfonylamino)-5-methylphenoxymethyl]cinnamic acid

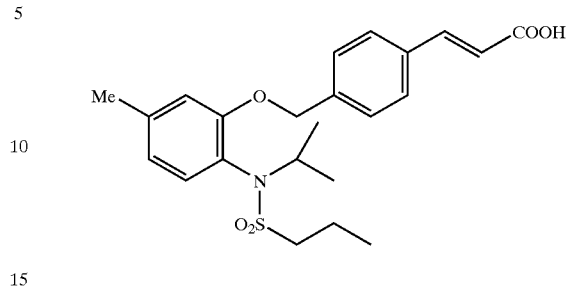

TLC: Rf 0.44 (CHCl$_3$:MeOH=9:1); NMR: δ 7.79 (1H, d, J=16.0 Hz), 7.53 (4H, m), 7.14 (1H, m), 6.80 (2H, m), 6.47 (1H, d, J=16.0 Hz), 5.07 (2H, s), 4.31 (1H, m), 2.94 (2H, m), 1.79 (2H, m), 1.23 (3H, d, J=6.6 Hz), 1.08 (3H, d, J=6.6 Hz), 0.83 (3H, t, J=7.2 Hz).

EXAMPLE 18(102)

4-[2-(N-ethyl-phenylsulfonylamino)-5-trifluoromethyl-phenoxymethyl]cinnamic acid

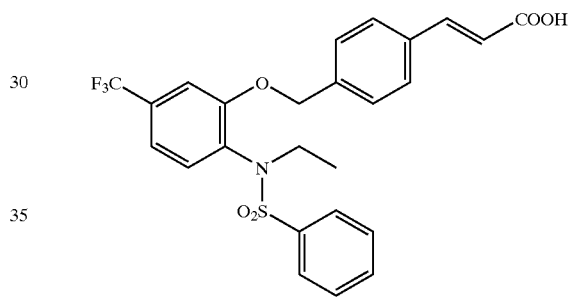

TLC: Rf 0.37 (CHCl$_3$:MeOH=9:1); NMR: δ 7.79 (1H, d, J=16.0 Hz), 7.60–7.71 (2H, m), 7.15–7.55 (10H, m), 6.49 (1H, d, J=16.0 Hz), 4.89 (2H, s), 3.67 (2H, q, J=7.0 Hz), 1.09 (3H, t, J=7.0 Hz).

EXAMPLE 18(103)

4-[2-(N-cyclopropylmethyl-phenylsulfonylamino)-5-trifluoromethylphenoxymethyl]cinnamic acid

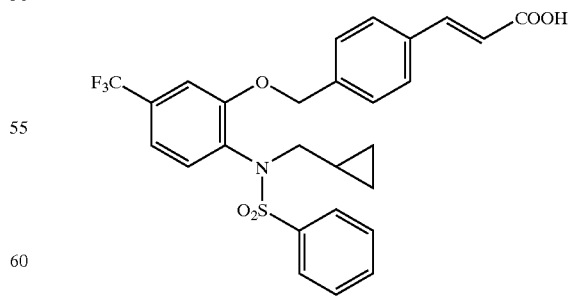

TLC: Rf 0.47 (CHCl$_3$:MeOH=9:1); NMR: δ 7.80 (1H, d, J=16.0 Hz), 7.14–7.55 (10H, m), 7.67 (2H, m), 6.49 (1H, d, J=16.0 Hz), 4.88 (2H, s), 3.49 (2H, d, J=7.0 Hz), 0.87 (1H, m), 0.37 (2H, m), 0.06 (2H, m).

EXAMPLE 18(104)

4-[2-(N-isopropyl-methylsulfonylamino)-5-trifluoromethyl-phenoxymethyl]cinnamic acid

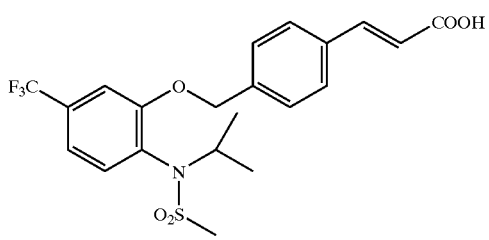

TLC: Rf 0.47 (CHCl$_3$:MeOH=9:1); NMR: δ 7.76 (1H, d, J=16.0 Hz), 7.61 (2H, d, J=8.4 Hz), 7.49 (2H, d, J=8.4 Hz), 7.37 (3H, m), 6.48 (1H, d, J=16.0 Hz), 5.14 (2H, s), 4.31 (1H, m), 2.89 (3H, s), 1.28 (3H, d, J=6.6 Hz), 1.09 (3H, d, J=6.6 Hz).

EXAMPLE 18(105)

4-[2-(N-benzyl-propylsulfonylamino)-5-trifluoromethyl-phenoxymethyl]cinnamic acid

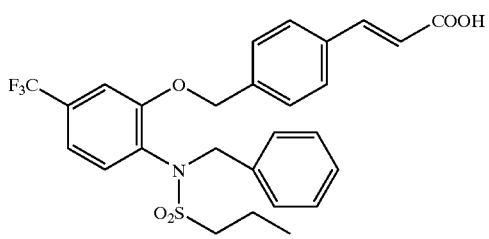

TLC: Rf 0.29 (CHCl$_3$:MeOH:AcOH =100:5:1); NMR: δ 7.82 (1H, d, J=16.2 Hz), 7.65 (2H, d, J=8.4 Hz), 7.51 (2H, d, J=8.4 Hz), 7.09–7.31 (8H, m), 6.52 (1H, d, J=16.2 Hz), 5.17 (2H, s), 4.78 (2H, s), 2.94 (2H, m), 1.80 (2H, m), 0.85 (2H, t, J=7.4 Hz).

EXAMPLE 18(106)

4-[2-(N-propyl-phenylsulfonylamino)-4-methylphenoxymethyl]cinnamic acid

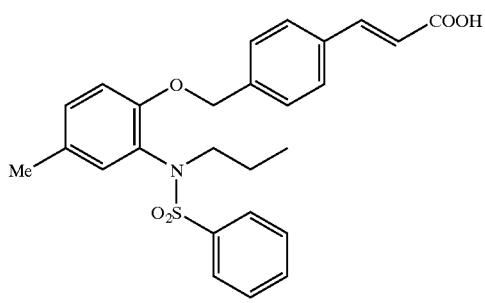

TLC: Rf 0.39 (CHCl$_3$:MeOH=9:1); NMR: δ 7.79 (1H, d, J=16.0 Hz), 7.70–7.65 (2H, m), 7.50 (2H, d, J=8.0 Hz), 7.42–7.38 (1H, m), 7.30 (2H, t, J=8.0 Hz), 7.16 (2H, d, J=8.0 Hz), 7.11 (1H, d, J=1.5 Hz), 7.07 (1H, dd, J=1.5, 8.0 Hz), 6.74 (1H, d, J=8.0 Hz), 6.47 (1H, d, J=16.0 Hz), 4.90–4.70 (2H, br), 3.70–3.50 (2H, br), 2.29 (3H, s), 1.55–1.45 (2H, m), 0.88 (3H, t, J=7.0 Hz).

EXAMPLE 18(107)

4-[2-[N-(prop-2-enyl)-phenylsulfonylamino]-5-trifluoromethylphenoxymethyl]cinnamic acid

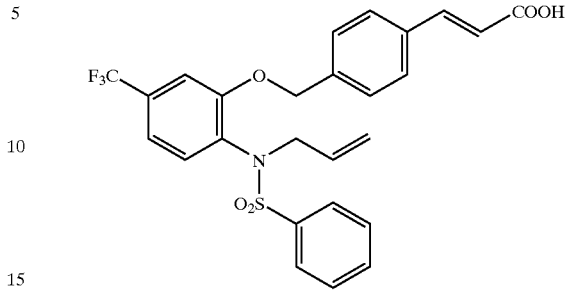

TLC: Rf 0.35 (CHCl$_3$:MeOH=9:1); NMR: δ 7.80 (1H, d, J=16.0 Hz), 7.71–7.68 (2H, m), 7.54 (2H, d, J=8.0 Hz), 7.49–7.45 (1H, m), 7.40 (1H, d, J=8.0 Hz), 7.38–7.33 (2H, m), 7.25 (1H, dd, J=2.0, 8.0 Hz), 7.19 (2H, d, J=8.0 Hz), 7.12 (1H, d, J=2.0 Hz), 6.49 (1H, d, J=16.0 Hz), 5.80–5.70 (1H, m), 5.07–5.02 (2H, m), 4.88 (2H, s), 4.5–4.3 (2H, m).

EXAMPLE 18(108)

4-[2-[N-(2-methylprop-2-enyl)-phenylsulfonylamino]-5-trifluoromethylphenoxymethyl]cinnamic acid

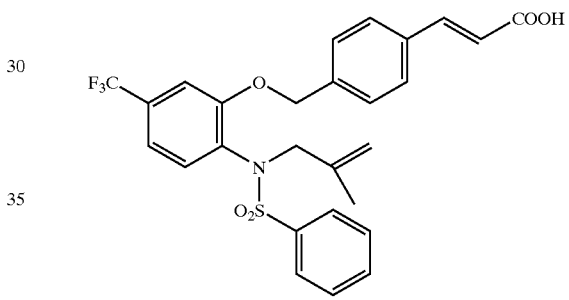

TLC: Rf 0.39 (CHCl$_3$:MeOH=9:1); NMR: δ 7.80 (1H, d, J=16.0 Hz), 7.68–7.63 (2H, m), 7.54 (2H, d, J=8.0 Hz), 7.48–7.44 (1H, m), 7.41 (1H, d, J=8.0 Hz), 7.35 (2H, t, J=8.0 Hz), 7.25 (1H, dd, J=1.5, 8.0 Hz), 7.17 (2H, d, J=8.0 Hz), 7.10 (1H, d, J=1.5 Hz), 6.50 (1H, d, J=16.0 Hz), 4.84 (2H, s), 4.73 (1H, s), 4.68 (1H, s), 4.20 (2H, s), 1.74 (3H, s).

EXAMPLE 18(109)

4-[2-[N-(prop-2-enyl)-2-furanylsulfonylamino]-5-methylphenoxymethyl]benzoic acid

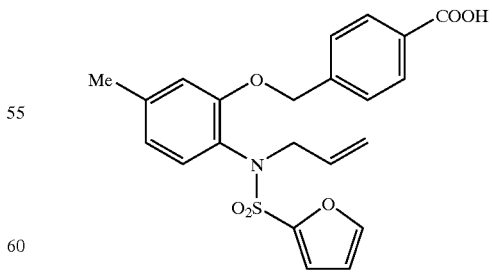

TLC: Rf 0.21 (hexane:AcOEt=1:1); NMR: δ 8.14–8.13 (2H, m), 7.45 (2H, d, J=8.5 Hz), 7.28 (1H, m), 7.10 (1H, d, J=7.5 Hz), 6.85 (1H, m), 6.84–6.76 (1H, m), 6.71 (1H, s), 6.34 (1H, m), 5.88–5.79 (1H, m), 5.11–5.02 (4H, m), 4.33 (2H, bs), 2.32 (3H, bs).

EXAMPLE 18(110)

4-[2-[N-(2-methylprop-2-enyl)-2-furanylsulfonylamino]-5-methylphenoxymethyl]benzoic acid

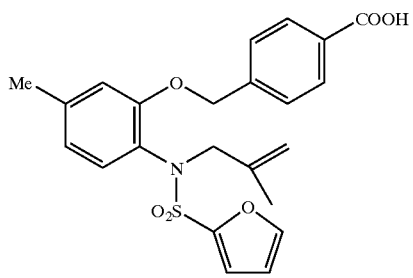

TLC: Rf 0.24 (hexane:AcOEt=1:1); NMR: δ 8.14–8.13 (2H, m), 7.44 (2H, d, J=8 Hz), 7.26 (1H, m), 7.13 (1H, d, J=8 Hz), 6.82 (1H, m), 6.78–6.69 (1H, m), 6.69 (1H, s), 6.33 (1H, m), 5.00 (2H, s), 4.76 (1H, dd, J=9.5, 1.5 Hz), 4.30 (2H, bs), 2.32 (3H, s), 1.78 (3H, s).

EXAMPLE 18(111)

4-[2-(N-isobutyl-phenylsulfonylamino)-4-methylphenoxymethyl]cinnamic acid

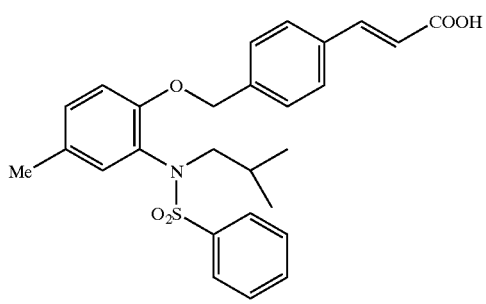

TLC: Rf 0.37 (CHCl₃:MeOH=9:1); NMR: δ 7.79 (1H, d, J=16.0 Hz), 7.70–7.60 (2H, m), 7.50 (2H, d, J=8.0 Hz), 7.40–7.35 (1H, m), 7.30–7.20 (2H, m), 7.20–7.10 (3H, m), 7.05 (1H, dd, J=2.0, 8.0 Hz), 6.72 (1H, d, J=8.0 Hz), 6.47 (1H, d, J=16.0 Hz), 4.9–4.5 (2H, m), 3.5–3.3 (2H, m), 2.29 (3H, s), 1.7–1.6 (1H, m), 1.0–0.8 (6H, m).

EXAMPLE 18(112)

4-[2-(N-benzyl-methylsulfonylamino)-5-trifluoromethylphenoxymethyl]cinnamic acid

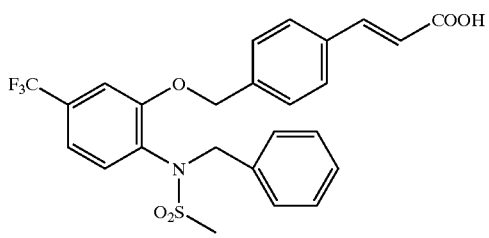

TLC: Rf 0.62 (CHCl₃:MeOH=9:1); NMR: δ 7.80 (1H, d, J=16.0 Hz), 7.64 (2H, d, J=8.4 Hz), 7.48 (2H, d, J=8.4 Hz), 7.24 (8H, m), 6.50 (1H, d, J=16.0 Hz), 5.18 (2H, s), 4.77 (2H, s), 2.88 (3H, s).

EXAMPLE 18(113)

4-[2-(N-isobutyl-2-furanylsulfonylamino)-4-methylphenoxymethyl]benzoic acid

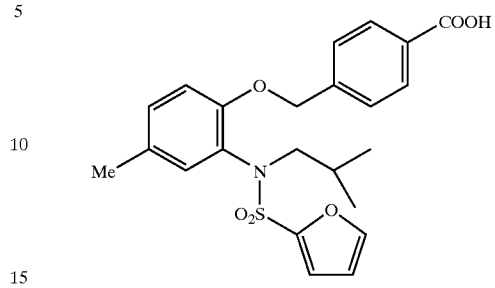

TLC: Rf 0.26 (AcOEt:hexane=1:1); NMR: δ 8.11 (2H, d, J=8 Hz), 7.41 (2H, d, J=8 Hz), 7.25 (1H, m), 7.09 (1H, d, J=2 Hz), 7.06 (1H, dt, J=8,2 Hz), 6.80 (1H, dd, J=4, 1 Hz), 6.76 (1H, d, J=8 Hz), 6.31 (1H, dd, J=2, 2 Hz), 5.20–4.80 (2H, brs), 3.53 (2H, brs), 2.28 (3H, s), 1.67 (1H, m), 0.92 (6H, brs).

EXAMPLE 18(114)

4-[2-(N-isopropyl-2-furanylsulfonylamino)-4-methylphenoxymethyl]benzoic acid

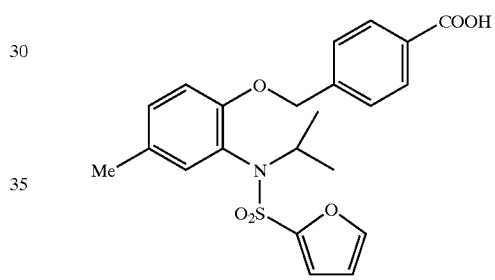

TLC: Rf 0.19 (AcOEt:hexane=1:1); NMR: δ 8.12 (2H, d, J=8 Hz), 7.55 (2H, d, J=8 Hz), 7.44 (1H, d, J=2 Hz), 7.11 (1H, dd, J=8, 2 Hz), 6.91 (1H, dd, J=3, 1 Hz), 6.87 (1H, d, J=3 Hz), 6.84 (1H, d, J=8 Hz), 6.42 (1H, dd, J=3, 1 Hz), 5.10 (2H, s), 4.48 (1H, m), 2.27 (3H, s), 1.12 (6H, d, J=7 Hz).

EXAMPLE 18(115)

4-[2-[N-(2-methylprop-2-enyl)-2-furanylsulfonylamino]-4-methylphenoxymethyl]benzoic acid

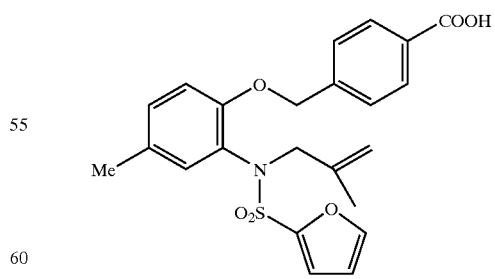

TLC: Rf 0.21 (AcOEt:hexane=1:1); NMR: δ 8.12 (2H, d, J=8 Hz), 7.42 (2H, d, J=8 Hz), 7.26 (1H, m), 7.07 (1H, d, J=2 Hz), 7.06 (1H, dd, J=8, 2 Hz), 6.83 (1H, d, J=3 Hz), 6.75 (1H, d, J=8 Hz), 6.33 (1H, dd, J=3, 2 Hz), 4.97 (2H, s), 4.77 (2H, s), 4.30 (2H, s), 2.28 (3H, s), 1.79 (3H, s).

EXAMPLE 18(116)

4-[2-(N-isopropyl-2-furanylsulfonylamino)-5-methylphenoxymethyl]cinnamic acid

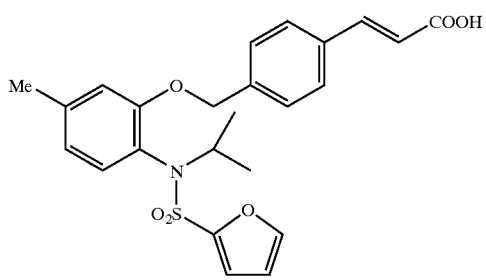

TLC: Rf 0.20 (hexane:AcOEt=1:1); NMR: δ 7.80 (1H, d, J=16 Hz), 7.61–7.45 (4H, m), 7.43 (1H, m), 6.93–6.88 (2H, m), 6.79–6.73 (2H, m), 6.47 (1H, d, J=16 Hz), 6.41 (1H, dd, J=3.5, 2 Hz), 5.07 (2H, s), 4.56–4.43 (1H, m), 2.34 (3H, s), 1.10 (6H, dd, J=6.5, 4 Hz).

EXAMPLE 18(117)

4-[2-(N-isopropyl-2-furanylsulfonylamino)-5-trifluoromethylphenoxymethyl]cinnamic acid

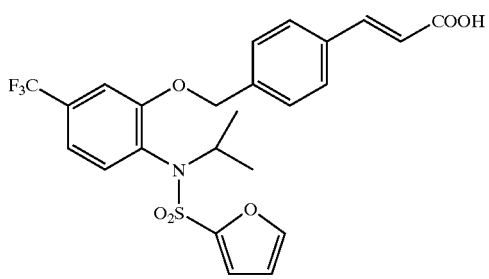

TLC: Rf 0.18 (hexane:AcOEt=1:1); NMR: δ 7.80 (1H, d, J=16 Hz), 7.63–7.51 (4H, m), 7.46 (1H, dd, J=1.5, 1 Hz), 7.23–7.20 (3H, m), 6.94 (1H, dd, J=3.5, 1 Hz), 6.52–6.43 (3H, m), 5.14 (2H, s), 4.51–4.41 (1H, m), 1.09 (6H, dd, J=6.5, 1 Hz).

EXAMPLE 18(118)

4-[2-(N-isopropyl-2-furanylsulfonylamino)-4-trifluoromethylphenoxymethyl]benzoic acid

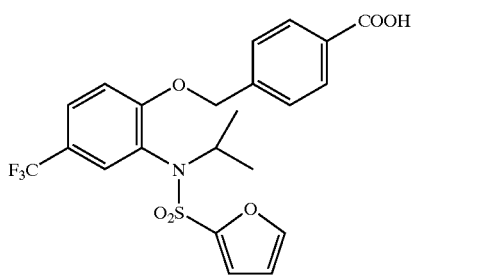

TLC: Rf 0.35 (AcOEt hexane:AcOH=50:50:1); NMR: δ 8.16 (2H, d, J=8.5 Hz), 7.60 (3H, m), 7.38 (1H, dd, J=1.0, 2.0 Hz), 7.26 (1H, m), 7.05 (1H, d, J=9.0 Hz), 6.95 (1H, d, J=3.0 Hz), 6.47 (1H, dd, J=2.0, 3.5 Hz), 5.22 (2H, s), 4.52 (1H, sept, J=7.0 Hz), 1.12 (3H, d, J=7.0 Hz), 1.10 (3H, d, J=7.0 Hz).

EXAMPLE 18(119)

4-[2-(N-isobutyl-2-furanylsulfonylamino)-4-trifluoromethylphenoxymethyl]benzoic acid

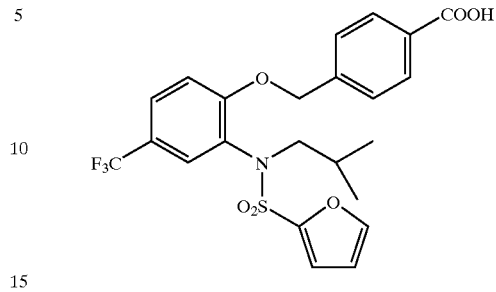

TLC: Rf 0.35 (AcOEt:hexane:AcOH=50:50:1); NMR: δ 8.15 (2H, d, J=9.0 Hz), 7.55 (1H, m), 7.48 (2H, d, J=9.0 Hz), 7.44 (1H, d, J=2.0 Hz), 7.35 (1H, dd, J=1.0, 2.0 Hz), 6.99 (1H, d, J=9.0 Hz), 6.86 (1H, dd, J=1.0, 2.0 Hz), 6.39 (1H, dd, J=2.0, 4.0 Hz), 5.12 (2H, br), 3.52 (2H, d, J=7.0 Hz), 1.64 (1H, m), 0.92 (6H, d, J=6.5 Hz).

EXAMPLE 18(120)

4-[2-(N-isopropyl-phenylsulfonylamino)-4-trifluoromethylphenoxymethyl]cinnamic acid

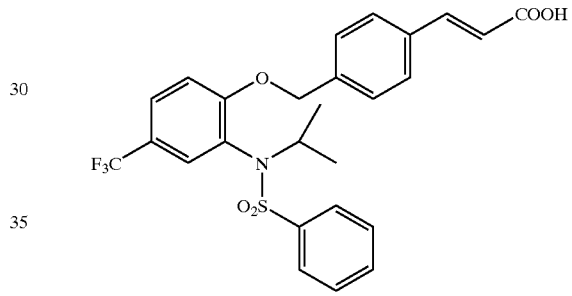

TLC: Rf 0.35 (AcOEt:hexane:AcOH=50:50:1); NMR: δ 7.81 (3H, m), 7.58–7.62 (3H, m), 7.53 (1H, m), 7.49 (2H, d, J=8.0 Hz), 7.41 (2H, m), 7.24 (1H, d, J=2.0 Hz), 7.07 (1H, d, J=8.5 Hz), 6.49 (1H, d, J=16.5 Hz), 5.13 (1H, d, J=12.5 Hz), 5.12 (1H, d, J=12.5 Hz), 4.40 (1H, sept, J=6.5 Hz), 4.07 (3H, d, J=6.5 Hz), 1.02 (3H, d, J=6.5 Hz).

EXAMPLE 18(121)

4-[2-(N-isobutyl-2-furanylsulfonylamino)-5-chlorophenoxymethyl]benzoic acid

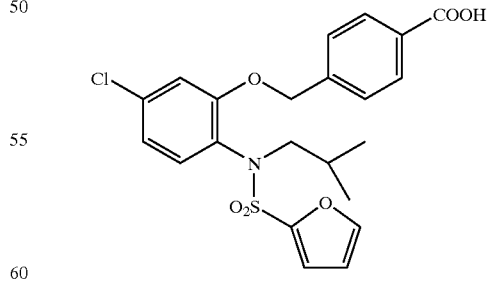

TLC: Rf 0.36 (AcOEt:hexane:AcOH=50:50:1); NMR: δ 8.14 (2H, d, J=8.5 Hz), 7.44 (2H, d, J=8.5 Hz), 7.26 (1H, m), 7.21 (1H, d, J=9.0 Hz), 6.98 (1H, dd, J=2.5, 8.0 Hz), 6.91 (1H, d, J=2.5 Hz), 6.82 (1H, d, J=4.5 Hz), 6.34 (1H, d, J=2.0, 3.0 Hz), 5.00 (2H, br), 3.51 (2H, brs), 1.65 (1H, m), 0.91 (6H, d, J=6.5 Hz).

EXAMPLE 18(122)
4-[2-(N-isopropyl-2-furanylsulfonylamino)-5-chlorophenoxymethyl]cinnamic acid

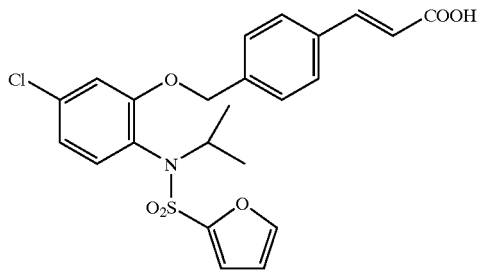

TLC: Rf 0.49 (CHCl₃:MeOH=9:1); NMR: δ 7.80 (1H, d, J=16.2 Hz), 7.60 (2H, d, J=8.4 Hz), 7.50 (2H, d, J=8.4 Hz), 7.45–7.42 (1H, m), 7.02–6.90 (4H, m), 6.53–6.40 (2H, m), 5.07 (2H, s), 4.60–4.40 (1H, m), 1.10 (3H, d, J=6.6 Hz), 1.07 (3H, d, J=6.6 Hz).

EXAMPLE 18(123)
4-[2-(N-isobutyl-2-furanylsulfonylamino)-5-chlorophenoxymethyl]cinnamic acid

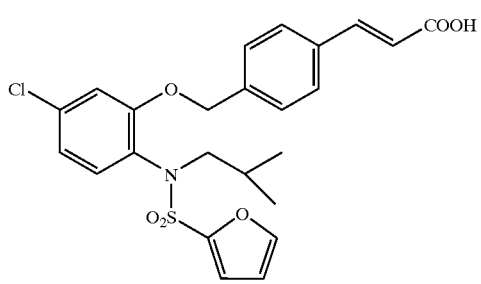

TLC: Rf 0.49 (CHCl₃:MeOH=9:1); NMR: δ 7.80 (1H, d, J=15.8 Hz), 7.58 (2H, d, J=8.0 Hz), 7.37 (2H, d, J=8.0 Hz), 7.25 (1H, dd, J=1.0, 1.8 Hz), 7.20 (1H, d, J=8.2 Hz), 7.00–6.90 (2H, m), 6.81 (1H, dd, J=1.0, 3.6 Hz), 6.49 (1H, d, J=15.8 Hz), 6.33 (1H, dd, J=1.8, 3.6 Hz), 4.95 (2H, s), 3.60–3.40 (2H, m), 1.80–1.50 (1H, m), 0.90 (6H, d, J=6.6 Hz).

EXAMPLE 18(124)
4-[2-(N-isobutyl-2-furanylsulfonylamino)-5-trifluoromethylphenoxymethyl]benzoic acid

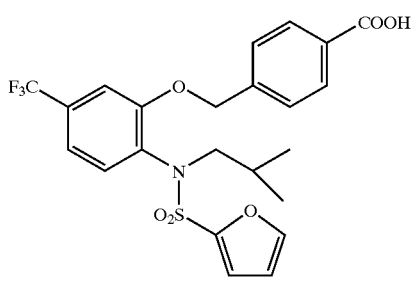

TLC: Rf 0.20 (hexane:AcOEt=1:1); NMR: δ 8.18–8.14 (2H, m), 7.48–7.40 (2H, m), 7.30–7.26 (2H, m), 7.16 (1H, m), 6.84 (1H, dd, J=3.5, 1 Hz), 6.35 (1H, dd, J=3.5, 2 Hz), 5.07 (2H, s), 3.54 (2H, d, J=7 Hz), 1.64 (1H, sept., J=7 Hz), 0.90 (6H, d, J=7 Hz).

EXAMPLE 18(125)
4-[2-(N-isobutyl-2-furanylsulfonylamino)-4-chlorophenoxymethyl]benzoic acid

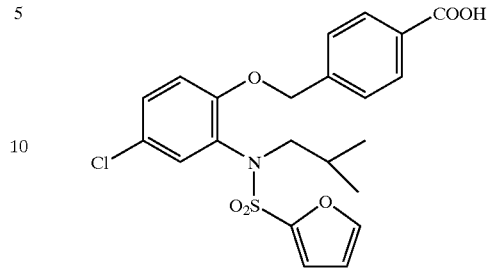

TLC: Rf 0.36 (CHCl₃:MeOH=9:1); NMR: δ 8.14 (2H, d, J=8.4 Hz), 7.44 (2H, d, J=8.4 Hz), 7.34–7.20 (3H, m), 6.90–6.80 (2H, m), 6.37 (1H, dd, J=1.8, 3.0 Hz), 5.03 (2H, s), 3.51 (2H, d, J=7.2 Hz), 1.80–1.50 (1H, m), 0.91 (6H, d, J=6.6 Hz).

EXAMPLE 18(126)
4-[2-(N-isobutyl-2-furanylsulfonylamino)-4-methylphenoxymethyl]cinnamic acid

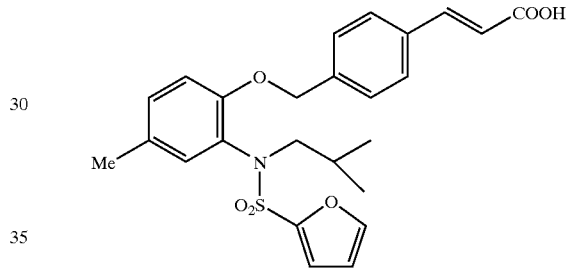

TLC: Rf 0.33 (CHCl₃:MeOH=9:1); NMR: δ 7.80 (1H, d, J=16.0 Hz), 7.57 (2H, d, J=8.0 Hz), 7.36 (2H, d, J=8.0 Hz), 7.28–7.22 (1H, m), 7.12–7.02 (2H, m), 6.84–6.74 (2H, m), 6.48 (1H, d, J=16.0 Hz), 6.32 (1H, dd, J=1.8, 3.6 Hz), 4.92 (2H, s), 3.54 (2H, d, J=7.0 Hz), 2.28 (3H, s), 1.80–1.60 (1H, m), 0.92 (6H, d, J=6.6 Hz).

EXAMPLE 18(127)
4-[2-(N-isobutyl-4-ethoxyphenylsulfonylamino)-5-trifluoromethylphenoxymethyl]benzoic acid

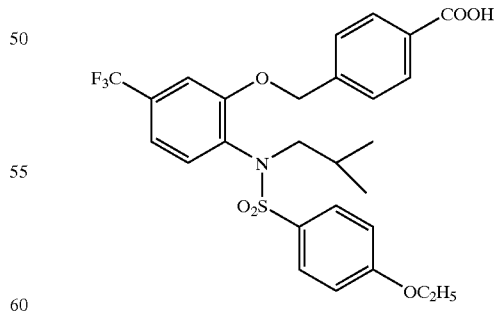

TLC: Rf 0.35 (CHCl₃:MeOH:AcOH=100:5:1); NMR: δ 8.09 (2H, d, J=8.5 Hz), 7.52 (2H, d, J=8.5 Hz), 7.46 (1H, d, J=8.5 Hz), 7.25–7.29 (3H, m), 7.13 (1H, brd, J=1.5 Hz), 6.73 (2H, d, J=9.0 Hz), 4.92 (2H, br), 3.96 (2H, q, J=7.5 Hz), 3.40 (2H, brs), 1.59 (1H, m), 1.42 (3H, t, J=7.5 Hz), 0.90 (6H, brd, J=6.0 Hz).

EXAMPLE 18(128)

4-[2-(N-methyl-phenylsulfonylamino)-4-chlorophenoxymethyl]benzoic acid

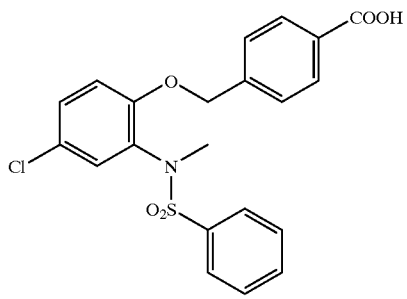

TLC: Rf 0.43 (CHCl₃:MeOH:H₂O=9:1:0.1); NMR (DMSO-d₆): δ 7.88 (2H, d, J=8.6 Hz), 7.66–7.38 (6H, m), 7.25–7.11 (4H, m), 4.95 (2H, s), 3.15 (3H, s).

EXAMPLE 19

Methyl 4-[2-(N-cyclopentylmethyl-phenylsulfonylamino)-5-trifluoromethylphenoxymethyl]benzoate

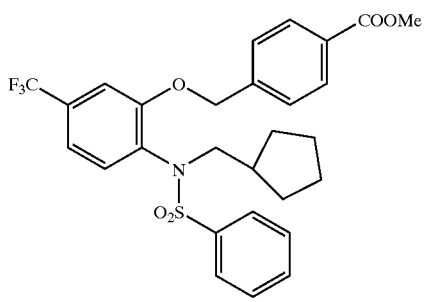

To a solution of methyl 4-(2-phenylsulfonylamino-5-trifluoromethyl-phenoxymethyl)benzoate (251 mg; prepared in Example 15), triphenylphosphine (142 mg) and cyclopentylmethanol (54 mg) in THF (2 ml), diethyl azodicarboxylate (89 μl; abbreviated as DEAD) was added at 0° C. The mixture was stirred overnight at room temperature. The reaction solution was purified on silica gel chromatography (hexane: AcOEt=7:1) to give the title compound (333 mg) having the following physical data.

TLC: Rf 0.51 (hexane: AcOEt=3:1); NMR: δ 8.01 (2H, d, J=8.4 Hz), 7.63–7.58 (2H, m), 7.48–7.25 (5H, m), 7.17 (2h, D, J=8.4 Hz), 7.09 (1H, d, J=1.4 Hz), 4.83 (2H, br), 3.95 (3H, s), 3.55 (2H, d-like), 1.92–1.09 (9H, m).

EXAMPLE 20

4-[2-(N-cyclopentylmethyl-phenylsulfonylamino)-5-trifluoromethylphenoxymethyl]benzoic acid

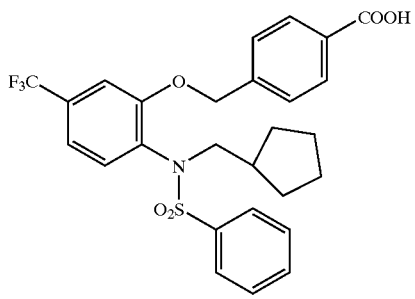

By using methyl 4-[2-(N-cyclopentylmethyl-phenylsulfonylamino)-5-trifluoromethylphenoxymethyl] benzoate (prepared in Example 19.), the title compounds having the following physical data was obtained by the same procedure as Example 2.

TLC: Rf 0.40 (CHCl₃:MeOH:H₂O=9:1:0.1); NMR: δ 8.09 (2H, d, J=8.2 Hz), 7.65–7.61 (2H, m), 7.47–7.20 (7H, m), 7.11 (1H, d, J=1.8 Hz), 4.89 (2H, br), 3.59–3.51 (2H, m), 1.93–1.10 (9H, m).

EXAMPLE 20(1)–20(30)

By using the corresponding compounds, the title compounds having the following physical data were obtained by the same procedure as Reference Example 6→Reference Example 7→Example 7→Example 19→Example 2 or Reference Example 8→Reference Example 9→Reference Example 10→Example 9→Example 19→Example 2.

EXAMPLE 20(1)

4-[2-(N-cyclopropylmethyl-phenylsulfonylamino)-5-trifluoromethylphenoxy-methyl]benzoic acid

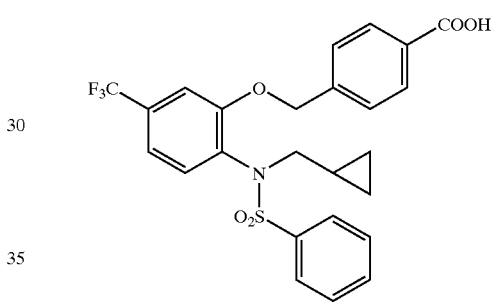

TLC: Rf 0.43 (CHCl₃:MeOH:H₂O=9:1:0.1); NMR: δ 8.09 (2H, d, J=8.2 Hz), 7.70–7.65 (2H, m), 7.54–7.22 (7H, m), 7.14 (1H, d, J=1.8 Hz), 4.93 (2H, s), 3.51 (2H, d, J=7.2 Hz), 0.96–0.81 (1H, m), 0.44–0.35 (2H, m), 0.10–0.02 (2H, m).

EXAMPLE 20(2)

4-[2-(N-t-butylmethyl-phenylsulfonylamino)-5-trifluoromethylphenoxymethyl]benzoic acid

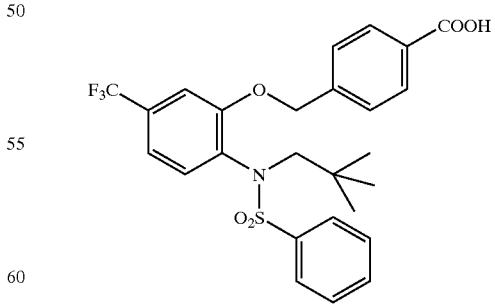

TLC: Rf 0.5 (CHCl₃:MeOH=9:1); NMR: δ 8.12 (2H, d, J=8.0 Hz), 7.6–7.4 (4H, m), 7.4–7.2 (5H, m), 7.09 (1H, d, J=1.8 Hz), 5.02 (1H, d, J=12.4 Hz), 4.72 (1H, d, J=12.4 Hz), 3.53 (2H, s), 0.86 (9H, s).

EXAMPLE 20(3)

4-[2-(N-isopropyl-phenylsulfonylamino)-5-trifluoromethylphenoxymethyl]phenylacetic acid

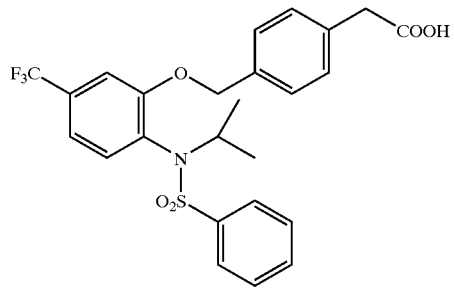

TLC: Rf 0.47 (CHCl₃:MeOH:AcOH=100:5:1); NMR: δ 7.79 (2H, d, J=7.6 Hz), 7.20–7.50 (10H, m), 5.01 (2H, s), 4.28 (1H, sept, J=6.6 Hz), 3.71 (2H, s), 1.08 (3H, d, J=6.6 Hz), 1.01 (3H, d, J=6.6 Hz).

EXAMPLE 20(4)

4-[2-(N-isopropyl-propylsulfonylamino)-5-trifluoromethylphenoxymethyl]benzoic acid

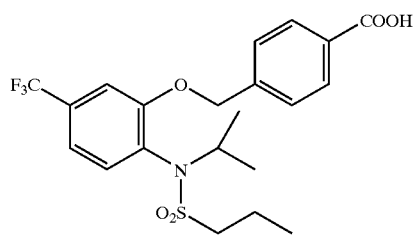

TLC: Rf 0.33 (CHCl₃:MeOH=20:1); NMR (CD₃Cl): δ 8.13 (2H, d, J=8.0 Hz), 7.54 (2H, d, J=8.0 Hz), 7.30–7.46 (3H, m), 5.19 (2H, s), 4.32 (1H, sept, J=6.2 Hz), 2.96 (2H, m), 1.78 (2H, m), 1.27 (2H, d, J=6.4 Hz), 1.12 (2H, d, J=6.4 Hz), 0.85 (3H, t, J=7.4 Hz).

EXAMPLE 20(5)

4-[2-(N-isopropyl-pentylsulfonylamino)-5-trifluoromethylphenoxymethyl]benzoic acid

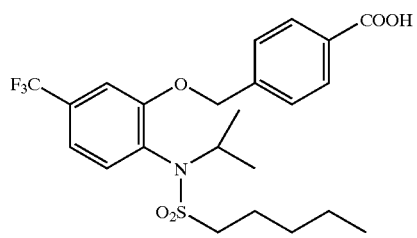

TLC: Rf 0.40 (CHCl₃:MeOH=20:1); NMR (CD₃Cl): δ 8.17 (2H, d, J=8.4 Hz), 7.59 (2H, d, J=8.4 Hz), 7.12–7.41 (3H, m), 5.18 (2H, s), 4.32 (1H, sept, J=6.6 Hz), 2.97 (2H, m), 1.74 (2H, m), 1.02–1.35 (8H, m), 0.82 (3H, t, J=6.8 Hz).

EXAMPLE 20(6)

4-[2-(N-isopropyl-butylsulfonylamino)-5-trifluoromethylphenoxymethyl]benzoic acid

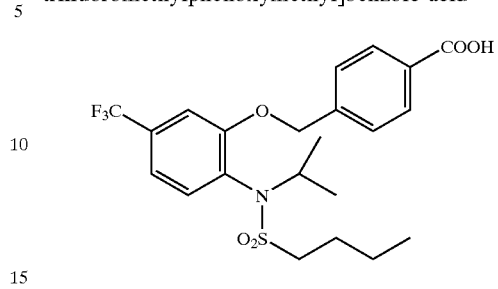

TLC: Rf 0.40 (CHCl₃:MeOH=9:1); NMR: δ 8.17 (2H, d, J=8.2 Hz), 7.59 (2H, d, J=8.2 Hz), 7.40 (1H, d, J=7.8 Hz), 7.3–7.2 (2H, m), 5.18 (2H, s), 4.4–4.2 (1H, m), 3.1–2.9 (2H, m), 1.8–1.6 (2H, m), 1.4–1.0 (8H, m), 0.92 (3H, t, J=7.2 Hz).

EXAMPLE 20(7)

4-[2-(N-isopropyl-hexylsulfonylamino)-5-trifluoromethylphenoxymethyl]benzoic acid

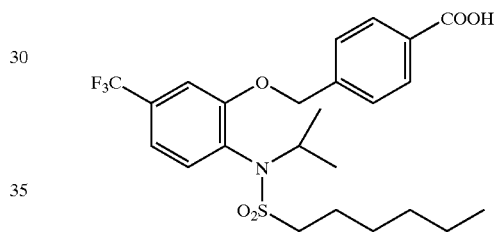

TLC: Rf 0.44 (CHCl₃:MeOH=9:1); NMR: δ 8.18 (2H, d, J=8.0 Hz), 7.59 (2H, d, J=8.0 Hz), 7.40 (1H, d, J=8.0 Hz), 7.3–7.2 (2H, m), 5.18 (2H, s), 4.4–4.2 (1H, m), 3.0–2.9 (2H, m), 1.8–1.6 (2H, m), 1.3–1.0 (12H, m), 0.85 (3H, t, J=7.4 Hz).

EXAMPLE 20(8)

4-[2-(N-isopropyl-heptylsulfonylamino)-5-trifluoromethylphenoxymethyl]benzoic acid

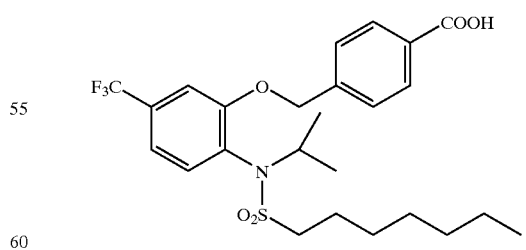

TLC: Rf 0.48 (CHCl₃:MeOH=9:1); NMR: δ 8.18 (2H, d, J=8.0 Hz), 7.59 (2H, d, J=8.0 Hz), 7.40 (1H, d, J=8.0 Hz), 7.3–7.2 (2H, m), 5.18 (2H, s), 4.4–4.2 (1H, m), 3.0–2.9 (2H, m), 1.9–1.6 (2H, m), 1.4–1.0 (14H, m), 0.86 (3H, t, J=6.2 Hz).

EXAMPLE 20(9)

4-[2-(N-isopropyl-4-hydroxyphenylsulfonylamino)-5-trifluoromethylphenoxymethyl]benzoic acid

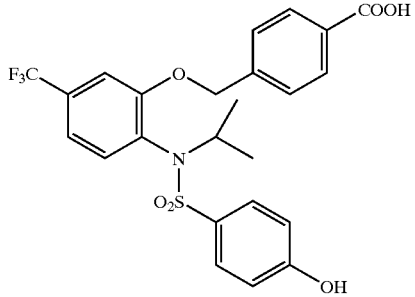

TLC: Rf 0.28 (CHCl$_3$:MeOH=9:1); NMR: δ 8.13 (2H, d, J=8.2 Hz), 7.66 (2H, d, J=9.2 Hz), 7.50 (2H, d, J=8.2 Hz), 7.3–7.2 (3H, m), 6.72 (2H, d, J=9.2 Hz), 5.10 (2H, s), 4.4–4.2 (1H, m), 3.0–1.5 (2H, br), 1.10 (3H, d, J=6.6 Hz), 1.03 (3H, d, J=6.6 Hz).

EXAMPLE 20(10)

4-[2-(N-isopropyl-butylsulfonylamino)-5-methylphenoxymethyl]benzoic acid

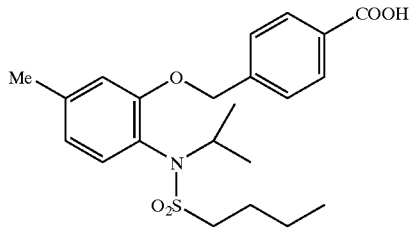

TLC: Rf 0.41 (CHCl$_3$:MeOH=9:1); NMR: δ 8.15 (2H, d, J=8.6 Hz), 7.57 (2H, d, J=8.6 Hz), 7.15 (1H, d, J=8.4 Hz), 6.9–6.8 (2H, m), 5.13 (2H, s), 4.4–4.2 (1H, m), 3.1–2.9 (2H, m), 2.36 (3H, s), 1.8–1.6 (2H, m), 1.3–1.2 (5H, m), 1.10 (3H, d, J=6.6 Hz), 0.81 (3H, t, J=7.4 Hz).

EXAMPLE 20(11)

4-[2-(N-isopropyl-hexylsulfonylamino)-5-methylphenoxymethyl]benzoic acid

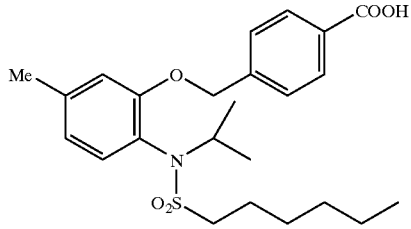

TLC: Rf 0.47 (CHCl$_3$:MeOH=9:1); NMR: δ 8.15 (2H, d, J=8.4 Hz), 7.57 (2H, d, J=8.4 Hz), 7.15 (1H, d, J=8.4 Hz), 7.1–7.0 (2H, m), 5.13 (2H, s), 4.4–4.2 (1H, m), 3.0–2.9 (2H, m), 2.36 (3H, s), 1.8–1.6 (2H, m), 1.3–1.0 (12H, m), 0.84 (3H, t, J=6.4 Hz).

EXAMPLE 20(12)

4-[2-(N-isopropyl-heptylsulfonylamino)-5-methylphenoxymethyl]benzoic acid

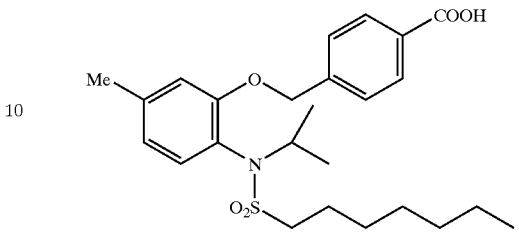

TLC: Rf 0.47 (CHCl$_3$:MeOH=9:1); NMR: δ 8.15 (2H, d, J=8.0 Hz), 7.57 (2H, d, J=8.0 Hz), 7.15 (1H, d, J=8.4 Hz), 6.9–6.8 (2H, m), 5.13 (2H, s), 4.4–4.2 (1H, m), 3.0–2.9 (2H, m), 2.36 (3H, s), 1.9–1.6 (2H, m), 1.3–1.0 (14H, m), 0.85 (3H, t, J=6.2 Hz).

EXAMPLE 20(13)

4-[2-(N-isopropyl-methylsulfonylamino)-5-methylphenoxymethyl]benzoic acid

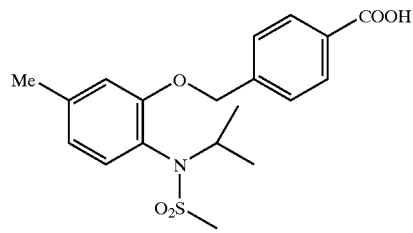

TLC: Rf 0.13 (hexane:AcOEt=1:1); NMR: δ 8.17–8.13 (2H, m), 7.58–7.53 (2H, m), 7.17–7.12 (1H, m), 6.8 (2H, m), 5.1 (2H, m), 4.33 (1H, sept., J=6.5 Hz), 2.90 (3H, s), 2.36 (3H, s), 1.26 (3H, d, J=6.5 Hz), 1.09 (3H, d, J=6.5 Hz).

EXAMPLE 20(14)

4-[2-(N-isopropyl-ethylsulfonylamino)-5-methylphenoxymethyl]benzoic acid

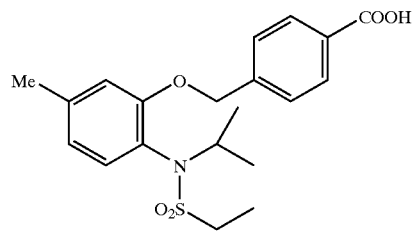

TLC: Rf 0.20 (hexane:AcOEt=1:1); NMR: δ 8.17–8.13 (2H, m), 7.59–7.55 (2H, m), 7.17–7.13 (1H, m), 6.8 (2H, m), 5.1 (2H, m), 4.33 (1H, sept., J=7 Hz), 3.01 (2H, q, J=7 Hz), 2.36 (3H, s), 1.29–1.20 (6H, m), 1.09 (3H, d, J=6.5 Hz).

EXAMPLE 20(15)
4-[2-(N-isopropyl-2-phenylethylsulfonylamino)-5-methylphenoxymethyl]benzoic acid

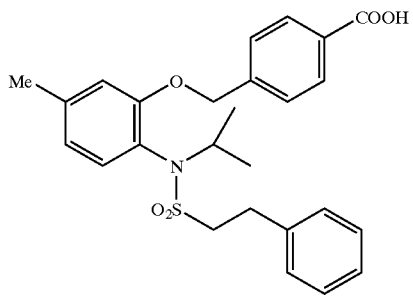

TLC: Rf 0.24 (hexane:AcOEt=1:1); NMR: δ 8.00–7.96 (2H, m), 7.44–7.40 (2H, m), 7.26–7.14 (4H, m), 7.05–7.01 (2H, m), 6.85–6.81 (2H, m), 5.07 (2H, s), 4.42–4.27 (1H, m), 3.4–3.2 (2H, m), 3.2–3.0 (2H, m), 2.36 (3H, s), 1.25 (3H, d, J=6.5 Hz), 1.09 (3H, d, J=6.5 Hz).

EXAMPLE 20(16)
4-[2-(N-isopropyl-benzylsulfonylamino)-5-methylphenoxymethyl]benzoic acid

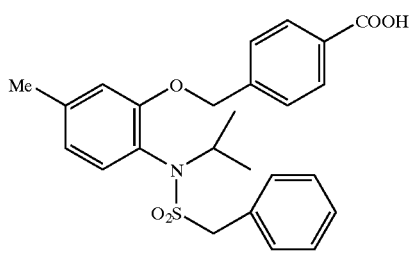

TLC: Rf 0.22 (hexane:AcOEt=1:1); NMR: δ 8.15–8.11 (2H, m), 7.63–7.59 (2H, m), 7.3 (2H, m), 6.92–6.88 (1H, m), 6.81–6.70 (2H, m), 5.2 (2H, m), 4.29 (2H, s), 4.18–4.02 (1H, m), 2.35 (3H, s), 1.12 (3H, d, J=6.5 Hz), 1.04 (3H, d, J=6.5 Hz).

EXAMPLE 20(17)
4-[2-(N-t-butylmethyl-phenylsulfonylamino)-4-methylphenoxymethyl]benzoic acid

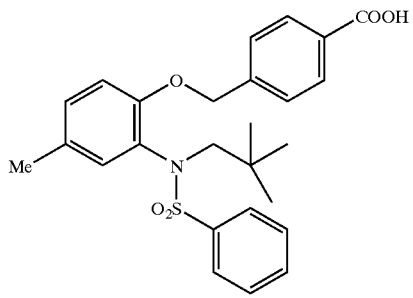

TLC: Rf 0.37 (CHCl$_3$:MeOH=9:1); NMR: δ 8.08 (2H, d, J=8 Hz), 7.55 (2H, m), 7.39 (1H, m), 7.32–7.20 (4H, m), 7.17 (1H, d, J=2 Hz), 7.03 (1H, dd, J=8 and 2 Hz), 6.68 (1H, d, J=8 Hz), 4.90 (1H, d, J=13 Hz), 4.59 (1H, d, J=13 Hz), 3.57 (1H, d, J=14 Hz), 3.50 (1H, d, J=14 Hz), 2.28 (3H, s), 0.88 (9H, s).

EXAMPLE 20(18)
4-[2-(N-isopropyl-methylsulfonylamino)-5-trifluoromethylphenoxymethyl]benzoic acid

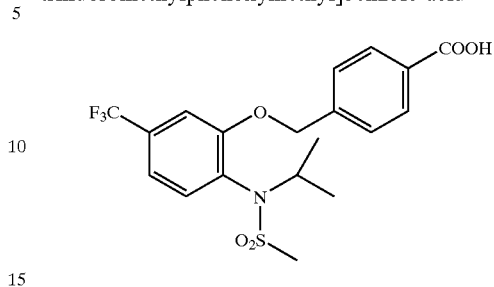

TLC: Rf 0.32 (CHCl$_3$:MeOH=9:1); NMR: δ 8.17 (2H, d, J=8.5 Hz), 7.58 (2H, d, J=8.5 Hz), 7.43–7.23 (3H, m), 5.20 (2H, s), 4.32 (1H, m), 2.91 (3H, s), 1.29 (3H, d, J=7 Hz), 1.10 (3H, d, J=7 Hz).

EXAMPLE 20(19)
4-[2-(N-isopropyl-ethylsulfonylamino)-5-trifluoromethylphenoxymethyl]benzoic acid

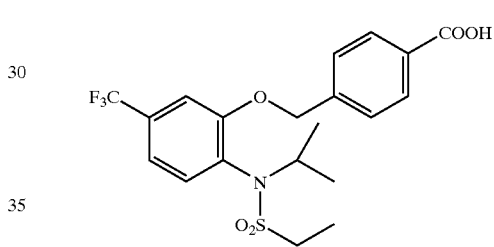

TLC: Rf 0.36 (CHCl$_3$:MeOH=9:1); NMR: δ 8.18 (2H, d, J=8.5 Hz), 7.59 (2H, d, J=8.5 Hz), 7.43–7.23 (3H, m), 5.19 (2H, s), 4.33 (1H, m), 3.03 (2H, q, J=7.5 Hz), 1.32–1.17 (6H, m), 1.09 (3H, d, J=7 Hz).

EXAMPLE 20(20)
4-[2-(N-isopropyl-cyclopentylmethylsulfonylamino)-5-methylphenoxymethyl]benzoic acid

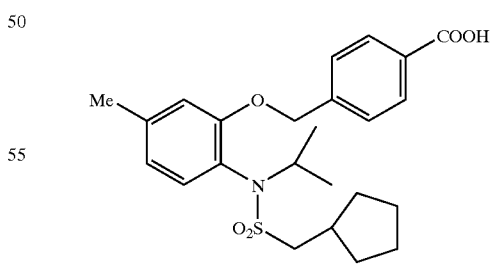

TLC: Rf 0.26 (hexane:AcOEt=1:1); NMR: δ 8.17–8.13 (2H, m), 7.59–7.55 (2H, m), 7.16–7.12 (1H, m), 6.83–6.80 (2H, m), 5.13 (2H, s), 4.31 (1H, sept., J=7 Hz), 3.04–3.00 (2H, m), 2.36 (3H, s), 2.4–2.2 (1H, m), 2.0–1.8 (2H, m), 1.6–1.4 (4H, m), 1.24 (3H, d, J=7 Hz), 1.3–1.1 (2H, m), 1.09 (3H, d, J=7 Hz).

EXAMPLE 20(21)

4-[2-(N-cyclohexylmethyl-propylsulfonylamino)-5-methylphenoxymethyl]benzoic acid

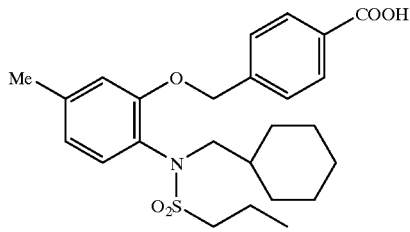

TLC: Rf 0.43 (CHCl$_3$:MeOH=9:1); NMR: δ 8.16 (2H, d, J=8.6 Hz), 7.54 (2H, d, J=8.6 Hz), 7.26 (1H, d, J=8.6 Hz), 6.9–6.8 (2H, m), 5.17 (2H, s), 3.5–3.4 (2H, m), 2.9–2.8 (2H, m), 2.35 (3H, s), 2.0–1.0 (13H, m), 0.84 (3H, t, J=8.0 Hz), 4.0–1.0 (1H, br).

EXAMPLE 20(22)

4-[2-(N-cyclopentylmethyl-propylsulfonylamino)-5-methylphenoxymethyl]benzoic acid

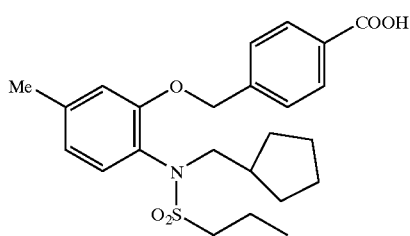

TLC: Rf 0.38 (CHCl$_3$:MeOH=9:1); NMR: δ 8.16 (2H, d, J=8.4 Hz), 7.54 (2H, d, J=8.4 Hz), 7.26 (1H, d, J=8.4 Hz), 6.9–6.8 (2H, m), 5.17 (2H, s), 3.6–3.5 (2H, m), 2.9–2.8 (2H, m), 2.35 (3H, s), 2.0–1.0 (11H, m), 0.84 (3H, t, J=7.6 Hz), 6.0–4.0 (1H, br).

EXAMPLE 20(23)

4-[2-(N-isopropyl-propylsulfonylamino)-5-trifluoromethylphenoxymethyl]cinnamic acid

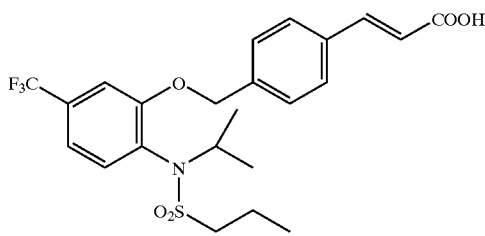

TLC: Rf 0.32 (CHCl$_3$:MeOH:AcOH=100:5:1); NMR: δ 7.80 (1H, d, J=16.2 Hz), 7.61 (2H, d, J=8.6 Hz), 7.51 (2H, d, J=8.6 Hz), 7.39 (1H, d, J=8.8 Hz), 7.24–7.33 (2H, m), 6.49 (1H, d, J=16.2 Hz), 5.12 (2H, s), 4.31 (1H, m), 2.95 (2H, m), 1.77 (2H, m), 1.26 (3H, d, J=6.6 Hz), 1.09 (3H, d, J=6.6 Hz), 0.82 (3H, t, J=7.2 Hz).

EXAMPLE 20(24)

4-[2-(N-isopropyl-pentylsulfonylamino)-5-trifluoromethylphenoxymethyl]cinnamic acid

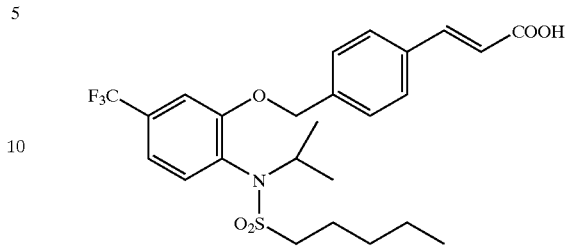

TLC: Rf 0.27 (CHCl$_3$:MeOH:AcOH=100:5:1); NMR: δ 7.80 (1H, d, J=16.0 Hz), 7.61 (2H, d, J=8.4 Hz), 7.51 (2H, d, J=8.4 Hz), 7.39 (1H, m), 7.24–7.33 (2H, m), 6.48 (1H, d, J=16.0 Hz), 5.12 (2H, s), 4.31 (1H, sept, J=6.6 Hz), 2.96 (2H, m), 1.72 (2H, m), 1.26 (3H, d, J=6.6 Hz), 1.05–1.23 (7H, m), 0.83 (3H, t, J=6.2 Hz).

EXAMPLE 20(25)

4-[2-(N-isopropyl-2-furanylsulfonylamino)-5-trifluoromethylphenoxymethyl]benzoic acid

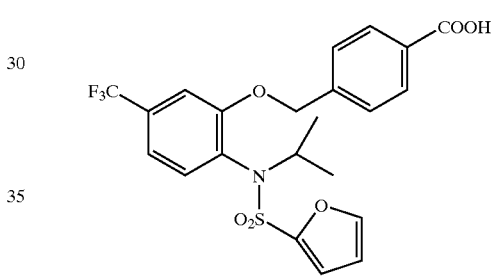

TLC: Rf 0.22 (hexane:AcOEt=1:1); NMR: δ 8.15 (2H, d, J=8 Hz), 7.59 (2H, d, J=8 Hz), 7.46 (1H, dd, J=2, 1 Hz), 7.23 (3H, m), 6.94 (1H, dd, J=3.5, 1 Hz), 6.44 (1H, dd, J=3.5, 2 Hz), 5.18 (2H, s), 4.49 (1H, m), 1.10 (6H, dd, J=7, 2.5 Hz).

EXAMPLE 20(26)

4-[2-(N-isopropyl-2-thienylsulfonylamino)-5-trifluoromethylphenoxymethyl]benzoic acid

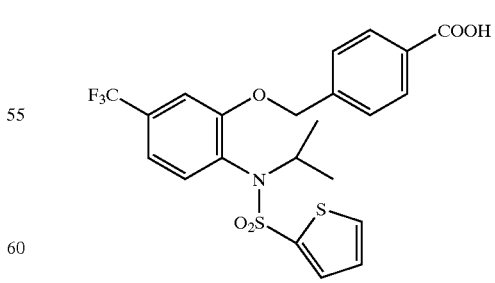

TLC: Rf 0.24 (hexane:AcOEt=1:1); NMR: δ 8.15 (2H, d, J=8.5 Hz), 7.57 (2H, d, J=8.5 Hz), 7.54–7.51 (2H, m), 7.25 (3H, m), 7.01–6.99 (1H, m), 5.19 (2H, s), 4.49–4.44 (1H, m), 1.10 (6H, d, J=6.5 Hz).

EXAMPLE 20(27)
4-[2-(N-isopropyl-4-chlorophenylsulfonylamino)-5-trifluoromethylphenoxymethyl]benzoic acid

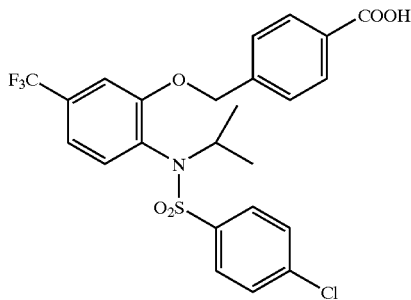

TLC: Rf 0.43 (CHCl₃:MeOH=10:1); NMR (DMSO-d₆): δ 7.93 (2H, d, J=8.4 Hz), 7.73 (2H, d, J=8.4 Hz), 7.56 (1H, s), 7.50–7.28 (6H, m), 5.22 (2H, s), 4.38 (1H, sept, J=6.6 Hz), 1.00 (3H, d, J=6.6 Hz), 0.93 (3H, d, J=6.6 Hz).

EXAMPLE 20(28)
4-[2-(N-isopropyl-4-ethylphenylsulfonylamino)-5-trifluoromethylphenoxymethyl]benzoic acid

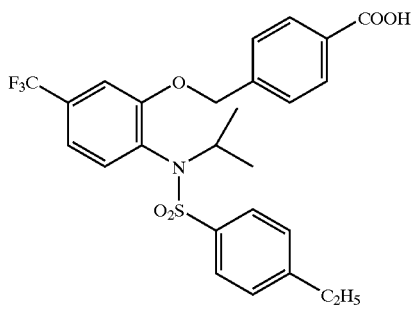

TLC: Rf 0.40 (CHCl₃:MeOH=10:1); NMR (DMSO-d₆): δ 7.94 (2H, d, J=8.4 Hz), 7.66 (2H, d, J=8.4 Hz), 7.55 (1H, d, J=1 Hz), 7.49 (2H, d, J=8.4 Hz), 7.39 (1H, dd, J=8.4 Hz, 1 Hz), 7.32 (1H, d, J=8.4 Hz), 7.23 (2H, d, J=8.4 Hz), 5.25 (2H, s), 4.14 (1H, sept, J=6.6 Hz), 2.61 (2H, q, J=7.4 Hz), 1.14 (3H, t, J=7.4 Hz), 1.00 (3H, d, J=6.6 Hz), 0.93 (3H, d, J=6.6 Hz).

EXAMPLE 20(29)
4-[2-(N-isopropyl-4-propylphenylsulfonylamino)-5-trifluoromethylphenoxymethyl]benzoic acid

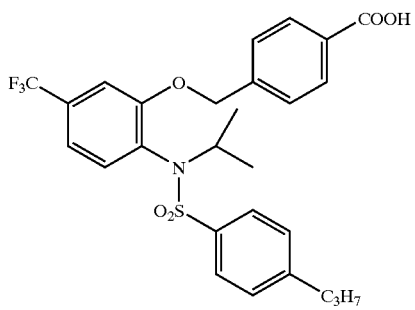

TLC: Rf 0.41 (CHCl₃:MeOH=10:1); NMR (DMSO-d₆): δ 7.94 (2H, d, J=8.4 Hz), 7.65 (2H, d, J=8.4 Hz), 7.55 (1H, d, J=1 Hz), 7.50 (2H, d, J=8.4 Hz), 7.39 (1H, dd, J=8.4 Hz, 1 Hz), 7.32 (1H, d, J=8.4 Hz), 7.20 (2H, d, J=8.4 Hz), 5.25 (2H, s), 4.13 (1H, sept, J=6.6 Hz), 2.55 (2H, t, J=7.4 Hz), 1.54 (2H, tq, J=7.4 Hz, 7.4 Hz), 0.97 (3H, d, J=6.6 Hz), 0.90 (3H, d, J=6.6 Hz), 0.84 (3H, t, J=7.4 Hz).

EXAMPLE 20(30)
4-[2-(N-isopropyl-4-butylphenylsulfonylamino)-5-trifluoromethylphenoxymethyl]benzoic acid

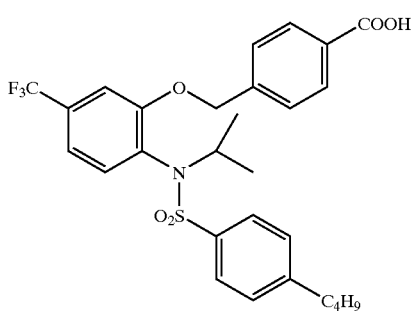

TLC: Rf 0.41 (CHCl₃:MeOH=10:1); NMR (DMSO-d₆): δ 7.94 (2H, d, J=8.4 Hz), 7.65 (2H, d, J=8.4 Hz), 7.55 (1H, d, J=1 Hz), 7.49 (2H, d, J=8.4 Hz), 7.38 (1H, dd, J=8.4 Hz, 1 Hz), 7.33 (1H, d, J=8.4 Hz), 7.20 (2H, d, J=8.4 Hz), 5.24 (2H, s), 4.14 (1H, sept, J=6.6 Hz), 2.57 (2H, t, J=7.4 Hz), 1.49 (2H, m), 1.25 (2H, m), 0.98 (3H, d, J=6.6 Hz), 0.89 (3H, d, J=6.6 Hz), 0.87 (3H, t, J=7.4 Hz).

EXAMPLE 21—21(16)

By using 2-nitrophenol or the corresponding compounds, the title compounds having the following physical data were obtained by the same procedure as Reference Example 6→Reference Example 12→Reference Example 2→Example 2.

EXAMPLE 21
4-(2-phenylsulfonylaminophenoxymethyl)benzoic acid

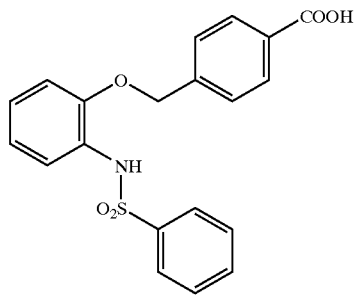

TLC: Rf 0.35 (AcOEt:hexane:AcOH=6:13:1); NMR (DMSO-d₆): δ 12.86 (1H, brs), 9.53 (1H, brs), 7.91 (2H, d, J=8.0 Hz), 7.66 (2H, d, J=8.0 Hz), 7.52 (1H, t, J=7.0 Hz), 7.45–7.25 (5H, m), 7.08 (1H, t, J=9.0 Hz), 6.95–6.80 (2H, m), 4.91 (2H, s).

EXAMPLE 21(1)
4-[2-(4-chlorophenylsulfonylamino)phenoxymethyl]benzoic acid

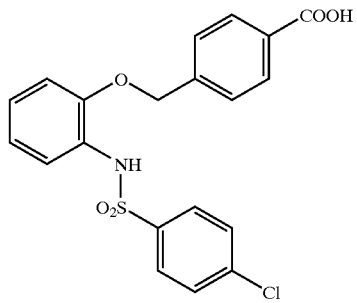

TLC: Rf 0.39 (AcOEt:hexane:AcOH=6:13:1); NMR (DMSO-d$_6$): δ 12.85 (1H, brs), 9.68 (1H, brs), 7.93 (2H, d, J=8.5 Hz), 7.60 (2H, d, J=8.5 Hz), 7.36 (4H, d, J=8.5 Hz), 7.35–7.25 (1H, m), 7.12 (1H, dt, J=7.5, 2.0 Hz), 6.96–6.85 (2H, m), 4.92 (2H, s).

EXAMPLE 21(2)
4-(2-phenylsulfonylamino-4-fluorophenoxymethyl)benzoic acid

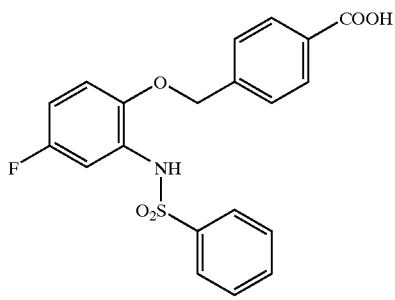

TLC: Rf 0.37 (AcOEt:hexane:AcOH=6:13:1); NMR (DMSO-d$_6$): δ 12.95 (1H, brs), 9.90 (1H, brs), 7.90 (2H, d, J=8.5 Hz), 7.72 (2H, d, J=7.0 Hz), 7.58 (1H, m), 7.46 (2H, t, J=7.5 Hz), 7.37 (2H, d, J=8.5 Hz), 7.10 (1H, d, J=9.5 Hz), 6.92 (2H, d, J=7.0 Hz), 4.95 (2H, s).

EXAMPLE 21(3)
4-(2-phenylsulfonylamino-5-fluorophenoxymethyl)benzoic acid

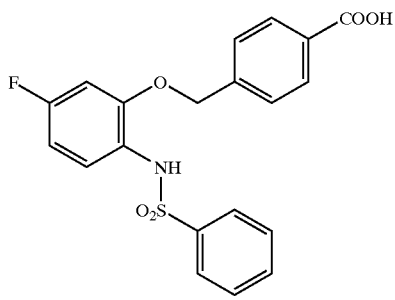

TLC: Rf 0.42 (AcOEt:hexane:AcOH=6:13:1); NMR (DMSO-d$_6$): δ 12.95 (1H, brs), 9.65 (1H, brs), 7.91 (2H, d, J=8.5 Hz), 7.60 (2H, d, J=7.0 Hz), 7.52 (1H, t, J=7.0 Hz), 7.39 (2H, d, J=7.5 Hz), 7.35 (2H, d, J=7.5 Hz), 7.26 (1H, dd, J=7.0, 6.5 Hz), 6.84 (1H, dd, J=11.0, 2.5 Hz), 6.75 (1H, dt, J=8.5, 2.5 Hz), 4.90 (2H, s).

EXAMPLE 21(4)
4-(2-phenylsulfonylamino-4-bromophenoxymethyl)benzoic acid

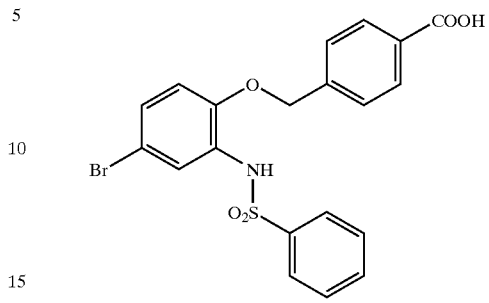

TLC: Rf 0.25 (AcOEt:hexane:AcOH=6:13:1); NMR (DMSO-d$_6$): δ 12.97 (1H, brs), 9.97 (1H, brs), 7.90 (2H, d, J=8.0 Hz), 7.69 (2H, dd, J=7.5, 2 Hz), 7.58 (1H, tt, J=7.5, 2 Hz), 7.46 (2H, d, J=7.5 Hz), 7.39 (1H, d, J=2.5 Hz), 7.36 (2H, d, J=8.0 Hz), 7.27 (1H, dd, J=9.0, 2.5 Hz), 6.89 (1H, d, J=9 Hz), 4.97 (2H, s).

EXAMPLE 21(5)
4-(2-phenylsulfonylamino-5-chlorophenylthiomethyl)benzoic acid

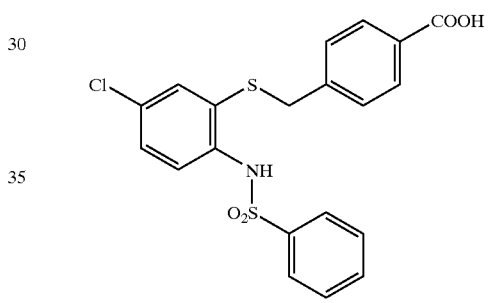

TLC: Rf 0.50 (CHCl$_3$:MeOH:AcOH=100:5:1); NMR: δ 7.99 (2H, d, J=8.4 Hz), 7.78 (2H, m), 7.41–7.62 (5H, m), 7.23 (1H, dd, J=2.6, 8.8 Hz), 7.08 (1H, d, J=2.6 Hz), 7.05 (2H, d, J=8.6 Hz), 3.71 (2H, s).

EXAMPLE 21(6)
4-(2-phenylsulfonylamino-4-methoxyphenoxymethyl)benzoic acid

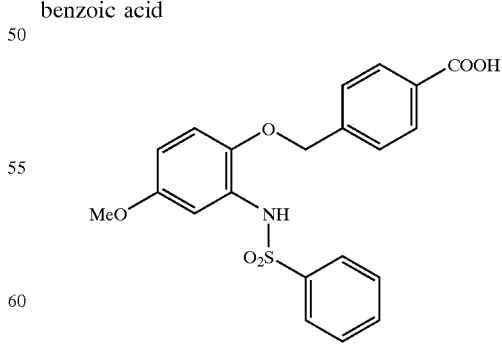

TLC: Rf 0.38 (CHCl$_3$:MeOH=17:3); NMR (DMSO-d$_6$): δ 7.90 (2H, d, J=8.5 Hz), 7.71 (2H, d, J=8.0 Hz), 7.64–7.35 (5H, m), 6.90–6.80 (2H, m), 6.44 (1H, dd, J=9.0 and 3.0 Hz), 4.89 (2H, s), 3.65 (3H, m).

EXAMPLE 21(7)

4-(2-phenylsulfonylamino-4-trifluoromethylphenoxymethyl)benzoic acid

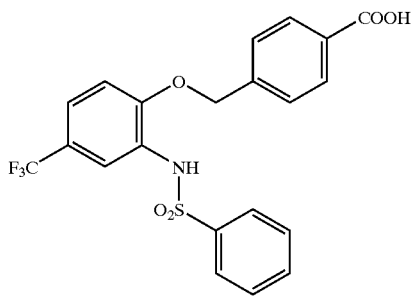

TLC: Rf 0.32 (CHCl₃:MeOH=17:3); NMR (DMSO-d₆): δ 7.92 (2H, d, J=8.5 Hz), 7.69 (2H, d, J=8.0 Hz), 7.63–7.34 (7H, m), 7.11 (1H, d, J=8.5 Hz), 5.09 (2H, s).

EXAMPLE 21(8)

4-(2-phenylsulfonylamino-4-methylphenoxymethyl)benzoic acid

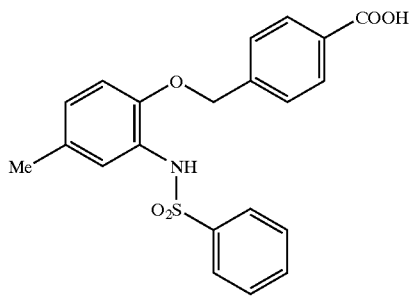

TLC: Rf 0.43 (AcOEt:hexane:AcOH=7:12:1); NMR (DMSO-d₆): δ 7.89 (2H, d, J=8.0 Hz), 7.66 (2H, d, J=7.0 Hz), 7.60–7.48 (1H, m), 7.41 (2H, d, J=8.0 Hz), 7.35 (2H, d, J=8 Hz), 7.11 (1H, d, J=2.0 Hz), 6.90 (1H, dd, J=8.0, 2.0 Hz), 6.76 (1H, d, J=8 Hz), 4.88 (2H, s), 2.19 (3H, s).

EXAMPLE 21(9)

4-(2-phenylsulfonylamino-5-methylphenoxymethyl)benzoic acid

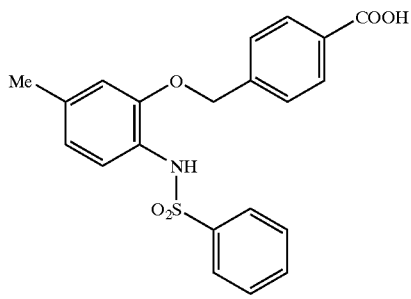

TLC: Rf 0.43 (AcOEt:hexane:AcOH=7:12:1); NMR (DMSO-d₆): δ 7.91 (2H, d, J=8.5 Hz), 7.62 (2H, d, J=7.0 Hz), 7.57–7.45 (1H, m), 7.44–7.30 (4H, m), 7.14 (1H, d, J=8.0 Hz), 6.75 (1H, s), 6.71 (1H, d, J=8.0 Hz), 4.88 (2H, s), 2.21 (3H, s).

EXAMPLE 21(10)

4-(2-benzylsulfonylamino-5-chlorophenoxymethyl)benzoic acid

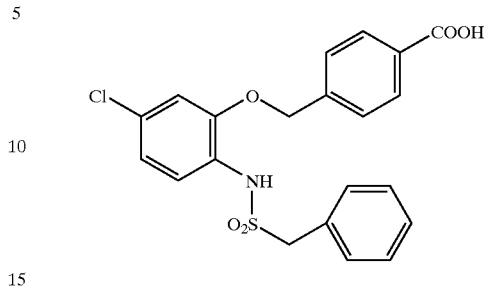

TLC: Rf 0.52 (CHCl₃:MeOH:AcOH=100:5:1); NMR (DMSO-d₆): δ 7.96 (2H, d, J=8.0 Hz), 7.67 (2H, d, J=8.0 Hz), 7.29 (5H, s), 7.21 (1H, d, J=8.2 Hz), 7.20 (1H, d, J=2.4 Hz), 6.95 (1H, dd, J=2.4, 8.2 Hz), 5.31 (2H, s), 4.38 (2H, s).

EXAMPLE 21(11)

4-(2-phenylsulfonylamino-5-methoxyphenoxymethyl)benzoic acid

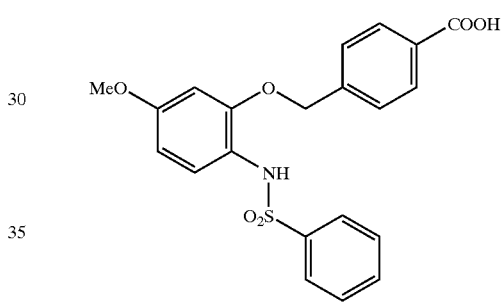

TLC: Rf 0.40 (CHCl₃:MeOH=4:1); NMR (DMSO-d₆): δ 7.90 (2H, d, J=8.5 Hz), 7.59 (2H, d, J=8 Hz), 7.51 (1H, t, J=8 Hz), 7.44–7.28 (4H, m), 7.15 (1H, d, J=8.5 Hz), 6.54–6.47 (2H, m), 4.86 (2H, s), 3.69 (3H, s).

EXAMPLE 21(12)

3-(2-phenylsulfonylamino-5-chlorophenoxymethyl)benzoic acid

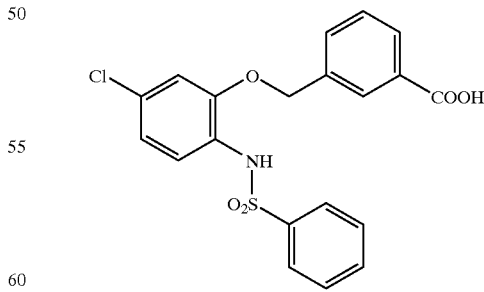

TLC: Rf 0.48 (AcOEt:hexane:AcOH=7:12:1); NMR (DMSO-d₆): δ 13.03 (1H, brs), 9.80 (1H, brs), 7.98 (1H, s), 7.95–7.86 (1H, m), 7.66 (2H, d, J=7.0 Hz), 7.58–7.46 (3H, m), 7.40 (2H, t, J=7.0 Hz), 7.27 (1H, d, J=8.5 Hz), 7.07 (1H, d, J=2.5 Hz), 6.96 (1H, dd, J=8.5, 2.5 Hz), 4.96 (2H, s).

EXAMPLE 21(13)

4-(2-phenylsulfonylamino-4-chloro-5-methylphenoxymethyl)benzoic acid

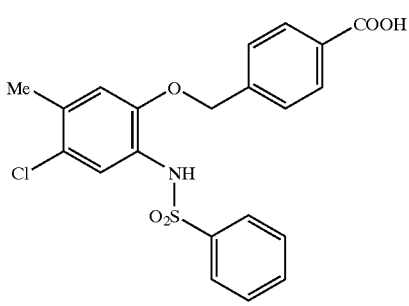

TLC: Rf 0.44 (CHCl$_3$:MeOH=4:1); NMR (DMSO-d$_6$): δ 7.91 (2H, d, J=8 Hz), 7.66 (2H, d, J=7 Hz), 7.55 (1H, t, J=7.5 Hz), 7.47–7.30 (4H, m), 7.25 (1H, s), 6.98 (1H, s), 4.93 (2H, s), 2.23 (3H, s).

EXAMPLE 21(14)

4-(2-phenylsulfonylamino-4,5-dichlorophenoxymethyl)benzoic acid

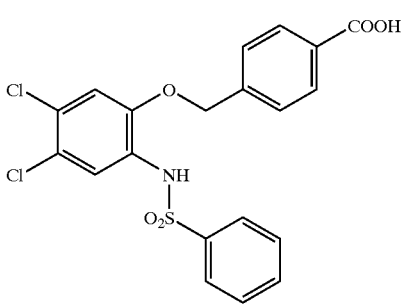

TLC: Rf 0.42 (CHCl$_3$:MeOH=4:1); NMR (DMSO-d$_6$): δ 7.92 (2H, d, J=8 Hz), 7.69 (2H, d, J=7.5 Hz), 7.58 (1H, t, J=7.5 Hz), 7.50–7.31 (5H, m), 7.26 (1H, s), 5.01 (2H, s).

EXAMPLE 21(15)

4-(2-phenylsulfonylamino-5-chlorophenoxymethyl)phthalic acid

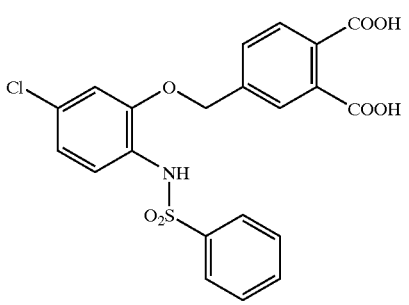

TLC: Rf 0.36 (CHCl$_3$:MeOH:AcOH=15:4:1); NMR (DMSO-d$_6$,): δ 13.23 (2H, brs), 9.86 (1H, s), 7.74–7.58 (4H, m), 7.56–7.30 (4H, m), 7.29 (1H, d, J=8.5 Hz), 7.06 (1H, d, J=2.0 Hz), 6.98 (1H, dd, J=8.5, 2 Hz), 4.94 (2H, s).

EXAMPLE 21(16)

4-(2-phenylsulfonylamino-5-chlorophenoxy)benzoic acid

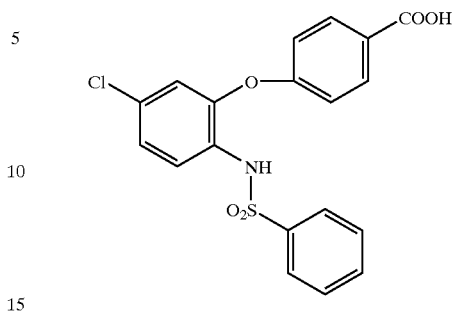

TLC: Rf 0.46 (CHCl$_3$:MeOH=9:1); NMR: δ 7.99 (2H, d, J=9.0 Hz), 7.8–7.7 (3H, m), 7.6–7.5 (1H, m), 7.5–7.3 (2H, m), 7.15 (1H, dd, J=2.2, 8.8 Hz), 6.97 (1H, s), 6.77 (1H, d, J=2.2 Hz), 6.65 (2H, d, J=9.0 Hz).

REFERENCE EXAMPLE 18

Methyl 4-[3-(2-nitro-5-chlorophenoxy)propyl]benzoate (a) OH Having Compound

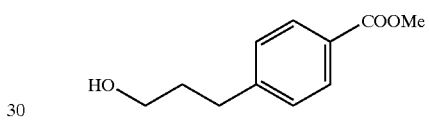

To a solution of methyl 4-(2-methoxycarbonylethyl)benzoate (1.0 g) in mixture of THF-MeOH (12 ml; THF:MeOH=5:1), sodium boron hydride (85 mg) was added. The mixture was stirred for 19 hours at room temperature. To the reaction mixture, ammonium chloride was added. After an excess of reagent was decomposed, the mixture was extracted with ethyl acetate. The organic layer was washed, dried over and concentrated under the reduced pressure. The residue was purified on silica gel column chromatography (AcOEt:hexane=2:3) to give the OH having compound (692 mg) having the following physical data.

TLC: Rf 0.38 (hexane: AcOEt=1:1).

(b) Title Compound

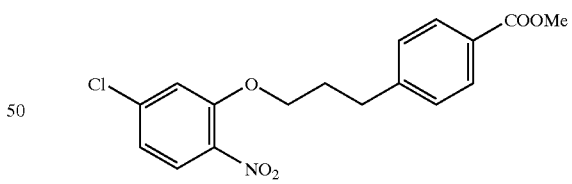

To a solution of 2-nitro-5-chlorophenol (150 mg) in THF (2.0 ml), the OH having compound prepared in the above (a) (168 mg) and triphenylphosphine (227 mg) were added in a stream of argon. After then, DEAD (136 μl was added dropwise thereto at 0° C. The reaction mixture was stirred for 24 hours at room temperature. After stirring, the mixture was quenched by adding iced water and extracted with ethyl acetate. The organic layer was washed, dried over and concentrated under the reduced pressure. The residue was purified on silica gel column chromatography (hexane: AcOEt=10:1→5:1) to give the title compound (309 mg) having the following physical data. TLC : Rf 0.24 (hexane:AcOEt=5:1).

EXAMPLE 22

4-[3-(2-phenylsulfonylamino-5-chlorophenoxy)propyl]benzoic acid

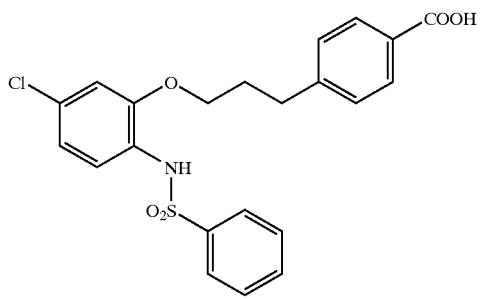

By using methyl 4-[3-(2-nitro-5-chlorophenoxy)propyl]benzoate (prepared in Reference Example 18.), the title compound having the following physical data was obtained by the same procedure as Reference Example 12→Reference Example 2→Example 2.

TLC: Rf 0.41 (CHCl$_3$:MeOH:AcOH=100:5:1); NMR: δ 8.04 (2H, d, J=8.4 Hz), 7.73 (2H, m), 7.50 (2H, m), 7.40 (2H, m), 7.21 (2H, d, J=8.2 Hz), 5.92 (1H, brs), 6.91 (1H, dd, J=2.2, 8.6 Hz), 6.67 (1H, d, J=2.2 Hz), 3.75 (2H, t, J=6.2 Hz), 2.70 (2H, t, J=7.0 Hz), 1.98 (2H, m).

EXAMPLE 22(1)–22(4)

By using corresponding diester, halfester or 4-acetylbenzoic acid, the title compounds having the following physical data were obtained by the same procedure as Reference Example 18→Reference Example 12→Reference Example 2→Example 2.

EXAMPLE 22(1)

trans-4-(2-phenylsulfonylamino-5-chlorophenoxymethyl)cyclohexanoic acid

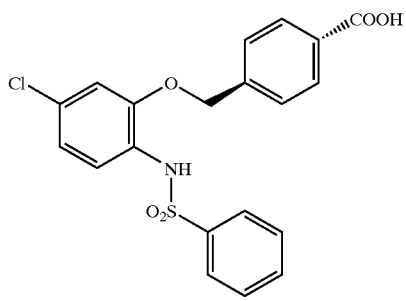

TLC: Rf 0.39 (CHCl$_3$:MeOH:AcOH=100:5:1); NMR: δ 7.70 (2H, m), 7.36–7.59 (4H, m), 6.92 (1H, brs), 6.91 (1H, dd, J=2.2, 8.4 Hz), 6.70 (1H, d, J=2.2 Hz), 3.55 (2H, d, J=6.2 Hz), 2.31 (1H, tt, J=3.8, 12.0 Hz), 2.00–2.19 (2H, m), 1.35–1.85 (5H, m), 0.95 (2H, m).

EXAMPLE 22(2)

cis-4-(2-phenylsulfonylamino-5-chlorophenoxymethyl)cyclohexanoic acid

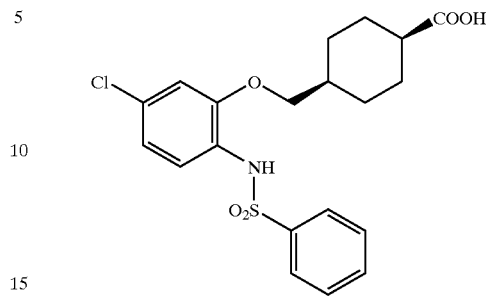

TLC: Rf 0.53 (CHCl$_3$:MeOH:AcOH=100:5:1); NMR: δ 7.70 (2H, m), 7.35–7.57 (4H, m), 6.89 (1H, dd, J=2.2, 8.6 Hz), 6.84 (1H, brs), 6.69 (1H, d, J=2.2 Hz), 3.58 (2H, d, J=6.4 Hz), 2.70 (1H, m), 1.98–2.15 (2H, m), 1.43–1.80 (5H, m), 1.15–1.40 (2H, m).

EXAMPLE 22(3)

6-(2-phenylsulfonylamino-5-chlorophenoxymethyl)nicotinic acid

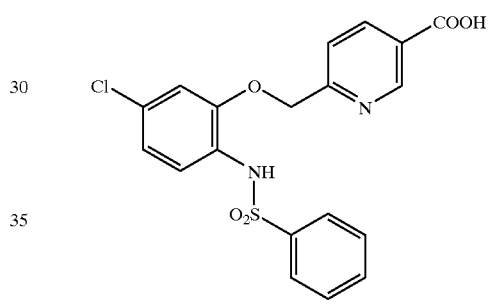

TLC: Rf 0.40 (CHCl$_3$:MeOH:AcOH=100:10:1); NMR (DMSO-d$_6$): δ 9.90 (1H, brs), 9.02 (1H, d, J=1.6 Hz), 8.27 (1H, dd, J=2.2, 8.4 Hz), 7.62 (2H, m), 7.49 (2H, m), 7.31–7.39 (2H, m), 7.31 (1H, d, J=8.6 Hz), 7.08 (1H, d, J=2.2 Hz), 7.02 (1H, dd, J=2.2, 8.6 Hz), 4.96 (2H, s).

EXAMPLE 22(4)

4-[1 RS-(2-phenylsulfonylamino-5-chlorophenoxy)ethyl]benzoic acid

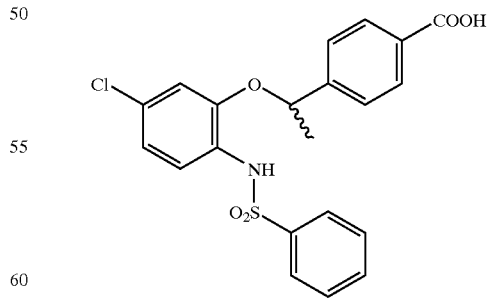

TLC: Rf 0.48 (CHCl$_3$:MeOH=9:1); NMR: δ 12.0–10.0 (1H, br), 8.00 (2H, d, J=8.4 Hz), 7.78 (2H, d, J=7.8 Hz), 7.7–7.4 (4H, m), 7.1–7.0 (3H, m), 6.88 (1H, dd, J=2.2, 8.8 Hz), 6.45 (1H, s), 5.14 (1H, q, J=6.4 Hz), 1.50 (3H, d, J=6.4 Hz).

REFERENCE EXAMPLE 19

2-nitro-5-trifluoromethylphenyl methoxymethyl ether

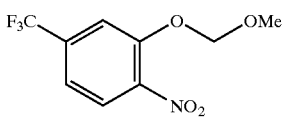

To a solution of 2-nitro-5-trifluoromethylphenol (400 mg) in DMF (4.0 ml), sodium hydride (77 mg) was added at 0° C. in a stream of argon. The mixture was stirred for 30 minutes. After stirring, methoxymethyl chloride (147 μl) was added dropwise thereto. The mixture was stirred for 20 minutes. The reaction mixture was quenched by iced water and extracted with ethyl acetate. The layer containing ethyl acetate was washed, dried over and concentrated under the reduced pressure. The residue was purified on silica gel column chromatography (hexane:AcOEt=20:1) to give the title compound (353 mg) having the following physical data.

TLC:Rf 0.44 (hexane:AcOEt=10:1).

REFERENCE EXAMPLE 20

2-amino-5-trifluoromethylphenyl methoxymethyl ether

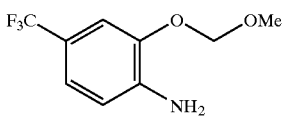

To a solution of 2-nitro-5-trifluoromethylphenyl methoxymethyl ether (353 mg; prepared in Reference Example 19.) in MeOH (3.5 ml), 10% Pd—C (30 mg) was added in a stream of argon. The mixture was stirred vigorously at room temperature under hydrogen atmosphere. The reaction mixture was filtered through celite and concentrated under the reduced pressure to give the title compound (313 mg) having the following physical data.

TLC: Rf 0.44 (hexane:AcOEt=3:1).

REFERENCE EXAMPLE 21

Methyl N-(2-methoxymethoxy-4-trifluoromethylphenyl)-phenylsulfonylaminoacetate

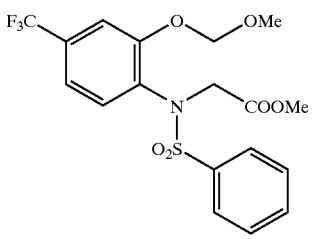

By using 2-amino-5-trifluoromethylphenyl methoxymethyl ether (313 mg; prepared in Reference Example 20.), the title compound (625 mg) having the following physical data was obtained by the same procedure as Reference Example 2→Example 17.

TLC: Rf 0.66 (benzene:acetone=9:1).

REFERENCE EXAMPLE 22

1,1-dimethyl-2-[N-(2-methoxymethoxy-4-trifluoromethyl-phenyl)-phenylsulfonylamino]ethanol

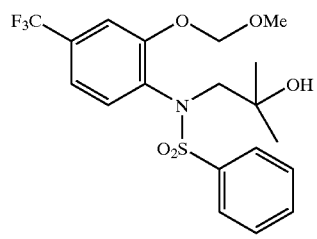

To a solution of methyl N-(2-methoxymethoxy-4-trifluoromethylphenyl)-phenylsulfonylaminoacetate (525 mg; prepared in Reference Example 21.) in THF (6.0 ml), methylmagnesium bromide (2.67 ml) was added dropwise in a stream of argon at 0° C. The mixture was stirred for 30 minutes. The reaction mixture was quenched by iced water, extracted with ethyl acetate, washed, dried over and concentrated under the reduced pressure. The residue was purified on silica gel column chromatography (hexane:AcOEt=2:1) to give the title compound (380 mg) having the following physical data.

TLC: Rf 0.26 (hexane:AcOEt=2:1).

REFERENCE EXAMPLE 23

1,1-dimethyl-2-[N-(2-hydroxy-4-trifluoromethylphenyl)-phenylsulfonylamino]ethanol

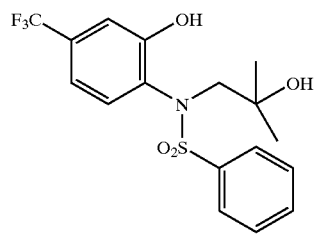

To a solution of 1,1-dimethyl-2-[N-(2-methoxymethoxy-4-trifluoromethylphenyl)-phenylsulfonylamino]ethanol (380 mg; prepared in Reference Example 22.) in THF (4.0 ml), 6N HCl (0.8 ml) was added. The mixture was stirred for 2 days at room temperature. The reaction mixture was diluted with ethyl acetate, washed, dried over and concentrated under the reduced pressure. The residue was purified on silica gel column chromatography (hexane:AcOEt=2:1) to give the title compound (291 mg) having the following physical data.

TLC: Rf 0.29 (benzene:acetone=9:1).

REFERENCE EXAMPLE 24

2-(N-isopropyl-phenylsulfonylamino)-5-trifluoromethyl-phenol

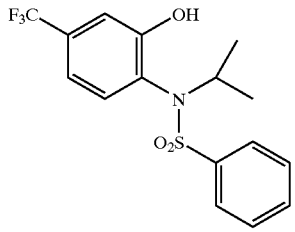

By using 2-amino-5-trifluoromethylphenyl methoxymethyl ether (prepared in Reference Example 20.), the title compound having the following physical data was obtained by the same procedure as Reference Example 2→Example 17→Reference Example 23.

TLC: Rf 0.57 (hexane:AcOEt=5:2).

EXAMPLE 23

4-[2-[N-(2-hydroxy-2-methylpropyl)-phenylsulfonylamino]-5-trifluoromethyl-phenoxymethyl]benzoic acid

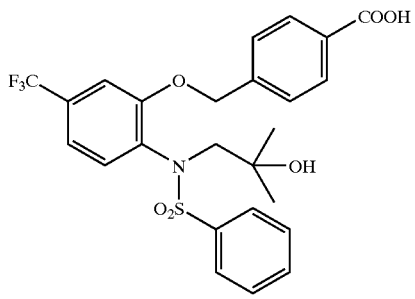

By using 1,1-dimethyl-2-[N-(2-hydroxy-4-trifluoromethylphenyl)-phenylsulfonylamino]ethanol (prepared in Reference Example 23.), the title compound having the following physical data was obtained by the same procedure as Reference Example 6→Example 2.

TLC: Rf 0.48 (CHCl₃:MeOH:AcOH=100:5:1); NMR (CD₃COCD₃): δ 8.03 (2H, brd, J=8.2 Hz), 7.47–7.66 (4H, m), 7.30–7.47 (6H, m), 5.21 (1H, m), 4.89 (1H, m), 3.79 (2H, s), 1.20 (6H, s).

EXAMPLE 23(1)–23(3)

By using 2-[N-(2-hydroxy-2-methylpropyl)-phenylsulfonylamino]-5-trifluoromethylphenol (prepared in Reference Example 23.), the title compounds having the following physical data were obtained by the same procedure as Reference Example 6→Example 2.

EXAMPLE 23(1)

4-[2-[N-(2-hydroxy-2-methylpropyl)-phenylsulfonylamino]-5-trifluoromethyl-phenoxymethyl]cinnamic acid

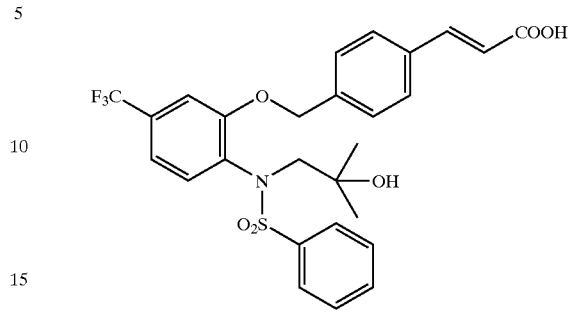

TLC: Rf 0.53 (CHCl₃:MeOH=9:1); NMR: δ 7.80 (1H, d, J=16.0 Hz), 7.54 (6H, m), 7.35 (6H, m), 6.49 (1H, d, J=16.0 Hz), 4.99 (1H, m), 4.81 (1H, m), 3.63 (2H, m), 1.21 (6H, s).

EXAMPLE 23(2)

4-[2-[N-(2-hydroxy-2-methylpropyl)-phenylsulfonylamino]-5-methylphenoxymethyl]benzoic acid

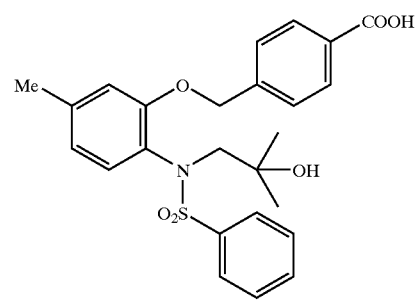

TLC: Rf 0.45 (CHCl₃:MeOH=9:1); NMR: δ 8.09 (2H, d, J=8.4 Hz), 7.60 (2H, m), 7.28–7.44 (5H, m), 7.06 (1H, m), 6.71 (2H, m), 5.00 (1H, d, J=2.8 Hz), 4.74 (1H, d, J=12.8 Hz), 3.69 (1H, d, J=14.2 Hz), 3.57 (1H, d, J=114.2 Hz), 2.33 (3H, s), 2.13 (1H, s), 1.25 (3H, bs), 1.19 (3H, bs).

EXAMPLE 23(3)

4-[2-[N-(2-hydroxy-2-methylpropyl)-2-furanylsulfonylamino]-5-trifluoromethylphenoxymethyl]benzoic acid

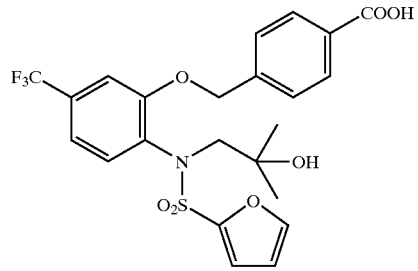

TLC: Rf 0.42 (CHCl₃:MeOH=9:1); NMR: δ 8.15 (2H, d, J=8.4 Hz), 7.52 (2H, d, J=8.4 Hz), 7.21–7.34 (4H, m), 6.82 (1H, m), 6.38 (1H, m), 5.12 (2H, m), 3.76 (2H, m), 2.12 (1H, s), 1.23 (6H, bs).

EXAMPLE 24

4-[2-(N-isopropyl-phenylsulfonylamino)-5-trifluoromethylphenoxymethyl]phenoxy acetic acid

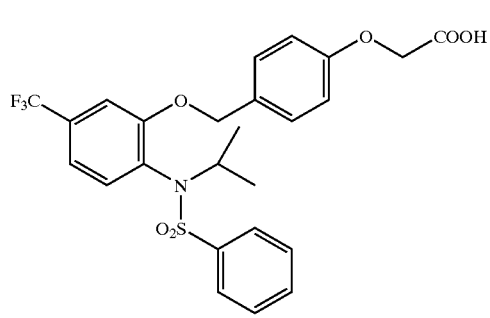

By using 2-(N-isopropyl-phenylsulfonylamino)-5-trifluoromethylphenol (prepared in Reference Example 24.), the title compound having the following physical data was obtained by the same procedure as Reference Example 18 (b)→Example 2.

TLC: Rf 0.39 (AcOEt:hexane:AcOH=9:10:1); NMR: δ 7.80 (2H, d, J=7.5 Hz), 7.49 (1H, t, J=7.5 Hz), 7.40–7.20 (7H, m), 6.95 (2H, d, J=8.5 Hz), 4.98 (2H, s), 4.72 (2H, s), 4.28 (1H, qn, J=6.5 Hz), 1.06 (3H, d, J=6.5 Hz), 1.01 (3H, d, J=6.5 Hz).

EXAMPLE 24(1)–24(10)

By using the corresponding compounds, the title compounds having the following physical data were obtained by the same procedure as Reference Example 18 (b)→Example 2.

EXAMPLE 24(1)

5-[2-(N-isopropyl-phenylsulfonylamino)-5-trifluoromethylphenoxymethyl]thiophene-2-carboxylic acid

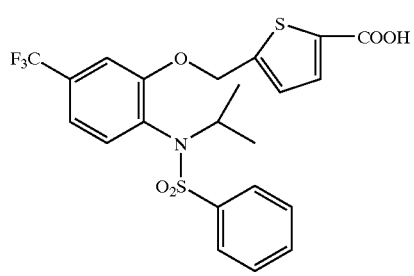

TLC: Rf 0.54 (CHCl$_3$:MeOH:AcOH=90:9:1); NMR: δ 7.9–7.7 (3H, m), 7.6–7.3 (3H, m), 7.3–7.2 (3H, m), 7.16 (1H, d, J=4.0 Hz), 5.20 (2H, s), 4.5–4.3 (1H, m), 1.10 (3H, d, J=3.8 Hz), 1.32 (3H, d, J=3.8 Hz).

EXAMPLE 24(2)

5-[2-(N-isopropyl-phenylsulfonylamino)-5-trifluoromethylphenoxymethyl]furan-2-carboxylic acid

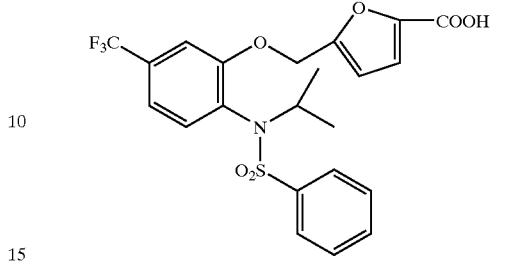

TLC: Rf 0.17 (CHCl$_3$:MeOH=5:1); NMR: δ 7.76 (2H, d, J=8 Hz), 7.54–7.29 (3H, m), 7.29–7.13 (4H, m), 6.52 (1H, m), 5.00 (2H, s), 4.31 (1H, m), 0.98 (6H, m).

EXAMPLE 24(3)

4-[2-(N-isopropyl-phenylsulfonylamino)-5-methylphenoxymethyl]phenoxyacetic acid

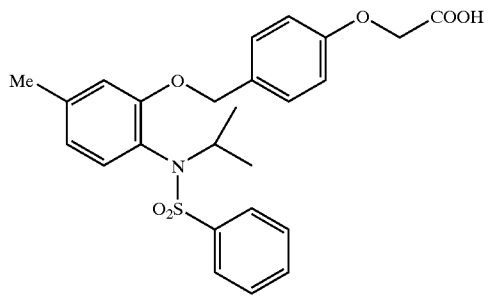

TLC: Rf 0.09 (AcOEt); NMR: δ 7.81 (2H, d, J=7.5 Hz), 7.50–7.30 (5H, m), 7.00–6.91 (3H, m), 6.82–6.73 (2H, m), 4.91 (2H, s), 4.71 (2H, s), 4.27 (1H, sept, J=7 Hz), 2.36 (3H, s), 1.05 (3H, d, J=7 Hz), 1.01 (3H, d, J=7 Hz).

EXAMPLE 24(4)

5-[2-(N-isopropyl-phenylsulfonylamino)-5-methylphenoxymethyl]thiophene-2-carboxylic acid

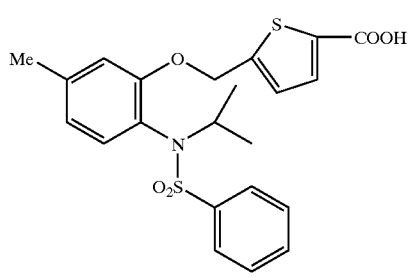

TLC: Rf 0.30 (CHCl$_3$:MeOH=9:1); NMR: δ 7.9–7.7 (3H, m), 7.5–7.4 (1H, m), 7.4–7.3 (2H, m), 7.12 (1H, d, J=3.6 Hz), 7.01 (1H, d, J=8.2 Hz), 6.9–6.7 (2H, m), 5.12 (2H, s), 4.5–4.3 (1H, m), 2.38 (3H, s), 1.51 (3H, d, J=2.4 Hz), 1.05 (3H, d, J=2.4 Hz).

EXAMPLE 24(5)

4-[2-(N-isopropyl-phenylsulfonylamino)-5-methylphenoxymethyl]cinnamic acid

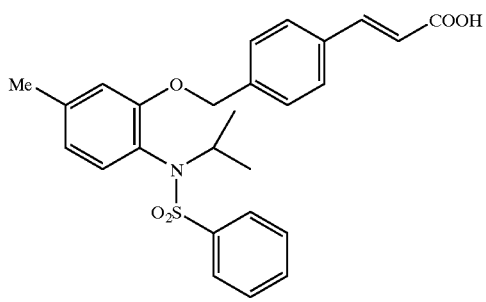

TLC: Rf 0.39 (hexane:AcOEt=1:2); NMR: δ 7.86–7.78 (3H, m), 7.60–7.26 (7H, m), 6.97 (1H, d, J=8 Hz), 6.80–6.74 (2H, m), 6.48 (1H, d, J=16 Hz), 5.01 (2H, s), 4.36 (1H, sept., J=6.5 Hz), 1.05 (6H, d, J=6.5 Hz).

EXAMPLE 24(6)

4-[2-(N-isopropyl-phenylsulfonylamino)-5-chlorophenoxymethyl]phenoxyacetic acid

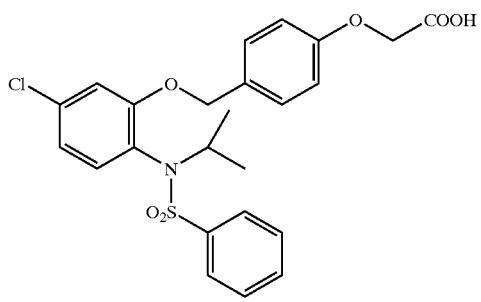

TLC: Rf 0.10 (CHCl$_3$:MeOH=10:1); NMR: δ 7.80–7.76 (2H, m), 7.52–7.44 (1H, m), 7.35–7.26 (4H, m), 7.05–6.91 (5H, m), 4.91 (2H, s), 4.72 (2H, s), 4.28 (1H, sept., J=7 Hz), 1.05 (3H, d, J—7 Hz), 1.00 (2H, d, J=7 Hz).

EXAMPLE 24(7)

4-[2-(N-isopropyl-phenylsulfonylamino)-5-chlorophenoxymethyl]cinnamic acid

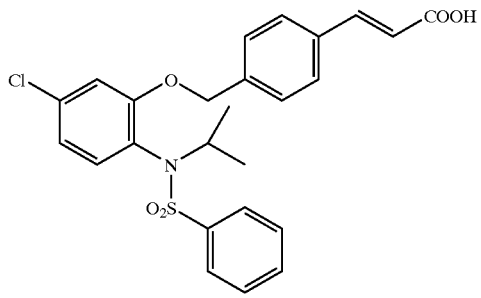

TLC: Rf 0.31 (hexane:AcOEt=1:1); NMR: δ 7.85–7.77 (2H, m), 7.60–7.35 (7H, m), 7.05–6.90 (3H, m), 6.48 (1H, d, J=16 Hz), 5.01 (2H, s), 4.36 (1H, sept., J=6.5 Hz), 1.04 (6H, d, J=7 Hz).

EXAMPLE 24(8)

5-[2-(N-isopropyl-phenylsulfonylamino)-5-chlorophenoxymethyl]thiophene-2-carboxylic acid

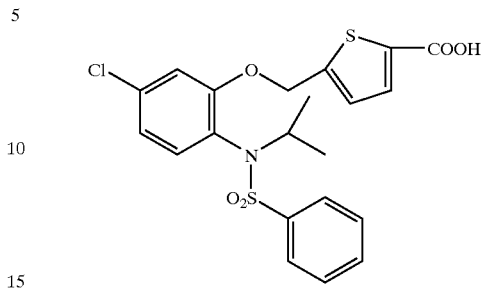

TLC: Rf 0.42 (CHCl$_3$:MeOH=9:1); NMR: δ 7.8–7.7 (3H, m), 7.5–7.3 (3H, m), 7.2–6.9 (4H, m), 5.15 (1H, d, J=13.2 Hz), 5.08 (1H, d, J=13.2 Hz), 4.5–4.3 (1H, m), 5.5–4.0 (1H, br), 1.08 (3H, d, J=2.6 Hz), 1.05 (3H, d, J=2.6 Hz).

EXAMPLE 24(9)

5-[2-(N-isopropyl-phenylsulfonylamino)-5-chlorophenoxymethyl]furan-2-carboxylic acid

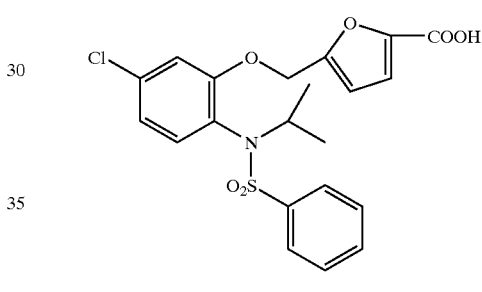

TLC: Rf 0.37 (CHCl$_3$:MeOH=9:1); NMR: δ 7.9–7.7 (2H, m), 7.6–7.4 (3H, m), 7.31 (1H, d, J=3.4 Hz), 7.0–6.9 (3H, m), 6.63 (1H, d, J=3.4 Hz), 5.03 (1H, d, J=13.2 Hz), 4.96 (1H, d, J=13.2 Hz), 5.5–4.5 (1H, br), 4.4–4.2 (1H, m), 1.03 (6H, d, J=6.6 Hz).

EXAMPLE 24(10)

4-[2-[2-(N-isopropyl-phenylsulfonylamino)-5-trifluoromethylphenoxy]-ethyl]benzoic acid

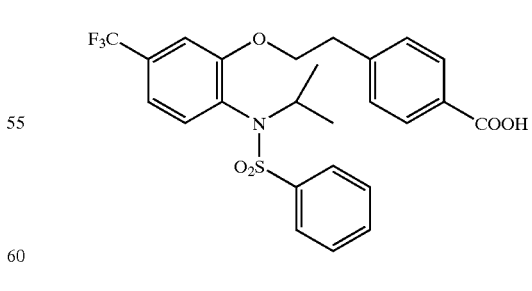

TLC: Rf 0.40 (CHCl$_3$:MeOH=9:1); NMR: δ 8.07 (2H, d, J=8.5 Hz), 7.83 (2H, d, J=7 Hz), 7.65–7.45 (5H, m), 7.39 (2H, d, J=8.5 Hz), 7.25–7.08 (3H, m), 4.37 (1H, m), 4.25–4.05 (2H, m), 3.08 (2H, d, J=7 Hz), 0.99 (3H, d, J=6.5 Hz), 0.84 (3H, d, J=6.5 Hz).

EXAMPLE 25

2-methoxy-4-[2-(N-isopropyl-phenylsulfonylamino)-5-trifluoromethylphenoxymethyl]benzoic acid

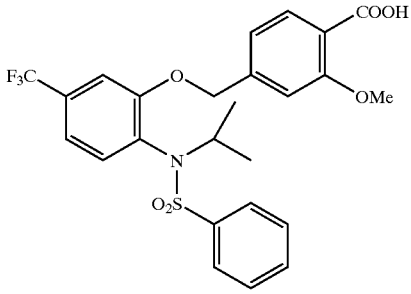

By using 2-(N-isopropyl-phenylsulfonylamino)-5-trifluoromethylphenol (prepared in Reference Example 24.), the title compound having the following physical data was obtained by the same procedure as Reference Example 6→Example 2.

TLC: Rf 0.49 (CHCl$_3$:MeOH=9:1); NMR: δ 11.0–10.6 (1H, br), 8.21 (1H, d, J=7.8 Hz), 7.9–7.8 (2H, m), 7.71 (1H, d, J=0.6 Hz), 7.7–7.4 (3H, m), 7.3–7.2 (2H, m), 7.2–7.1 (1H, m), 7.00 (1H, d, J=7.8 Hz), 5.22 (2H, s), 4.6–4.4 (1H, m), 4.18 (3H, s), 1.08 (3H, d, J=6.6 Hz), 0.92 (3H, d, J=6.6 Hz).

EXAMPLE 26

2-hydroxy-4-[2-(N-isopropyl-phenylsulfonylamino)-5-trifluoromethylphenoxymethyl]benzoic acid

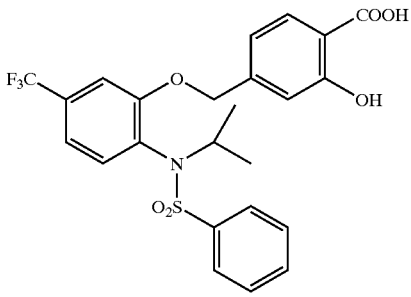

By using 2-(N-isopropyl-phenylsulfonylamino)-5-trifluoromethylphenol (prepared in Reference Example 24.), the title compound having the following physical data was obtained by the same procedure as Reference Example 6→Reference Example 23→Example 2.

TLC: Rf 0.56 (CHCl$_3$:MeOH:AcOH=90:9:1); NMR: δ 10.51 (1H, s), 7.95 (1H, d, J=8.0 Hz), 7.9–7.8 (2H, m), 7.6–7.4 (3H, m), 7.3–7.2 (3H, m), 7.1–7.0 (2H, m), 5.05 (2H, s), 4.5–4.3 (1H, m), 1.09 (3H, d, J=5.0 Hz), 1.06 (3H, d, J=5.0 Hz).

EXAMPLE 26(1)–26(2)

By using the corresponding compounds, the title compounds having the following physical data were obtained by the same procedure as Reference Example 6→Reference Example 23→Example 2.

EXAMPLE 26(1)

2-hydroxy-4-[2-(N-isopropyl-phenylsulfonylamino)-5-methylphenoxymethyl]benzoic acid

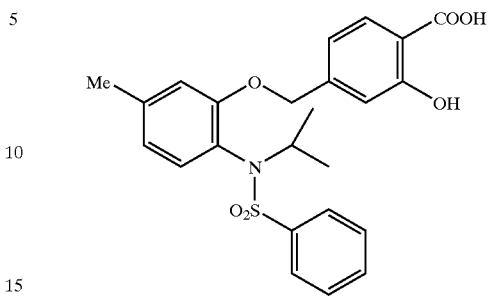

TLC: Rf 0.20 (CHCl$_3$:MeOH=17:3); NMR: δ 10.50 (1H, s), 7.92 (1H, d, J=8.5 Hz), 7.83 (2H, m), 7.54–7.32 (3H, m), 7.05–6.93 (3H, m), 6.81–6.72 (2H, m), 4.97 (2H, s), 4.42 (1H, m), 2.35 (3H, s), 1.13–0.98 (6H, m).

EXAMPLE 26(2)

2-hydroxy-4-[2-(N-isopropyl-phenylsulfonylamino)-5-chlorophenoxymethyl]benzoic acid

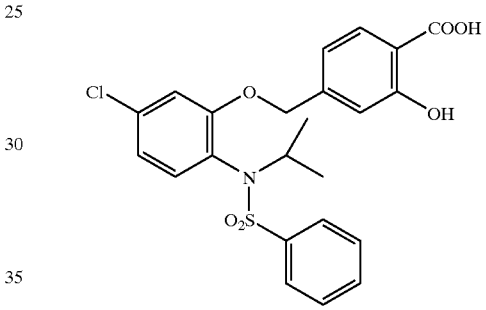

TLC: Rf 0.21 (CHCl$_3$:MeOH=9:1); NMR: δ 7.93 (1H, d, J=8.0 Hz), 7.9–7.7 (2H, m), 7.6–7.3 (3H, m), 7.1–6.9 (5H, m), 4.97 (2H, s), 4.5–4.3 (1H, m), 3.0–2.0 (2H, br), 1.07 (3H, d, J=6.2 Hz), 1.04 (3H, d, J=6.2 Hz).

REFERENCE EXAMPLE 25

4-phenylsulfonylamino-3-nitrobenzotrifluoride

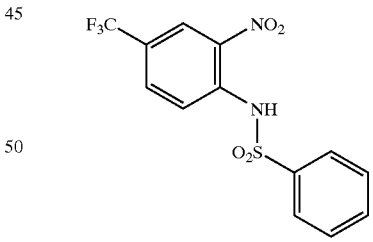

To a solution of 4-amino-3-nitrobenzotrifluoride (3.09 g) in THF sodium hydride (660 mg) was added. The mixture was stirred for 30 minutes at room temperature. After stirring, benzenesulfonylchloride (3.18 g) was added thereto. The mixture was stirred for 2 hours at room temperature. In addition, sodium hydride (420 mg) was added thereto. The mixture was stirred for 1 hour. The reaction mixture was acidified by adding an aqueous solution of ammonium chloride and extracted with ethyl acetate. The organic layer was washed, dried over, filtered and concentrated to give the title compound (4.86 g) having the following physical data.

TLC: Rf 0.31 (hexane:AcOEt=3:1).

REFERENCE EXAMPLE 26

4-phenylsulfonylamino-3-aminobenzotrifluoride

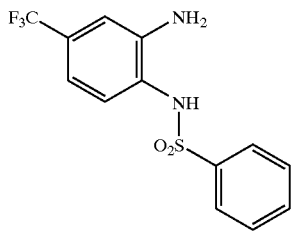

By using 4-phenylsulfonylamino-3-nitrobenzotrifluoride (2.4 g; prepared in Reference Example 25.), the title compound (1.7 g) having the following physical data was obtained by the same procedure as Reference Example 12.

TLC: Rf 0.17 (hexane:AcOEt=3:1).

EXAMPLE 27

Methyl 4-(2-phenylsulfonylamino-5-trifluoromethylphenyl-aminomethyl)-benzoate

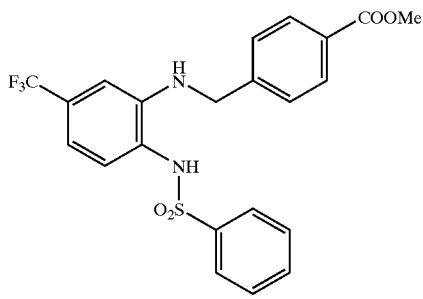

To a solution of 4-phenylsulfonylamino-3-aminobenzotrifluoride (100 mg; prepared in Reference Example 26) and terephthal aldehyde acid methyl ester (78 mg) in MeOH (2 ml), acetic acid (1.5 ml) was added. The mixture was stirred for 2 hours at room temperature. After stirring, a solution of sodium cyanoborohydride (30 mg) in MeOH (2 ml) was added. The mixture was stirred for 2 hours at room temperature. The reaction solution was extracted with $H_2O$-AcOEt, washed, dried over, filtered and concentrated. The precipitate was washed with hexane to give the title compound (146 mg) having the following physical data.

TLC: Rf 0.27 (hexane:AcOEt=2:1); NMR: δ 8.02 (2H, m), 7.76 (2H, m), 7.6–7.4 (5H, m), 6.74–6.70 (2H, m), 6.55–6.50 (1H, m), 6.02 (1H, bs), 5.35 (1H, m), 4.40 (2H, m), 3.92 (3H, s).

EXAMPLE 28

4-[2-(N-isopropyl-phenylsulfonylamino)-5-trifluoromethyl-phenylaminomethyl]benzoic acid

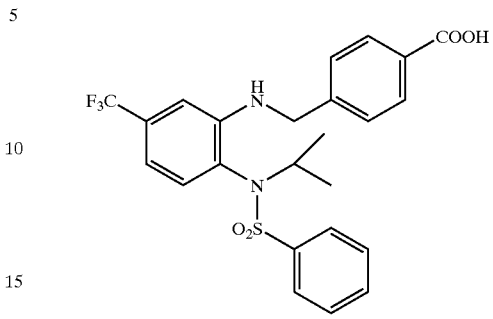

By using methyl 4-(2-phenylsulfonylamino-5-trifluoromethylphenylaminomethyl)benzoate (prepared in Example 27.), the title compound having the following physical data was obtained by the same procedure as Example 17→Example 2.

TLC: Rf 0.45 (hexane:AcOEt=1:1); NMR: δ 8.10 (2H, d, J=8.5 Hz), 7.8–7.7 (2H, m), 7.6–7.4 (5H, m), 6.8–6.7 (2H, m), 6.7–6.6 (1H, m), 5.34 (1H, m), 4.69 (1H, sept, J=7 Hz), 4.45 (2H, d, J=6 Hz), 1.15 (3H, d, J=7 Hz), 1.01 (3H, d, J=7 Hz).

EXAMPLE 29

Methyl 4-[N-methyl-[2-(N-isopropyl-phenylsulfonyl-amino)-5-trifluoromethylphenyl]aminomethyl]benzoate

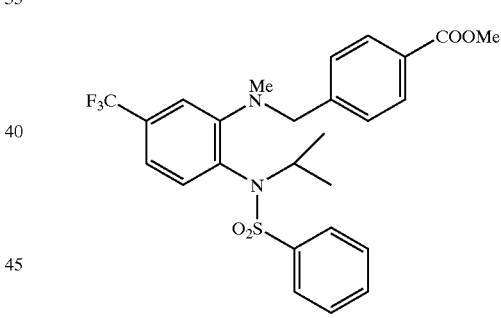

Methyl 4-[2-(N-isopropyl-phenylsulfonylamino)-5-trifluoromethyl-phenyl]aminomethyl]benzoate (200 mg) prepared by the same procedure as Example 17 by using methyl 4-(2-phenylsulfonylamino-5-trifluoromethyl-phenylaminomethyl)benzoate (prepared in Example 27) was dissolved in DMF (5 ml). Sodium hydride (64 mg) and methyl iodide (200 µl) were added thereto. The mixture was stirred for 24 hours at 60° C. The reaction mixture was extracted with $H_2O$-AcOEt, washed, dried over, filtered and concentrated under the reduced pressure. The residue was purified on silica gel column chromatography (hexane:AcOEt=5:1) to give the title compound (105 mg) having the following physical data.

TLC: Rf 0.54 ($CH_2Cl_2$); NMR: δ 8.0 (2H, m), 7.9 (2H, m), 7.6–7.5 (3, m), 7.4 (2H, m), 7.4–7.2 (2H, m), 7.0 (1H, m), 4.6–4.3 (2H, m), 3.92 (3H, m), 2.72 (3, s), 1.2 (3H, m), 0.8 (3H, m).

EXAMPLE 30

4-[N-methyl-[2-(N-isopropyl-phenylsulfonylamino)-5-trifluoromethylphenyl]aminomethyl]benzoic acid

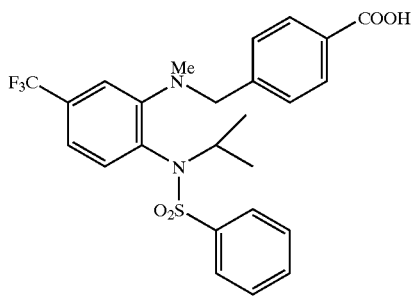

By using methyl 4-[N-methyl-[2-(N-isopropyl-phenylsulfonylamino)-5-trifluoromethylphenyl]aminomethyl]benzoate (prepared in Example 29.), the title compound having the following physical data was obtained by the same procedure as Example 2.

TLC: Rf 0.45 (hexane:AcOEt=1:1); NMR: δ 8.09 (2H, d, J=8 Hz), 7.9 (2H, m), 7.7–7.4 (5H, m), 7.2 (2H, m), 7.0 (1H, m), 4.6–4.4 (3H, m), 2.75 (3H, s), 1.26 (3H, d, J=7 Hz), 0.85 (3H, d, J=7 Hz).

REFERENCE EXAMPLE 27

Methyl 2-t-butoxycarbonylamino-5-trifluoromethylbenzoate

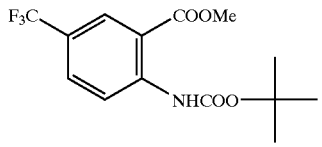

4-t-butoxycarbonylaminobenzotrifluoride (3.90 g) was dissolved in THF. At −50° C., t-butyl lithium (30 ml) was added dropwise thereto. The mixture was stirred for 3 hours with keeping at −50° C. Carbon dioxide gas was bubbled into this mixture under stirring (the temperature increased to about −30° C.). The solvent was distilled out. The back-extractration of the residue was 2N NaOH-ether mixture solution was carried out. The aqueous layer was acidified by adding 2N HCl, extracted with ether, washed and dried over. In addition, the layer containing ether was washed, dried over, filtered and concentrated after combining the said layer containing ether to give the crude compound. Such crude compound was dissolved in ether. A solution of diazomethane in ether was added thereto until the reaction solution became yellow. The reaction solution was concentrated and purified on silica gel column chromatography (hexane:AcOEt=20:1→10:1) to give the title compound (3.80 g) having the following physical data.

TLC: Rf 0.70 (hexane:AcOEt=3:1).

REFERENCE EXAMPLE 28

Methyl 2-amino-5-trifluoromethylbenzoate

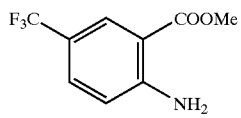

To a solution of methyl 2-t-butoxycarbonylamino-5-trifluoromethyl-benzoate (3.80 g; prepared in Reference Example 27.) in methylene chloride (30 ml), trifluoroacetic acid (6 ml) was added. The mixture was stirred for 8 hours at room temperature. The solvent was distilled off azeotropically with toluene three times. To the reaction mixture, an aqueous sodium hydrogencarbonate solution was added to neutralize. The mixture was extracted with ethyl acetate, washed, dried, filtered and concentrated under the reduced pressure. The residue was purified on silica gel column chromatography (hexane:AcOEt=5:1) to give the title compound (2.35 g) having the following physical data.

TLC: Rf 0.20 (hexane:AcOEt=5:1).

EXAMPLE 31

4-[2-(N-isopropyl-phenylsulfonylamino)-5-trifluoromethyl-benzoylamino]benzoic acid

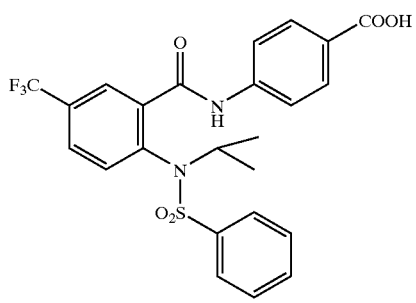

By using methyl 2-amino-5-trifluoromethylbenzoate (prepared in Reference Example 28.), the title compound having the following physical data was obtained by the same procedure as Reference Example 2→Reference Example 3→Example 1→Example 2.

TLC: Rf 0.25 (hexane:AcOEt=1:2); NMR: δ 10.01 (1H, s), 8.18–8.14 (3H, m), 7.93 (8H, m), 6.64 (1H, d, J=8 Hz), 4.67 (1H, sept., J=6.5 Hz), 1.09 (3H, d, J=6.5 Hz), 0.86 (3H, d, J=6.5 Hz).

REFERENCE EXAMPLE 29

Methyl 4-[2-[N-[1,3-bis(t-butyldimethylsilyloxy)prop-2-yl]-phenylsulfonylamino]-5-trifluoromethylphenoxymethyl]benzoate (a) 1,3-diOTBs Having Compound (Intermediate)

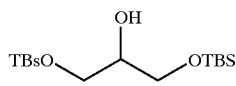

To a solution of glycerol (2 g) in DMF (15 ml), solution of t-butyldimethylsilylchloride (6.5 g) and imidazole (3.3 g) in DMF (8 ml) was added dropwise slowly at 0° C. The solution was stirred for 3 hours at room temperature. The reaction mixture was poured into water, extracted with AcOEt-hexane (AcOEt:hexane=1:1) mixture solution and purified on silica gel column chromatography to give the 1,3-diOTBs having compound (5.8 g) having the following physical data.

TLC: Rf 0.5 (hexane:AcOEt=9:1).

(b) Title Compound

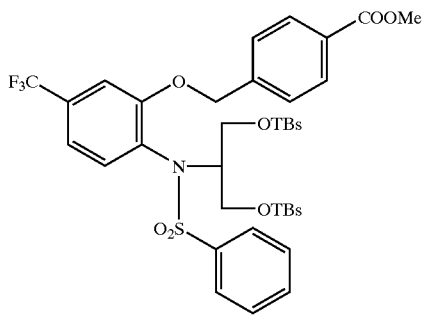

By using methyl 4-(2-phenylsulfonylamino-5-trifluoromethylphenoxymethyl)benzoate (180 mg; prepared in Example 15.) and the 1,3-diOTBs having compound prepared in the above (a) (247 mg), the title compound (200 mg) having the following physical data was obtained by the same procedure as Example 19.

TLC: Rf 0.28 (hexane:AcOEt=9:1).

EXAMPLE 32

Methyl 4-[2-[N-(1,3-dihydroxyprop-2-yl)-phenylsulfonyl-amino]-5-trifluoromethylphenoxymethyl]benzoate

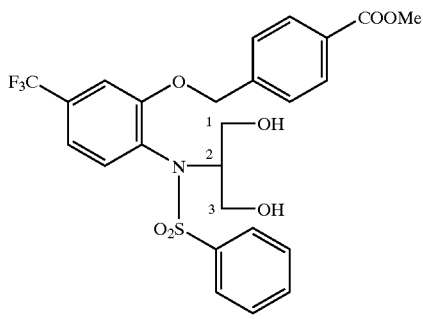

To a solution of methyl 4-[2-[N-[1,3-bis(t-butyldimethyl-silyloxy)prop-2-yl]-phenylsulfonylamino]-5-trifluoromethylphenoxymethyl]benzoate (200 mg; prepared in Reference Example 29.) in THF (3 ml), a solution of tetrabutylammonium fluoride (0.57 ml) in THF (1 M) was added. The solution was stirred for 3 hours at room temperature. To the reaction compound, water was added. The mixture was extracted with ethyl acetate, washed, dried over and purified on silica gel column chromatography (110 mg) having the following physical data.

TLC: Rf 0.50 (CH$_2$Cl$_2$:MeOH=9:1); NMR: δ 8.08 (2H, d, J=8.2 Hz), 7.78 (2H, d, J=7.2 Hz), 7.70–7.24 (8H, m), 5.14 (1H, d, J=12.0 Hz), 5.06 (1H, d, J=2.0 Hz), 4.50–4.30 (1H, m), 3.93 (3H, s), 3.80–3.20 (4H, m), 2.72 (1H, dd, J=3.6, 18.2 Hz).

EXAMPLE 33

4-[2-[N-(1,3-dihydroxyprop-2-yl)-phenylsulfonylamino]-5-trifluoromethylphenoxymethyl]benzoic acid

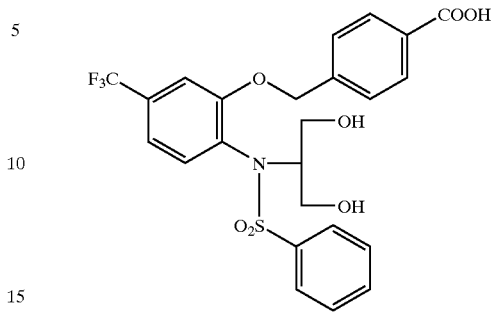

By using methyl 4-[2-[N-(1,3-dihydroxyprop-2-yl)-phenylsulfonylamino]-5-trifluoromethylphenoxymethyl]benzoate (prepared in Example 32.), the title compound having the following physical data was obtained by the same procedure as Example 2.

TLC: Rf 0.51 (AcOEt:AcOH=99:1); NMR: δ 8.13 (2H, d, J=8.4 Hz), 7.8–7.7 (2H, m), 7.6–7.2 (8H, m), 5.17 (1H, d, J=11.4 Hz), 5.08 (1H, d, J=11.4 Hz), 4.5–4.3 (1H, m), 3.6–3.5 (2H, m), 3.4–3.2 (2H, m).

EXAMPLE 34

4-[2-[N-(1,3-dimethoxyprop-2-yl)-phenylsulfonylamino]-5-trifluoromethylphenoxymethyl]benzoic acid

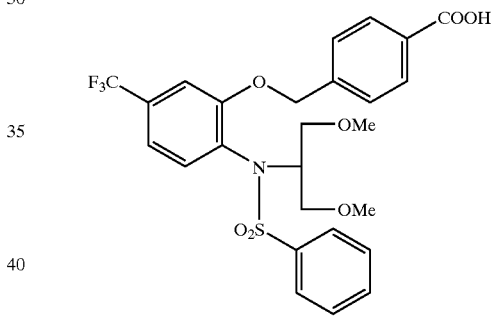

By using methyl 4-[2-[N-(1,3-dihydroxyprop-2-yl)-phenylsulfonylamino]-5-trifluoromethylphenoxymethyl]benzoate (prepared in Example 32.), the title compound having the following physical data was obtained by the same procedure as Reference Example 19→Example 2

TLC: Rf 0.57 (CHCl$_3$:MeOH=9:1); NMR: δ 8.18 (2H, d, J=8.2 Hz), 7.8–7.7 (2H, m), 7.63 (2H, d, J=8.2 Hz), 7.6–7.4 (3H, m), 7.3–7.2 (3H, m),5.18 (2H, s), 4.5–4.4 (1H, m), 3.7–3.6 (1H, m), 3.5–3.0 (3H, m), 3.09 (3H, s), 3.04 (3H, s).

REFERENCE EXAMPLE 30

2-(N-isopropyl-methylsulfonylamino)-5-trifluoromethylphenyl methoxymethyl ether

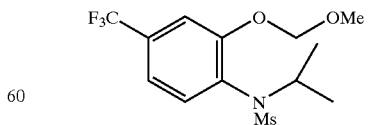

By using 2-amino-5-trifluoromethylphenyl methoxymethyl ether and mesylchloride, the title compound having the following physical data was obtained by the same procedure as Reference Example 2→Example 17.

TLC: Rf 0.40 (hexane:AcOEt=2:1).

REFERENCE EXAMPLE 31

2-(N-isopropyl-2-hydroxyhexylsulfonylamino)-5-trifluoromethylphenyl methoxymethyl ether

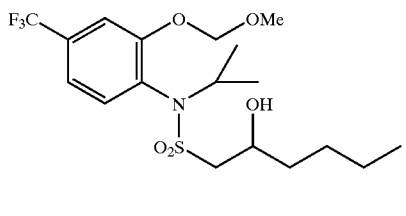

To a solution of 2-(N-isopropyl-methylsulfonylamino)-5-trifluoromethyl-phenyl methoxymethyl ether (135 mg; prepared in Reference Example 30.) in THF (3.0 ml), hexamethylphosphoramide (420 µl) was added in a stream of argon. At −78° C., n-butyl lithium (742 µl) was added dropwise thereto. The mixture was stirred for 1.5 hours. To the mixture, a solution of valeraldehyde (102 mg) in THF (1.0 ml) was added dropwise. The mixture was stirred for 30 minutes. To the reaction mixture, water was added. The mixture was extracted with ethyl acetate, washed, dried over and concentrated with the reduced pressure. The residue was purified on silica gel column chromatography (hexane:AcOEt=4:1) to give the title compound (69 mg) having the following physical data.

TLC: Rf 0.49 (hexane:AcOEt=2:1).

REFERENCE EXAMPLE 32

2-(N-isopropyl-1-hexenylsulfonylamino)-5-trifluoromethyl-phenyl methoxymethyl ether

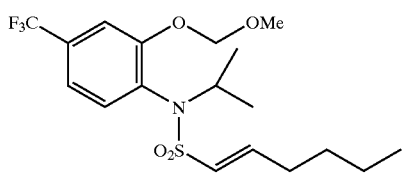

To a solution of 2-(N-isopropyl-2-hydroxyhexylsulfonylamino)-5-trifluoromethylphenyl methoxymethyl ether (160 mg; prepared in Reference Example 31) in methylene chloride (2.0 ml), triethylamine (104 µl) and mesylchloride (35 µl) were added in a stream of argon at 0° C. The mixture was stirred for 10 minutes. To the mixture, 1,5-diazabicyclo[5,4,0]undecene (134 µl) was added. The mixture was stirred for 2 hours at room temperature. To the reaction mixture, diluted HCl was added. The mixture was extracted with ethyl acetate, washed, dried over and concentrated with the reduced pressure. The residue was purified on silica gel column chromatography (hexane:AcOEt=8:1) to give the title compound (140 mg) having the following physical data.

TLC : Rf 0.37 (hexane:AcOEt=3:1).

EXAMPLE 35

4-[2-(N-isopropyl-1-hexenylsulfonylamino)-5-trifluoromethylphenoxymethyl]benzoic acid

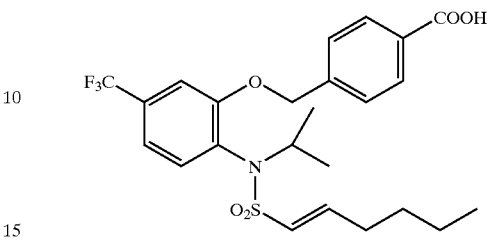

By using 2-(N-isopropyl-1-hexenylsulfonylamino)-5-trifluoromethylphenyl methoxymethyl ether (prepared in Reference Example 32.), the title compound having the following physical data was obtained by the same procedure as Reference Example 23→Reference Example 6→Example 2.

TLC: Rf 0.44 (CHCl$_3$:MeOH:AcOH=100:5:1); NMR: δ 8.19 (2H, d, J=8.2 Hz), 7.62 (2H, d, J=8.2 Hz), 7.22–7.45 (3H, m), 6.68 (1H, td, J=7.0, 15.0 Hz), 6.09 (1H, td, J=1.4, 15.0 Hz), 5.19 (2H, s), 4.15 (1H, m), 1.97 (2H, m), 1.16–1.40 (7H, m), 1.03 (3H, d, J=6.8 Hz), 0.86 (3H, m).

REFERENCE EXAMPLE 33

Methyl 4-(2-cyclopentylsulfinylamino-5-trifluoromethylphenoxymethyl)-benzoate

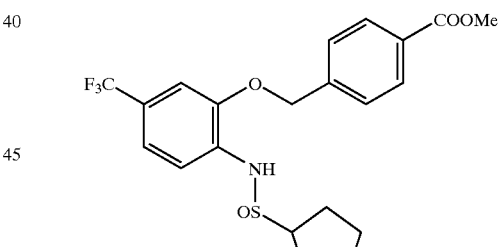

To a solution of methyl 4-(2-amino-5-trifluoromethylphenoxymethyl)-benzoate (300 mg) in methylene chloride (3.0 ml), pyridine (187 µl) and triphenylphosphine (315 mg) were added in a stream of argon. At 0° C., cyclopentylsulfonylchloride (202 mg) was added dropwise thereto. The mixture was stirred for 6 hours at room temperature. To the reaction mixture, water was added. The mixture was extracted with ethyl acetate, washed, dried over and concentrated with the reduced pressure. The residue was purified on silica gel column chromatography (hexane:AcOEt= 2:1→1:1) to give the title compound (309 mg) having the following physical data.

TLC: Rf 0.23 (hexane:AcOEt=2:1).

EXAMPLE 36

Methyl 4-(2-cyclopentylsulfonylamino-5-trifluoromethyl-phenoxymethyl)-benzoate

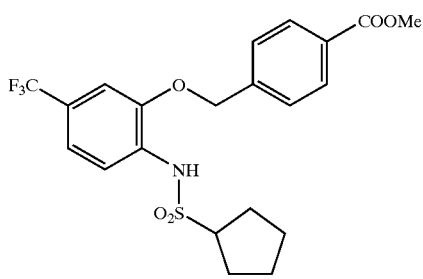

To a solution of methyl 4-(2-cyclopentylsulfinylamino-5-trifluoromethylphenoxymethyl)benzoate (305 mg; prepared in Reference Example 33.) in methylene chloride (4.0 ml), meta-chloroperbenzoic acid (456 mg) was added at 0° C. The mixture was stirred for 1 hour. The reaction mixture was diluted with ethyl acetate, washed, dried over and concentrated under the reduced pressure to give the title compound (317 mg) having the following physical data.

TLC: Rf 0.56 (hexane:AcOEt=2:1); NMR: δ 8.11 (2H, d, J=8.6 Hz), 7.73 (1H, brd, J=9.0 Hz), 7.47 (2H, d, J=8.6 Hz), 7.25 (1H, m), 7.15 (1H, d, J=1.4 Hz), 6.95 (1H, brs), 5.21 (2H, s), 3.95 (3H, s), 3.54 (1H, m), 1.53–2.16 (8H, m).

EXAMPLE 37

4-[2-(N-isopropyl-cyclopentylsulfonylamino)-5-trifluoromethylphenoxymethyl]benzoic acid

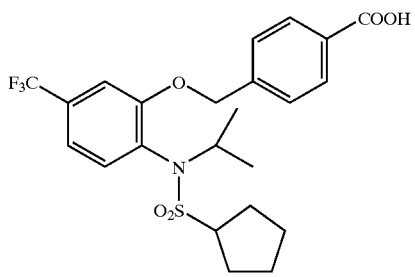

By using methyl 4-(2-cyclopentylsulfonylamino-5-trifluoromethylphenoxymethyl)benzoate (prepared in Example 36.), the title compound having the following physical data was obtained by the same procedure as Example 17→Example 2.

TLC: Rf 0.40 (CHCl$_3$:MeOH:AcOH=100:5:1); NMR: δ 8.17 (2H, d, J=8.4 Hz), 7.61 (2H, d, J=8.4 Hz), 7.38 (1H, d, J=8.0 Hz), 7.28 (2H, m), 5.17 (2H, s), 4.36 (1H, sept, J=6.6 Hz), 3.51 (1H, m), 1.84–2.10 (3H, m), 1.61–1.84 (3H, m), 1.30–1.56 (2H, m), 1.24 (3H, d, J=6.6 Hz), 1.08 (3H, d, J=6.6 Hz).

EXAMPLE 37(1)–37(7)

By using the corresponding compounds, the title compounds having the following physical data were obtained by the same procedure as Reference Example 33→Example 36→Example 17→Example 2.

EXAMPLE 37(1)

4-[2-(N-isopropyl-cyclohexylsulfonylamino)-5-trifluoromethylphenoxymethyl]benzoic acid

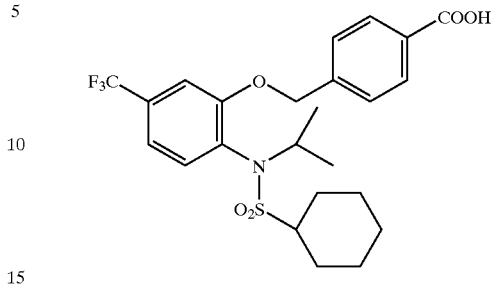

TLC: Rf 0.27 (AcOEt:hexane=1:1); NMR: δ 8.17 (2H, d, J=8 Hz), 7.61 (2H, d, J=8 Hz), 7.42 (1H, d, J=8 Hz), 7.28 (1H, d, J=8 Hz), 7.26 (1H, s), 5.19 (2H, s), 4.32 (1H, m), 2.88 (1H, m), 2.25–2.04 (2H, m), 1.92–1.35 (5H, m), 1.30–0.60 (9H, m).

EXAMPLE 37(2)

4-[2-(N-isopropyl-cyclohexylsulfonylamino)-5-methylphenoxymethyl]benzoic acid

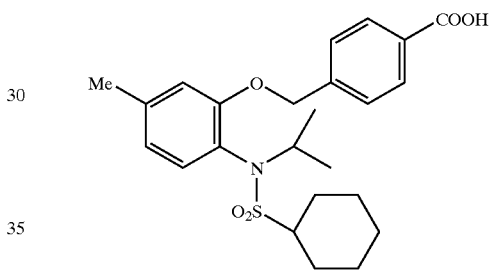

TLC: Rf 0.37 (CHCl$_3$:MeOH:AcOH=100:5:1); NMR: δ 8.15 (2H, d, J=8.6 Hz), 7.59 (2H, d, J=8.6 Hz), 7.17 (1H, d, J=8.4 Hz), 6.82 (2H, m), 5.13 (2H, s), 4.32 (1H, m), 2.88 (1H, tt, J=3.2, 12.0 Hz), 2.35 (3H, s), 2.15 (2H, m), 1.36–1.90 (5H, m), 1.23 (3H, d, J=6.6 Hz), 1.12 (3H, d, J=6.6 Hz), 0.82 (1H, m).

EXAMPLE 37(3)

4-[2-(N-isopropyl-isopropylsulfonylamino)-5-trifluoromethylphenoxymethyl]benzoic acid

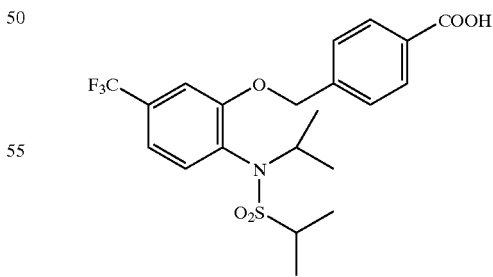

TLC: Rf 0.34 (CHCl$_3$:MeOH:AcOH=100:5:1); NMR: δ 8.18 (2H, d, J=8.4 Hz), 7.60 (2H, d, J=8.4 Hz), 7.42 (1H, d, J=8.0 Hz), 7.23–7.33 (2H, m), 5.17 (2H, s), 4.32 (1H, sept, J=6.6 Hz), 3.17 (1H, sept, J=7.0 Hz), 1.32 (3H, d, J=7.0 Hz), 1.25 (3H, d, J=6.6 Hz), 1.19 (3H, d, J=7.0 Hz), 1.09 (3H, d, J=6.6 Hz).

EXAMPLE 37(4)
4-[2-(N-isopropyl-isopropylsulfonylamino)-5-methylphenoxymethyl]benzoic acid

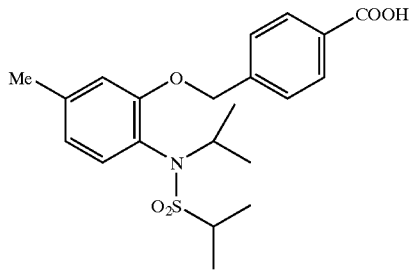

TLC: Rf 0.46 (CHCl₃:MeOH:AcOH=100:5:1); NMR: δ 8.15 (2H, d, J=8.2 Hz), 7.57 (2H, d, J=8.2 Hz), 7.16 (1H, d, J=8.4 Hz), 6.81 (2H, m), 5.11 (2H, s), 4.31 (1H, sept, J=6.6 Hz), 3.16 (1H, sept, J=6.8 Hz), 2.36 (3H, s), 1.31 (3H, d, J=6.8 Hz), 1.23 (3H, d, J=6.6 Hz), 1.18 (3H, d, J=6.6 Hz), 1.08 (3H, d, J=6.8 Hz).

EXAMPLE 37(5)
4-[2-(N-isopropyl-isopropylsulfonylamino)-5-trifluoromethylphenoxymethyl]cinnamic acid

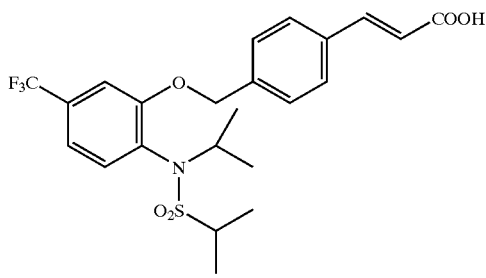

TLC: Rf 0.20 (AcOEt:hexane=1:1); NMR: δ 7.79 (1H, d, J=15 Hz), 7.61 (2H, d, J=8 Hz), 7.50 (2H, d, J=8 Hz), 7.40 (1H, d, J=8 Hz), 7.34–7.20 (2H, m), 6.48 (1H, d, J=15 Hz), 5.12 (2H, s), 4.31 (1H, m), 3.14 (1H, m), 1.31 (3H, d, J=7 Hz), 1.25 (3H, d, J=7 Hz), 1.15 (3H, d, J=7 Hz), 1.07 (3H, d, J=7 Hz).

EXAMPLE 37(6)
4-[2-(N-isopropyl-cyclopentylsulfonylamino)-5-trifluoromethylphenoxymethyl]cinnamic acid

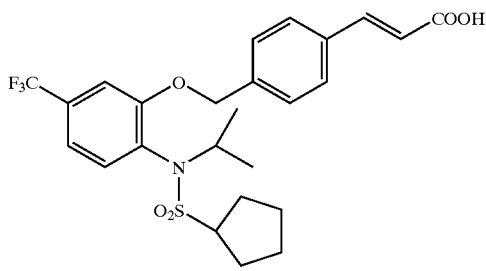

TLC: Rf 0.24 (AcOEt:hexane=1:1); NMR: δ 7.80 (1H, d, J=15 Hz), 7.61 (2H, d, J=8 Hz), 7.53 (2H, d, J=8 Hz), 7.38 (1H, d, J=8 Hz), 7.30–7.22 (2H, m), 6.48 (1H, d, J=15 Hz), 5.13 (2H, s), 4.35 (1H, m), 3.49 (1H, m), 2.20–1.16 (1H, m), 1.07 (3H, d, J=7 Hz).

Example 37(7)
4-[2-(N-isopropyl-cyclohexylsulfonylamino)-5-trifluoromethylphenoxymethyl]cinnamic acid

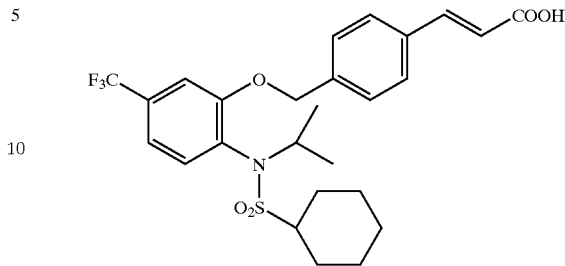

TLC: Rf 0.27 (AcOEt:hexane=1:1); NMR: δ 7.80 (1H, d, J=15 Hz), 7.61 (2H, d, J=8 Hz), 7.52 (2H, d, J=8 Hz), 7.41 (1H, d, J=8 Hz), 7.34–7.20 (2H, m), 6.48 (1H, d, J=15 Hz), 5.13 (2H, s), 4.32 (1H, m), 2.87 (1H, m), 2.21–2.00 (2H, m), 1.90–1.34 (5H, m), 1.26 (3H, d, J=7 Hz), 1.18–0.60 (6H, m).

REFERENCE EXAMPLE 34
Methyl 4-(3-nitro-5-trifluoromethylpyridine-2-yloxymethyl)benzoate

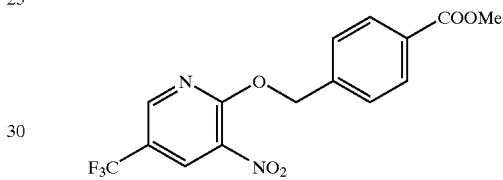

To a solution of 2-hydroxy-3-nitro-5-trifluoromethylpyridine (1.0 g) in toluene (10 ml), methyl 4-chloromethylbenzoate (1.32 g) and silver oxide (1.23 g) were added in a stream of argon. The mixture was refluxed for 18 hours with heating. The reaction mixture was filtered. The filtrate was concentrated. The residue was recrystallized from ethyl acetate to give the title compound (982 mg) having the following physical data.

TLC: Rf 0.34 (hexane:AcOEt=3:1).

EXAMPLE 38
4-(3-phenylsulfonylamino-5-trifluoromethylpyridine-2-yloxymethyl)benzoic acid

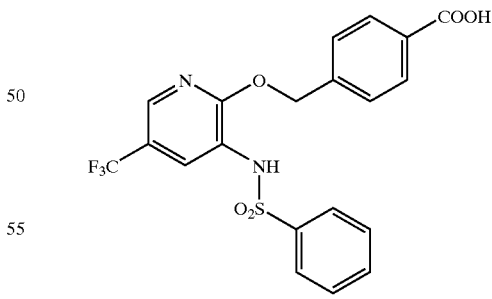

By using methyl 4-(3-nitro-5-trifluoromethylpyridine-2-yloxymethyl)benzoate (prepared in Reference Example 34.), the title compound having the following physical data was obtained by the same procedure as Reference Example 12→Reference Example 2→Example 2.

TLC: Rf 0.50 (CHCl₃:MeOH:AcOH=100:5:1); NMR (DMSO-d₆): δ 12.94 (1H, m), 10.46 (1H, m), 8.33 (1H, m), 7.89 (2H, d, J=8.4 Hz), 7.85 (1H, d, J=2.2 Hz), 7.73 (2H, m), 7.43–7.65 (3H, m), 7.36 (2H, d, J=8.4 Hz), 5.33 (2H, s).

REFERENCE EXAMPLE 35

4-[2-(N-methoxymethoxycarbonylmethyl-phenylsulfonylamino)-5-trifluoromethylphenoxymethyl]benzoic acid-.methoxymethyl ester

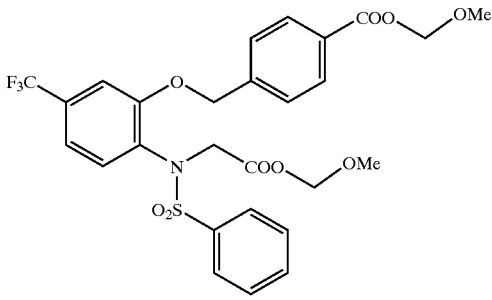

4-[2-(N-carboxymethyl-phenylsulfonylamino)-5-trifluoromethyl-phenoxymethyl]benzoic acid (446 mg) prepared by the same procedure as Example 17→Example 2 by using methyl 4-(2-phenylsulfonylamino-5-trifluoromethylphenoxymethyl)benzoate (prepared in Example 15) was dissolved in DMF (5 ml). To the solution, methoxymethyl chloride (160 μl) and triethylamine (300 μl) were added dropwise. The mixture was stirred for 2 hours at room temperature. Water was added thereto. The mixture was extracted with ethyl acetate, washed, dried over, filtered and concentrated to give the title compound (476 mg) having the following physical data.

TLC: Rf 0.20 (hexane:AcOEt=3:1).

REFERENCE EXAMPLE 36

4-[2-[N-(N,N-dimethylaminocarbonylmethyl)-phenylsulfonylamino]-5-trifluoromethylphenoxymethyl]benzoic acid. methoxymethyl ester

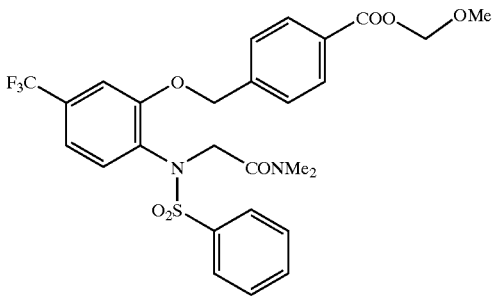

To a solution of 4-[2-(N-methoxymethoxycarbonyl-methyl-phenylsulfonylamino)-5-trifluoromethylphenoxymethyl]benzoic acid. methoxymethyl ester (476 mg; prepared in Reference Example 35) in THF (2 ml), dimethylamine(0.8 ml) was added. The mixture was stirred for 3 days at room temperature. The solvent was distilled off. The residue was purified on silica gel column chromatography (hexane:AcOEt=2:1→1:1) to give the title compound (290 mg) having the following physical data.

TLC: Rf 0.26 (hexane:AcOEt=1:1).

EXAMPLE 39

4-[2-[N-(N,N-dimethylaminocarbonylmethyl)-phenylsulfonylamino]-5-trifluoromethylphenoxymethyl]benzoic acid

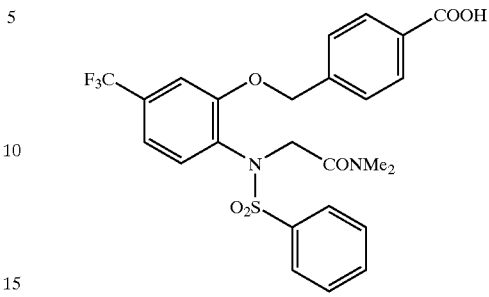

By using 4-[2-[N-(N,N-dimethylaminocarbonylmethyl)-phenylsulfonylamino]-5-trifluoromethylphenoxymethyl]benzoic acid methoxymethyl ester (prepared in Reference Example 36.), the title compound having the following physical data was obtained by the same procedure as Reference Example 23.

TLC: Rf 0.24 (AcOEt); NMR: δ 8.10–8.06 (2H, m), 7.71–6.64 (3H, m), 7.55–7.47 (1H, m), 7.42–7.10 (6H, m), 4.94 (2H, s), 4.56 (2H, s), 3.04 (3H, s), 2.86 (3H, s).

REFERENCE EXAMPLE 37

Methyl 4-phenylsulfonylamino-3-methoxybenzoate

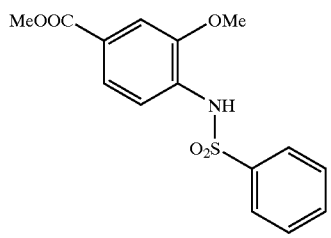

By using 4-nitro-3-hydroxybenzoic acid, the title compound having the following physical data was obtained by the same procedure as Reference Example 6→Reference Example 12→Reference Example 2:

TLC: Rf 0.12 (hexane:AcOEt=3:1).

REFERENCE EXAMPLE 38

1-methyl-1-(4-phenylsulfonylamino-3-methoxyphenyl)ethanol

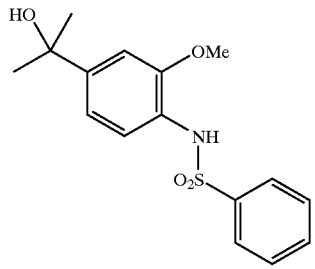

To a suspension of methyl 4-phenylsulfonylamino-3-methoxybenzoate (3.2 g; prepared in Reference Example 37.) in THF (50 ml), methyl lithium in ether (38.8 ml) was added dropwise at −65° C. The mixture was slowly warmed to 5° C. over a period of 3 hours under stirring. The reaction mixture was neutralized by adding diluted HCl and extracted with ethyl acetate. The organic layer was washed, dried over and concentrated to give the title compound having the following physical data.

TLC: Rf 0.18 (hexane:AcOEt=1:1).

REFERENCE EXAMPLE 39

1-methyl-1-[4-(N-acetyl-phenylsulfonylamino)-3-methoxyphenyl]ethanol

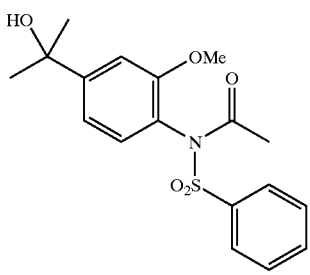

To a solution of 1-methyl-1-(4-phenylsulfonylamino-3-methoxyphenyl)-ethanol (2.65 g; prepared in Reference Example 38.) in methylene chloride (15 ml), acetic anhydride (3.05 ml) and triethylamine (4.60 ml) were added. The mixture was stirred overnight at room temperature. The solvent was distilled off. The residue was purified on silica gel column chromatography (hexane:AcOEt=3:4) to give the title compound (2.33 g) having the following physical data.

TLC: Rf 0.19 (hexane:AcOEt=1:1).

REFERENCE EXAMPLE 40

2-(N-acetyl-phenylsulfonylamino)-5-isopropylphenyl methyl ether

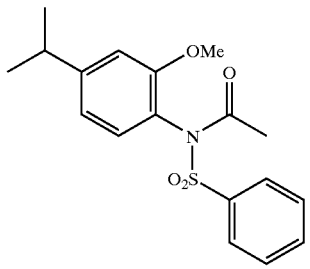

To a solution of 1-methyl-1-[4-(N-acetyl-phenylsulfonylamino)-3-methoxyphenyl]ethanol (2.50 g; prepared in Reference Example 39.) in methylene chloride (10 ml), trifluoroacetic acid (10 ml) and triethylsilane (3.3 ml) were added at 0° C. The mixture was stirred for 1 hour at room temperature. The reaction mixture was added to saturated sodium hydrogencarbonate carefully The mixture was extracted with ethyl acetate. The organic layer was washed, dried over and concentrated. The residue was purified on silica gel column chromatography (hexane:AcOEt=3:1) to give the title compound (2.33 g) having the following physical data.

TLC: Rf 0.24 (hexane:AcOEt=1:1).

REFERENCE EXAMPLE 41

2-(N-acetyl-phenylsulfonylamino)-5-isopropylphenol

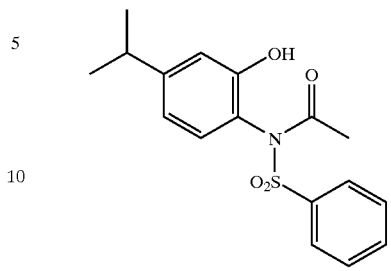

To a solution of 2-(N-acetyl-phenylsulfonylamino)-5-isopropylphenyl methyl ether (2.28 g; prepared in Reference Example 40.) in methylene chloride (15 ml), boron tribromide (1.36 ml) was added at 0° C. The mixture was stirred for 5 hours at 10° C. The reaction mixture was poured into iced water, extracted with ethyl acetate. The organic layer was washed, dried over and concentrated. The residue was purified on silica gel column chromatography (benzene:AcOEt=23:2) and recrystallized from AcOEt-hexane mixture solution to give the title compound (1.55 g) having the following physical data.

TLC: Rf 0.24 (benzene:AcOEt=9:1).

REFERENCE EXAMPLE 42

Methyl 4-[2-(N-acetyl-phenylsulfonylamino)-5-isopropylphenoxymethyl]benzoate

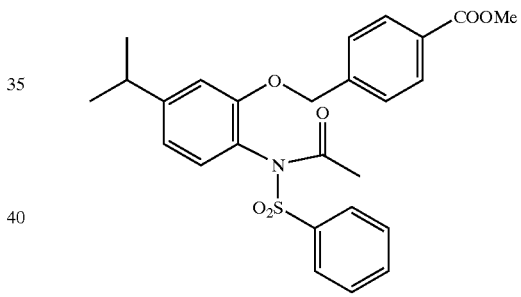

By using 2-(N-acetyl-phenylsulfonylamino)-5-isopropylphenol (1.50 g; prepared in Reference Example 41.), the title compound (2.22 g) having the following physical data was obtained by the same procedure as Reference Example 6.

TLC: Rf 0.24 (hexane:AcOEt=7:3).

REFERENCE EXAMPLE 43

4-(phenylsulfonylamino)-3-methoxybenzyl alcohol

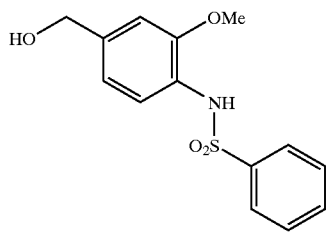

A solution of methyl 4-phenylsulfonylamino-3-methoxybenzoate (1.5 g; prepared in Reference Example 37.) in THF (90 ml) was cooled to −78° C. in a stream of argon. The solution of diisobutylaluminum hydride (1.0 M) in hexane (22 ml) was added dropwise thereto. The mixture was stirred for 4 hours at −78° C. After the temperature increased to room temperature, the mixture was diluted with ether (100 ml). A saturated aqueous sodium sulfate (1.5 ml) was added thereto slowly. The mixture was stirred for 30 minutes, dried over, filtered and concentrated to give the title compound (1.5 g)

TLC: Rf 0.31 (AcOEt:hexane=2:1).

REFERENCE EXAMPLE 44
4-phenylsulfonylamino-3-methoxybenzaldehyde

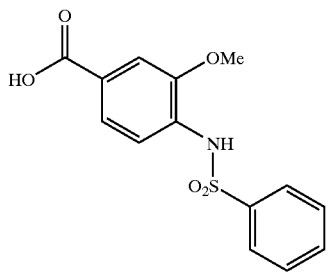

To a solution of 4-phenylsulfonylamino-3-methoxybenzyl alcohol (522 mg; prepared in Reference Example 43.) in methylene chloride (15 ml), manganese dioxide (3 g) was added in a stream of argon. The solution was stirred for 1 hour at room temperature. After the termination of reaction, the reaction mixture was filtered. The filtrate was concentrated to give the title compound (404 mg) having the following physical data.

TLC: Rf 0.57 (AcOEt:hexane=3:2).

REFERENCE EXAMPLE 45
1-(4-phenylsulfonylamino-3-methoxyphenyl)ethanol

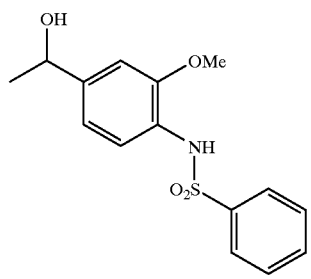

A solution of 4-phenylsulfonylamino-3-methoxybenzaldehyde (400 mg; prepared in Reference Example 44.) in THF (10 ml) was cooled to at −78° C. mg; prepared in Reference Example 44.) in THF (10 ml) was cooled to at −78° C. in a stream of argon. A solution of methyl lithium (1.0M) in diethyl ether (3.4 ml) was added dropwise thereto. The mixture was stirred for 20 minutes. After the termination of reaction, a mixture of $H_2O$+1N HCl was added thereto to stop the reaction. The mixture was extracted with ethyl acetate three times. The organic layer was washed, dried over and purified on silica gel column chromatography (AcOEt:hexane=1:1) to give the title compound (421 mg) having the following physical data.

TLC: Rf 0.34 (AcOEt:hexane=3:2).

EXAMPLE 40
4-(2-phenylsulfonylamino-5-isopropylphenoxymethyl) benzoic acid

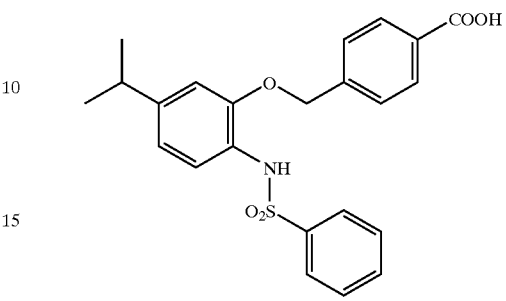

By using methyl 4-[2-(N-acetyl-phenylsulfonylamino)-5-isopropyl-phenoxymethyl]benzoate (2.00 g; prepared in Reference Example 42.), the title compound (1.66 g) having the following physical data was obtained by the same procedure as Example 2.

TLC: Rf 0.49 ($CHCl_3$:MeOH=4:1); NMR (DMSO-$d_6$): δ 7.84 (2H, d, J=8.5 Hz), 7.79–7.53 (5H, m), 7.41 (2H, d, J=8.5 Hz), 6.90 (1H, d, J=8 Hz), 6.63 (1H, d, J=2 Hz), 6.55 (1H, dd, J=8 and 2 Hz), 4.82 (2H, s), 2.72 (1H, m), 1.10 (6H, d, J=7 Hz).

EXAMPLE 41

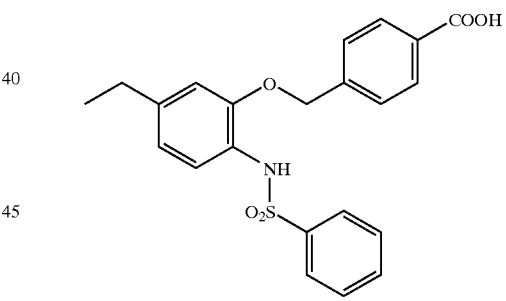

By using 1-(4-phenylsulfonylamino-3-methoxyphenyl) ethanol (prepared in Reference Example 45.), the title compound having the following physical data was obtained by the same procedure as Reference Example 40→Reference Example 39→Reference Example 41→Reference Example 6→Example 2.

TLC: Rf 0.29 (AcOEt:hexane:AcOH=5:14:1); NMR (DMSO-$d_6$): δ 12.87 (1H, brs), 9.53 (1H, brs), 7.83 (2H, d, J=8.5 Hz), 7.78–7.50 (5H, m), 7.39 (2H, d, J=8.0 Hz), 6.86 (2H, d, J=8.0 Hz), 6.57 (1H, d, J=2.0 Hz), 6.50 (1H, dd, J=8, 2 Hz), 4.82 (2H, brs), 2.44 (2H, q, J=7.5 Hz), 1.08 (3H, t, J=7.5 Hz).

EXAMPLE 42
4-(2-phenylsulfonylamino-5-hydroxymethylphenoxymethyl)benzoic acid

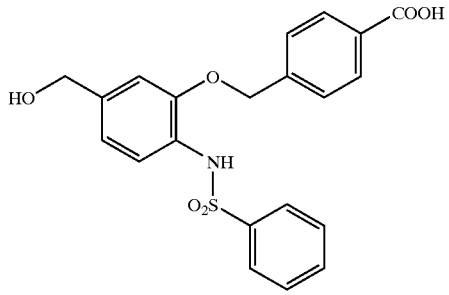

By using methyl 4-nitro-3-hydroxybenzoate, the title compound having the following physical data was obtained by the same procedure as Reference Example 19→Reference Example 20→Reference Example 2→Reference Example 43→Reference Example 39→Reference Example 23→Reference Example 6→Example 2.

TLC: Rf 0.39 (AcOEt:hexane:AcOH=13:6:1); NMR (DMSO-$d_6$): δ 12.83 (1H, brs), 9.56 (1H, s), 7.83 (2H, d, J=8.5 Hz), 7.78–7.50 (5H, m), 7.38 (2H, d, J=8.5 Hz), 6.88 (1H, d, J=8.0 Hz), 6.74 (1H, s), 6.56 (1H, d, J=8.0 Hz), 5.10 (1H, brt, J=5.5 Hz), 4.83 (2H, s), 4.34 (2H, d, J=5.5 Hz).

REFERENCE EXAMPLE 46
Methyl 4-chloro-2-hydroxybenzoate

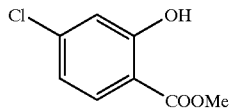

To a solution of 4-chloro-2-hydroxybenzoic acid (5.0 g) in ether (50 ml), diazomethane in ether was added until the reaction was terminated at 0° C. The reaction mixture was concentrated under the reduced pressure. The residue was purified on silica gel column chromatography (hexane:AcOEt=4:1) to give the title compound (5.4 g) having the following physical data.

TLC: Rf 0.60 (hexane:AcOEt=2:1).

REFERENCE EXAMPLE 47
2-hydroxymethyl-5-chlorophenol

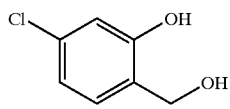

To a solution of lithium aluminum hydride (1.1 g) in THF (50 ml),

To a solution of lithium aluminum hydride (1.1 g) in THF (50 ml), methyl 4-chloro-2-hydroxybenzoate (5.38 g; prepared in Reference Example 46.) in THF (50 ml) was added dropwise in a stream of argon at 0° C. After the solution was warmed to at room temperature, the solution was stirred for 30 minutes. To the reaction mixture, water was added. The mixture was extracted with mixture solution of ether-AcOEt, washed, dried over and concentrated under the reduced pressure. The residue was recrystallized from mixture solution of hexane-AcOEt to give the title compound (3.92 g) having the following physical data.

TLC: Rf 0.60 (hexane:AcOEt=1:1).

REFERENCE EXAMPLE 48
Methyl 4-(2-mesyloxymethyl-5-chlorophenoxymethyl)benzoate

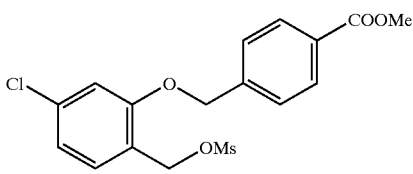

By using 2-hydroxymethyl-5-chlorophenol (prepared in Reference Example 47.), the title compound having the following physical data was obtained by the same procedure as Reference Example 6→Reference Example 8.

TLC: Rf 0.60 (benzene:acetone=9:1).

REFERENCE EXAMPLE 49
Methyl 4-(2-azidomethyl-5-chlorophenoxymethyl)benzoate

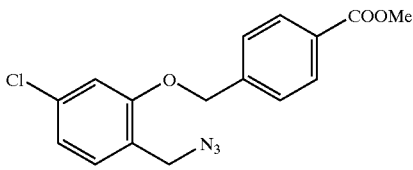

To a solution of methyl 4-(2-mesyloxymethyl-5-chlorophenoxymethyl)-benzoate (628 mg; prepared in Reference Example 48.) in DMF (5.0 ml), sodium azide (530 mg) was added in a stream of argon. The mixture was stirred for 40 minutes at 60° C. The reaction mixture was diluted with ethyl acetate. The impurity was filtered with celite. The filtrate was washed, dried over and concentrated under the reduced pressure. The residue was purified on silica gel column chromatography (hexane:AcOEt=10:1) to give the title compound (404 mg) having the following physical data.

TLC: Rf 0.56 (hexane:AcOEt=4:1).

REFERENCE EXAMPLE 50
Methyl 4-(2-aminomethyl-5-chlorophenoxymethyl)benzoate

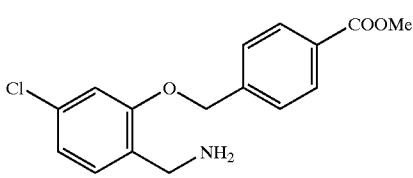

To a solution of methyl 4-(2-azidomethyl-5-chlorophenoxymethyl)-benzoate (389 mg; prepared in Reference Example 49) in THF (4.0 ml), triphenylphosphine (462 mg) was added at room temperature. The mixture was stirred for 3 hours. After stirring, water was added thereto. The mixture was stirred for 15 hours. The reaction mixture was concentrated under the reduced pressure. the residue was purified on silica gel column chromatography ($CHCL_3$:MeOH=50:1→10:1) to give the title compound (339 mg) having the following physical data.

TLC: Rf 0.22 ($CHCl_3$:MeOH=10:1).

EXAMPLE 43

4-(2-phenylsulfonylaminomethyl-5-chlorophenoxymethyl)benzoic acid

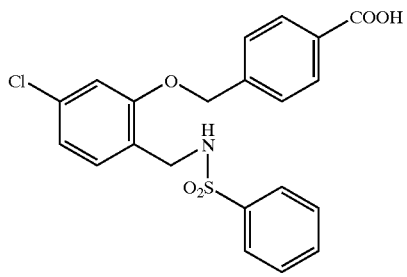

By using methyl 4-(2-aminomethyl-5-chlorophenoxymethyl)benzoate (prepared in Reference Example 50.), the title compound having the following physical data was obtained by the same procedure as Reference Example 2→Example 2.

TLC: Rf 0.49 (CHCl$_3$:MeOH:AcOH=100:5:1); NMR (DMSO-d$_6$): δ 7.94 (2H, d, J=8.0 Hz), 7.77 (2H, m), 7.45–7.70 (5H, m), 7.25 (1H, d, J=8.2 Hz), 7.05 (1H, d, J=1.8 Hz), 6.94 (1H, dd, J=0.8, 8.2 Hz), 5.20 (2H, s), 4.00 (2H, s).

EXAMPLE 44

4-[2-(N-isopropyl-phenylsulfonylamino)-5-trifluoromethylphenoxymethyl]phenylpropiolic acid

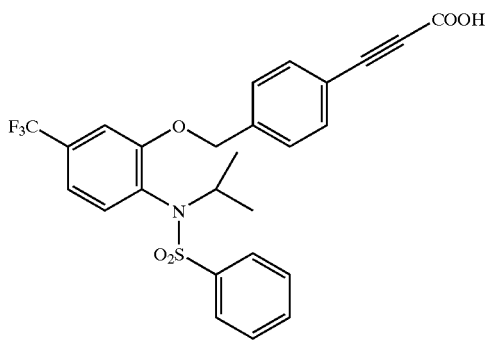

By using 4-[2-(N-isopropyl-phenylsulfonylamino)-5-trifluoromethylphenoxymethyl]benzoic acid (prepared in Example 18 (9).), the title compound having the following physical data was obtained by the same procedure as Reference Example 13→Reference Example 14→Reference Example 15→Example 2.

TLC: Rf 0.32 (CHCl$_3$:MeOH=8:2); NMR: δ 7.80 (2H, d, J=8 Hz), 7.64 (2H, d, J=8 Hz), 7.68–7.26 (8H, m), 5.09 (2H, s), 4.38 (1H, sept, J=6.5 Hz), 1.04 (6H, d, J=6.5 Hz).

EXAMPLE 45

4-[2-[2-(N-isopropyl-phenylsulfonylamino)-5-trifluoromethylphenyl]ethyl]benzoic acid

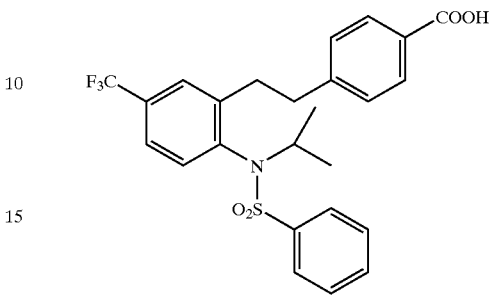

By using methyl 4-[2-(2-t-butoxycarbonylamino-5-trifluoromethylphenyl)-(EZ)-vinyl]benzoate, the title compound having the following physical data was obtained by the same procedure as Reference Example 20→Reference Example 23→Reference Example 2→Example 17→Example 2.

TLC: Rf 0.46 (CHCl$_3$:MeOH=9:1); NMR: δ 8.09 (2H, d, J=8.2 Hz), 7.8–7.7 (2H, m), 7.7–7.3 (7H, m), 6.88 (1H, d, J=8.2 Hz), 4.7–4.5 (1H, m), 3.4–3.1 (2H, m), 3.1–2.9 (2H, m), 1.03 (3H, d, J=6.8 Hz), 0.93 (3H, d, J=6.8 Hz).

EXAMPLE 46

4-(2-phenylsulfonylamino-4-chlorophenoxymethyl)benzyl alcohol

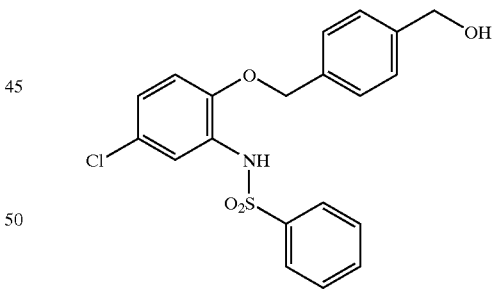

By using methyl 4-(2-phenylsulfonylamino-4-chlorophenoxymethyl)-benzoate (prepared in Example 7 (a).), the title compound having the following physical data was obtained by the same procedure as Reference Example 43.

TLC:Rf 0.24 (hexane:AcOEt=1:1); NMR: δ 7.75 (2H, m), 7.60 (1H, d, J=2.4 Hz), 7.55 (1H, m), 7.45 (2H, m), 7.36 (2H, d, J=8.0 Hz), 7.13 (2H, d, J=8.0 Hz), 7.03 (1H, brs), 6.96 (1H, dd, J=2.4, 8.8 Hz), 6.68 (1H, d, J=8.8 Hz), 4.86 (2H, s), 4.73 (2H, d, J=5.8 Hz), 1.74 (1H, t, J=5.8 Hz).

EXAMPLE 47

4-[N-[2-(4-chlorophenylsulfonylamino)-5-chlorophenyl]aminosulfonyl]benzoic acid

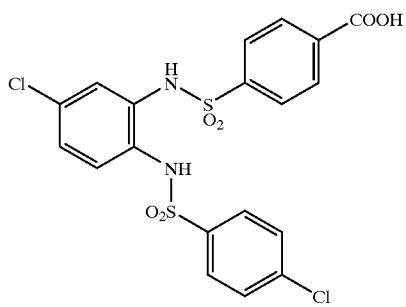

By using 2-nitro-4-chloroaniline, the title compound having the following physical data was obtained by the same procedure as Reference Example 2→Reference Example 12→Reference Example 2→Example 2.

TLC: Rf 0.22 (CHCl$_3$:MeOH:H$_2$O=8:2:0.2); NMR (DMSO-d$_6$): δ 9.68 (1H, br), 8.11 (2H, d, J=8.4 Hz), 7.84 (2H, d, J=8.4 Hz), 7.69 (2H, d, J=8.8 Hz), 7.62 (2H, d, J=8.8 Hz), 7.12 (1H, dd, J=2.4 and 8.4 Hz), 7.02 (1H, d, J=2.4 Hz), 6.97 (1H, d, J=8.4 Hz).

EXAMPLE 48

4-[2-[2-(N-isopropyl-phenylsulfonylamino)-5-trifluoromethylphenyl]-(E)-vinyl]benzoic acid

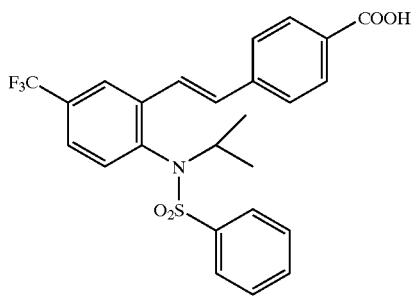

By using methyl 4-[2-(2-t-butoxycarbonylamino-5-trifluoromethylphenyl)-(E)-vinyl]benzoate, the title compound having the following physical data was obtained by the same procedure as Reference Example 23→Reference Example 2→Example 17→Example 2.

TLC: Rf 0.45 (CHCl$_3$:MeOH=9:1); NMR: δ 8.2–8.0 (3H, m), 7.9–7.7 (2H, m), 7.6–7.4 (7H, m), 7.2–7.0 (2H, m), 4.8–4.6 (1H, m), 1.08 (3H, d, J=5.0 Hz), 1.05 (3H, d, J=5.0 Hz).

EXAMPLE 48(1)

4-[2-[2-(N-isopropyl-phenylsulfonylamino)-5-trifluoromethylphenyl]-(Z)-vinyl]benzoic acid

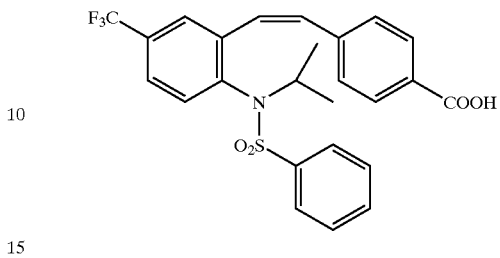

By using methyl 4-[2-(2-t-butoxycarbonylamino-5-trifluoromethylphenyl)-(Z)-vinyl]benzoate, the title compound having the following physical data was obtained by the same procedure as Reference Example 23→Reference Example 2→Example 17→Example 2.

TLC: Rf 0.51 (CHCl$_3$:MeOH=9:1); NMR: δ 7.97 (2H, d, J=8.4 Hz), 7.9–7.7 (2H, m), 7.7–7.4 (5H, m), 7.31 (2H, d, J=8.4 Hz), 7.1–6.9 (2H, m), 6.77 (1H, d, J=12.4 Hz), 4.7–4.5 (1H, m), 1.19 (3H, d, J=6.6 Hz), 1.04 (3H, d, J=6.6 Hz).

EXAMPLE 49

4-(2-benzoylamino-5-chlorophenoxymethyl)benzoic acid

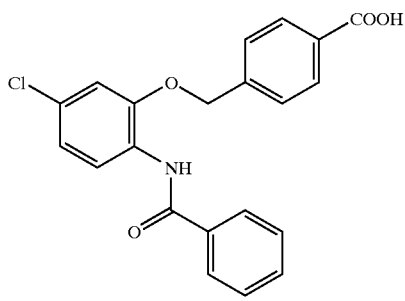

By using 2-nitro-5-chlorophenol, the title compound having the following physical data was obtained by the same procedure as Reference Example 6→Reference Example 12→Example 11→Example 2.

TLC: Rf 0.51 (CHCl$_3$:MeOH:AcOH=100:5:1); NMR (DMSO-d$_6$): δ 12.92 (1H, brs), 9.64 (1H, s), 7.94 (4H, m), 7.75 (1H, d, J=8.6 Hz), 7.47–7.68 (5H, m), 7.23 (1H, d, J=2.2 Hz), 7.05 (1H, dd, J=2.2, 8.6 Hz), 5.32 (2H, s).

EXAMPLE 50–50(2)

By using 4-(2-phenylsulfonylamino-5-isopropylphenoxymethyl)-benzoic acid (prepared in Example 40.) or 4-(2-phenylsulfonylamino-5ethylphenoxymethyl)benzoic acid (prepared in Example 41.), the title compounds having the following physical data were obtained by the same procedure as Reference Example 1→Example 17→Example 2.

EXAMPLE 50
4-[2-(N-isopropyl-phenylsulfonylamino)-5-isopropylphenoxymethyl]benzoic acid

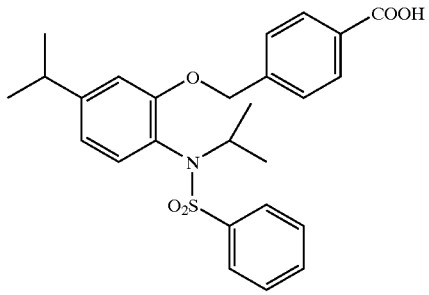

TLC: Rf 0.13 (CHCl$_3$:MeOH=19:1); NMR (DMSO-d$_6$) δ 7.85 (2H, d, J=8 Hz), 7.79–7.52(5H, m), 7.40 (2H, d, J=8 Hz), 7.01 (1H, d, J=8 Hz), 6.73 (1H, d, J=2 Hz), 6.65 (1H, dd, J=8 and 2 Hz), 4.83 (2H, brs), 4.47 (1H, m), 2.80 (1H, m), 1.1 4 (6H, d, J=7 Hz), 0.95 (6H, d, J=7 Hz).

EXAMPLE 50(1)
4-[2-(N-methyl-phenylsulfonylamino)-5-isopropylphenoxymethyl]benzoic acid

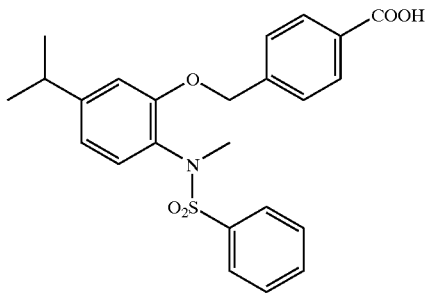

TLC: Rf 0.13 (CHCl$_3$:MeOH=19:1); NMR (DMSO-d$_6$): δ 7.85 (2H, d, J=8 Hz), 7.76–7.53 (5H, m), 7.39 (2H, d, J=8 Hz), 6.98 (1H, d, J=8 Hz), 6.77 (1H, d, J=2 Hz), 6.70 (1H, dd, J=8 and 2 Hz), 4.78 (2H, brs), 3.33 (3H, s), 2.82 (1H, m), 1.15 (6H, d, J=7 Hz).

EXAMPLE 50(2)
4-[2-(N-isopropyl-phenylsulfonylamino)-5-ethylphenoxymethyl]benzoic acid

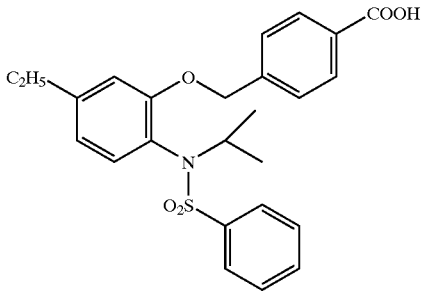

TLC: Rf 0.40 (AcOEt:hexane:AcOH=5:14:1); NMR: δ 7.97 (2H, d, J=8.0 Hz), 7.82–7.70 (2H, m), 7.62–7.32 (5H, m), 7.05 (1H, d, J=8.0 Hz), 6.60 (1H, dd, J=8, 1.5 Hz), 6.53 (1H, d, J=1.5 Hz), 4.86 (2H, brs), 4.36 (1H, qn, J=6.0 Hz), 2.55 (2H, q, J=7.5 Hz), 1.18 (3H, t, J=7.5 Hz), 1.02 (6H, brd, J=6.0 Hz).

EXAMPLE 51
4-[2-(N-isopropyl-phenylsulfonylamino)-5-trifluoromethylphenoxymethyl]cinnamic acid sodium salt

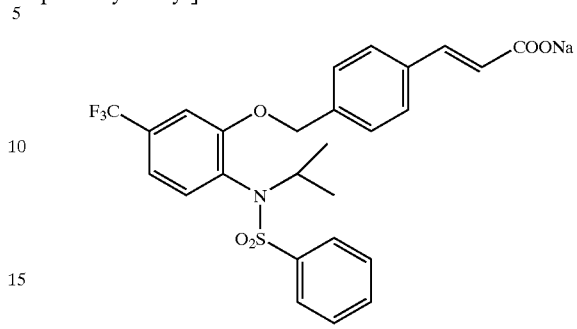

To a solution of 4-[2-(N-isopropyl-phenylsulfonylamino)-5-trifluoromethylphenoxymethyl]cinnamic acid (425 mg; prepared in Example 18(40).) in MeOH (5 ml), 2N NaOH (0.41 ml) was added. The mixture was stirred at room temperature. The mixture was distilled off azeotropically with benzene three times to give the title compound (430 mg) having the following physical data.

TLC: Rf 0.19 (hexane:AcOEt=1:1); NMR: δ 7.60 (2H, d, J=7 Hz), 7.40–6.97 (11H, m), 6.47 (1H, d, J=16 Hz), 4.62 (2H, bs), 4.20–4.08 (1H, m), 0.77 (6H, d, J=5 Hz).

EXAMPLE 52(1)–52(5)

By using methyl 4-(2-amino-5-trifluoromethylphenoxymethyl)benzoate (prepared in Reference Example 17.) and the corresponding benzenesulfonylchloride derivatives, the title compounds having the following physical data were obtained by the same procedure as Example 4→Example 19 (isopropanol was used instead of cyclopentylmethanol.) →Example 2.

EXAMPLE 52(1)
4-[2-(N-isopropyl-4-propoxyphenylsulfonylamino)-5-trifluoromethylphenoxymethyl]benzoic acid

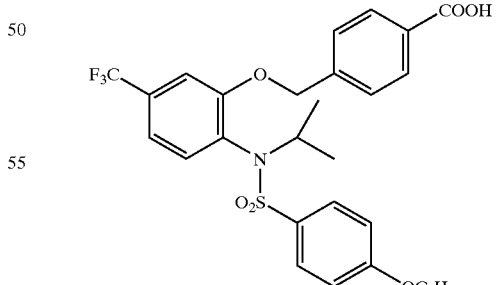

TLC: Rf 0.55 (CHCl$_3$:MeOH=9:1); NMR: δ 8.16 (2H, d, J=8.8 Hz), 7.71 (2H, d, J=8.8 Hz), 7.54 (2H, d, J=8.8 HZ), 7.30–7.22 (3H, m), 6.80 (2H, d, J=8.8 Hz), 5.14 (2H, s), 4.44–4.24 (1H, m), 3.92 (2H, t, J=6.6 Hz), 1.91–1.72 (2H, m), 1.14–0.98 (9H, m).

EXAMPLE 52(2)
4-[2-(N-isopropyl-4-ethylthiophenylsulfonylamino)-5-trifluoromethylphenoxymethyl]benzoic acid

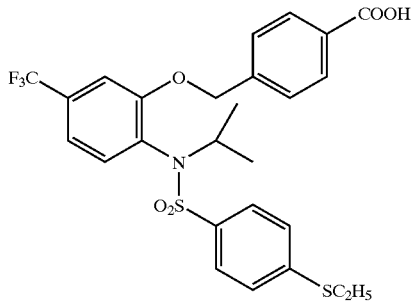

TLC: Rf 0.64 (CHCl₃:MeOH=9:1); NMR: δ 8.17 (2H, d, J=8.4 Hz), 7.66 (2H, d, J=8.4 Hz), 7.53 (2H, d, J=8.4 Hz), 0.30–7.20 (3H, m), 7.16 (2H, d, J=8.4 Hz), 5.12 (2H, s), 4.44–4.22 (1H, m), 2.98 (2H, q, J=7.6 Hz), 1.36 (3H, t, J=7.6 Hz), 1.09 (3H, d, J=6.6 Hz), 1.05 (3H, d, J=6.6 Hz).

EXAMPLE 52(3)
4-[2-(N-isopropyl-4-methylthiophenylsulfonylamino)-5-trifluoromethylphenoxymethyl]benzoic acid

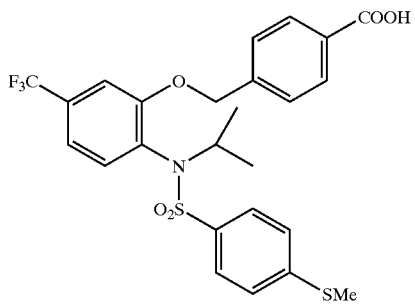

TLC: Rf 0.56 (CHCl₃:MeOH=9:1); NMR: δ 8.16 (2H, d, J=8.4 Hz), 7.67 (2H, d, J=8.4 Hz), 7.52 (2H, d, J=8.4 Hz), 7.30–7.20 (3H, m), 7.12 (2H, d, J=8.4 Hz), 5.12 (2H, s), 4.46–4.24 (1H, m), 2.48 (3H, s), 1.09 (3H, d, J=7.0 Hz), 1.05 (3H, d, J=7.0 Hz).

EXAMPLE 52(4)
4-[2-(N-isopropyl-4-butoxyphenylsulfonylamino)-5-trifluoromethylphenoxymethyl]benzoic acid

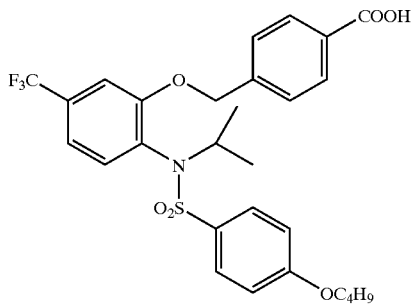

TLC: Rf 0.51 (CHCl₃:MeOH=9:1); NMR: δ 8.16 (2H, d, J=8.4 Hz), 7.71 (2H, d, J=8.8 Hz), 7.54 (2H, d, J=8.4 Hz), 7.30–7.22 (3H, m), 6.79 (2H, d, J=8.8 Hz), 5.14 (2H, s), 4.42–4.27 (1H, m), 3.96 (2H, t, J=6.2 Hz), 1.87–1.70 (2H, m), 1.60–1.40 (2H, m), 1.14–0.92 (9H, m).

EXAMPLE 52(5)
4-[2-(N-isopropyl-4-isopropoxyphenylsulfonylamino)-5-trifluoromethylphenoxymethyl]benzoic acid

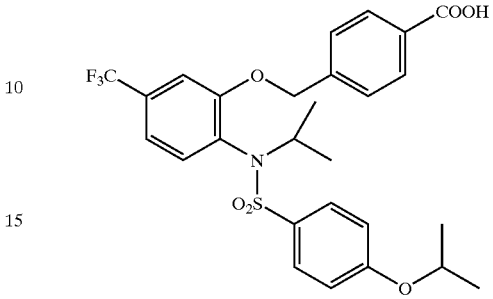

TLC: Rf 0.68 (CHCl₃:MeOH=9:1); NMR: δ 8.17 (2H, d, J=8.0 Hz), 7.71 (2H, d, J=8.8 Hz), 7.56 (2H, d, J=8.0 Hz), 7.30–7.22 (3H, m), 6.78 (2H, d, J=8.8 Hz), 5.15 (2H, s), 4.62–4.50 (1H, m), 4.40–4.23 (1H, m), 1.35 (6H, d, J=5.8 Hz), 1.08 (3H, d, J=7.4 Hz), 1.04 (3H, d, J=7.4 Hz).

EXAMPLE 53(1)–53(3)

By using methyl 4-(2-amino-5-chlorophenoxymethyl)benzoate (prepared in Reference Example 7.) or methyl 4-(2-amino-5-trifluoromethylphenoxymethyl)benzoate (prepared in Reference Example 17.), the title compounds having the following physical data were obtained by the same procedure as Example 27 (the corresponding aldehyde was used.)→Example 11→Example 2.

EXAMPLE 53(1)
4-[2-(N-isobutyl-benzoylamino)-5-chlorophenoxymethyl]benzoic acid

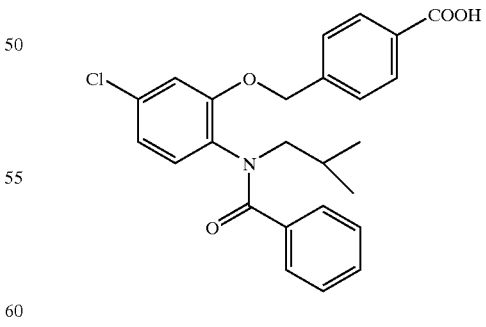

TLC: Rf 0.53 (CHCl₃:MeOH=5:1); NMR(CDCl₃+1 drop of CD₃OD): δ 8.08 (2H, d, J=8 Hz), 7.44–7.04 (8H, m), 6.94–6.80 (1H, m), 6.73 (1H, s), 5.03 (1H, d, J=13 Hz), 4.82 (1H, d, J=13 Hz), 3.91 (1H, dd, J=15, 7 Hz), 3.49 (1H, dd, J=15, 7 Hz), 2.10–1.60 (1H, m), 0.98 (6H, d, J=7 Hz).

EXAMPLE 53(2)
4-[2-(N-isopropyl-benzoylamino)-5-trifluoromethylphenoxymethyl]benzoic acid

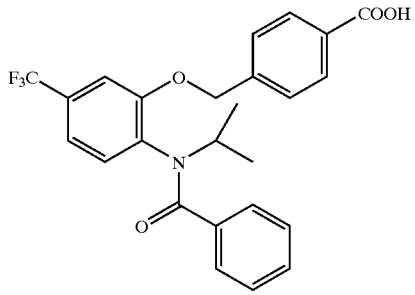

TLC: Rf 0.49 (CHCl₃:MeOH=9:1); NMR: δ 8.18 (2H, d, J=8.4 Hz), 7.52–7.35 (3H, m), 7.30–7.03 (6H, m), 7.02–6.92 (1H, m), 5.20–4.90 (2H, m), 4.90–4.70 (1H, m), 1.50–1.00 (6H, m).

EXAMPLE 53(3)
4-[2-(N-isopropyl-2-furoylamino)-5-trifluoromethylphenoxymethyl]benzoic acid

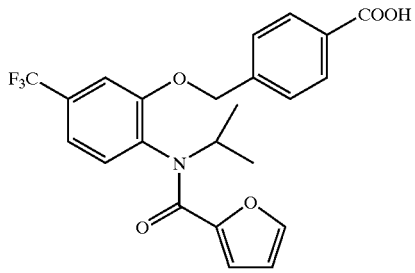

TLC: Rf 0.43 (CHCl₃:MeOH=9:1); NMR: δ 8.09 (2H, d, J=7.8 Hz), 7.43–7.22 (5H, m), 7.15 (1H, s), 6.25–6.20 (1H, m), 6.16–6.08 (1H, br), 5.20–4.84 (3H, m), 1.40–1.00 (6H, m).

EXAMPLE 54
4-(2-benzoylamino-5-chlorobenzoylamino)benzoic acid

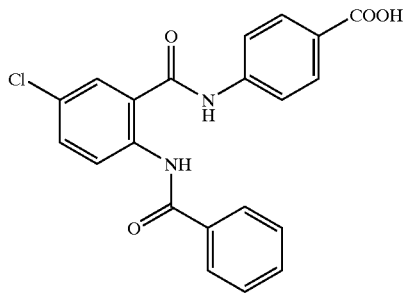

By using 2-nitro-5-chlorobenzoic acid chloride (prepared in Reference Example 13.), the title compound having the following physical data was obtained by the same procedure as Example 11→Reference Example 10→Example 11→Example 2.

TLC: Rf 0.52 (AcOEt:hexane:AcOH=7:12:1); NMR (DMSO-d₆): δ 12.77 (1H, brs), 11.33 (1H, s), 10.85 (1H, s), 8.36 (1H, d, J=9.0 Hz), 8.02–7.78 (7H, m), 7.69 (1H, dd, J=9.0, 2.5 Hz), 7.64–7.48 (3H, m).

EXAMPLE 55(1)–55(2)

By using 2-nitro-5-chlorobenzoic acid chloride (prepared in Reference Example 13.), the title compounds having the following physical data were obtained by the same procedure as Example 11→Reference Example 10→Reference Example 2→Example 2.

EXAMPLE 55(1)
4-[2-(2-thienylsulfonylamino)-5-chlorobenzoylamino]benzoic acid

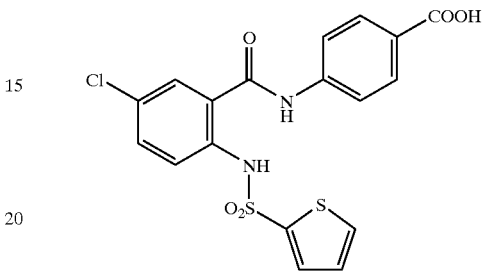

TLC: Rf 0.18 (CHCl₃:MeOH=9:1); NMR (DMSO-d₆): δ 12.73 (1H, br), 10.68 (1H, brs), 10.48 (1H, brs), 7.93 (2H, d, J=8.8 Hz), 7.87 (1H, dd, J=1.2 and 3.6 Hz), 7.81 (1H, d, J=2.2 Hz), 7.76 (2H, d, J=8.8 Hz), 7.61–7.53 (2H, m), 7.41 (1H, d, J=8.8 Hz), 7.05 (1H, dd, J=3.8 and 4.0 Hz).

Example 55(2)
4-(2-butylsulfonylamino-5-chlorobenzoylamino)benzoic acid

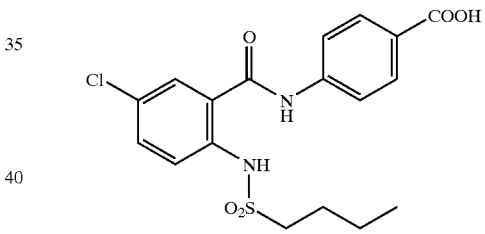

TLC: Rf 0.26 (CHCl₃:MeOH=9:1); NMR (DMSO-d₆): δ 12.77 (1H, brs), 10.80 (1H, brs), 9.94 (1H, s), 7.93 (2H, d, J=8.8 Hz), 7.88 (1H, d, J=2.2 Hz), 7.82 (2H, d, J=8.8 Hz), 7.61 (1H, dd, J=2.2 and 8.8 Hz), 7.54 (1H, d, J=8.8 Hz), 3.18 (2H, t-like), 1.66–1.51 (2H, m), 1.37–1.19 (2H, m), 0.74 (3H, t, J=7.2 Hz).

REFERENCE EXAMPLE 51
Methyl 4-(2-nitro-5-methylphenylthiomethyl)benzoate

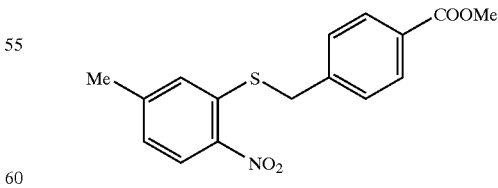

To a solution of methyl 4-acetylthiomethylbenzoate (794 mg) in MeOH (5.0 ml), sodium methoxide (191 mg) and 3-fluoro-4-nitrotoluene (500 mg) were added suceedingly in a stream of argon at 0° C. The mixture was warmed slowly to become at room temperature. The mixture was stirred for 4 hours. To the reaction mixture, a saturated aqueous ammonium chloride was added. The mixture was extracted with ethyl acetate, washed, dried over and concentrated under the reduced pressure. The residue was recrystrallized from ethanol to give the title compound (646 mg) having the following physical data.

TLC: Rf 0.49 (hexane:CH$_2$Cl$_2$:AcOEt=8:4:1).

EXAMPLE 56

4-[2-(N-isopropyl-2-furanylsulfonylamino)-5-methylphenylthiomethyl]benzoic acid

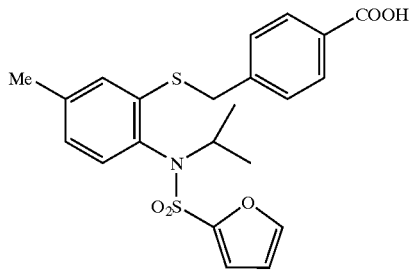

By using methyl 4-(2-nitro-5-methylphenylthiomethyl) benzoate (prepared in Reference Example 51.), the title compound having the following physical data was obtained by the same procedure as Reference Example 11→Reference Example 2→Example 17→Example 2.

TLC: Rf 0.45 (CHCl$_3$:MeOH:AcOH=100:5:1); NMR: δ 8.04 (2H, d, J=8.4 Hz), 7.58 (1H, dd, J=0.8, 1.8 Hz), 7.48 (2H, d, J=8.4 Hz), 7.08 (1H, m), 6.91–6.98 (2H, m), 6.84 (1H, d, J=8.0 Hz), 6.50 (1H, dd, J=2.0, 3.8 Hz), 4.47 (1H, sept, J=6.8 Hz), 4.19 (2H, s), 2.28 (3H, s), 1.16 (3H, d, J=6.8 Hz), 1.06 (3H, d, J=6.8 Hz).

EXAMPLE 57

4-[2-(N-isobutyl-2-thienylsulfonylamino)-5-trifluoromethylphenoxymethyl]cinnamic acid

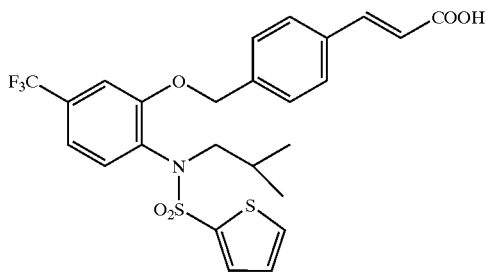

By using 2-nitro-5-trifluoromethylphenol, the title compound having the following physical data was obtained by the same procedure as Reference Example 18 (b)→Reference Example 12→Reference Example 2→Example 17→Example 2.

TLC: Rf 0.51 (CHCl$_3$:MeOH:AcOH=100:5:1); NMR: δ 7.80 (1H, d, J=16.2 Hz), 7.57 (2H, d, J=8.0 Hz), 7.22–7.46 (6H, m), 7.16 (1H, m), 6.93 (1H, dd, J=4.0, 5.2 Hz), 6.49 (1H, d, J=16.2 Hz), 4.94 (2H, brs), 3.45 (2H, d, J=7.2 Hz), 1.62 (1H, m), 0.91 (6H, d, J=6.6 Hz).

EXAMPLE 58

6-[2-(N-isopropyl-phenylsulfonylamino)-5-trifluoromethylphenoxymethyl]-2-naphthalic acid

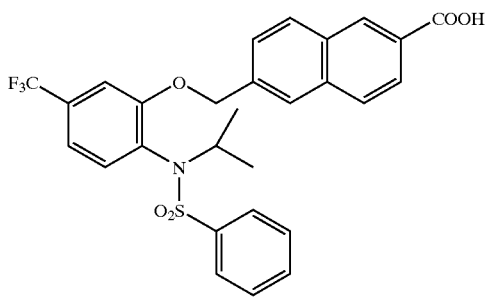

By using 2-(N-isopropyl-phenylsulfonylamino)-5-trifluoromethylphenol (prepared in Reference Example 24.) and ethyl 6-hydroxymethyl-2-naphthate, the title compound having the following physical data was obtained by the same procedure as Reference Example 18 (b)→Example 2.

TLC: Rf 0.55 (CHCl$_3$:MeOH:AcOH=100:5:1); NMR: δ 8.74 (1H, s), 8.17 (1H, dd, J=1.8, 8.8 Hz), 8.03 (1H, d, J=8.4 Hz), 8.03 (1H, brs), 7.95 (1H, d, J=8.8 Hz), 7.79–7.87 (2H, m), 7.61 (1H, dd, J=1.4, 8.4 Hz), 7.43 (1H, m), 7.32 (3H, m), 7.26 (2H, m), 5.26 (2H, s), 4.39 (1H, m), 1.08 (3H, d, J=6.6 Hz), 1.06 (3H, d, J=6.6 Hz).

EXAMPLE 59(1)–59(3)

By using 2-nitro-5-trifluoromethylphenol, the title compounds having the following physical data were-obtained by the same procedure as Reference Example 18 (b)→Reference Example 12→Example 27→Example 11→Example 2.

EXAMPLE 59(1)

4-[2-(N-isopropyl-2-furoylamino)-5-trifluoromethylphenoxymethyl]cinnamic acid

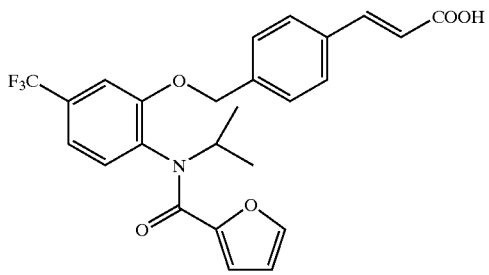

TLC: Rf 0.44 (CHCl$_3$:MeOH=9:1); NMR: δ 7.76 (1H, d, J=16.2 Hz), 7.52 (2H, d, J=8.4 Hz), 7.38 (1H, d, J=8.4 Hz), 7.32 (1H, d, J=8.4 Hz), 7.28–7.20 (3H, m), 7.17 (1H, s), 6.45 (1H, d, J=16.2 Hz), 6.24–6.19 (1H, m), 6.11–6.00 (1H, br), 5.20–4.80 (3H, m), 1.40–1.00 (6H, m).

EXAMPLE 59(2)

4-[2-(N-isobutyl-2-furoylamino)-5-trifluoromethylphenoxymethyl]cinnamic acid

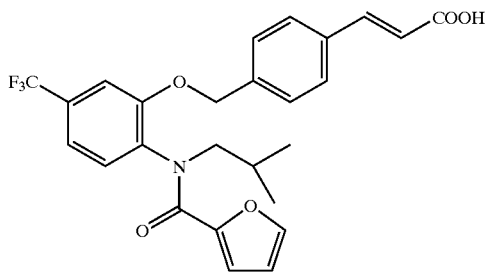

TLC: Rf 0.49 (CHCl$_3$:MeOH=9:1); NMR: δ 7.76 (1H, d, J=15.9 Hz), 7.52 (2H, d, J=8.4 Hz), 7.39 (1H, d, J=8.1 Hz), 7.33–7.15 (5H, m), 6.45 (1H, d, J=15.9 Hz), 6.28–6.10 (2H, m), 5.20–4.90 (2H, m), 4.00–3.80 (1H, br), 3.60–3.30 (1H, br), 2.00–1.80 (1H, m), 0.95 (6H, d, J=6.6 Hz).

EXAMPLE 59(3)

4-[2-(N-isopropyl-butyrylamino)-5-trifluoromethylphenoxymethyl]cinnamic acid

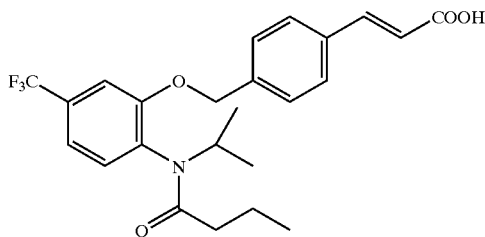

TLC: Rf 0.42 (CHCl$_3$:MeOH=9:1); NMR: δ 7.78 (1H, d, J=15.9 Hz), 7.58 (2H, d, J=8.1 Hz), 7.42 (2H, d, J=8.1 Hz), 7.35–7.20 (3H, m), 6.48 (1H, d, J=15.9 Hz), 5.20–4.93 (3H, m), 1.90 (2H, dt, J=2.7, 7.5 Hz), 1.64–1.50 (2H, m), 1.17 (3H, d, J=6.6 Hz), 0.94 (3H, d, J=6.6 Hz), 0.79 (3H, t, J=7.2 Hz).

EXAMPLE 60(1)–60(2)

By using 2-nitro-5-trifluoromethylphenol, the title compounds having the following physical data were obtained by the same procedure as Reference Example 18 (b)→Reference Example 12→Reference Example 2→Example 19→Example 2.

EXAMPLE 60(1)

4-[2-(N-isopropyl-4-ethoxyphenylsulfonylamino)-5-trifluoromethylphenoxymethyl]cinnamic acid

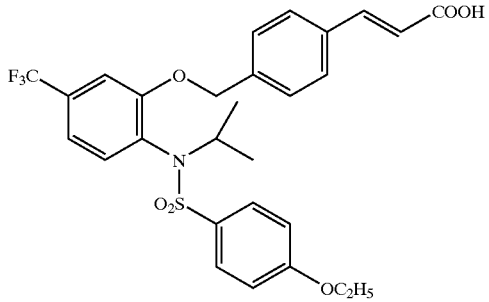

TLC: Rf 0.51 (CHCl$_3$:MeOH=9:1); NMR: δ 7.82 (1H, d, J=16.0 Hz), 7.72 (2H, d, J=8.8 Hz), 7.61 (2H, d, J=8.6 Hz), 7.48 (2H, d, J=8.6 Hz), 7.28–7.22 (3H, m), 6.77 (2H, d, J=8.8 Hz), 6.50 (1H, d, J=16.0 Hz), 5.10 (2H, s), 4.40–4.20 (1H, m), 4.01 (2H, q, J=6.8 Hz), 1.43 (3H, t, J=6.8 Hz), 1.07 (3H, d, J=6.6 Hz), 1.03 (3H, d, J=6.6 Hz).

EXAMPLE 60(2)

4-[2-(N-isobutyl-4-ethoxyphenylsulfonylamino)-5-trifluoromethylphenoxymethyl]cinnamic acid

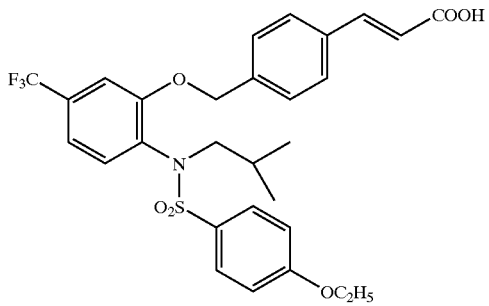

TLC: Rf 0.57 (CHCl$_3$:MeOH=9:1); NMR: δ 7.81 (1H, d, J=15.6 Hz), 7.60–7.47 (3H, m), 7.44 (1H, d, J=8.2 Hz), 7.30–7.10 (5H, m), 6.73(2H, d, J=8.8 Hz), 6.50 (1H, d, J=15.6 Hz), 5.00–4.80 (2H, br), 3.95 (2H, q, J=7.0 Hz), 3.39 (2H, d, J=6.8 Hz), 1.70–1.50 (1H, m), 1.41 (3H, t, J=6.8 Hz), 0.88 (6H, d, J=6.6 Hz).

EXAMPLE 61

4-[2-(N-isopropyl-3-ethoxyphenylsulfonylamino)-5-trifluoromethylphenoxymethyl]benzoic acid

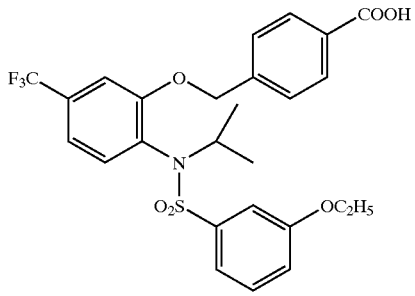

By using methyl 4-(2-amino-5-trifluoromethylphenoxymethyl)benzoate (prepared in Reference Example 17.), the title compound having the following physical data was obtained by the same procedure as Example 4→Example 19→Example 2.

TLC: Rf 0.63 (CHCl$_3$:MeOH=9:1); NMR: δ 8.15 (2H, d, J=8.4 Hz), 7.53 (2H, d, J=8.4 Hz), 7.40–7.20 (6H, m), 7.02 (1H, ddd, J=1.2, 2.4, 8.0 Hz), 5.13 (2H, s), 4.52–4.36 (1H, m), 3.98 (2H, q, J=6.8 Hz), 1.40 (3H, t, J=6.8 Hz), 1.08 (3H, d, J=6.6 Hz), 1.06 (3H, d, J=6.6 Hz).

EXAMPLE 62(1)–62(2)

By using 2-nitrobenzoic acid chloride, the title compounds having the following physical data were obtained by the same procedure as Example 11→Reference Example 20→Reference Example 2→Example 2.

EXAMPLE 62(1)

4-[2-(3-chlorophenylsulfonylamino)benzoylamino]benzoic acid

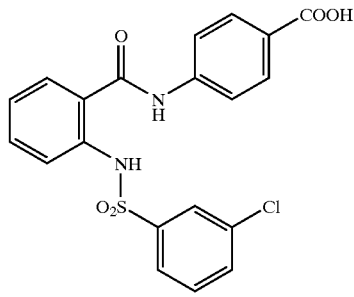

TLC: Rf 0.38 (CHCl$_3$:MeOH=9:1); NMR (DMSO-d$_6$): δ 10.59 (1H, s), 10.44 (1H, s), 7.95 (2H, d, J=8.4 Hz), 7.86–7.60 (6H, m), 7.58–7.45 (2H, m), 7.38–7.25 (2H, m).

EXAMPLE 62(2)

4-[2-(4-bromophenylsulfonylamino)benzoylamino]benzoic acid

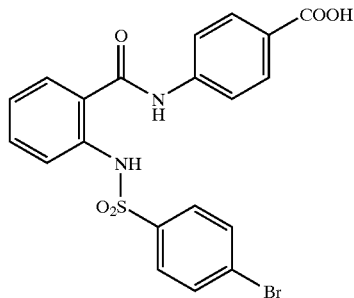

TLC: Rf 0.39 (CHCl$_3$:MeOH=9:1); NMR (DMSO-d$_6$): δ 10.55 (1H, s), 10.38 (1H, s), 7.96 (2H, d, J=8.8 Hz), 7.90–7.45 (8H, m), 7.44–7.25 (2H, m).

FORMULATION EXAMPLE 1

The following compounds were admixed in conventional method and punched out to obtain 100 tablets each containing 5 mg of active ingredient.

| | |
|---|---|
| 4-(2-phenylsulfonylamino-5-chlorobenzoylamino)benzoic acid (prepared in Example 2.) | 500 mg |
| Cellulose calcium glycolate (disintegrating agent) | 200 mg |
| Magnesium stearate (lubricating agent) | 100 mg |
| Micro crystalline cellulose | 9.2 g |

We claim:
1. A sulfonamide or carboamide derivative of the formula (1):

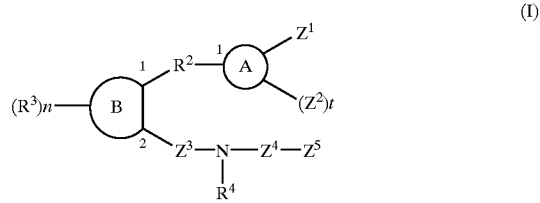

wherein

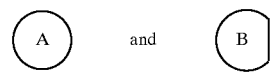

each, independently, is C5–15 carbocyclic ring or 5–7 membered heterocyclic ring containing one or two oxygen, sulfur or nitrogen atom(s), $Z^1$ is
—COR$^1$,
—C1–4 alkylene-COR$^1$,
—CH=CH—COR$^1$,
C≡COR$^1$,
(wherein, R$^1$ is hydroxy, C1–4 alkoxy or formula: NR$^6$R$^7$
wherein, R$^6$ and R$^7$ each, independently, is H or C1–4 alkyl)), or
C1–5 alkylene-OH, $Z^2$ is H, C1–4 alkyl, C1–4 alkoxy, nitro, halogen, trifluoromethyl, trifluoromethoxy, hydroxy or COR$^1$ (wherein R$^1$ is as defined hereinbefore), $Z^3$ is single bond or C104 alkylene, $Z^4$ is SO$_2$ or CO, $Z^5$ is
(1) C1–8 alkyl, C2–8 alkenyl, or C2–8 alkynyl,
(2) phenyl, C3–7 cycloalkyl, or 5–7 membered heterocyclic ring containing one or two oxygen, sulfur or nitrogen atom(s), or
(3) C1–4 alkyl, C2–4 alkenyl or C2–4 alkynyl substituted by phenyl or C3–7 cycloalkyl (phenyl, C3–7 cycloalkyl and 5–7 membered heterocyclic ring containing one or two oxygen, sulfur or nitrogen atom(s) mentioned in the above (2) and (3) may be substituted by 1–5 of R$^5$ (wherein R$^5$ (if two or more R$^5$, each independently) is H, C1–6 alkyl, C1–6 alkoxy, C1–6 alkylthio, nitro, halogen, tifluoromethyl, trifluoromethoxy or hydroxy)), $R^2$ is
CONR$^8$,
NR$^8$CO,
CONR$^8$—C1–4 alkylene,
C1–4 alkylene-CONR$^8$,
NR$^8$CO—C1–4 alkylene, C1–4 alkylene-NR⁸CO,
C1–3 alkylene-CONR⁸—C1–3 alkylene, or
C1–3 alkylene-NR⁸CO—C13 alkylene
(wherein each R⁸ is H or C1–4 alkyl),
O, S, NZ⁶ (wherein Z⁶ is H or C1–4 alkyl),
Z⁷-C1–4 alkylene,
C1–4 alkylene-Z⁷, or
C1–3 alkylene-Z⁷-C1–3 alkylene
(wherein each Z⁷ is O, S or NZ⁶ (wherein Z⁶ is as defined hereinbefore))
CO,
CO—C1–4 alkylene,
C1–4 alkylene-CO,
C1–3 alkylene-CO—C1–3 alkylene,
C2–4 alkylene,
C2–4 alkenylene, or
C2–4 alkynylene,
R³ is H, C1–6 alkyl, C1–6 alkoxy, C1–6 alkylthio, nitro, halogen, frifluoromethyl, trifluoromethoxy, hydroxy or hydroxymethyl,
R⁴ is
(1) H,
(2) C1–8 alkyl, C2–8 alkenyl, or C2–8 alkynyl,
(3) C1–6 alkyl substituted by one or two substituent(s) selected from the group consisting of COOZ⁸, CONZ⁹Z¹⁰, and OZ⁸ (wherein Z⁸, Z⁹ and Z¹⁰ each, independently, is H or C1–4 alkyl) and C1–4 alkoxy-C1–4 alkoxy,
(4) C3–7 cycloalkyl, or
(5) C1–4 alkyl, C2–4 alkenyl or C2–4 alkynyl substituted by phenyl or C3–7 cycloalkyl (phenyl and C3–7 cycloalkyl mentioned in the above (4) and (5) may be substituted by 1–5 of R⁵ (wherein R⁵ is as defined hereinbefore)), and n and t each, independently, is an integer of 1–4,
with the proviso that (1) R² and Z³ should be connected at the 1- or 2-position of

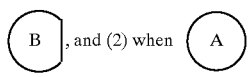

is a benzene ring and (Z²)t is other than COR¹, Z¹ should be connected at the 3- or 4-position of the benzene ring), or a non-toxic salt thereof.; with the proviso that when

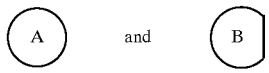

are each C5–15 carbocyclic ring, R² is not —CONH— or —O—C1–4 alkylene.

2. A compound according to claim 1, wherein

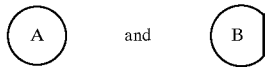

is C5–15 carbocyclic ring and Z⁵ is C1–8 alkyl, C2–8 alkenyl, C2–8 alkynyl, or group containing phenyl or C3–7 cycloalkyl.

3. A compound according to claim 1, wherein at least one of

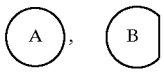

and Z⁵ is 5–7 membered heterocyclic ring containing one or two oxygen, sulfur or nitrogen atom(s).

4. A compound according to claim 1, wherein

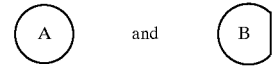

is C5–15 carbocyclic ring and Z⁵ is 5–7 membered heterocyclic ring containing one or two oxygen, sulfur or nitrogen atom(s).

5. A compound according to claim 1, wherein one of

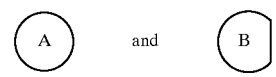

is 5–7 membered heterocyclic ring containing one or two oxygen, sulfur or nitrogen atom(s) and the other is C5–15 carbocyclic ring.

6. A compound according to claim 1, wherein R² is
CONR⁸,
CONR⁸—C1–4 alkylene,
C1–4 alkylene-CONR⁸,
C1–3 alkylene-CONR⁸—C1–3 alkylene,
NR⁸CO,
NR⁸CO—C1–4 alkylene,
C1–4 alkylene-NR⁸CO or
C1–3 alkylene-NR⁸CO—C1–3 alkylene
(wherein each R⁸ is H or C1–4 alkyl.).

7. A compound according to claim 1, wherein R² is
O, S, NZ⁶
(wherein Z⁶ is H or C1–4 alkyl.),
Z7-C1–4 alkylene,
C1–4 alkylene-Z⁷, or
C1–3 alkylene-Z⁷-C1–3 alkylene
(wherein each Z⁷ is O, S or NZ⁶ (wherein Z⁶ is as defined hereinbefore)).

8. A compound according to claim 1, wherein R² is C2–4 alkylene, C2–4 alkenylene or C2–4 alkynylene.

9. A compound according to claim 1, wherein R² is CO,
CO—C1–4 alkylene,
C1–4 alkylene-CO or
C1–3 alkylene-CO—C1–3 alkylene.

10. A compound according to claim 1 which is selected from
(1) 4-[2-[2-(4-chlorophenylsulfonylamino)-5-chlorophenyl]-(E)-vinyl]benzoic acid,
(2) 4-[2-[2-(4-chlorophenylsulfonylamino)-5-chlorophenyl]-(Z)-vinyl-]benzoic acid,
(3) 4-[2-[2-(4-chlorophenyl)sulfonylamino-5-chlorophenyl]ethyl]benzoic acid,
(4) 4-[2-[2-(4-chlorophenylsulfonylamino)-5-chlorophenyl-]ethynyl]benzoic acid,
(5) 4-[2-[2-(N-isopropyl-phenylsulfonylamino)-5-trifluoromethylphenyl]ethyl]benzoic acid, (6) 4-[2-[2-(N-isopropyl-phenylsul-fonylamino)-5-trifluoromethylphenyl]-(E)-vinyl]benzoic acid and (7) 4-[2-[2-(N-isopropyl-phenylsulfonylamino)-5-trifluoromethylphenyl]-(Z)-vi-nyl]benzoic acid, and methyl esters thereof.

11. A compound according to claim 1 which is selected from (1) 5-[2-(N-isopropyl-phenylsulfonylamino)-5-methylphenoxymethyl]furan-2-carb-oxylic acid, (2) 6-(2-phenylsulfonylamino-5-chlorophenoxymethyl) nicotinic acid, (3) 5-[2-(N-isopropyl-phenylsulfonylamino)-5-trifluoromethylphenoxymethyl]-thiophene-2-carboxylic acid, (4) 5-[2-(N-isopropyl-phenylsulfonylamino)-5-trifluoromethylphenoxymethyl]-furan-2-carboxylic acid, (5) 5-[2-(N-isopropyl-phenylsulfonylamino)-5-methylphenoxymethyl]-thiophene-2-carboxylic acid, (6) 5-[2-(N-isopropyl-phenylsulfonylamino)-5-chloroph-enoxymethyl]thiophene-2-carboxylic acid, (7) 5-[2-(N-isopropyl-phenylsulf-onylamino)-5-chlorophenoxymethyl]furan-2-carboxylic acid and (8) 4-(3-phenylsulfonylamino-5-trifluoromethylpyridine-2-yloxymethyl)benzoic acid, and methyl esters thereof.

12. A prostaglandin $E_2$ antagonist or agonist which comprises the sulfonamide or carboamide derivative of the formula (I) depicted in claim 1 or a non-toxic salt thereof as an active ingredient.

13. A compound of claim 11, wherein the compound is 5-[2-(N-isopropyl-phenylsulfonylamino)-5-trifluoromethylphenoxymethyl]-thiophene-2-carboxylic acid.

\* \* \* \* \*